(12) United States Patent
Schupp et al.

(10) Patent No.: US 12,404,558 B2
(45) Date of Patent: Sep. 2, 2025

(54) METHODS AND ASSAYS FOR DETECTION AND SUBTYPING OF MICROBIAL PATHOGENS

(71) Applicants: The Translational Genomics Research Institute, Phoenix, AZ (US); Arizona Board of Regents on Behalf of Northern Arizona University, Flagstaff, AZ (US)

(72) Inventors: James Schupp, Flagstaff, AZ (US); Jason Sahl, Phoenix, AZ (US); Paul Keim, Flagstaff, AZ (US); David Engelthaler, Flagstaff, AZ (US); David Wagner, Phoenix, AZ (US); Viacheslav Fofanov, Phoenix, AZ (US)

(73) Assignees: The Translational Genomics Research Institute, Phoenix, AZ (US); Arizona Board of Regents on Behalf of Northern Arizona University, Flagstaff, AZ (US)

( * ) Notice: Subject to any disclaimer, the term of this patent is extended or adjusted under 35 U.S.C. 154(b) by 1071 days.

(21) Appl. No.: 17/426,600

(22) PCT Filed: Jan. 28, 2020

(86) PCT No.: PCT/US2020/015395
§ 371 (c)(1),
(2) Date: Jul. 28, 2021

(87) PCT Pub. No.: WO2020/159977
PCT Pub. Date: Aug. 6, 2020

(65) Prior Publication Data
US 2022/0090172 A1 Mar. 24, 2022

Related U.S. Application Data

(60) Provisional application No. 62/798,463, filed on Jan. 29, 2019.

(51) Int. Cl.
*C12Q 1/689* (2018.01)
*C12Q 1/04* (2006.01)
(Continued)

(52) U.S. Cl.
CPC ............... *C12Q 1/689* (2013.01); *C12Q 1/04* (2013.01); *C12Q 1/6844* (2013.01); *C12Q 1/686* (2013.01);
(Continued)

(58) Field of Classification Search
CPC ...................................................... C12Q 1/689
See application file for complete search history.

(56) References Cited

U.S. PATENT DOCUMENTS

2004/0259226 A1* 12/2004 Robey ................. C12Q 1/689
435/252.3
2006/0003352 A1* 1/2006 Lipkin .................. C12Q 1/686
435/6.14
(Continued)

FOREIGN PATENT DOCUMENTS

WO 2015/070187 A2 5/2015

OTHER PUBLICATIONS

Genbank CP019726.1—Bacillus anthracis strain Sterne 34F2 genome—NCBI (Year: 2017).*
(Continued)

*Primary Examiner* — Aaron A Priest
*Assistant Examiner* — Tian Yu
(74) *Attorney, Agent, or Firm* — FULLER IP LAW LLC; Rodney J. Fuller

(57) ABSTRACT

The present invention provides methods of detecting a biothreat agent in a sample, comprising detecting at least one biothreat-specific amplicon in the sample. The methods also
(Continued)

encompass confirming the absence of the biothreat agent by detecting Near Neighbor specific amplicons to avoid false positive results.

20 Claims, 27 Drawing Sheets

Specification includes a Sequence Listing.

(51) Int. Cl.
*C12Q 1/6844* (2018.01)
*C12Q 1/686* (2018.01)
*C12R 1/07* (2006.01)

(52) U.S. Cl.
CPC ... *C12Q 2600/156* (2013.01); *C12Q 2600/16* (2013.01); *C12R 2001/07* (2021.05)

(56) References Cited

U.S. PATENT DOCUMENTS

| | | | | |
|---|---|---|---|---|
| 2006/0057603 | A1* | 3/2006 | Radnedge | C12Q 1/689 435/6.12 |
| 2013/0149708 | A1 | 6/2013 | Riojas et al. | |
| 2016/0326572 | A1 | 11/2016 | Schupp et al. | |
| 2018/0173843 | A1 | 6/2018 | Lemmer et al. | |

OTHER PUBLICATIONS

Afshinnekoo, E., et al. Geospatial Resolution of Human and Bacterial Diversity with City-Scale Metagenomics. Cell Systems 2015; 1(1):72-87.

Agaisse, H., et al. PlcR is a pleiotropic regulator of extracellular virulence factor gene expression in Bacillus thuringiensis. Microbiology 1999; 32(5):1043-1053.

Slamti, L., et al. Distinct mutations in PlcR explain why some strains of Bacillus cereus group are nonhemolytic. Journal of Bacteriology 2004; 186(11):3531-3538.

Kolsto, A., et al. What Sets Bacillus anthracis Apart from Other Bacillus Species? Annual Review of Microbiology 2009; 63(1):451-476.

Lau, S. Y., et al. Cell Division Defects in *Escherichia coli* Deficient in the Multidrug Efflux Transporter AcrEF-TolC. J Bacteriol 2005; 187(22):7815-7825.

Nagakubo, S., et al. The putative response regulator BaeR stimulates multidrug resistance of *Escherichia coli* via a hovel multidrug exporter system, MdtABC. J Bacteriol 2002; 184(15):4161-4167.

Tanabe, H., et al. Growth phase-dependent transcription of emrKY, a homolog of multidrug efflux emrAB genes of *Escherichia coil*, is induced by tetracycline. J Gen Appl Microbiol 1997; 43(5):257-263.

Sulavik, M. C., et al. Antibiotic susceptibility profiles of Escherichia coli strains lacking multidrug efflux pump genes. Antimicrob Agents Chemother 2001; 45(4):1126-1136.

Bharat, A., et al. Effect of Variants of Penicillin-Binding Protein 2 on Cephalosporin and Carbapenem Susceptibilities in Neisseria gonorrhoeae. Antimicrob Agents Chemother 2015; 59(8):5003-5006.

Sun, S., et al. Resistance to β-Lactam Antibiotics Conferred by Point Mutations in Penicillin-Binding Proteins PBP3, PBP4 and PBP6 in *Salmonella enterica*. PLoS One 2014; 9:e97202.

Scholz, P., et al. Complete nucleotide sequence and gene organization of the broad-host-range plasmid RSF1010. Gene 1989; 75(2):271-288.

Agerso, Y., et al. Identification of Tet 39, a novel class of tetracycline resistance determinant in *Acinetobacter* spp. of environmental and clinical origin. J Antimicrob Chemother 2005; 55(4):566-569.

Liu, B., et al. ARDB—Antibiotic Resistance Genes Database. Nucl Acids Res 2009; 37 (suppl 1): D443-D447.

McArthur, A. G., et al. The comprehensive antibiotic resistance database. Antimicrob Agents Chemother 2013; 57(7):3348-3357.

Goodwin, S., et al. Coming of age: ten years of next-generation sequencing technologies. Nat Rev Genet 2016; 17(6):333-351.

GenBank submission EF410354, Feb. 12, 2007 (online); Retrieved May 27, 2020 from the internet <URL: https://www.ncbi.nlm.nih.gov/nuccore/EF410354>nt 1344-1363.

GenBank submission CP003187, Jan. 30, 2014 (online); Retrieved May 27, 2020 from the internet <URL: https://www.ncbi.nlm.nih.gov/nuccore/CP003187>nt 4396310-4396329, nt 4396521-4396542.

* cited by examiner

| Species | Yersinia pestis | | Yersinia pestis specific SNP | | | | | | Yersinia PGM pigmentation locus | | Yersinia pestis pla plasmid specific | Yersinia enterocolitica specific | Yersinia pestis AMR specific SNP | Yersinia pestis pIP1202 plasmid | | |
|---|---|---|---|---|---|---|---|---|---|---|---|---|---|---|---|---|
| pestis | + | + | + | + | + | + | + | + | + | + | + | - | - | - | - | - |
| pestis | + | + | + | + | + | + | + | + | + | + | + | - | - | - | - | - |
| pestis | + | + | + | + | + | + | + | + | + | + | + | - | - | - | - | - |
| pestis | + | + | + | + | + | + | + | + | + | + | + | - | - | - | - | - |
| pestis | + | + | + | + | + | + | + | + | + | + | + | - | - | - | - | - |
| pestis | + | + | + | + | + | + | + | + | - | - | + | - | - | - | - | - |
| pestis | - | - | - | + | - | - | - | - | - | + | - | - | - | - | - | - |
| pestis | + | + | + | + | + | + | + | + | + | + | + | - | - | - | - | - |
| pestis | + | + | + | + | + | + | + | + | + | + | + | - | - | - | - | - |
| pestis | + | + | + | + | + | + | + | + | + | + | + | - | - | - | - | - |
| pestis | + | + | + | + | + | + | + | + | - | - | + | - | - | - | - | - |
| pestis | + | + | + | + | + | + | + | + | + | + | + | - | - | - | - | - |
| pestis | + | + | + | + | + | + | + | + | + | + | + | - | - | - | - | - |
| pestis | + | + | + | + | + | + | + | + | - | - | - | - | - | - | - | - |
| pestis | + | + | + | + | + | + | + | + | + | + | - | - | - | - | - | - |
| pestis | - | - | - | - | - | - | - | - | - | - | - | - | - | - | - | - |
| pestis | - | - | - | - | - | - | - | - | - | - | - | - | - | - | - | - |
| pestis | - | - | - | - | - | - | - | - | - | - | - | - | - | - | - | - |
| pestis | + | + | + | + | + | + | + | + | + | + | + | - | - | - | - | - |
| pestis | + | + | + | + | + | + | + | + | - | - | + | - | - | - | - | - |
| pestis | + | + | + | + | + | + | + | + | + | + | + | - | - | - | - | - |
| pestis | + | + | + | + | + | + | + | + | + | + | - | - | - | - | - | - |
| pestis | + | + | + | + | + | + | + | + | + | + | + | - | - | - | - | - |
| pestis | + | + | + | + | + | + | + | + | + | + | + | - | - | - | - | - |
| pestis | + | + | + | + | + | + | + | + | + | + | + | - | - | - | - | - |
| pestis | + | + | + | + | + | + | + | + | + | + | + | - | - | - | - | - |
| pestis | + | + | + | + | + | + | + | + | + | + | + | - | - | - | - | - |
| pestis | + | + | + | + | + | + | + | + | + | + | + | - | - | - | - | - |
| pestis | + | + | + | + | + | + | + | + | + | + | + | - | - | - | - | - |
| pestis | + | + | + | + | + | + | + | + | + | + | + | - | - | - | - | - |
| pestis | + | + | + | + | + | + | + | + | + | + | + | - | - | - | - | - |
| pestis | + | + | + | + | + | + | + | + | + | + | + | - | - | - | - | - |
| pestis | + | + | + | + | + | + | + | + | + | + | + | - | - | - | - | - |
| pestis | - | + | + | - | + | + | + | + | + | + | + | - | - | - | - | - |
| pestis | + | + | + | + | + | + | + | + | + | + | + | - | - | - | - | - |
| pestis | + | + | + | + | + | + | + | + | + | + | + | - | - | - | - | - |
| pestis | + | + | + | + | + | + | + | + | + | + | + | - | - | - | - | - |
| pestis | + | + | + | + | + | + | + | + | + | + | + | - | - | - | - | - |
| pestis | + | + | + | + | + | + | + | + | + | + | + | - | - | - | - | - |
| pestis | + | + | + | + | + | + | + | + | + | + | + | - | - | - | - | - |
| pestis | + | + | + | + | + | + | + | + | + | + | + | - | - | - | - | - |
| pestis | + | + | + | + | + | + | + | + | + | + | + | - | - | - | - | - |
| pestis | + | + | + | + | + | + | + | + | + | + | + | - | - | - | - | - |
| pestis | + | + | + | + | + | + | + | + | + | + | + | - | - | - | - | - |

FIG. 4B

| Species | Yersinia pestis | | Yersinia pestis specific SNP | | | | | | Yersinia PsaM pigmentation locus | | Yersinia pestis pla plasmid specific | Yersinia enterocolitica specific | Yersinia pestis AMR specific SNP | Yersinia pestis pIP1202 plasmid | | |
|---|---|---|---|---|---|---|---|---|---|---|---|---|---|---|---|---|
| pestis | + | + | + | + | + | + | + | + | + | + | + | - | - | - | - | - |
| pestis | + | + | + | + | + | + | + | + | + | + | + | - | - | - | - | - |
| pestis | + | + | + | + | + | + | + | + | + | + | + | - | - | - | - | - |
| pestis | + | + | + | + | + | + | + | + | + | + | + | - | - | - | - | - |
| pestis | + | + | + | + | + | + | + | + | + | + | + | - | - | - | - | - |
| pestis | + | + | + | + | + | + | + | + | + | + | + | - | - | - | - | - |
| pestis | + | + | + | + | + | + | + | + | + | + | + | - | - | - | - | - |
| pestis | + | + | + | + | + | + | + | + | + | + | + | - | - | - | - | - |
| pestis | + | + | + | + | + | + | + | + | + | + | + | - | - | - | - | - |
| pestis | + | + | + | + | + | + | + | + | + | + | + | - | - | - | - | - |
| pestis | + | + | + | + | + | + | + | + | + | + | + | - | - | - | - | - |
| pestis | + | + | + | + | + | + | + | + | + | + | + | - | - | - | - | - |
| pestis | + | + | + | + | + | + | + | + | + | + | + | - | - | - | - | - |
| pestis | + | + | + | + | + | + | + | + | + | + | + | - | - | - | - | - |
| pestis | + | + | + | + | + | + | + | + | + | + | - | - | - | - | - | - |
| pestis | + | + | + | + | + | + | + | + | + | + | + | - | - | - | - | - |
| pestis | + | + | + | + | + | + | + | + | + | + | + | - | - | - | - | - |
| pestis | + | + | + | + | + | + | + | + | + | + | + | - | - | - | - | - |
| pestis | + | + | + | + | + | + | + | + | + | + | + | - | - | - | - | - |
| pestis | + | + | + | + | + | + | + | + | + | + | + | - | - | - | - | - |
| pestis | + | + | + | + | + | + | + | - | + | + | + | - | - | - | - | - |
| pestis | + | + | + | + | + | + | + | + | + | + | + | - | - | - | - | - |
| pestis | + | + | + | + | + | + | + | + | + | + | + | - | - | - | - | - |
| pestis | + | + | + | + | + | + | + | + | + | + | + | - | - | - | - | - |
| pestis | + | + | + | + | + | + | + | + | + | + | + | - | - | - | - | - |
| pestis | + | + | + | + | + | + | + | + | + | + | + | - | - | - | - | - |
| pestis | + | + | + | + | + | + | + | + | + | + | - | - | - | - | - | - |
| pestis | + | + | + | + | + | + | + | + | - | - | + | - | - | - | - | - |
| pestis | + | + | + | + | + | + | + | + | + | + | + | - | - | - | - | - |
| pestis | + | + | + | + | + | + | + | + | + | + | + | - | - | - | - | - |
| pestis | + | + | + | + | + | + | + | + | + | + | + | - | - | - | - | - |
| pestis | + | + | + | + | + | + | + | + | + | + | - | - | - | - | - | - |
| pestis | + | + | + | + | + | + | + | + | + | + | - | - | - | - | - | - |
| pestis | + | + | + | + | + | + | + | + | + | + | - | - | - | - | - | - |
| pestis | + | + | + | + | + | + | + | + | + | + | + | - | - | - | - | - |
| pestis | + | + | + | + | + | + | + | + | + | + | - | - | - | - | - | - |
| pestis | + | + | + | + | + | + | + | + | + | + | - | - | - | - | - | - |
| pestis | + | + | + | + | + | + | + | + | + | + | + | - | - | - | - | - |
| pestis | + | + | + | + | + | + | + | + | + | + | - | - | - | - | - | - |
| pestis | + | + | + | + | + | + | + | + | + | + | + | - | - | - | - | - |
| pestis | + | + | + | + | + | + | + | + | + | + | + | - | - | - | - | - |
| pestis | + | + | + | + | + | + | + | + | + | + | + | - | - | - | - | - |
| pestis | + | + | + | + | + | + | + | + | + | + | + | - | - | - | - | - |
| pestis | + | + | + | + | + | + | + | + | - | - | - | - | - | - | - | - |

FIG. 4C

| Species | Yersinia pestis | | Yersinia pestis specific SNP | | | | | | Yersinia PGM pigmentation locus | | Yersinia pestis pla plasmid specific | Yersinia enterocolitica specific | Yersinia pestis AMR specific SNP | Yersinia pestis pIP1202 plasmid | | |
|---|---|---|---|---|---|---|---|---|---|---|---|---|---|---|---|---|
| pestis | + | + | + | + | + | + | + | + | + | + | - | - | - | - | - | - |
| pestis | + | + | + | + | + | + | + | + | + | + | - | - | - | - | - | - |
| pestis | + | + | + | + | + | + | + | + | + | + | + | - | - | - | - | - |
| pestis | + | + | + | + | + | + | + | + | + | + | + | - | - | - | - | - |
| pestis | + | + | + | + | + | + | + | + | - | - | - | - | - | - | - | - |
| pestis | - | - | + | - | - | + | + | - | + | + | + | - | - | - | - | - |
| pestis | + | + | + | + | + | + | + | + | - | - | - | - | - | - | - | - |
| pestis | + | + | + | + | + | + | + | + | - | - | + | - | - | - | - | - |
| pestis | + | + | + | + | + | + | + | + | + | + | + | - | - | - | - | - |
| pestis | + | + | + | + | + | + | + | + | + | + | + | - | - | - | - | - |
| pseudotuberculosis | - | - | - | - | - | - | - | - | - | - | - | - | - | - | - | - |
| pseudotuberculosis | - | - | - | - | - | - | - | - | - | - | - | - | - | - | - | - |
| pseudotuberculosis | - | - | - | - | - | - | - | - | - | - | - | - | - | - | - | - |
| pseudotuberculosis | - | - | - | - | - | - | - | - | + | + | - | - | - | - | - | - |
| pseudotuberculosis | - | - | - | - | - | - | - | - | - | - | - | - | - | - | - | - |
| pseudotuberculosis | - | - | - | - | - | - | - | - | - | - | - | - | - | - | - | - |
| pseudotuberculosis | - | - | - | - | - | - | - | - | - | - | - | - | - | - | - | - |
| pseudotuberculosis | - | - | - | - | - | - | - | - | + | + | - | - | - | - | - | - |
| pseudotuberculosis | - | - | - | - | - | - | - | - | + | - | - | - | - | - | - | - |
| pseudotuberculosis | - | - | - | - | + | - | - | - | + | + | - | - | - | - | - | - |
| pseudotuberculosis | - | - | - | - | - | - | - | - | - | - | - | - | - | - | - | - |
| pseudotuberculosis | - | - | - | - | - | - | - | - | - | - | - | - | - | - | - | - |
| pseudotuberculosis | - | - | - | - | - | - | - | - | - | - | - | - | - | - | - | - |
| pseudotuberculosis | - | - | - | - | - | - | - | - | - | - | - | - | - | - | - | - |
| pseudotuberculosis | - | - | - | - | - | - | - | - | - | - | - | - | - | - | - | - |
| pseudotuberculosis | - | - | - | - | - | - | - | - | - | - | - | - | - | - | - | - |
| pseudotuberculosis | - | - | - | - | - | - | - | - | - | - | - | - | - | - | - | - |
| pseudotuberculosis | - | - | - | - | - | - | - | - | - | - | - | - | - | - | - | - |
| pseudotuberculosis | - | - | - | - | - | - | - | - | + | - | - | - | - | - | - | - |
| pseudotuberculosis | - | - | - | - | - | - | - | - | - | - | - | - | - | - | - | - |
| pseudotuberculosis | - | - | - | - | - | - | - | - | - | - | - | - | - | - | - | - |
| pseudotuberculosis | - | - | - | - | - | - | - | - | - | - | - | - | - | - | - | - |
| pseudotuberculosis | - | - | - | - | - | - | - | - | - | - | - | - | - | - | - | - |
| pseudotuberculosis | - | - | - | - | - | - | - | - | + | + | - | - | - | - | - | - |
| pseudotuberculosis | - | - | - | - | - | - | - | - | - | - | - | - | - | - | - | - |
| pseudotuberculosis | - | - | - | - | - | - | - | - | - | - | - | - | - | - | - | - |
| pseudotuberculosis | - | - | - | - | - | - | - | - | + | + | - | - | - | - | - | - |
| pseudotuberculosis | - | - | - | - | - | - | - | - | - | - | - | - | - | - | - | - |
| pseudotuberculosis | - | - | - | - | + | - | - | - | + | - | - | - | - | - | - | - |
| pseudotuberculosis | - | - | - | - | - | - | - | - | - | - | - | - | - | - | - | - |
| pseudotuberculosis | - | - | - | - | - | - | - | - | - | - | - | - | - | - | - | - |
| pseudotuberculosis | - | - | - | - | - | - | - | - | - | - | - | - | - | - | - | - |
| pseudotuberculosis | - | - | - | - | - | - | - | - | - | - | - | - | - | - | - | - |
| frederiksenii | - | - | - | - | - | - | - | - | - | - | - | - | - | - | - | - |
| enterolitica | - | - | - | - | - | - | - | - | - | - | - | + | - | - | - | - |

FIG. 4D

| Species | Subspecies | Francisella tularensis species specific duplicate marker | Francisella novicida | Francisella noatunensis | Francisella philomiragia | Francisella tularensis specific SNP assay | Francisella tularensis A1-clade | Francisella tularensis A2-clade | Francisella tularensis B-clade | Francisella tularensis A-clade |
|---|---|---|---|---|---|---|---|---|---|---|
| tularensis | tularensis | + | + | - | - | - | + | + | + | - | + |
| tularensis | tularensis | + | + | - | - | - | + | + | + | - | + |
| tularensis | tularensis | + | + | - | - | - | + | - | + | - | + |
| tularensis | tularensis | + | + | - | - | - | + | - | + | - | + |
| tularensis | tularensis | + | + | - | - | - | + | + | + | - | + |
| tularensis | tularensis | + | + | - | - | - | + | - | - | - | + |
| tularensis | tularensis | + | + | - | - | - | + | - | - | + | + |
| tularensis | tularensis | - | - | - | - | - | - | - | - | - | - |
| tularensis | tularensis | - | - | - | - | - | - | - | - | - | - |
| tularensis | tularensis | - | - | - | - | - | - | - | - | - | - |
| tularensis | tularensis | + | + | - | - | - | + | + | + | - | + |
| tularensis | tularensis | + | + | - | - | - | + | + | + | - | + |
| tularensis | tularensis | + | + | - | - | - | + | + | + | - | + |
| tularensis | tularensis | + | + | - | - | - | + | + | + | - | + |
| tularensis | tularensis | + | + | - | - | - | + | + | + | - | + |
| tularensis | tularensis | + | + | - | - | - | + | + | + | - | + |
| tularensis | tularensis | + | + | - | - | - | + | - | - | + | + |
| tularensis | tularensis | + | + | - | - | - | + | + | + | - | + |
| tularensis | tularensis | + | + | - | - | - | + | + | + | - | + |
| tularensis | tularensis | + | + | - | - | - | + | + | + | - | + |
| tularensis | tularensis | + | + | - | - | - | + | + | + | - | + |
| tularensis | tularensis | + | + | - | - | - | + | + | + | - | + |
| tularensis | tularensis | + | + | - | - | - | + | + | + | - | + |
| tularensis | tularensis | + | + | - | - | - | + | + | + | - | + |
| tularensis | tularensis | + | + | - | - | - | + | + | + | - | + |
| tularensis | tularensis | + | + | - | - | - | + | + | + | - | + |
| tularensis | tularensis | + | + | - | - | - | + | + | + | - | + |
| tularensis | tularensis | + | + | - | - | - | + | + | + | - | + |
| tularensis | tularensis | + | + | - | - | - | + | + | + | - | + |
| tularensis | tularensis | + | + | - | - | - | + | + | + | - | + |
| tularensis | tularensis | + | + | - | - | - | + | + | + | - | + |
| tularensis | tularensis | + | + | - | - | - | + | + | + | - | + |
| tularensis | tularensis | + | + | - | - | - | + | + | + | - | + |
| tularensis | tularensis | + | + | - | - | - | + | + | + | - | + |
| tularensis | tularensis | + | + | - | - | - | + | + | + | - | + |
| tularensis | tularensis | + | + | - | - | - | + | + | + | - | + |

| Species | Subspecies | Francisella tularensis | Francisella tularensis species specific duplicate marker | Francisella novicida | Francisella noatunensis | | Francisella philomiragia | | Francisella tularensis specific SNP assay | | | Francisella tularensis A1-clade | Francisella tularensis A2-clade | Francisella tularensis B-clade | Francisella tularensis A-clade |
|---|---|---|---|---|---|---|---|---|---|---|---|---|---|---|---|
| tularensis | novacida | - | - | - | - | - | - | - | + | - | + | - | - | - | - |
| tularensis | novacida | - | - | - | - | - | + | + | + | - | + | - | - | - | - |
| tularensis | novacida | - | - | - | - | - | - | - | + | - | + | - | - | - | - |
| tularensis | mediaasiatica | - | - | - | - | - | - | - | - | - | - | - | - | - | - |
| tularensis | mediaasiatica | + | + | - | - | - | - | - | + | + | + | - | - | - | + |
| tularensis | holarctica/japonica | + | + | - | - | - | - | - | + | + | + | - | - | + | - |
| tularensis | holarctica/japonica | + | + | - | - | - | - | - | + | + | + | - | - | + | - |
| tularensis | holarctica/japonica | + | + | - | - | - | - | - | + | + | + | - | - | + | - |
| tularensis | holarctica/japonica | + | + | - | - | - | - | - | + | + | + | - | - | + | - |
| tularensis | holarctica/japonica | + | + | - | - | - | - | - | + | + | + | - | - | + | - |
| tularensis | holarctica/japonica | + | + | - | - | - | - | - | + | + | + | - | - | + | - |
| tularensis | holarctica | + | + | - | - | - | - | - | + | + | - | - | - | + | - |
| tularensis | holarctica | + | + | - | - | - | - | - | + | + | + | - | - | + | - |
| tularensis | holarctica | + | + | - | - | - | - | - | + | + | + | - | - | + | - |
| tularensis | holarctica | - | - | - | - | - | - | - | - | - | - | - | - | - | - |
| tularensis | holarctica | - | - | - | - | - | - | - | - | - | - | - | - | - | - |
| tularensis | holarctica | - | - | - | - | - | - | - | + | - | - | - | - | + | - |
| tularensis | holarctica | + | + | - | - | - | - | - | + | + | + | - | - | + | - |
| tularensis | holarctica | - | - | - | - | - | - | - | - | - | - | - | - | - | - |
| tularensis | holarctica | - | - | - | - | - | - | - | + | + | - | - | - | - | - |
| tularensis | holarctica | - | - | - | - | - | - | - | - | - | - | - | - | - | - |
| tularensis | holarctica | + | + | - | - | - | - | - | + | + | + | - | - | + | - |
| tularensis | holarctica | + | + | - | - | - | - | - | + | + | + | - | - | + | - |
| tularensis | holarctica | + | + | - | - | - | - | - | + | + | + | - | - | + | - |
| tularensis | holarctica | + | + | - | - | - | - | - | + | + | + | - | - | + | - |
| tularensis | holarctica | + | + | - | - | - | - | - | + | + | + | - | - | + | - |
| tularensis | holarctica | + | + | - | - | - | - | - | + | + | + | - | - | + | - |
| tularensis | holarctica | + | + | - | - | - | - | - | + | + | + | - | - | + | - |
| tularensis | holarctica | + | + | - | - | - | - | - | + | + | + | - | - | + | - |
| tularensis | holarctica | + | + | - | - | - | - | - | + | + | + | - | - | + | - |
| tularensis | holarctica | + | + | - | - | - | - | - | + | + | + | - | - | + | - |
| tularensis | holarctica | + | + | - | - | - | - | - | + | + | + | - | - | + | - |
| tularensis | holarctica | + | + | - | - | - | - | - | + | + | + | - | - | + | - |
| tularensis | holarctica | + | + | - | - | - | - | - | + | - | - | - | - | + | - |
| tularensis | holarctica | + | + | - | - | - | - | - | + | + | + | - | - | + | - |
| tularensis | holarctica | + | + | - | - | - | - | - | + | + | + | - | - | + | - |
| tularensis | holarctica | + | + | - | - | - | - | - | + | + | + | - | - | + | - |
| tularensis | holarctica | - | - | - | - | - | - | - | - | - | - | - | - | - | - |
| tularensis | holarctica | + | + | - | - | - | - | - | + | + | + | - | - | + | - |

FIG. 5C

| Species | Subspecies | Francisella tularensis | Francisella tularensis species specific duplicate marker | Francisella navicida | Francisella noatunensis | Francisella philomiragia | Francisella tularensis specific SnP assay | Francisella tularensis A1-clade | Francisella tularensis A2-clade | Francisella tularensis B-clade | Francisella tularensis A-clade |
|---|---|---|---|---|---|---|---|---|---|---|---|
| tularensis | holarctica | - | - | - | - | - | + | + | + | - | - |
| tularensis | holarctica | + | + | - | - | - | + | - | - | + | - |
| tularensis | holarctica | - | - | - | - | - | + | - | - | + | - |
| tularensis | holarctica | - | + | - | - | - | + | - | - | + | - |
| tularensis | holarctica | + | + | - | - | - | + | - | - | + | - |
| tularensis | holarctica | + | + | - | - | - | + | - | - | + | - |
| tularensis | holarctica | + | + | - | - | - | + | - | - | + | - |
| tularensis | holarctica | - | - | - | - | - | + | - | - | + | - |
| tularensis | holarctica | + | - | - | - | - | + | - | - | + | - |
| tularensis | holarctica | + | + | - | - | - | + | - | - | + | - |
| tularensis | holarctica | - | - | - | - | - | + | - | - | - | - |
| tularensis | holarctica | - | - | - | - | - | + | + | + | - | - |
| tularensis | holarctica | + | - | - | - | - | + | - | - | + | - |
| tularensis | holarctica | + | + | - | - | - | + | + | - | + | - |
| tularensis | holarctica | + | + | - | - | - | + | - | - | + | - |
| tularensis | holarctica | + | + | - | - | - | + | - | - | + | - |
| tularensis | holarctica | - | - | - | - | - | + | - | - | + | - |
| tularensis | holarctica | + | + | - | - | - | + | - | - | + | - |
| tularensis | holarctica | + | + | - | - | - | + | - | - | + | - |
| tularensis | holarctica | + | + | - | - | - | + | - | - | + | - |
| tularensis | holarctica | - | - | - | - | - | + | - | - | + | - |
| tularensis | holarctica | - | - | - | - | - | - | - | - | - | - |
| tularensis | holarctica | - | - | - | - | - | - | - | - | - | - |
| tularensis | holarctica | - | - | - | - | - | - | - | - | - | - |
| tularensis | holarctica | + | + | - | - | - | - | - | - | + | - |
| tularensis | holarctica | + | + | - | - | - | + | - | - | + | - |
| tularensis | holarctica | - | - | - | - | - | + | - | - | + | - |
| tularensis | holarctica | + | + | - | - | - | + | - | - | + | - |
| tularensis | holarctica | - | - | - | - | - | + | + | - | + | - |
| tularensis | holarctica | - | - | - | - | - | + | + | + | + | - |
| tularensis | holarctica | - | - | - | - | - | + | + | + | - | - |
| tularensis | holarctica | - | - | - | - | - | + | + | - | - | - |
| tularensis | holarctica | - | - | - | - | - | + | + | - | - | - |
| tick endosymbiont |  |  |  |  |  |  |  |  |  |  |  |
| tick endosymbiont |  |  |  |  |  |  |  |  |  |  |  |
| philomiragia |  | - | - | - | - | + | + | - | - | - | - |

FIG. 5D

| Species | Subspecies | Francisella tularensis | Francisella tularensis species specific duplicate marker | Francisella novicida | Francisella noatunensis | Francisella philomiragia | Francisella tularensis specific SNP assay | Francisella tularensis A1-clade | Francisella tularensis A2-clade | Francisella tularensis B-clade | Francisella tularensis A-clade |
|---|---|---|---|---|---|---|---|---|---|---|---|
| | philomiragia | - | - | - | - | + | + | - | - | - | - |
| | philomiragia | - | - | - | - | + | + | - | - | - | - |
| | philomiragia | - | - | - | - | + | + | - | - | - | - |
| | philomiragia | - | - | - | - | + | + | - | - | - | - |
| | philomiragia | - | - | - | - | + | + | - | - | - | - |
| | philomiragia | - | - | - | - | + | + | - | - | - | - |
| | philomiragia | - | - | - | - | + | + | - | - | - | - |
| | philomiragia | - | - | - | - | + | + | - | - | - | - |
| | philomiragia | - | - | - | - | + | + | - | - | - | - |
| | philomiragia | - | - | - | - | + | + | - | - | - | - |
| | philomiragia | - | - | - | - | + | + | - | - | - | - |
| | philomiragia | - | - | - | - | + | + | - | - | - | - |
| | philomiragia | - | - | - | - | + | + | - | - | - | - |
| | philomiragia | - | - | - | - | + | + | - | - | - | - |
| | philomiragia | - | - | - | - | + | + | - | - | - | - |
| | philomiragia | - | - | - | - | + | + | - | - | - | - |
| | philomiragia | - | - | - | - | + | + | - | - | - | - |
| | philomiragia | - | - | - | - | + | + | - | - | - | - |
| | philomiragia | - | - | - | - | + | + | - | - | - | - |
| | philomiragia | - | - | - | - | + | + | - | - | - | - |
| | philomiragia | - | - | - | - | + | + | - | - | - | - |
| | philomiragia | - | - | - | - | + | + | - | - | - | - |
| | philomiragia | - | - | - | - | + | + | - | - | - | - |
| | philomiragia | - | - | - | - | + | + | - | - | - | - |
| | philomiragia | - | - | - | - | + | + | - | - | - | - |
| | philomiragia | - | - | - | - | + | + | - | - | - | - |
| | philomiragia | - | - | - | - | + | + | - | - | - | - |
| | philomiragia | - | - | - | - | + | + | - | - | - | - |
| | philomiragia | - | - | - | - | + | + | - | - | - | - |
| | philomiragia | - | - | - | - | + | + | - | - | - | - |
| | philomiragia | - | - | - | - | + | + | - | - | - | - |
| | philomiragia | - | - | - | - | + | + | - | - | - | - |
| | philomiragia | - | - | - | - | + | + | - | - | - | - |
| | philomiragia | - | - | - | - | + | + | - | - | - | - |
| | philomiragia | - | - | - | - | + | + | - | - | - | - |
| | philomiragia | - | - | - | - | + | + | - | - | - | - |
| | hispaniensis | - | - | - | - | - | - | - | - | - | - |

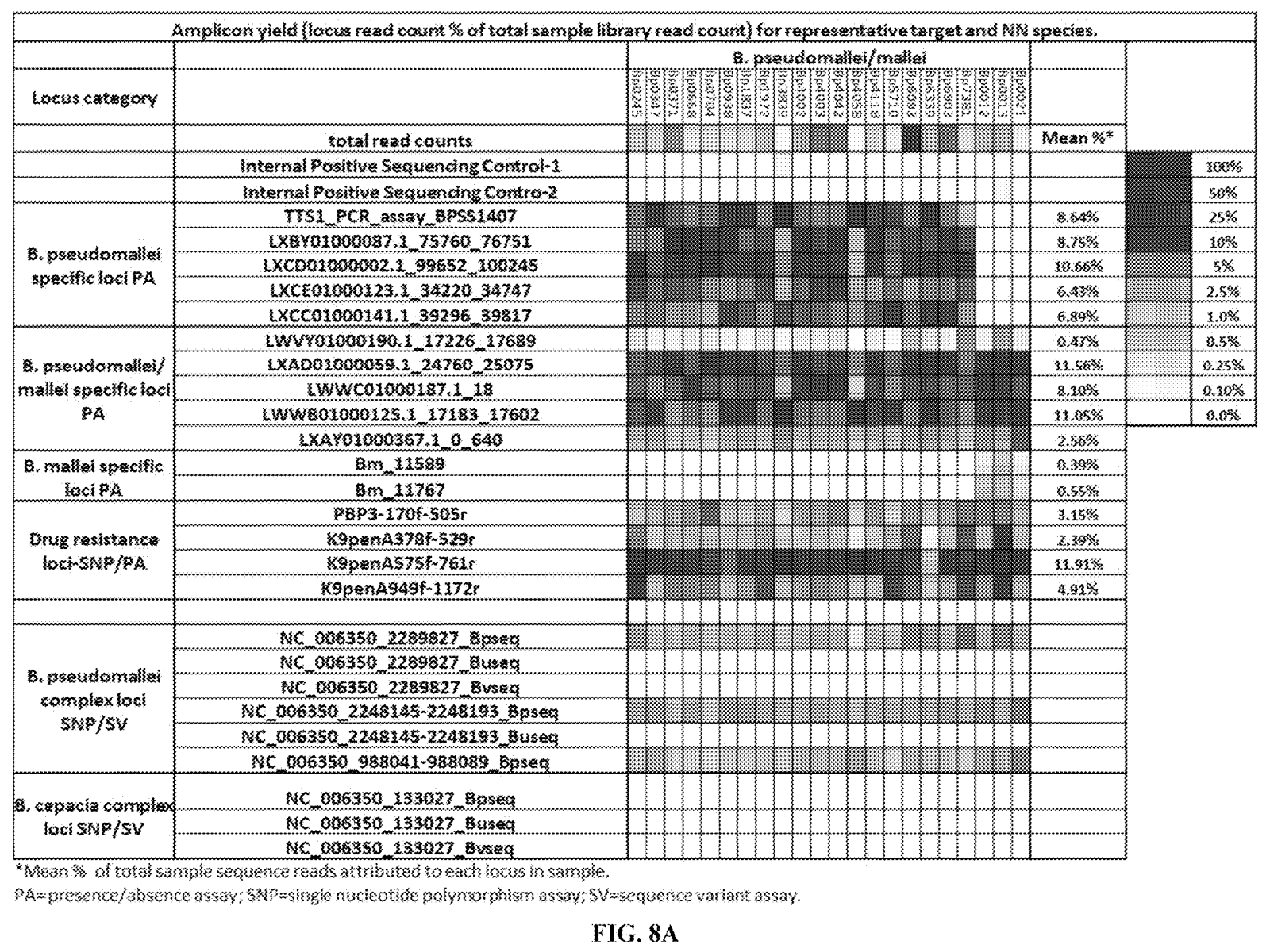

| Locus category | Amplicon yield (locus read count % of total sample library read count) for representative target and NN species. | | | | | | | | | | | | | | | | | | | | | | Mean %* |
|---|---|---|---|---|---|---|---|---|---|---|---|---|---|---|---|---|---|---|---|---|---|---|---|
| | | | | | | | | | | | | | B. pseudomallei/mallei | | | | | | | | | | |
| | | Bp0245 | Bp0347 | Bp0371 | Bp0668 | Bp0784 | Bp0938 | Bp1837 | Bp1973 | Bp3839 | Bp4

Amplicon yield (locus read count % of total sample library read count) for representative target and NN species.

| Locus category | | F. tularensis | | F. tularensis spp. novicida/novicida-like | | F. philomiragia | | Mean %* |
|---|---|---|---|---|---|---|---|---|
| | Total read counts | F0003, F0005, F0007, F0016-h, F0017-h, F0080, F0309, F0311, F0319, F0325 | | F1074, F1106, F1107, F1108, F1110, F0364, F0528, F0051, F0052, F0771 | | F1075, F1076, F1077, F1078, F1079, F1080, F1082, F1083, F1092, F1093, F1094, F1095, F1096, F1104, F1105, F0046, F0048, F0344 | | |
| F. tularensis specific loci PA | Ft_dup_CP080915.1_197 | | | | | | | 6.52% |
| | Ftularensis_CP080915.1_1782 | | | | | | | 11.72% |
| | Ftularensis_CP080915.1_731 | | | | | | | 0.02% |
| NN loci SNP/SV | FtLVS_AM233362_1562618 | | | | | | | 19.24% |
| | FtLVS_AM233362_1642765 | | | | | | | 13.72% |
| | FtLVS_AM233362_1646546 | | | | | | | 0.88% |
| | FtA | | | | | | | 14.10% |
| | FtA1 | | | | | | | 16.13% |
| | FtA2 | | | | | | | 3.83% |
| | FtB | | | | | | | 13.21% |
| NN species loci PA | Ftnovicida_CP009444.1_569 | | | | | | | |
| | Fphilom_CP009444.1_285 | | | | | | | |
| | Fphilom_CP009444.1_569 | | | | | | | |

Legend: 100%, 50%, 25%, 10%, 5%, 2.5%, 1.0%, 0.5%, 0.25%, 0

SEQUENCE LISTING

```
<160> NUMBER OF SEQ ID NOS: 470

<210> SEQ ID NO 1
<211> LENGTH: 20
<212> TYPE: DNA
<213> ORGANISM: Artificial Sequence
<220> FEATURE:
<223> OTHER INFORMATION: Primer

<400> SEQUENCE: 1
acgtcaggtg attattggac                                              20

<210> SEQ ID NO 2
<211> LENGTH: 20
<212> TYPE: DNA
<213> ORGANISM: Artificial Sequence
<220> FEATURE:
<223> OTHER INFORMATION: Primer

<400> SEQUENCE: 2
caacaattat atccgccatt                                              20

<210> SEQ ID NO 3
<211> LENGTH: 20
<212> TYPE: DNA
<213> ORGANISM: Artificial Sequence
<220> FEATURE:
<223> OTHER INFORMATION: Primer

<400> SEQUENCE: 3
gaagatgtac gctcgatagg                                              20
```

```
<210> SEQ ID NO 4
<211> LENGTH: 20
<212> TYPE: DNA
<213> ORGANISM: Artificial Sequence
<220> FEATURE:
<223> OTHER INFORMATION: Primer

<400> SEQUENCE: 4
gaaattcttt ttgccatcac                                                   20

<210> SEQ ID NO 5
<211> LENGTH: 20
<212> TYPE: DNA
<213> ORGANISM: Artificial Sequence
<220> FEATURE:
<223> OTHER INFORMATION: Primer

<400> SEQUENCE: 5
cacaattgaa tgaaaatgct                                                   20

<210> SEQ ID NO 6
<211> LENGTH: 20
<212> TYPE: DNA
<213> ORGANISM: Artificial Sequence
<220> FEATURE:
<223> OTHER INFORMATION: Primer

<400> SEQUENCE: 6
cacgaaacct gtttaccttt                                                   20

<210> SEQ ID NO 7
<211> LENGTH: 20
<212> TYPE: DNA
<213> ORGANISM: Artificial Sequence
<220> FEATURE:
<223> OTHER INFORMATION: Primer

<400> SEQUENCE: 7
gatattcgac gagctttctg                                                   20

<210> SEQ ID NO 8
<211> LENGTH: 20
<212> TYPE: DNA
<213> ORGANISM: Artificial Sequence
<220> FEATURE:
<223> OTHER INFORMATION: Primer

<400> SEQUENCE: 8
tattcatcgt catcctcctc                                                   20

<210> SEQ ID NO 9
<211> LENGTH: 20
<212> TYPE: DNA
<213> ORGANISM: Artificial Sequence
<220> FEATURE:
<223> OTHER INFORMATION: Primer

<400> SEQUENCE: 9
tattgaacgc attgaatcag                                                   20

<210> SEQ ID NO 10
<211> LENGTH: 20
<212> TYPE: DNA
<213> ORGANISM: Artificial Sequence
<220> FEATURE:
<223> OTHER INFORMATION: Primer
```

-continued

<400> SEQUENCE: 10
tattggtaag caaaccgtct                                          20

<210> SEQ ID NO 11
<211> LENGTH: 20
<212> TYPE: DNA
<213> ORGANISM: Artificial Sequence
<220> FEATURE:
<223> OTHER INFORMATION: Primer

<400> SEQUENCE: 11
ggttcaggac aaaatgtagc                                          20

<210> SEQ ID NO 12
<211> LENGTH: 20
<212> TYPE: DNA
<213> ORGANISM: Artificial Sequence
<220> FEATURE:
<223> OTHER INFORMATION: Primer

<400> SEQUENCE: 12
taacttctga agcgaaaacc                                          20

<210> SEQ ID NO 13
<211> LENGTH: 20
<212> TYPE: DNA
<213> ORGANISM: Artificial Sequence
<220> FEATURE:
<223> OTHER INFORMATION: Primer

<400> SEQUENCE: 13
gcgaatttta gacgacaatc                                          20

<210> SEQ ID NO 14
<211> LENGTH: 20
<212> TYPE: DNA
<213> ORGANISM: Artificial Sequence
<220> FEATURE:
<223> OTHER INFORMATION: Primer

<400> SEQUENCE: 14
taaccgtgct taattcgttt                                          20

<210> SEQ ID NO 15
<211> LENGTH: 20
<212> TYPE: DNA
<213> ORGANISM: Artificial Sequence
<220> FEATURE:
<223> OTHER INFORMATION: Primer

<400> SEQUENCE: 15
attaataagg cgactggtga                                          20

<210> SEQ ID NO 16
<211> LENGTH: 20
<212> TYPE: DNA
<213> ORGANISM: Artificial Sequence
<220> FEATURE:
<223> OTHER INFORMATION: Primer

<400> SEQUENCE: 16
ttacccatcc agaatgagac                                          20

<210> SEQ ID NO 17

```
<211> LENGTH: 20
<212> TYPE: DNA
<213> ORGANISM: Artificial Sequence
<220> FEATURE:
<223> OTHER INFORMATION: Primer

<400> SEQUENCE: 17
acaattctta aaaggcgaca                                                     20

<210> SEQ ID NO 18
<211> LENGTH: 20
<212> TYPE: DNA
<213> ORGANISM: Artificial Sequence
<220> FEATURE:
<223> OTHER INFORMATION: Primer

<400> SEQUENCE: 18
tgtagcgtct ccgatatttt                                                     20

<210> SEQ ID NO 19
<211> LENGTH: 20
<212> TYPE: DNA
<213> ORGANISM: Artificial Sequence
<220> FEATURE:
<223> OTHER INFORMATION: Primer

<400> SEQUENCE: 19
catggggctt tctattatgt                                                     20

<210> SEQ ID NO 20
<211> LENGTH: 22
<212> TYPE: DNA
<213> ORGANISM: Artificial Sequence
<220> FEATURE:
<223> OTHER INFORMATION: Primer

<400> SEQUENCE: 20
ttcgttcttt cataagtttc ct                                                  22

<210> SEQ ID NO 21
<211> LENGTH: 20
<212> TYPE: DNA
<213> ORGANISM: Artificial Sequence
<220> FEATURE:
<223> OTHER INFORMATION: Primer

<400> SEQUENCE: 21
ttggagtttg ttttgctttt                                                     20

<210> SEQ ID NO 22
<211> LENGTH: 21
<212> TYPE: DNA
<213> ORGANISM: Artificial Sequence
<220> FEATURE:
<223> OTHER INFORMATION: Primer

<400> SEQUENCE: 22
gtaacaatta atccacgtcc t                                                   21

<210> SEQ ID NO 23
<211> LENGTH: 20
<212> TYPE: DNA
<213> ORGANISM: Artificial Sequence
<220> FEATURE:
<223> OTHER INFORMATION: Primer

<400> SEQUENCE: 23
```
ttatcgtcca ttctttcgtc                                               20

<210> SEQ ID NO 24
<211> LENGTH: 20
<212> TYPE: DNA
<213> ORGANISM: Artificial Sequence
<220> FEATURE:
<223> OTHER INFORMATION: Primer

<400> SEQUENCE: 24
aaacctaatg aaacgggatt                                               20

<210> SEQ ID NO 25
<211> LENGTH: 20
<212> TYPE: DNA
<213> ORGANISM: Artificial Sequence
<220> FEATURE:
<223> OTHER INFORMATION: Primer

<400> SEQUENCE: 25
tatgaaagga gccgtaaaac                                               20

<210> SEQ ID NO 26
<211> LENGTH: 20
<212> TYPE: DNA
<213> ORGANISM: Artificial Sequence
<220> FEATURE:
<223> OTHER INFORMATION: Primer

<400> SEQUENCE: 26
tgaatatgaa gcggaaaact                                               20

<210> SEQ ID NO 27
<211> LENGTH: 20
<212> TYPE: DNA
<213> ORGANISM: Artificial Sequence
<220> FEATURE:
<223> OTHER INFORMATION: Primer

<400> SEQUENCE: 27
tcgaacatac ctccatttct                                               20

<210> SEQ ID NO 28
<211> LENGTH: 20
<212> TYPE: DNA
<213> ORGANISM: Artificial Sequence
<220> FEATURE:
<223> OTHER INFORMATION: Primer

<400> SEQUENCE: 28
aaagatagct ttgcacttgg                                               20

<210> SEQ ID NO 29
<211> LENGTH: 20
<212> TYPE: DNA
<213> ORGANISM: Artificial Sequence
<220> FEATURE:
<223> OTHER INFORMATION: Primer

<400> SEQUENCE: 29
tttttcgtaa gcatcttcaa                                               20

<210> SEQ ID NO 30
<211> LENGTH: 20
<212> TYPE: DNA

```
<213> ORGANISM: Artificial Sequence
<220> FEATURE:
<223> OTHER INFORMATION: Primer

<400> SEQUENCE: 30
tttgatgtga aggtgagaca                                               20

<210> SEQ ID NO 31
<211> LENGTH: 20
<212> TYPE: DNA
<213> ORGANISM: Artificial Sequence
<220> FEATURE:
<223> OTHER INFORMATION: Primer

<400> SEQUENCE: 31
ggttacagga cggattgata                                               20

<210> SEQ ID NO 32
<211> LENGTH: 20
<212> TYPE: DNA
<213> ORGANISM: Artificial Sequence
<220> FEATURE:
<223> OTHER INFORMATION: Primer

<400> SEQUENCE: 32
tcccaccaat atcaaagaac                                               20

<210> SEQ ID NO 33
<211> LENGTH: 20
<212> TYPE: DNA
<213> ORGANISM: Artificial Sequence
<220> FEATURE:
<223> OTHER INFORMATION: Primer

<400> SEQUENCE: 33
tgagcctacc tagtgattgg                                               20

<210> SEQ ID NO 34
<211> LENGTH: 24
<212> TYPE: DNA
<213> ORGANISM: Artificial Sequence
<220> FEATURE:
<223> OTHER INFORMATION: Primer

<400> SEQUENCE: 34
ttggataaat tccacaaatt cctc                                          24

<210> SEQ ID NO 35
<211> LENGTH: 20
<212> TYPE: DNA
<213> ORGANISM: Artificial Sequence
<220> FEATURE:
<223> OTHER INFORMATION: Primer

<400> SEQUENCE: 35
cgccagcgta ttatataggt                                               20

<210> SEQ ID NO 36
<211> LENGTH: 20
<212> TYPE: DNA
<213> ORGANISM: Artificial Sequence
<220> FEATURE:
<223> OTHER INFORMATION: Primer

<400> SEQUENCE: 36
gctaattctg ggttgtgttt                                               20
```

```
<210> SEQ ID NO 37
<211> LENGTH: 19
<212> TYPE: DNA
<213> ORGANISM: Artificial Sequence
<220> FEATURE:
<223> OTHER INFORMATION: Primer

<400> SEQUENCE: 37
tcggtaagta tcaccctca                                              19

<210> SEQ ID NO 38
<211> LENGTH: 19
<212> TYPE: DNA
<213> ORGANISM: Artificial Sequence
<220> FEATURE:
<223> OTHER INFORMATION: Primer

<400> SEQUENCE: 38
tgcttctgta taacgcatt                                              19

<210> SEQ ID NO 39
<211> LENGTH: 20
<212> TYPE: DNA
<213> ORGANISM: Artificial Sequence
<220> FEATURE:
<223> OTHER INFORMATION: Primer

<400> SEQUENCE: 39
cagtcggtaa cgttattggt                                             20

<210> SEQ ID NO 40
<211> LENGTH: 20
<212> TYPE: DNA
<213> ORGANISM: Artificial Sequence
<220> FEATURE:
<223> OTHER INFORMATION: Primer

<400> SEQUENCE: 40
taactcagat gcaattggtg                                             20

<210> SEQ ID NO 41
<211> LENGTH: 20
<212> TYPE: DNA
<213> ORGANISM: Artificial Sequence
<220> FEATURE:
<223> OTHER INFORMATION: Primer

<400> SEQUENCE: 41
attgtagagg gtgactctgc                                             20

<210> SEQ ID NO 42
<211> LENGTH: 19
<212> TYPE: DNA
<213> ORGANISM: Artificial Sequence
<220> FEATURE:
<223> OTHER INFORMATION: Primer

<400> SEQUENCE: 42
tatcaaaatc tccgccaat                                              19

<210> SEQ ID NO 43
<211> LENGTH: 20
<212> TYPE: DNA
<213> ORGANISM: Artificial Sequence
<220> FEATURE:
```

-continued

<223> OTHER INFORMATION: Primer

<400> SEQUENCE: 43
ttcttcggaa gttctcagtt                                                    20

<210> SEQ ID NO 44
<211> LENGTH: 19
<212> TYPE: DNA
<213> ORGANISM: Artificial Sequence
<220> FEATURE:
<223> OTHER INFORMATION: Primer

<400> SEQUENCE: 44
cggacacata cgaccatag                                                     19

<210> SEQ ID NO 45
<211> LENGTH: 20
<212> TYPE: DNA
<213> ORGANISM: Artificial Sequence
<220> FEATURE:
<223> OTHER INFORMATION: Primer

<400> SEQUENCE: 45
aagtttgagg tgtggaaatg                                                    20

<210> SEQ ID NO 46
<211> LENGTH: 20
<212> TYPE: DNA
<213> ORGANISM: Artificial Sequence
<220> FEATURE:
<223> OTHER INFORMATION: Primer

<400> SEQUENCE: 46
tcgaaatgag ttccaatttt                                                    20

<210> SEQ ID NO 47
<211> LENGTH: 21
<212> TYPE: DNA
<213> ORGANISM: Artificial Sequence
<220> FEATURE:
<223> OTHER INFORMATION: Primer

<400> SEQUENCE: 47
caaaactaat aggggagggt g                                                  21

<210> SEQ ID NO 48
<211> LENGTH: 19
<212> TYPE: DNA
<213> ORGANISM: Artificial Sequence
<220> FEATURE:
<223> OTHER INFORMATION: Primer

<400> SEQUENCE: 48
ccgagaacct acctcgtta                                                     19

<210> SEQ ID NO 49
<211> LENGTH: 20
<212> TYPE: DNA
<213> ORGANISM: Artificial Sequence
<220> FEATURE:
<223> OTHER INFORMATION: Primer

<400> SEQUENCE: 49
aggagatgag agttttgcac                                                    20

```
<210> SEQ ID NO 50
<211> LENGTH: 19
<212> TYPE: DNA
<213> ORGANISM: Artificial Sequence
<220> FEATURE:
<223> OTHER INFORMATION: Primer

<400> SEQUENCE: 50 accccccataa ttaccatga                                                19

<210> SEQ ID NO 51
<211> LENGTH: 20
<212> TYPE: DNA
<213> ORGANISM: Artificial Sequence
<220> FEATURE:
<223> OTHER INFORMATION: Primer

<400> SEQUENCE: 51
cgttgcgtaa gtatgtgcta                                                20

<210> SEQ ID NO 52
<211> LENGTH: 20
<212> TYPE: DNA
<213> ORGANISM: Artificial Sequence
<220> FEATURE:
<223> OTHER INFORMATION: Primer

<400> SEQUENCE: 52
aggtggcgta attaacgtag                                                20

<210> SEQ ID NO 53
<211> LENGTH: 20
<212> TYPE: DNA
<213> ORGANISM: Artificial Sequence
<220> FEATURE:
<223> OTHER INFORMATION: Primer

<400> SEQUENCE: 53
cgaaaagttg tcgacctaat                                                20

<210> SEQ ID NO 54
<211> LENGTH: 20
<212> TYPE: DNA
<213> ORGANISM: Artificial Sequence
<220> FEATURE:
<223> OTHER INFORMATION: Primer

<400> SEQUENCE: 54
actgcgttca cgaagaatag                                                20

<210> SEQ ID NO 55
<211> LENGTH: 20
<212> TYPE: DNA
<213> ORGANISM: Artificial Sequence
<220> FEATURE:
<223> OTHER INFORMATION: Primer

<400> SEQUENCE: 55
tctcttgatt caacgtttcc                                                20

<210> SEQ ID NO 56
<211> LENGTH: 20
<212> TYPE: DNA
<213> ORGANISM: Artificial Sequence
<220> FEATURE:
<223> OTHER INFORMATION: Primer
```

<400> SEQUENCE: 56
gatgcaaaac caattcactt                                              20

<210> SEQ ID NO 57
<211> LENGTH: 20
<212> TYPE: DNA
<213> ORGANISM: Artificial Sequence
<220> FEATURE:
<223> OTHER INFORMATION: Primer

<400> SEQUENCE: 57
gtgaaacatc gcttttagg                                               20

<210> SEQ ID NO 58
<211> LENGTH: 20
<212> TYPE: DNA
<213> ORGANISM: Artificial Sequence
<220> FEATURE:
<223> OTHER INFORMATION: Primer

<400> SEQUENCE: 58
tccgcaatga tatacttcaa                                              20

<210> SEQ ID NO 59
<211> LENGTH: 20
<212> TYPE: DNA
<213> ORGANISM: Artificial Sequence
<220> FEATURE:
<223> OTHER INFORMATION: Primer

<400> SEQUENCE: 59
atacggtgaa aatgaagcag                                              20

<210> SEQ ID NO 60
<211> LENGTH: 19
<212> TYPE: DNA
<213> ORGANISM: Artificial Sequence
<220> FEATURE:
<223> OTHER INFORMATION: Primer

<400> SEQUENCE: 60
cgtctttggt aatcgttca                                               19

<210> SEQ ID NO 61
<211> LENGTH: 20
<212> TYPE: DNA
<213> ORGANISM: Artificial Sequence
<220> FEATURE:
<223> OTHER INFORMATION: Primer

<400> SEQUENCE: 61
tcgtcgtcac cgggatggtc                                              20

<210> SEQ ID NO 62
<211> LENGTH: 20
<212> TYPE: DNA
<213> ORGANISM: Artificial Sequence
<220> FEATURE:
<223> OTHER INFORMATION: Primer

<400> SEQUENCE: 62
ggcctttgcc cgcatactcg                                              20

<210> SEQ ID NO 63
<211> LENGTH: 20

```
<212> TYPE: DNA
<213> ORGANISM: Artificial Sequence
<220> FEATURE:
<223> OTHER INFORMATION: Primer

<400> SEQUENCE: 63
tcgcawgaag tgcgttgccg                                               20

<210> SEQ ID NO 64
<211> LENGTH: 20
<212> TYPE: DNA
<213> ORGANISM: Artificial Sequence
<220> FEATURE:
<223> OTHER INFORMATION: Primer

<400> SEQUENCE: 64
gccgcttgcg aagcgatgat                                               20

<210> SEQ ID NO 65
<211> LENGTH: 20
<212> TYPE: DNA
<213> ORGANISM: Artificial Sequence
<220> FEATURE:
<223> OTHER INFORMATION: Primer

<400> SEQUENCE: 65
cgcgcttgcc caactaccag                                               20

<210> SEQ ID NO 66
<211> LENGTH: 20
<212> TYPE: DNA
<213> ORGANISM: Artificial Sequence
<220> FEATURE:
<223> OTHER INFORMATION: Primer

<400> SEQUENCE: 66
gcgcaacggt gcgagacaat                                               20

<210> SEQ ID NO 67
<211> LENGTH: 20
<212> TYPE: DNA
<213> ORGANISM: Artificial Sequence
<220> FEATURE:
<223> OTHER INFORMATION: Primer

<400> SEQUENCE: 67
aatccatgca tgtcgygccc                                               20

<210> SEQ ID NO 68
<211> LENGTH: 20
<212> TYPE: DNA
<213> ORGANISM: Artificial Sequence
<220> FEATURE:
<223> OTHER INFORMATION: Primer

<400> SEQUENCE: 68
gcgatcgctc aacgggcttc                                               20

<210> SEQ ID NO 69
<211> LENGTH: 20
<212> TYPE: DNA
<213> ORGANISM: Artificial Sequence
<220> FEATURE:
<223> OTHER INFORMATION: Primer

<400> SEQUENCE: 69
```

```
tcgcatttgc ayacgctccc                                                    20

<210> SEQ ID NO 70
<211> LENGTH: 20
<212> TYPE: DNA
<213> ORGANISM: Artificial Sequence
<220> FEATURE:
<223> OTHER INFORMATION: Primer

<400> SEQUENCE: 70
agtgcgcaaa cttggcgagg                                                    20

<210> SEQ ID NO 71
<211> LENGTH: 30
<212> TYPE: DNA
<213> ORGANISM: Artificial Sequence
<220> FEATURE:
<223> OTHER INFORMATION: Primer

<400> SEQUENCE: 71
caccgaaaga tttcagttcc gcctcattca                                         30

<210> SEQ ID NO 72
<211> LENGTH: 26
<212> TYPE: DNA
<213> ORGANISM: Artificial Sequence
<220> FEATURE:
<223> OTHER INFORMATION: Primer

<400> SEQUENCE: 72
ggccgtcgat ggtttcgtcg gttttc                                             26

<210> SEQ ID NO 73
<211> LENGTH: 25
<212> TYPE: DNA
<213> ORGANISM: Artificial Sequence
<220> FEATURE:
<223> OTHER INFORMATION: Primer

<400> SEQUENCE: 73
tgcattgagc acggcacgca gattc                                              25

<210> SEQ ID NO 74
<211> LENGTH: 32
<212> TYPE: DNA
<213> ORGANISM: Artificial Sequence
<220> FEATURE:
<223> OTHER INFORMATION: Primer

<400> SEQUENCE: 74
gaaaaattta tcggatcgag caccatggtt tg                                      32

<210> SEQ ID NO 75
<211> LENGTH: 22
<212> TYPE: DNA
<213> ORGANISM: Artificial Sequence
<220> FEATURE:
<223> OTHER INFORMATION: Primer

<400> SEQUENCE: 75
atacgcggcg cggctcattt cg                                                 22

<210> SEQ ID NO 76
<211> LENGTH: 24
<212> TYPE: DNA
<213> ORGANISM: Artificial Sequence
```

-continued

```
<220> FEATURE:
<223> OTHER INFORMATION: Primer

<400> SEQUENCE: 76
gcgtcgcgct cgtcgatacg gtca                                          24

<210> SEQ ID NO 77
<211> LENGTH: 25
<212> TYPE: DNA
<213> ORGANISM: Artificial Sequence
<220> FEATURE:
<223> OTHER INFORMATION: Primer

<400> SEQUENCE: 77
tgcgcagcga gtggttcagg ttgtc                                         25

<210> SEQ ID NO 78
<211> LENGTH: 26
<212> TYPE: DNA
<213> ORGANISM: Artificial Sequence
<220> FEATURE:
<223> OTHER INFORMATION: Primer

<400> SEQUENCE: 78
cgacgatacg gatacggcac ggaagc                                        26

<210> SEQ ID NO 79
<211> LENGTH: 18
<212> TYPE: DNA
<213> ORGANISM: Artificial Sequence
<220> FEATURE:
<223> OTHER INFORMATION: Primer

<400> SEQUENCE: 79
ccgcgccggc cgcagacc                                                 18

<210> SEQ ID NO 80
<211> LENGTH: 22
<212> TYPE: DNA
<213> ORGANISM: Artificial Sequence
<220> FEATURE:
<223> OTHER INFORMATION: Primer

<400> SEQUENCE: 80
cgggcgtgcc ggactcctcg tc                                            22

<210> SEQ ID NO 81
<211> LENGTH: 20
<212> TYPE: DNA
<213> ORGANISM: Artificial Sequence
<220> FEATURE:
<223> OTHER INFORMATION: Primer

<400> SEQUENCE: 81
cctttgcggc aagcgtcgaa                                               20

<210> SEQ ID NO 82
<211> LENGTH: 20
<212> TYPE: DNA
<213> ORGANISM: Artificial Sequence
<220> FEATURE:
<223> OTHER INFORMATION: Primer

<400> SEQUENCE: 82
gagccaacgc acatggacgg                                               20
```

<210> SEQ ID NO 83
<211> LENGTH: 20
<212> TYPE: DNA
<213> ORGANISM: Artificial Sequence
<220> FEATURE:
<223> OTHER INFORMATION: Primer

<400> SEQUENCE: 83
ccagtcgggc cgggaaaaac                                            20

<210> SEQ ID NO 84
<211> LENGTH: 20
<212> TYPE: DNA
<213> ORGANISM: Artificial Sequence
<220> FEATURE:
<223> OTHER INFORMATION: Primer

<400> SEQUENCE: 84
ggcggcaaaa gcgtcgatga                                            20

<210> SEQ ID NO 85
<211> LENGTH: 20
<212> TYPE: DNA
<213> ORGANISM: Artificial Sequence
<220> FEATURE:
<223> OTHER INFORMATION: Primer

<400> SEQUENCE: 85
gccggaaccg tcgagcattg                                            20

<210> SEQ ID NO 86
<211> LENGTH: 20
<212> TYPE: DNA
<213> ORGANISM: Artificial Sequence
<220> FEATURE:
<223> OTHER INFORMATION: Primer

<400> SEQUENCE: 86
tggattcgac tgcctccgct                                            20

<210> SEQ ID NO 87
<211> LENGTH: 20
<212> TYPE: DNA
<213> ORGANISM: Artificial Sequence
<220> FEATURE:
<223> OTHER INFORMATION: Primer

<400> SEQUENCE: 87
tcgatatccg ccgtctcgcc                                            20

<210> SEQ ID NO 88
<211> LENGTH: 20
<212> TYPE: DNA
<213> ORGANISM: Artificial Sequence
<220> FEATURE:
<223> OTHER INFORMATION: Primer

<400> SEQUENCE: 88
atgtgtcggt gggcttcggt                                            20

<210> SEQ ID NO 89
<211> LENGTH: 20
<212> TYPE: DNA
<213> ORGANISM: Artificial Sequence
<220> FEATURE:
<223> OTHER INFORMATION: Primer

```
<400> SEQUENCE: 89
gaaaggcgat gtgccgagcg                                              20

<210> SEQ ID NO 90
<211> LENGTH: 20
<212> TYPE: DNA
<213> ORGANISM: Artificial Sequence
<220> FEATURE:
<223> OTHER INFORMATION: Primer

<400> SEQUENCE: 90
ttcggagaag cgccaaacgc                                              20

<210> SEQ ID NO 91
<211> LENGTH: 26
<212> TYPE: DNA
<213> ORGANISM: Artificial Sequence
<220> FEATURE:
<223> OTHER INFORMATION: Primer

<400> SEQUENCE: 91
cgcggacagc atcgattacg tgaatc                                       26

<210> SEQ ID NO 92
<211> LENGTH: 24
<212> TYPE: DNA
<213> ORGANISM: Artificial Sequence
<220> FEATURE:
<223> OTHER INFORMATION: Primer

<400> SEQUENCE: 92
ccgccgaatc cgatgctcaa tttc                                         24

<210> SEQ ID NO 93
<211> LENGTH: 31
<212> TYPE: DNA
<213> ORGANISM: Artificial Sequence
<220> FEATURE:
<223> OTHER INFORMATION: Primer

<400> SEQUENCE: 93
gacctgcagc aggtattcga cattatcgtt c                                 31

<210> SEQ ID NO 94
<211> LENGTH: 26
<212> TYPE: DNA
<213> ORGANISM: Artificial Sequence
<220> FEATURE:
<223> OTHER INFORMATION: Primer

<400> SEQUENCE: 94
agcttcgcat acagcacttc cgccag                                       26

<210> SEQ ID NO 95
<211> LENGTH: 22
<212> TYPE: DNA
<213> ORGANISM: Artificial Sequence
<220> FEATURE:
<223> OTHER INFORMATION: Primer

<400> SEQUENCE: 95
gcgctgcccg tttcaccact gg                                           22

<210> SEQ ID NO 96
```

```
<211> LENGTH: 25
<212> TYPE: DNA
<213> ORGANISM: Artificial Sequence
<220> FEATURE:
<223> OTHER INFORMATION: Primer

<400> SEQUENCE: 96
cgtgacgccg tcgggaaaga tcatc                                  25

<210> SEQ ID NO 97
<211> LENGTH: 29
<212> TYPE: DNA
<213> ORGANISM: Artificial Sequence
<220> FEATURE:
<223> OTHER INFORMATION: Primer

<400> SEQUENCE: 97
ctgaccgaac gatggctgga gatacatgc                              29

<210> SEQ ID NO 98
<211> LENGTH: 26
<212> TYPE: DNA
<213> ORGANISM: Artificial Sequence
<220> FEATURE:
<223> OTHER INFORMATION: Primer

<400> SEQUENCE: 98
caaatgggaa gcgagctccc ttccga                                 26

<210> SEQ ID NO 99
<211> LENGTH: 25
<212> TYPE: DNA
<213> ORGANISM: Artificial Sequence
<220> FEATURE:
<223> OTHER INFORMATION: Primer

<400> SEQUENCE: 99
cggacgcctg tcgcccgaaa cctat                                  25

<210> SEQ ID NO 100
<211> LENGTH: 21
<212> TYPE: DNA
<213> ORGANISM: Artificial Sequence
<220> FEATURE:
<223> OTHER INFORMATION: Primer

<400> SEQUENCE: 100
cgcgagcacg ccgagcgaca t                                      21

<210> SEQ ID NO 101
<211> LENGTH: 22
<212> TYPE: DNA
<213> ORGANISM: Artificial Sequence
<220> FEATURE:
<223> OTHER INFORMATION: Primer

<400> SEQUENCE: 101
cgtcgacgcc ccgggctttc tg                                     22

<210> SEQ ID NO 102
<211> LENGTH: 21
<212> TYPE: DNA
<213> ORGANISM: Artificial Sequence
<220> FEATURE:
<223> OTHER INFORMATION: Primer

<400> SEQUENCE: 102
```
cgccgcgcac cggtttcaat c                                                    21

<210> SEQ ID NO 103
<211> LENGTH: 25
<212> TYPE: DNA
<213> ORGANISM: Artificial Sequence
<220> FEATURE:
<223> OTHER INFORMATION: Primer

<400> SEQUENCE: 103
cgaaaataat tttcggccgg cgcac                                                25

<210> SEQ ID NO 104
<211> LENGTH: 27
<212> TYPE: DNA
<213> ORGANISM: Artificial Sequence
<220> FEATURE:
<223> OTHER INFORMATION: Primer

<400> SEQUENCE: 104
cgacaggcat cgggcgacta ctaccag                                              27

<210> SEQ ID NO 105
<211> LENGTH: 25
<212> TYPE: DNA
<213> ORGANISM: Artificial Sequence
<220> FEATURE:
<223> OTHER INFORMATION: Primer

<400> SEQUENCE: 105
caacgggcga gtttgcaacg gaatc                                                25

<210> SEQ ID NO 106
<211> LENGTH: 23
<212> TYPE: DNA
<213> ORGANISM: Artificial Sequence
<220> FEATURE:
<223> OTHER INFORMATION: Primer

<400> SEQUENCE: 106
gccggcttgg cttcgtcctt gtc                                                  23

<210> SEQ ID NO 107
<211> LENGTH: 19
<212> TYPE: DNA
<213> ORGANISM: Artificial Sequence
<220> FEATURE:
<223> OTHER INFORMATION: Primer

<400> SEQUENCE: 107
cggcatgcgc ggccgaatc                                                       19

<210> SEQ ID NO 108
<211> LENGTH: 21
<212> TYPE: DNA
<213> ORGANISM: Artificial Sequence
<220> FEATURE:
<223> OTHER INFORMATION: Primer

<400> SEQUENCE: 108
atcgcgccct gcagcgagca c                                                    21

<210> SEQ ID NO 109
<211> LENGTH: 20
<212> TYPE: DNA

<210> SEQ ID NO 110
<211> LENGTH: 20
<212> TYPE: DNA
<213> ORGANISM: Artificial Sequence
<220> FEATURE:
<223> OTHER INFORMATION: Primer

<400> SEQUENCE: 109
gccagcgcat ccaccaacat                                               20

<210> SEQ ID NO 110
<211> LENGTH: 20
<212> TYPE: DNA
<213> ORGANISM: Artificial Sequence
<220> FEATURE:
<223> OTHER INFORMATION: Primer

<400> SEQUENCE: 110
agaggaagaa gggcgaggcg                                               20

<210> SEQ ID NO 111
<211> LENGTH: 20
<212> TYPE: DNA
<213> ORGANISM: Artificial Sequence
<220> FEATURE:
<223> OTHER INFORMATION: Primer

<400> SEQUENCE: 111
cgcgcarytc gtcgtcctcg                                               20

<210> SEQ ID NO 112
<211> LENGTH: 20
<212> TYPE: DNA
<213> ORGANISM: Artificial Sequence
<220> FEATURE:
<223> OTHER INFORMATION: Primer

<400> SEQUENCE: 112
cgaacctsgt gcmggtrcag                                               20

<210> SEQ ID NO 113
<211> LENGTH: 20
<212> TYPE: DNA
<213> ORGANISM: Artificial Sequence
<220> FEATURE:
<223> OTHER INFORMATION: Primer

<400> SEQUENCE: 113
cacgttgccs ggraartacg                                               20

<210> SEQ ID NO 114
<211> LENGTH: 20
<212> TYPE: DNA
<213> ORGANISM: Artificial Sequence
<220> FEATURE:
<223> OTHER INFORMATION: Primer

<400> SEQUENCE: 114
ccgtcgacaa gatcgcgcts                                               20

<210> SEQ ID NO 115
<211> LENGTH: 19
<212> TYPE: DNA
<213> ORGANISM: Artificial Sequence
<220> FEATURE:
<223> OTHER INFORMATION: Primer

<400> SEQUENCE: 115
cagaacgcgc trtyccacg                                                19

<210> SEQ ID NO 116
<211> LENGTH: 20
<212> TYPE: DNA
<213> ORGANISM: Artificial Sequence
<220> FEATURE:
<223> OTHER INFORMATION: Primer

<400> SEQUENCE: 116
tgccgcgtga tccattgcat                                                  20

<210> SEQ ID NO 117
<211> LENGTH: 27
<212> TYPE: DNA
<213> ORGANISM: Artificial Sequence
<220> FEATURE:
<223> OTHER INFORMATION: Primer

<400> SEQUENCE: 117 aggggtggt ttcctgagtg gcgtgac                                           27

<210> SEQ ID NO 118
<211> LENGTH: 26
<212> TYPE: DNA
<213> ORGANISM: Artificial Sequence
<220> FEATURE:
<223> OTHER INFORMATION: Primer

<400> SEQUENCE: 118
agcggtgtcg acgggtggaa aggatg                                           26

<210> SEQ ID NO 119
<211> LENGTH: 26
<212> TYPE: DNA
<213> ORGANISM: Artificial Sequence
<220> FEATURE:
<223> OTHER INFORMATION: Primer

<400> SEQUENCE: 119
acgggcgctt cacgatctcg gtgttc                                           26

<210> SEQ ID NO 120
<211> LENGTH: 25
<212> TYPE: DNA
<213> ORGANISM: Artificial Sequence
<220> FEATURE:
<223> OTHER INFORMATION: Primer

<400> SEQUENCE: 120
gcgcggcagt tcgatcaggc atttg                                            25

<210> SEQ ID NO 121
<211> LENGTH: 22
<212> TYPE: DNA
<213> ORGANISM: Artificial Sequence
<220> FEATURE:
<223> OTHER INFORMATION: Primer

<400> SEQUENCE: 121
gacggcgggc tttggggagt cc                                               22

<210> SEQ ID NO 122
<211> LENGTH: 20
<212> TYPE: DNA
<213> ORGANISM: Artificial Sequence
<220> FEATURE:

```
<223> OTHER INFORMATION: Primer

<400> SEQUENCE: 122
gctcgcgggc agcggtgtcg                                              20

<210> SEQ ID NO 123
<211> LENGTH: 21
<212> TYPE: DNA
<213> ORGANISM: Artificial Sequence
<220> FEATURE:
<223> OTHER INFORMATION: Primer

<400> SEQUENCE: 123
gacggccccg ggcggcttta c                                            21

<210> SEQ ID NO 124
<211> LENGTH: 26
<212> TYPE: DNA
<213> ORGANISM: Artificial Sequence
<220> FEATURE:
<223> OTHER INFORMATION: Primer

<400> SEQUENCE: 124
cgcggcagtt cgatcaggca tttgag                                       26

<210> SEQ ID NO 125
<211> LENGTH: 21
<212> TYPE: DNA
<213> ORGANISM: Artificial Sequence
<220> FEATURE:
<223> OTHER INFORMATION: Primer

<400> SEQUENCE: 125
gacggccccg ggcggcttta c                                            21

<210> SEQ ID NO 126
<211> LENGTH: 32
<212> TYPE: DNA
<213> ORGANISM: Artificial Sequence
<220> FEATURE:
<223> OTHER INFORMATION: Primer

<400> SEQUENCE: 126
cgaggggcga aattcccctt atagatcagt tg                                32

<210> SEQ ID NO 127
<211> LENGTH: 26
<212> TYPE: DNA
<213> ORGANISM: Artificial Sequence
<220> FEATURE:
<223> OTHER INFORMATION: Primer

<400> SEQUENCE: 127
cggtcgccac aaattcgcac gcactc                                       26

<210> SEQ ID NO 128
<211> LENGTH: 26
<212> TYPE: DNA
<213> ORGANISM: Artificial Sequence
<220> FEATURE:
<223> OTHER INFORMATION: Primer

<400> SEQUENCE: 128
agcgagcggc gcaacggaga atgatt                                       26
```

```
<210> SEQ ID NO 129
<211> LENGTH: 23
<212> TYPE: DNA
<213> ORGANISM: Artificial Sequence
<220> FEATURE:
<223> OTHER INFORMATION: Primer

<400> SEQUENCE: 129
gctgcgcggc caagcgaaaa acg                                               23

<210> SEQ ID NO 130
<211> LENGTH: 22
<212> TYPE: DNA
<213> ORGANISM: Artificial Sequence
<220> FEATURE:
<223> OTHER INFORMATION: Primer

<400> SEQUENCE: 130
cgcgaggacc gcagcgcaaa gc                                                22

<210> SEQ ID NO 131
<211> LENGTH: 24
<212> TYPE: DNA
<213> ORGANISM: Artificial Sequence
<220> FEATURE:
<223> OTHER INFORMATION: Primer

<400> SEQUENCE: 131
ggccgcagac cgtcaccgcg tatg                                              24

<210> SEQ ID NO 132
<211> LENGTH: 25
<212> TYPE: DNA
<213> ORGANISM: Artificial Sequence
<220> FEATURE:
<223> OTHER INFORMATION: Primer

<400> SEQUENCE: 132
gtcgcccgtc ttgttgccga gcatc                                             25

<210> SEQ ID NO 133
<211> LENGTH: 26
<212> TYPE: DNA
<213> ORGANISM: Artificial Sequence
<220> FEATURE:
<223> OTHER INFORMATION: Primer

<400> SEQUENCE: 133
gcccgtcaat ccgatgcmgt atctgg                                            26

<210> SEQ ID NO 134
<211> LENGTH: 24
<212> TYPE: DNA
<213> ORGANISM: Artificial Sequence
<220> FEATURE:
<223> OTHER INFORMATION: Primer

<400> SEQUENCE: 134
gcgccgatca rtggggtgga aatg                                              24

<210> SEQ ID NO 135
<211> LENGTH: 22
<212> TYPE: DNA
<213> ORGANISM: Artificial Sequence
<220> FEATURE:
<223> OTHER INFORMATION: Primer
```

<400> SEQUENCE: 135
catcgcggcg acgagcgttt cc					22

<210> SEQ ID NO 136
<211> LENGTH: 28
<212> TYPE: DNA
<213> ORGANISM: Artificial Sequence
<220> FEATURE:
<223> OTHER INFORMATION: Primer

<400> SEQUENCE: 136
ctcggtgatc ggcgaatagc ggatgaga					28

<210> SEQ ID NO 137
<211> LENGTH: 24
<212> TYPE: DNA
<213> ORGANISM: Artificial Sequence
<220> FEATURE:
<223> OTHER INFORMATION: Primer

<400> SEQUENCE: 137
gctgtgcgcg gcgacgcttc agta					24

<210> SEQ ID NO 138
<211> LENGTH: 26
<212> TYPE: DNA
<213> ORGANISM: Artificial Sequence
<220> FEATURE:
<223> OTHER INFORMATION: Primer

<400> SEQUENCE: 138
ccgatgtcgt tcgccgttcc gtagtc					26

<210> SEQ ID NO 139
<211> LENGTH: 24
<212> TYPE: DNA
<213> ORGANISM: Artificial Sequence
<220> FEATURE:
<223> OTHER INFORMATION: Primer

<400> SEQUENCE: 139
atccgccgtc ccgcccagca atag					24

<210> SEQ ID NO 140
<211> LENGTH: 29
<212> TYPE: DNA
<213> ORGANISM: Artificial Sequence
<220> FEATURE:
<223> OTHER INFORMATION: Primer

<400> SEQUENCE: 140
gggttcgccc agatttcgta ggtggtgag					29

<210> SEQ ID NO 141
<211> LENGTH: 22
<212> TYPE: DNA
<213> ORGANISM: Artificial Sequence
<220> FEATURE:
<223> OTHER INFORMATION: Primer

<400> SEQUENCE: 141
tcgccgtttc acgccccgca ac					22

<210> SEQ ID NO 142
<211> LENGTH: 22

```
<212> TYPE: DNA
<213> ORGANISM: Artificial Sequence
<220> FEATURE:
<223> OTHER INFORMATION: Primer

<400> SEQUENCE: 142
gcgccgaacg cgaggaacac ga                                            22

<210> SEQ ID NO 143
<211> LENGTH: 23
<212> TYPE: DNA
<213> ORGANISM: Artificial Sequence
<220> FEATURE:
<223> OTHER INFORMATION: Primer

<400> SEQUENCE: 143
gctcgcgaag ctcgcgctga acc                                           23

<210> SEQ ID NO 144
<211> LENGTH: 23
<212> TYPE: DNA
<213> ORGANISM: Artificial Sequence
<220> FEATURE:
<223> OTHER INFORMATION: Primer

<400> SEQUENCE: 144
ggatcgtgcc gtcgcccgca tac                                           23

<210> SEQ ID NO 145
<211> LENGTH: 25
<212> TYPE: DNA
<213> ORGANISM: Artificial Sequence
<220> FEATURE:
<223> OTHER INFORMATION: Primer

<400> SEQUENCE: 145
acaagcccgg ygtcgagatg gtgac                                         25

<210> SEQ ID NO 146
<211> LENGTH: 23
<212> TYPE: DNA
<213> ORGANISM: Artificial Sequence
<220> FEATURE:
<223> OTHER INFORMATION: Primer

<400> SEQUENCE: 146
cgcgtcggcc gaayggtcgt agt                                           23

<210> SEQ ID NO 147
<211> LENGTH: 23
<212> TYPE: DNA
<213> ORGANISM: Artificial Sequence
<220> FEATURE:
<223> OTHER INFORMATION: Primer

<400> SEQUENCE: 147
aatcgtcggc tgcgtcgcct tca                                           23

<210> SEQ ID NO 148
<211> LENGTH: 27
<212> TYPE: DNA
<213> ORGANISM: Artificial Sequence
<220> FEATURE:
<223> OTHER INFORMATION: Primer

<400> SEQUENCE: 148
```
cgggtagcgt gagtggaatt cgcagag                                              27

<210> SEQ ID NO 149
<211> LENGTH: 25
<212> TYPE: DNA
<213> ORGANISM: Artificial Sequence
<220> FEATURE:
<223> OTHER INFORMATION: Primer

<400> SEQUENCE: 149
cctcgaaggc ttcgggctga tccag                                                25

<210> SEQ ID NO 150
<211> LENGTH: 29
<212> TYPE: DNA
<213> ORGANISM: Artificial Sequence
<220> FEATURE:
<223> OTHER INFORMATION: Primer

<400> SEQUENCE: 150
gactaaccgc ttacgccacc cactcgttc                                            29

<210> SEQ ID NO 151
<211> LENGTH: 27
<212> TYPE: DNA
<213> ORGANISM: Artificial Sequence
<220> FEATURE:
<223> OTHER INFORMATION: Primer

<400> SEQUENCE: 151
aaagcgaata gtcgcgaagc ggcttga                                              27

<210> SEQ ID NO 152
<211> LENGTH: 29
<212> TYPE: DNA
<213> ORGANISM: Artificial Sequence
<220> FEATURE:
<223> OTHER INFORMATION: Primer

<400> SEQUENCE: 152
gcgatctcgg tgatgatctt gatgcagtg                                            29

<210> SEQ ID NO 153
<211> LENGTH: 22
<212> TYPE: DNA
<213> ORGANISM: Artificial Sequence
<220> FEATURE:
<223> OTHER INFORMATION: Primer

<400> SEQUENCE: 153
aacggcggcg tgaccgtcaa cg                                                   22

<210> SEQ ID NO 154
<211> LENGTH: 20
<212> TYPE: DNA
<213> ORGANISM: Artificial Sequence
<220> FEATURE:
<223> OTHER INFORMATION: Primer

<400> SEQUENCE: 154
cgctacgcgg ccacctgccc                                                      20

<210> SEQ ID NO 155
<211> LENGTH: 28
<212> TYPE: DNA
<213> ORGANISM: Artificial Sequence

```
<220> FEATURE:
<223> OTHER INFORMATION: Primer

<400> SEQUENCE: 155
cggagcttca gaacaacccg cgtgtaac                                              28

<210> SEQ ID NO 156
<211> LENGTH: 26
<212> TYPE: DNA
<213> ORGANISM: Artificial Sequence
<220> FEATURE:
<223> OTHER INFORMATION: Primer

<400> SEQUENCE: 156
ccttcggacc ttttcccgca actggc                                               26

<210> SEQ ID NO 157
<211> LENGTH: 22
<212> TYPE: DNA
<213> ORGANISM: Artificial Sequence
<220> FEATURE:
<223> OTHER INFORMATION: Primer

<400> SEQUENCE: 157
aattcggccg gcaggcggta cg                                                   22

<210> SEQ ID NO 158
<211> LENGTH: 19
<212> TYPE: DNA
<213> ORGANISM: Artificial Sequence
<220> FEATURE:
<223> OTHER INFORMATION: Primer

<400> SEQUENCE: 158
cgcgcgcagc cggcatttg                                                       19

<210> SEQ ID NO 159
<211> LENGTH: 27
<212> TYPE: DNA
<213> ORGANISM: Artificial Sequence
<220> FEATURE:
<223> OTHER INFORMATION: Primer

<400> SEQUENCE: 159
cccttcggtc cccaccagaa aaattcg                                              27

<210> SEQ ID NO 160
<211> LENGTH: 29
<212> TYPE: DNA
<213> ORGANISM: Artificial Sequence
<220> FEATURE:
<223> OTHER INFORMATION: Primer

<400> SEQUENCE: 160
agccgtacag gccaatgcag ccatctatg                                            29

<210> SEQ ID NO 161
<211> LENGTH: 24
<212> TYPE: DNA
<213> ORGANISM: Artificial Sequence
<220> FEATURE:
<223> OTHER INFORMATION: Primer

<400> SEQUENCE: 161
gcgccgcgtg ttcgtgacct tgtc                                                 24
```

-continued

```
<210> SEQ ID NO 162
<211> LENGTH: 22
<212> TYPE: DNA
<213> ORGANISM: Artificial Sequence
<220> FEATURE:
<223> OTHER INFORMATION: Primer

<400> SEQUENCE: 162
cgctgatcgg cgcatcggac ac                                              22

<210> SEQ ID NO 163
<211> LENGTH: 28
<212> TYPE: DNA
<213> ORGANISM: Artificial Sequence
<220> FEATURE:
<223> OTHER INFORMATION: Primer

<400> SEQUENCE: 163
atcgtgatat cgccggttcc tggttgtg                                        28

<210> SEQ ID NO 164
<211> LENGTH: 27
<212> TYPE: DNA
<213> ORGANISM: Artificial Sequence
<220> FEATURE:
<223> OTHER INFORMATION: Primer

<400> SEQUENCE: 164
cacgtttggc ggcagtgcaa ggtgtag                                         27

<210> SEQ ID NO 165
<211> LENGTH: 28
<212> TYPE: DNA
<213> ORGANISM: Artificial Sequence
<220> FEATURE:
<223> OTHER INFORMATION: Primer

<400> SEQUENCE: 165
tctgctgatc ggccttcgcc agatayac                                        28

<210> SEQ ID NO 166
<211> LENGTH: 34
<212> TYPE: DNA
<213> ORGANISM: Artificial Sequence
<220> FEATURE:
<223> OTHER INFORMATION: Primer

<400> SEQUENCE: 166
gcggatgaac aatttcctgt cgagcgacta ttac                                 34

<210> SEQ ID NO 167
<211> LENGTH: 27
<212> TYPE: DNA
<213> ORGANISM: Artificial Sequence
<220> FEATURE:
<223> OTHER INFORMATION: Primer

<400> SEQUENCE: 167
gcagggcgcc ttgatatccg ctatgag                                         27

<210> SEQ ID NO 168
<211> LENGTH: 25
<212> TYPE: DNA
<213> ORGANISM: Artificial Sequence
<220> FEATURE:
<223> OTHER INFORMATION: Primer
```

<400> SEQUENCE: 168
cggcgcaagg ttctcctgcc acatc                                          25

<210> SEQ ID NO 169
<211> LENGTH: 26
<212> TYPE: DNA
<213> ORGANISM: Artificial Sequence
<220> FEATURE:
<223> OTHER INFORMATION: Primer

<400> SEQUENCE: 169
gtgtgatcga ckgcgtcctc cctgag                                         26

<210> SEQ ID NO 170
<211> LENGTH: 25
<212> TYPE: DNA
<213> ORGANISM: Artificial Sequence
<220> FEATURE:
<223> OTHER INFORMATION: Primer

<400> SEQUENCE: 170
caagccgctg atacccgtgt cgctg                                          25

<210> SEQ ID NO 171
<211> LENGTH: 28
<212> TYPE: DNA
<213> ORGANISM: Artificial Sequence
<220> FEATURE:
<223> OTHER INFORMATION: Primer

<400> SEQUENCE: 171
gcgcttctcg gtgggtacga aaaacagc                                       28

<210> SEQ ID NO 172
<211> LENGTH: 28
<212> TYPE: DNA
<213> ORGANISM: Artificial Sequence
<220> FEATURE:
<223> OTHER INFORMATION: Primer

<400> SEQUENCE: 172
cgagtcggcc aagatcattc aggaccag                                       28

<210> SEQ ID NO 173
<211> LENGTH: 26
<212> TYPE: DNA
<213> ORGANISM: Artificial Sequence
<220> FEATURE:
<223> OTHER INFORMATION: Primer

<400> SEQUENCE: 173
caccttgaca ctgatccgcg gcgtag                                         26

<210> SEQ ID NO 174
<211> LENGTH: 36
<212> TYPE: DNA
<213> ORGANISM: Artificial Sequence
<220> FEATURE:
<223> OTHER INFORMATION: Primer

<400> SEQUENCE: 174
cttccttcgc acaaccgagc aaatactgag taaatc                              36

<210> SEQ ID NO 175

```
<211> LENGTH: 27
<212> TYPE: DNA
<213> ORGANISM: Artificial Sequence
<220> FEATURE:
<223> OTHER INFORMATION: Primer

<400> SEQUENCE: 175
gatcttgcga ccgatgctca gcgtgtg                                    27

<210> SEQ ID NO 176
<211> LENGTH: 25
<212> TYPE: DNA
<213> ORGANISM: Artificial Sequence
<220> FEATURE:
<223> OTHER INFORMATION: Primer

<400> SEQUENCE: 176
tggcgcgggc caaggatatc agttc                                      25

<210> SEQ ID NO 177
<211> LENGTH: 20
<212> TYPE: DNA
<213> ORGANISM: Artificial Sequence
<220> FEATURE:
<223> OTHER INFORMATION: Primer

<400> SEQUENCE: 177
gccttacgcc ttcgggatcg                                            20

<210> SEQ ID NO 178
<211> LENGTH: 20
<212> TYPE: DNA
<213> ORGANISM: Artificial Sequence
<220> FEATURE:
<223> OTHER INFORMATION: Primer

<400> SEQUENCE: 178
gaatgcgctc acccgatgct                                            20

<210> SEQ ID NO 179
<211> LENGTH: 20
<212> TYPE: DNA
<213> ORGANISM: Artificial Sequence
<220> FEATURE:
<223> OTHER INFORMATION: Primer

<400> SEQUENCE: 179
agcaagccat ccgcgtcatc                                            20

<210> SEQ ID NO 180
<211> LENGTH: 20
<212> TYPE: DNA
<213> ORGANISM: Artificial Sequence
<220> FEATURE:
<223> OTHER INFORMATION: Primer

<400> SEQUENCE: 180
caggatgcca ccgttggtga                                            20

<210> SEQ ID NO 181
<211> LENGTH: 20
<212> TYPE: DNA
<213> ORGANISM: Artificial Sequence
<220> FEATURE:
<223> OTHER INFORMATION: Primer

<400> SEQUENCE: 181
```
gccacaggca tggtgagcaa                                               20

<210> SEQ ID NO 182
<211> LENGTH: 21
<212> TYPE: DNA
<213> ORGANISM: Artificial Sequence
<220> FEATURE:
<223> OTHER INFORMATION: Primer

<400> SEQUENCE: 182
cggcattccc tcaatcacga a                                             21

<210> SEQ ID NO 183
<211> LENGTH: 19
<212> TYPE: DNA
<213> ORGANISM: Artificial Sequence
<220> FEATURE:
<223> OTHER INFORMATION: Primer

<400> SEQUENCE: 183
ctgcgtccca aaccgacga                                                19

<210> SEQ ID NO 184
<211> LENGTH: 20
<212> TYPE: DNA
<213> ORGANISM: Artificial Sequence
<220> FEATURE:
<223> OTHER INFORMATION: Primer

<400> SEQUENCE: 184
ccgtcgatgc cacgaatgaa                                               20

<210> SEQ ID NO 185
<211> LENGTH: 20
<212> TYPE: DNA
<213> ORGANISM: Artificial Sequence
<220> FEATURE:
<223> OTHER INFORMATION: Primer

<400> SEQUENCE: 185 cccccaaaaat cccgctctgg                                              20

<210> SEQ ID NO 186
<211> LENGTH: 20
<212> TYPE: DNA
<213> ORGANISM: Artificial Sequence
<220> FEATURE:
<223> OTHER INFORMATION: Primer

<400> SEQUENCE: 186
cggcacaaag ccggtgaaag                                               20

<210> SEQ ID NO 187
<211> LENGTH: 20
<212> TYPE: DNA
<213> ORGANISM: Artificial Sequence
<220> FEATURE:
<223> OTHER INFORMATION: Primer

<400> SEQUENCE: 187
tgccgttcag ttgggccttt                                               20

<210> SEQ ID NO 188
<211> LENGTH: 20
<212> TYPE: DNA

```
<213> ORGANISM: Artificial Sequence
<220> FEATURE:
<223> OTHER INFORMATION: Primer

<400> SEQUENCE: 188
tgccgcttcc aactgcttca                                               20

<210> SEQ ID NO 189
<211> LENGTH: 20
<212> TYPE: DNA
<213> ORGANISM: Artificial Sequence
<220> FEATURE:
<223> OTHER INFORMATION: Primer

<400> SEQUENCE: 189
gggcgggcca atcttttctg                                               20

<210> SEQ ID NO 190
<211> LENGTH: 20
<212> TYPE: DNA
<213> ORGANISM: Artificial Sequence
<220> FEATURE:
<223> OTHER INFORMATION: Primer

<400> SEQUENCE: 190
tccgcgatgt gaccaaacga                                               20

<210> SEQ ID NO 191
<211> LENGTH: 20
<212> TYPE: DNA
<213> ORGANISM: Artificial Sequence
<220> FEATURE:
<223> OTHER INFORMATION: Primer

<400> SEQUENCE: 191
tcggagattc cgacggacca                                               20

<210> SEQ ID NO 192
<211> LENGTH: 20
<212> TYPE: DNA
<213> ORGANISM: Artificial Sequence
<220> FEATURE:
<223> OTHER INFORMATION: Primer

<400> SEQUENCE: 192
ccgcatatcg ccctgacaca                                               20

<210> SEQ ID NO 193
<211> LENGTH: 20
<212> TYPE: DNA
<213> ORGANISM: Artificial Sequence
<220> FEATURE:
<223> OTHER INFORMATION: Primer

<400> SEQUENCE: 193
ggcaccgacg tgcaaaaagc                                               20

<210> SEQ ID NO 194
<211> LENGTH: 20
<212> TYPE: DNA
<213> ORGANISM: Artificial Sequence
<220> FEATURE:
<223> OTHER INFORMATION: Primer

<400> SEQUENCE: 194
ggccgatctc ggcactacga                                               20
```

<210> SEQ ID NO 195
<211> LENGTH: 20
<212> TYPE: DNA
<213> ORGANISM: Artificial Sequence
<220> FEATURE:
<223> OTHER INFORMATION: Primer

<400> SEQUENCE: 195
gcggggtacg ggctaaccaa                                               20

<210> SEQ ID NO 196
<211> LENGTH: 20
<212> TYPE: DNA
<213> ORGANISM: Artificial Sequence
<220> FEATURE:
<223> OTHER INFORMATION: Primer

<400> SEQUENCE: 196
tccgtacgct cgccacaaca                                               20

<210> SEQ ID NO 197
<211> LENGTH: 20
<212> TYPE: DNA
<213> ORGANISM: Artificial Sequence
<220> FEATURE:
<223> OTHER INFORMATION: Primer

<400> SEQUENCE: 197
gcaaaggcgc caggaaacaa                                               20

<210> SEQ ID NO 198
<211> LENGTH: 20
<212> TYPE: DNA
<213> ORGANISM: Artificial Sequence
<220> FEATURE:
<223> OTHER INFORMATION: Primer

<400> SEQUENCE: 198
accgccccga ttgaccaagt                                               20

<210> SEQ ID NO 199
<211> LENGTH: 20
<212> TYPE: DNA
<213> ORGANISM: Artificial Sequence
<220> FEATURE:
<223> OTHER INFORMATION: Primer

<400> SEQUENCE: 199
tccaggcggt tctccgattg                                               20

<210> SEQ ID NO 200
<211> LENGTH: 20
<212> TYPE: DNA
<213> ORGANISM: Artificial Sequence
<220> FEATURE:
<223> OTHER INFORMATION: Primer

<400> SEQUENCE: 200
gttgccgatg tcgaggcaca                                               20

<210> SEQ ID NO 201
<211> LENGTH: 20
<212> TYPE: DNA
<213> ORGANISM: Artificial Sequence
<220> FEATURE:

<223> OTHER INFORMATION: Primer

<400> SEQUENCE: 201
tcttcggcga gcgtctacgg					20

<210> SEQ ID NO 202
<211> LENGTH: 20
<212> TYPE: DNA
<213> ORGANISM: Artificial Sequence
<220> FEATURE:
<223> OTHER INFORMATION: Primer

<400> SEQUENCE: 202
cgcgtcggac gagtgtcgta					20

<210> SEQ ID NO 203
<211> LENGTH: 20
<212> TYPE: DNA
<213> ORGANISM: Artificial Sequence
<220> FEATURE:
<223> OTHER INFORMATION: Primer

<400> SEQUENCE: 203
ggctcacacg gctgggtcat					20

<210> SEQ ID NO 204
<211> LENGTH: 20
<212> TYPE: DNA
<213> ORGANISM: Artificial Sequence
<220> FEATURE:
<223> OTHER INFORMATION: Primer

<400> SEQUENCE: 204
acggcgtttt ggaccacgag					20

<210> SEQ ID NO 205
<211> LENGTH: 20
<212> TYPE: DNA
<213> ORGANISM: Artificial Sequence
<220> FEATURE:
<223> OTHER INFORMATION: Primer

<400> SEQUENCE: 205
ccgcctactg gtggcaggtg					20

<210> SEQ ID NO 206
<211> LENGTH: 20
<212> TYPE: DNA
<213> ORGANISM: Artificial Sequence
<220> FEATURE:
<223> OTHER INFORMATION: Primer

<400> SEQUENCE: 206
gccagtcccg ggaaggagtg					20

<210> SEQ ID NO 207
<211> LENGTH: 20
<212> TYPE: DNA
<213> ORGANISM: Artificial Sequence
<220> FEATURE:
<223> OTHER INFORMATION: Primer

<400> SEQUENCE: 207
gctcatcctg ccaggccagt					20

```
<210> SEQ ID NO 208
<211> LENGTH: 20
<212> TYPE: DNA
<213> ORGANISM: Artificial Sequence
<220> FEATURE:
<223> OTHER INFORMATION: Primer

<400> SEQUENCE: 208
gatacccacc gccggaacct                                               20

<210> SEQ ID NO 209
<211> LENGTH: 20
<212> TYPE: DNA
<213> ORGANISM: Artificial Sequence
<220> FEATURE:
<223> OTHER INFORMATION: Primer

<400> SEQUENCE: 209
agcggcggat tatgggcact                                               20

<210> SEQ ID NO 210
<211> LENGTH: 20
<212> TYPE: DNA
<213> ORGANISM: Artificial Sequence
<220> FEATURE:
<223> OTHER INFORMATION: Primer

<400> SEQUENCE: 210
acgctggggc tgttttgcag                                               20

<210> SEQ ID NO 211
<211> LENGTH: 20
<212> TYPE: DNA
<213> ORGANISM: Artificial Sequence
<220> FEATURE:
<223> OTHER INFORMATION: Primer

<400> SEQUENCE: 211
cgcccttcga gcttgcttcc                                               20

<210> SEQ ID NO 212
<211> LENGTH: 21
<212> TYPE: DNA
<213> ORGANISM: Artificial Sequence
<220> FEATURE:
<223> OTHER INFORMATION: Primer

<400> SEQUENCE: 212
ccgcaacagg tggcttctga c                                             21

<210> SEQ ID NO 213
<211> LENGTH: 20
<212> TYPE: DNA
<213> ORGANISM: Artificial Sequence
<220> FEATURE:
<223> OTHER INFORMATION: Primer

<400> SEQUENCE: 213
cgttgccccc gcccacgtag                                               20

<210> SEQ ID NO 214
<211> LENGTH: 20
<212> TYPE: DNA
<213> ORGANISM: Artificial Sequence
<220> FEATURE:
<223> OTHER INFORMATION: Primer
```

```
<400> SEQUENCE: 214
ccgtgtggcg cgtcctccat                                            20

<210> SEQ ID NO 215
<211> LENGTH: 20
<212> TYPE: DNA
<213> ORGANISM: Artificial Sequence
<220> FEATURE:
<223> OTHER INFORMATION: Primer

<400> SEQUENCE: 215
tgggctcatc ctcgcaaagc                                            20

<210> SEQ ID NO 216
<211> LENGTH: 20
<212> TYPE: DNA
<213> ORGANISM: Artificial Sequence
<220> FEATURE:
<223> OTHER INFORMATION: Primer

<400> SEQUENCE: 216
acgcgctcgg tggaaaacag                                            20

<210> SEQ ID NO 217
<211> LENGTH: 20
<212> TYPE: DNA
<213> ORGANISM: Artificial Sequence
<220> FEATURE:
<223> OTHER INFORMATION: Primer

<400> SEQUENCE: 217
tcacaccatg ggctccgaga                                            20

<210> SEQ ID NO 218
<211> LENGTH: 20
<212> TYPE: DNA
<213> ORGANISM: Artificial Sequence
<220> FEATURE:
<223> OTHER INFORMATION: Primer

<400> SEQUENCE: 218
cgggcgggta gacgagttcc                                            20

<210> SEQ ID NO 219
<211> LENGTH: 21
<212> TYPE: DNA
<213> ORGANISM: Artificial Sequence
<220> FEATURE:
<223> OTHER INFORMATION: Primer

<400> SEQUENCE: 219
accacgagtg tgtgcggcat t                                          21

<210> SEQ ID NO 220
<211> LENGTH: 20
<212> TYPE: DNA
<213> ORGANISM: Artificial Sequence
<220> FEATURE:
<223> OTHER INFORMATION: Primer

<400> SEQUENCE: 220
gcgctcgatg gttcccgaag                                            20

<210> SEQ ID NO 221
<211> LENGTH: 20
```

```
<212> TYPE: DNA
<213> ORGANISM: Artificial Sequence
<220> FEATURE:
<223> OTHER INFORMATION: Primer

<400> SEQUENCE: 221
cttgccttcc aggcgcacat                                              20

<210> SEQ ID NO 222
<211> LENGTH: 20
<212> TYPE: DNA
<213> ORGANISM: Artificial Sequence
<220> FEATURE:
<223> OTHER INFORMATION: Primer

<400> SEQUENCE: 222
tgccaagcgg aagctccttg                                              20

<210> SEQ ID NO 223
<211> LENGTH: 20
<212> TYPE: DNA
<213> ORGANISM: Artificial Sequence
<220> FEATURE:
<223> OTHER INFORMATION: Primer

<400> SEQUENCE: 223
gccgtgtccg catgatcctc                                              20

<210> SEQ ID NO 224
<211> LENGTH: 20
<212> TYPE: DNA
<213> ORGANISM: Artificial Sequence
<220> FEATURE:
<223> OTHER INFORMATION: Primer

<400> SEQUENCE: 224
cgctccagtg cgttgtcgag                                              20

<210> SEQ ID NO 225
<211> LENGTH: 20
<212> TYPE: DNA
<213> ORGANISM: Artificial Sequence
<220> FEATURE:
<223> OTHER INFORMATION: Primer

<400> SEQUENCE: 225
cactgttcgc atcggtattc                                              20

<210> SEQ ID NO 226
<211> LENGTH: 23
<212> TYPE: DNA
<213> ORGANISM: Artificial Sequence
<220> FEATURE:
<223> OTHER INFORMATION: Primer

<400> SEQUENCE: 226
ctygccgtgt ccgtcacgac aag                                          23

<210> SEQ ID NO 227
<211> LENGTH: 20
<212> TYPE: DNA
<213> ORGANISM: Artificial Sequence
<220> FEATURE:
<223> OTHER INFORMATION: Primer

<400> SEQUENCE: 227
```

-continued ggcgccttct ggtggtcctt                              20

<210> SEQ ID NO 228
<211> LENGTH: 20
<212> TYPE: DNA
<213> ORGANISM: Artificial Sequence
<220> FEATURE:
<223> OTHER INFORMATION: Primer

<400> SEQUENCE: 228
tggctttgcg accagtcgtg                              20

<210> SEQ ID NO 229
<211> LENGTH: 19
<212> TYPE: DNA
<213> ORGANISM: Artificial Sequence
<220> FEATURE:
<223> OTHER INFORMATION: Primer

<400> SEQUENCE: 229
atggcaarga ttctkgtrg                               19

<210> SEQ ID NO 230
<211> LENGTH: 17
<212> TYPE: DNA
<213> ORGANISM: Artificial Sequence
<220> FEATURE:
<223> OTHER INFORMATION: Primer

<400> SEQUENCE: 230
ttcacgatcc agccctt                                 17

<210> SEQ ID NO 231
<211> LENGTH: 20
<212> TYPE: DNA
<213> ORGANISM: Artificial Sequence
<220> FEATURE:
<223> OTHER INFORMATION: Primer

<400> SEQUENCE: 231
aacaagctaa aaccgaacaa                              20

<210> SEQ ID NO 232
<211> LENGTH: 20
<212> TYPE: DNA
<213> ORGANISM: Artificial Sequence
<220> FEATURE:
<223> OTHER INFORMATION: Primer

<400> SEQUENCE: 232
atagcctcaa ctgcttttg                               20

<210> SEQ ID NO 233
<211> LENGTH: 18
<212> TYPE: DNA
<213> ORGANISM: Artificial Sequence
<220> FEATURE:
<223> OTHER INFORMATION: Primer

<400> SEQUENCE: 233
cagtaccgac aaaacttc                                18

<210> SEQ ID NO 234
<211> LENGTH: 20
<212> TYPE: DNA
<213> ORGANISM: Artificial Sequence

```
<220> FEATURE:
<223> OTHER INFORMATION: Primer

<400> SEQUENCE: 234
tttactactc tgaaaacgag                                            20

<210> SEQ ID NO 235
<211> LENGTH: 20
<212> TYPE: DNA
<213> ORGANISM: Artificial Sequence
<220> FEATURE:
<223> OTHER INFORMATION: Primer

<400> SEQUENCE: 235
gcactacaaa tttaaatccc                                            20

<210> SEQ ID NO 236
<211> LENGTH: 20
<212> TYPE: DNA
<213> ORGANISM: Artificial Sequence
<220> FEATURE:
<223> OTHER INFORMATION: Primer

<400> SEQUENCE: 236
gtcgattatc aacctctatg                                            20

<210> SEQ ID NO 237
<211> LENGTH: 23
<212> TYPE: DNA
<213> ORGANISM: Artificial Sequence
<220> FEATURE:
<223> OTHER INFORMATION: Primer

<400> SEQUENCE: 237
gaaaggagtg cgggtaatag gtt                                        23

<210> SEQ ID NO 238
<211> LENGTH: 22
<212> TYPE: DNA
<213> ORGANISM: Artificial Sequence
<220> FEATURE:
<223> OTHER INFORMATION: Primer

<400> SEQUENCE: 238
ggcctgcaag tccaatatat gg                                         22

<210> SEQ ID NO 239
<211> LENGTH: 20
<212> TYPE: DNA
<213> ORGANISM: Artificial Sequence
<220> FEATURE:
<223> OTHER INFORMATION: Primer

<400> SEQUENCE: 239
ttaatatccc ggcactcata                                            20

<210> SEQ ID NO 240
<211> LENGTH: 22
<212> TYPE: DNA
<213> ORGANISM: Artificial Sequence
<220> FEATURE:
<223> OTHER INFORMATION: Primer

<400> SEQUENCE: 240
tccttaactg aataagtgct ca                                         22
```

```
<210> SEQ ID NO 241
<211> LENGTH: 19
<212> TYPE: DNA
<213> ORGANISM: Artificial Sequence
<220> FEATURE:
<223> OTHER INFORMATION: Primer

<400> SEQUENCE: 241
tttaatgaac ggtgcctag                                              19

<210> SEQ ID NO 242
<211> LENGTH: 19
<212> TYPE: DNA
<213> ORGANISM: Artificial Sequence
<220> FEATURE:
<223> OTHER INFORMATION: Primer

<400> SEQUENCE: 242
gtctgcgttt ctccagtat                                              19

<210> SEQ ID NO 243
<211> LENGTH: 26
<212> TYPE: DNA
<213> ORGANISM: Artificial Sequence
<220> FEATURE:
<223> OTHER INFORMATION: Primer

<400> SEQUENCE: 243
tctggcctgc taaataaaaa cgaacc                                      26

<210> SEQ ID NO 244
<211> LENGTH: 27
<212> TYPE: DNA
<213> ORGANISM: Artificial Sequence
<220> FEATURE:
<223> OTHER INFORMATION: Primer

<400> SEQUENCE: 244
caggcctcag cattttatta tggtgat                                     27

<210> SEQ ID NO 245
<211> LENGTH: 22
<212> TYPE: DNA
<213> ORGANISM: Artificial Sequence
<220> FEATURE:
<223> OTHER INFORMATION: Primer

<400> SEQUENCE: 245
ggggcggata ccttcaccta tg                                          22

<210> SEQ ID NO 246
<211> LENGTH: 23
<212> TYPE: DNA
<213> ORGANISM: Artificial Sequence
<220> FEATURE:
<223> OTHER INFORMATION: Primer

<400> SEQUENCE: 246
ctggggttca gtctggacga gat                                         23

<210> SEQ ID NO 247
<211> LENGTH: 21
<212> TYPE: DNA
<213> ORGANISM: Artificial Sequence
<220> FEATURE:
<223> OTHER INFORMATION: Primer
```

<400> SEQUENCE: 247
accatccggc gctaaatcgt c                                               21

<210> SEQ ID NO 248
<211> LENGTH: 23
<212> TYPE: DNA
<213> ORGANISM: Artificial Sequence
<220> FEATURE:
<223> OTHER INFORMATION: Primer

<400> SEQUENCE: 248
gaaatgcgcc tggtaagcag agt                                             23

<210> SEQ ID NO 249
<211> LENGTH: 20
<212> TYPE: DNA
<213> ORGANISM: Artificial Sequence
<220> FEATURE:
<223> OTHER INFORMATION: Primer

<400> SEQUENCE: 249
actcgggata ctccatactg                                                 20

<210> SEQ ID NO 250
<211> LENGTH: 18
<212> TYPE: DNA
<213> ORGANISM: Artificial Sequence
<220> FEATURE:
<223> OTHER INFORMATION: Primer

<400> SEQUENCE: 250
cgaaagcagt ggtcaatc                                                   18

<210> SEQ ID NO 251
<211> LENGTH: 20
<212> TYPE: DNA
<213> ORGANISM: Artificial Sequence
<220> FEATURE:
<223> OTHER INFORMATION: Primer

<400> SEQUENCE: 251
catgcgcttt acgttatatg                                                 20

<210> SEQ ID NO 252
<211> LENGTH: 18
<212> TYPE: DNA
<213> ORGANISM: Artificial Sequence
<220> FEATURE:
<223> OTHER INFORMATION: Primer

<400> SEQUENCE: 252
gcgttctgca ctctgtct                                                   18

<210> SEQ ID NO 253
<211> LENGTH: 19
<212> TYPE: DNA
<213> ORGANISM: Artificial Sequence
<220> FEATURE:
<223> OTHER INFORMATION: Primer

<400> SEQUENCE: 253
agcgacttcc gtgataaag                                                  19

<210> SEQ ID NO 254

```
<211> LENGTH: 19
<212> TYPE: DNA
<213> ORGANISM: Artificial Sequence
<220> FEATURE:
<223> OTHER INFORMATION: Primer

<400> SEQUENCE: 254
actcaggata ccgtgtggt                                                19

<210> SEQ ID NO 255
<211> LENGTH: 20
<212> TYPE: DNA
<213> ORGANISM: Artificial Sequence
<220> FEATURE:
<223> OTHER INFORMATION: Primer

<400> SEQUENCE: 255
ttcacgataa tcccctaatg                                               20

<210> SEQ ID NO 256
<211> LENGTH: 19
<212> TYPE: DNA
<213> ORGANISM: Artificial Sequence
<220> FEATURE:
<223> OTHER INFORMATION: Primer

<400> SEQUENCE: 256
ttctgtgctc tggctgata                                                19

<210> SEQ ID NO 257
<211> LENGTH: 20
<212> TYPE: DNA
<213> ORGANISM: Artificial Sequence
<220> FEATURE:
<223> OTHER INFORMATION: Primer

<400> SEQUENCE: 257
attatctgtg ccccttcttt                                               20

<210> SEQ ID NO 258
<211> LENGTH: 19
<212> TYPE: DNA
<213> ORGANISM: Artificial Sequence
<220> FEATURE:
<223> OTHER INFORMATION: Primer

<400> SEQUENCE: 258
ggagtggatg ccactaaac                                                19

<210> SEQ ID NO 259
<211> LENGTH: 20
<212> TYPE: DNA
<213> ORGANISM: Artificial Sequence
<220> FEATURE:
<223> OTHER INFORMATION: Primer

<400> SEQUENCE: 259
cctcacacaa caattcactg                                               20

<210> SEQ ID NO 260
<211> LENGTH: 20
<212> TYPE: DNA
<213> ORGANISM: Artificial Sequence
<220> FEATURE:
<223> OTHER INFORMATION: Primer

<400> SEQUENCE: 260
```
tttttccgac aaatttaagg                                                          20

<210> SEQ ID NO 261
<211> LENGTH: 20
<212> TYPE: DNA
<213> ORGANISM: Artificial Sequence
<220> FEATURE:
<223> OTHER INFORMATION: Primer

<400> SEQUENCE: 261
agcatgaagg ttgctaaaag                                                          20

<210> SEQ ID NO 262
<211> LENGTH: 20
<212> TYPE: DNA
<213> ORGANISM: Artificial Sequence
<220> FEATURE:
<223> OTHER INFORMATION: Primer

<400> SEQUENCE: 262
ggtgacttca aaaccgttag                                                          20

<210> SEQ ID NO 263
<211> LENGTH: 20
<212> TYPE: DNA
<213> ORGANISM: Artificial Sequence
<220> FEATURE:
<223> OTHER INFORMATION: Primer

<400> SEQUENCE: 263
gatgcttctg ctatcagstt                                                          20

<210> SEQ ID NO 264
<211> LENGTH: 20
<212> TYPE: DNA
<213> ORGANISM: Artificial Sequence
<220> FEATURE:
<223> OTHER INFORMATION: Primer

<400> SEQUENCE: 264
gtgtgrcttt gaastcttgt                                                          20

<210> SEQ ID NO 265
<211> LENGTH: 20
<212> TYPE: DNA
<213> ORGANISM: Artificial Sequence
<220> FEATURE:
<223> OTHER INFORMATION: Primer

<400> SEQUENCE: 265
gaagtggctc atgttagagg                                                          20

<210> SEQ ID NO 266
<211> LENGTH: 20
<212> TYPE: DNA
<213> ORGANISM: Artificial Sequence
<220> FEATURE:
<223> OTHER INFORMATION: Primer

<400> SEQUENCE: 266
agcgagccta tatgtaacca                                                          20

<210> SEQ ID NO 267
<211> LENGTH: 20
<212> TYPE: DNA

```
<213> ORGANISM: Artificial Sequence
<220> FEATURE:
<223> OTHER INFORMATION: Primer

<400> SEQUENCE: 267
tttaatgtcc gtcaacctct                                                  20

<210> SEQ ID NO 268
<211> LENGTH: 20
<212> TYPE: DNA
<213> ORGANISM: Artificial Sequence
<220> FEATURE:
<223> OTHER INFORMATION: Primer

<400> SEQUENCE: 268
acgagtttgt gagtcgctat                                                  20

<210> SEQ ID NO 269
<211> LENGTH: 20
<212> TYPE: DNA
<213> ORGANISM: Artificial Sequence
<220> FEATURE:
<223> OTHER INFORMATION: Primer

<400> SEQUENCE: 269
tgttacgtac aggctgtcaa                                                  20

<210> SEQ ID NO 270
<211> LENGTH: 20
<212> TYPE: DNA
<213> ORGANISM: Artificial Sequence
<220> FEATURE:
<223> OTHER INFORMATION: Primer

<400> SEQUENCE: 270
atcatatccc gtagcacaag                                                  20

<210> SEQ ID NO 271
<211> LENGTH: 20
<212> TYPE: DNA
<213> ORGANISM: Artificial Sequence
<220> FEATURE:
<223> OTHER INFORMATION: Primer

<400> SEQUENCE: 271
cataacccat cgcaatatct                                                  20

<210> SEQ ID NO 272
<211> LENGTH: 20
<212> TYPE: DNA
<213> ORGANISM: Artificial Sequence
<220> FEATURE:
<223> OTHER INFORMATION: Primer

<400> SEQUENCE: 272
aaattatctg tagcggcaaa                                                  20

<210> SEQ ID NO 273
<211> LENGTH: 20
<212> TYPE: DNA
<213> ORGANISM: Artificial Sequence
<220> FEATURE:
<223> OTHER INFORMATION: Primer

<400> SEQUENCE: 273
gtgtccaacg aaaccataat                                                  20
```

```
<210> SEQ ID NO 274
<211> LENGTH: 20
<212> TYPE: DNA
<213> ORGANISM: Artificial Sequence
<220> FEATURE:
<223> OTHER INFORMATION: Primer

<400> SEQUENCE: 274
tttggttgat tctgtcagtg                                               20

<210> SEQ ID NO 275
<211> LENGTH: 20
<212> TYPE: DNA
<213> ORGANISM: Artificial Sequence
<220> FEATURE:
<223> OTHER INFORMATION: Primer

<400> SEQUENCE: 275
aagcttaact ggtgattgga                                               20

<210> SEQ ID NO 276
<211> LENGTH: 20
<212> TYPE: DNA
<213> ORGANISM: Artificial Sequence
<220> FEATURE:
<223> OTHER INFORMATION: Primer

<400> SEQUENCE: 276
cgcctaacat cttatctgct                                               20

<210> SEQ ID NO 277
<211> LENGTH: 20
<212> TYPE: DNA
<213> ORGANISM: Artificial Sequence
<220> FEATURE:
<223> OTHER INFORMATION: Primer

<400> SEQUENCE: 277
gggtgatgca gtagagaaaa                                               20

<210> SEQ ID NO 278
<211> LENGTH: 20
<212> TYPE: DNA
<213> ORGANISM: Artificial Sequence
<220> FEATURE:
<223> OTHER INFORMATION: Primer

<400> SEQUENCE: 278
taccagatga acgaatagcc                                               20

<210> SEQ ID NO 279
<211> LENGTH: 20
<212> TYPE: DNA
<213> ORGANISM: Artificial Sequence
<220> FEATURE:
<223> OTHER INFORMATION: Primer

<400> SEQUENCE: 279
atcaagctca tcttcaaagc                                               20

<210> SEQ ID NO 280
<211> LENGTH: 20
<212> TYPE: DNA
<213> ORGANISM: Artificial Sequence
<220> FEATURE:
```

<223> OTHER INFORMATION: Primer

<400> SEQUENCE: 280
aaccatgttc agatccaaaa                                           20

<210> SEQ ID NO 281
<211> LENGTH: 20
<212> TYPE: DNA
<213> ORGANISM: Artificial Sequence
<220> FEATURE:
<223> OTHER INFORMATION: Primer

<400> SEQUENCE: 281
tacctctgcc aaaaattcat                                           20

<210> SEQ ID NO 282
<211> LENGTH: 20
<212> TYPE: DNA
<213> ORGANISM: Artificial Sequence
<220> FEATURE:
<223> OTHER INFORMATION: Primer

<400> SEQUENCE: 282
ggcatactca aggtagtggt                                           20

<210> SEQ ID NO 283
<211> LENGTH: 20
<212> TYPE: DNA
<213> ORGANISM: Artificial Sequence
<220> FEATURE:
<223> OTHER INFORMATION: Primer

<400> SEQUENCE: 283
tctttggtag cttgctgact                                           20

<210> SEQ ID NO 284
<211> LENGTH: 20
<212> TYPE: DNA
<213> ORGANISM: Artificial Sequence
<220> FEATURE:
<223> OTHER INFORMATION: Primer

<400> SEQUENCE: 284
cagacgacac ttggcttatt                                           20

<210> SEQ ID NO 285
<211> LENGTH: 18
<212> TYPE: DNA
<213> ORGANISM: Artificial Sequence
<220> FEATURE:
<223> OTHER INFORMATION: Primer

<400> SEQUENCE: 285
ggtaggataa ctaccaag                                             18

<210> SEQ ID NO 286
<211> LENGTH: 22
<212> TYPE: DNA
<213> ORGANISM: Artificial Sequence
<220> FEATURE:
<223> OTHER INFORMATION: Primer

<400> SEQUENCE: 286
gtcatgagtt ttaccaatac tc                                        22

```
<210> SEQ ID NO 287
<211> LENGTH: 20
<212> TYPE: DNA
<213> ORGANISM: Artificial Sequence
<220> FEATURE:
<223> OTHER INFORMATION: Primer

<400> SEQUENCE: 287
cttatgcagc aagaggaact                                               20

<210> SEQ ID NO 288
<211> LENGTH: 20
<212> TYPE: DNA
<213> ORGANISM: Artificial Sequence
<220> FEATURE:
<223> OTHER INFORMATION: Primer

<400> SEQUENCE: 288
atacaccggg ataggtttct                                               20

<210> SEQ ID NO 289
<211> LENGTH: 20
<212> TYPE: DNA
<213> ORGANISM: Artificial Sequence
<220> FEATURE:
<223> OTHER INFORMATION: Primer

<400> SEQUENCE: 289
ctgatggaag agagttcgag                                               20

<210> SEQ ID NO 290
<211> LENGTH: 20
<212> TYPE: DNA
<213> ORGANISM: Artificial Sequence
<220> FEATURE:
<223> OTHER INFORMATION: Primer

<400> SEQUENCE: 290
gtagatataa tcagcgccac                                               20

<210> SEQ ID NO 291
<211> LENGTH: 20
<212> TYPE: DNA
<213> ORGANISM: Artificial Sequence
<220> FEATURE:
<223> OTHER INFORMATION: Primer

<400> SEQUENCE: 291
cggtaagaat acgaccagag                                               20

<210> SEQ ID NO 292
<211> LENGTH: 20
<212> TYPE: DNA
<213> ORGANISM: Artificial Sequence
<220> FEATURE:
<223> OTHER INFORMATION: Primer

<400> SEQUENCE: 292
agaggatttc ttcctccttg                                               20

<210> SEQ ID NO 293
<211> LENGTH: 20
<212> TYPE: DNA
<213> ORGANISM: Artificial Sequence
<220> FEATURE:
<223> OTHER INFORMATION: Primer
```

<400> SEQUENCE: 293
aattctacaa gcacctggaa                                                                                  20

<210> SEQ ID NO 294
<211> LENGTH: 20
<212> TYPE: DNA
<213> ORGANISM: Artificial Sequence
<220> FEATURE:
<223> OTHER INFORMATION: Primer

<400> SEQUENCE: 294
tcctattaaa agcgccatag                                                                                  20

<210> SEQ ID NO 295
<211> LENGTH: 26
<212> TYPE: DNA
<213> ORGANISM: Artificial Sequence
<220> FEATURE:
<223> OTHER INFORMATION: Primer

<400> SEQUENCE: 295
gggcggacga aaaccttga gcacag                                                                            26

<210> SEQ ID NO 296
<211> LENGTH: 24
<212> TYPE: DNA
<213> ORGANISM: Artificial Sequence
<220> FEATURE:
<223> OTHER INFORMATION: Primer

<400> SEQUENCE: 296
gctcgggcgg acgaaaaccc ttga                                                                             24

<210> SEQ ID NO 297
<211> LENGTH: 28
<212> TYPE: DNA
<213> ORGANISM: Artificial Sequence
<220> FEATURE:
<223> OTHER INFORMATION: Primer

<400> SEQUENCE: 297
gcggcagccg ttgaggcaaa agtgatac                                                                         28

<210> SEQ ID NO 298
<211> LENGTH: 28
<212> TYPE: DNA
<213> ORGANISM: Artificial Sequence
<220> FEATURE:
<223> OTHER INFORMATION: Primer

<400> SEQUENCE: 298
gccgggatgc cttacctaga cgcaatga                                                                         28

<210> SEQ ID NO 299
<211> LENGTH: 28
<212> TYPE: DNA
<213> ORGANISM: Artificial Sequence
<220> FEATURE:
<223> OTHER INFORMATION: Primer

<400> SEQUENCE: 299
gccgggatgc cttacctaga cgcaatga                                                                         28

<210> SEQ ID NO 300
<211> LENGTH: 29

```
<212> TYPE: DNA
<213> ORGANISM: Artificial Sequence
<220> FEATURE:
<223> OTHER INFORMATION: Primer

<400> SEQUENCE: 300
cgagttccgt ccggttaagc gtgacagtc                                          29

<210> SEQ ID NO 301
<211> LENGTH: 17
<212> TYPE: DNA
<213> ORGANISM: Artificial Sequence
<220> FEATURE:
<223> OTHER INFORMATION: Primer

<400> SEQUENCE: 301
acccaactga atggagc                                                       17

<210> SEQ ID NO 302
<211> LENGTH: 43
<212> TYPE: DNA
<213> ORGANISM: Artificial Sequence
<220> FEATURE:
<223> OTHER INFORMATION: Primer

<400> SEQUENCE: 302
acccaactga atggagcggg cggacgaaaa cccttgagca cag                          43

<210> SEQ ID NO 303
<211> LENGTH: 19
<212> TYPE: DNA
<213> ORGANISM: Artificial Sequence
<220> FEATURE:
<223> OTHER INFORMATION: Primer

<400> SEQUENCE: 303
acgcacttga cttgtcttc                                                     19

<210> SEQ ID NO 304
<211> LENGTH: 47
<212> TYPE: DNA
<213> ORGANISM: Artificial Sequence
<220> FEATURE:
<223> OTHER INFORMATION: Primer

<400> SEQUENCE: 304
acgcacttga cttgtcttcg ccgggatgcc ttacctagac gcaatga                      47

<210> SEQ ID NO 305
<211> LENGTH: 24
<212> TYPE: DNA
<213> ORGANISM: Artificial Sequence
<220> FEATURE:
<223> OTHER INFORMATION: Primer

<400> SEQUENCE: 305
atccgccgtc ccgcccagca atag                                               24

<210> SEQ ID NO 306
<211> LENGTH: 29
<212> TYPE: DNA
<213> ORGANISM: Artificial Sequence
<220> FEATURE:
<223> OTHER INFORMATION: Primer

<400> SEQUENCE: 306
```
gggttcgccc agatttcgta ggtggtgag									29

<210> SEQ ID NO 307
<211> LENGTH: 37
<212> TYPE: DNA
<213> ORGANISM: Artificial Sequence
<220> FEATURE:
<223> OTHER INFORMATION: Primer

<400> SEQUENCE: 307
acccaactga atggagctcg tcgtcaccgg gatggtc									37

<210> SEQ ID NO 308
<211> LENGTH: 39
<212> TYPE: DNA
<213> ORGANISM: Artificial Sequence
<220> FEATURE:
<223> OTHER INFORMATION: Primer

<400> SEQUENCE: 308
acgcacttga cttgtcttcg gcctttgccc gcatactcg									39

<210> SEQ ID NO 309
<211> LENGTH: 37
<212> TYPE: DNA
<213> ORGANISM: Artificial Sequence
<220> FEATURE:
<223> OTHER INFORMATION: Primer

<400> SEQUENCE: 309
acccaactga atggagctcg cawgaagtgc gttgccg									37

<210> SEQ ID NO 310
<211> LENGTH: 39
<212> TYPE: DNA
<213> ORGANISM: Artificial Sequence
<220> FEATURE:
<223> OTHER INFORMATION: Primer

<400> SEQUENCE: 310
acgcacttga cttgtcttcg ccgcttgcga agcgatgat									39

<210> SEQ ID NO 311
<211> LENGTH: 37
<212> TYPE: DNA
<213> ORGANISM: Artificial Sequence
<220> FEATURE:
<223> OTHER INFORMATION: Primer

<400> SEQUENCE: 311
acccaactga atggagccgc gcttgcccaa ctaccag									37

<210> SEQ ID NO 312
<211> LENGTH: 39
<212> TYPE: DNA
<213> ORGANISM: Artificial Sequence
<220> FEATURE:
<223> OTHER INFORMATION: Primer

<400> SEQUENCE: 312
acgcacttga cttgtcttcg cgcaacggtg cgagacaat									39

<210> SEQ ID NO 313
<211> LENGTH: 37
<212> TYPE: DNA
<213> ORGANISM: Artificial Sequence

```
<220> FEATURE:
<223> OTHER INFORMATION: Primer

<400> SEQUENCE: 313
acccaactga atggagcaat ccatgcatgt cgygccc                              37

<210> SEQ ID NO 314
<211> LENGTH: 39
<212> TYPE: DNA
<213> ORGANISM: Artificial Sequence
<220> FEATURE:
<223> OTHER INFORMATION: Primer

<400> SEQUENCE: 314
acgcacttga cttgtcttcg cgatcgctca acgggcttc                            39

<210> SEQ ID NO 315
<211> LENGTH: 37
<212> TYPE: DNA
<213> ORGANISM: Artificial Sequence
<220> FEATURE:
<223> OTHER INFORMATION: Primer

<400> SEQUENCE: 315
acccaactga atggagctcg catttgcaya cgctccc                              37

<210> SEQ ID NO 316
<211> LENGTH: 39
<212> TYPE: DNA
<213> ORGANISM: Artificial Sequence
<220> FEATURE:
<223> OTHER INFORMATION: Primer

<400> SEQUENCE: 316
acgcacttga cttgtcttca gtgcgcaaac ttggcgagg                            39

<210> SEQ ID NO 317
<211> LENGTH: 37
<212> TYPE: DNA
<213> ORGANISM: Artificial Sequence
<220> FEATURE:
<223> OTHER INFORMATION: Primer

<400> SEQUENCE: 317
acccaactga atggagccct ttgcggcaag cgtcgaa                              37

<210> SEQ ID NO 318
<211> LENGTH: 39
<212> TYPE: DNA
<213> ORGANISM: Artificial Sequence
<220> FEATURE:
<223> OTHER INFORMATION: Primer

<400> SEQUENCE: 318
acgcacttga cttgtcttcg agccaacgca catggacgg                            39

<210> SEQ ID NO 319
<211> LENGTH: 37
<212> TYPE: DNA
<213> ORGANISM: Artificial Sequence
<220> FEATURE:
<223> OTHER INFORMATION: Primer

<400> SEQUENCE: 319
acccaactga atggagccca gtcgggccgg gaaaaac                              37
```

<210> SEQ ID NO 320
<211> LENGTH: 39
<212> TYPE: DNA
<213> ORGANISM: Artificial Sequence
<220> FEATURE:
<223> OTHER INFORMATION: Primer

<400> SEQUENCE: 320
acgcacttga cttgtcttcg gcggcaaaag cgtcgatga                    39

<210> SEQ ID NO 321
<211> LENGTH: 37
<212> TYPE: DNA
<213> ORGANISM: Artificial Sequence
<220> FEATURE:
<223> OTHER INFORMATION: Primer

<400> SEQUENCE: 321
acccaactga atggagcgcc ggaaccgtcg agcattg                      37

<210> SEQ ID NO 322
<211> LENGTH: 39
<212> TYPE: DNA
<213> ORGANISM: Artificial Sequence
<220> FEATURE:
<223> OTHER INFORMATION: Primer

<400> SEQUENCE: 322
acgcacttga cttgtcttct ggattcgact gcctccgct                    39

<210> SEQ ID NO 323
<211> LENGTH: 37
<212> TYPE: DNA
<213> ORGANISM: Artificial Sequence
<220> FEATURE:
<223> OTHER INFORMATION: Primer

<400> SEQUENCE: 323
acccaactga atggagctcg atatccgccg tctcgcc                      37

<210> SEQ ID NO 324
<211> LENGTH: 39
<212> TYPE: DNA
<213> ORGANISM: Artificial Sequence
<220> FEATURE:
<223> OTHER INFORMATION: Primer

<400> SEQUENCE: 324
acgcacttga cttgtcttca tgtgtcggtg ggcttcggt                    39

<210> SEQ ID NO 325
<211> LENGTH: 37
<212> TYPE: DNA
<213> ORGANISM: Artificial Sequence
<220> FEATURE:
<223> OTHER INFORMATION: Primer

<400> SEQUENCE: 325
acccaactga atggagcgaa aggcgatgtg ccgagcg                      37

<210> SEQ ID NO 326
<211> LENGTH: 39
<212> TYPE: DNA
<213> ORGANISM: Artificial Sequence
<220> FEATURE:
<223> OTHER INFORMATION: Primer

<400> SEQUENCE: 326
acgcacttga cttgtcttct tcggagaagc gccaaacgc                                    39

<210> SEQ ID NO 327
<211> LENGTH: 37
<212> TYPE: DNA
<213> ORGANISM: Artificial Sequence
<220> FEATURE:
<223> OTHER INFORMATION: Primer

<400> SEQUENCE: 327
acccaactga atggagcgcc agcgcatcca ccaacat                                      37

<210> SEQ ID NO 328
<211> LENGTH: 39
<212> TYPE: DNA
<213> ORGANISM: Artificial Sequence
<220> FEATURE:
<223> OTHER INFORMATION: Primer

<400> SEQUENCE: 328
acgcacttga cttgtcttca gaggaagaag ggcgaggcg                                    39

<210> SEQ ID NO 329
<211> LENGTH: 37
<212> TYPE: DNA
<213> ORGANISM: Artificial Sequence
<220> FEATURE:
<223> OTHER INFORMATION: Primer

<400> SEQUENCE: 329
acccaactga atggagccgc gcarytcgtc gtcctcg                                      37

<210> SEQ ID NO 330
<211> LENGTH: 39
<212> TYPE: DNA
<213> ORGANISM: Artificial Sequence
<220> FEATURE:
<223> OTHER INFORMATION: Primer

<400> SEQUENCE: 330
acgcacttga cttgtcttcc gaacctsgtg cmggtrcag                                    39

<210> SEQ ID NO 331
<211> LENGTH: 37
<212> TYPE: DNA
<213> ORGANISM: Artificial Sequence
<220> FEATURE:
<223> OTHER INFORMATION: Primer

<400> SEQUENCE: 331
acccaactga atggagccac gttgccsggr aartacg                                      37

<210> SEQ ID NO 332
<211> LENGTH: 39
<212> TYPE: DNA
<213> ORGANISM: Artificial Sequence
<220> FEATURE:
<223> OTHER INFORMATION: Primer

<400> SEQUENCE: 332
acgcacttga cttgtcttcc cgtcgacaag atcgcgcts                                    39

<210> SEQ ID NO 333

```
<211> LENGTH: 36
<212> TYPE: DNA
<213> ORGANISM: Artificial Sequence
<220> FEATURE:
<223> OTHER INFORMATION: Primer

<400> SEQUENCE: 333
acccaactga atggagccag aacgcgctrt yccacg                                 36

<210> SEQ ID NO 334
<211> LENGTH: 39
<212> TYPE: DNA
<213> ORGANISM: Artificial Sequence
<220> FEATURE:
<223> OTHER INFORMATION: Primer

<400> SEQUENCE: 334
acgcacttga cttgtcttct gccgcgtgat ccattgcat                              39

<210> SEQ ID NO 335
<211> LENGTH: 44
<212> TYPE: DNA
<213> ORGANISM: Artificial Sequence
<220> FEATURE:
<223> OTHER INFORMATION: Primer

<400> SEQUENCE: 335
acccaactga atggagcagg gggtggtttc ctgagtggcg tgac                        44

<210> SEQ ID NO 336
<211> LENGTH: 45
<212> TYPE: DNA
<213> ORGANISM: Artificial Sequence
<220> FEATURE:
<223> OTHER INFORMATION: Primer

<400> SEQUENCE: 336
acgcacttga cttgtcttca gcggtgtcga cgggtggaaa ggatg                       45

<210> SEQ ID NO 337
<211> LENGTH: 43
<212> TYPE: DNA
<213> ORGANISM: Artificial Sequence
<220> FEATURE:
<223> OTHER INFORMATION: Primer

<400> SEQUENCE: 337
acccaactga atggagcacg ggcgcttcac gatctcggtg ttc                         43

<210> SEQ ID NO 338
<211> LENGTH: 44
<212> TYPE: DNA
<213> ORGANISM: Artificial Sequence
<220> FEATURE:
<223> OTHER INFORMATION: Primer

<400> SEQUENCE: 338
acgcacttga cttgtcttcg cgcggcagtt cgatcaggca tttg                        44

<210> SEQ ID NO 339
<211> LENGTH: 41
<212> TYPE: DNA
<213> ORGANISM: Artificial Sequence
<220> FEATURE:
<223> OTHER INFORMATION: Primer

<400> SEQUENCE: 339
```

```
acccaactga atggagcatc cgccgtcccg cccagcaata g                    41
```

<210> SEQ ID NO 340
<211> LENGTH: 48
<212> TYPE: DNA
<213> ORGANISM: Artificial Sequence
<220> FEATURE:
<223> OTHER INFORMATION: Primer

<400> SEQUENCE: 340

```
acgcacttga cttgtcttcg ggttcgccca gatttcgtag gtggtgag             48
```

<210> SEQ ID NO 341
<211> LENGTH: 43
<212> TYPE: DNA
<213> ORGANISM: Artificial Sequence
<220> FEATURE:
<223> OTHER INFORMATION: Primer

<400> SEQUENCE: 341

```
acccaactga atggagccgg tcgccacaaa ttcgcacgca ctc                  43
```

<210> SEQ ID NO 342
<211> LENGTH: 45
<212> TYPE: DNA
<213> ORGANISM: Artificial Sequence
<220> FEATURE:
<223> OTHER INFORMATION: Primer

<400> SEQUENCE: 342

```
acgcacttga cttgtcttca gcgagcggcg caacggagaa tgatt                45
```

<210> SEQ ID NO 343
<211> LENGTH: 42
<212> TYPE: DNA
<213> ORGANISM: Artificial Sequence
<220> FEATURE:
<223> OTHER INFORMATION: Primer

<400> SEQUENCE: 343

```
acgcacttga cttgtcttcg ctgcgcggcc aagcgaaaaa cg                   42
```

<210> SEQ ID NO 344
<211> LENGTH: 39
<212> TYPE: DNA
<213> ORGANISM: Artificial Sequence
<220> FEATURE:
<223> OTHER INFORMATION: Primer

<400> SEQUENCE: 344

```
acccaactga atggagccgc gaggaccgca gcgcaaagc                       39
```

<210> SEQ ID NO 345
<211> LENGTH: 41
<212> TYPE: DNA
<213> ORGANISM: Artificial Sequence
<220> FEATURE:
<223> OTHER INFORMATION: Primer

<400> SEQUENCE: 345

```
acccaactga atggagcggc cgcagaccgt caccgcgtat g                    41
```

<210> SEQ ID NO 346
<211> LENGTH: 44
<212> TYPE: DNA

```
<213> ORGANISM: Artificial Sequence
<220> FEATURE:
<223> OTHER INFORMATION: Primer

<400> SEQUENCE: 346
acgcacttga cttgtcttcg tcgcccgtct tgttgccgag catc        44

<210> SEQ ID NO 347
<211> LENGTH: 37
<212> TYPE: DNA
<213> ORGANISM: Artificial Sequence
<220> FEATURE:
<223> OTHER INFORMATION: Primer

<400> SEQUENCE: 347
acccaactga atggagcttt ttcgtaagca tcttcaa             37

<210> SEQ ID NO 348
<211> LENGTH: 39
<212> TYPE: DNA
<213> ORGANISM: Artificial Sequence
<220> FEATURE:
<223> OTHER INFORMATION: Primer

<400> SEQUENCE: 348
acgcacttga cttgtcttct ttgatgtgaa ggtgagaca           39

<210> SEQ ID NO 349
<211> LENGTH: 37
<212> TYPE: DNA
<213> ORGANISM: Artificial Sequence
<220> FEATURE:
<223> OTHER INFORMATION: Primer

<400> SEQUENCE: 349
acccaactga atggagcacg tcaggtgatt attggac             37

<210> SEQ ID NO 350
<211> LENGTH: 39
<212> TYPE: DNA
<213> ORGANISM: Artificial Sequence
<220> FEATURE:
<223> OTHER INFORMATION: Primer

<400> SEQUENCE: 350
acgcacttga cttgtcttcc aacaattata tccgccatt           39

<210> SEQ ID NO 351
<211> LENGTH: 37
<212> TYPE: DNA
<213> ORGANISM: Artificial Sequence
<220> FEATURE:
<223> OTHER INFORMATION: Primer

<400> SEQUENCE: 351
acccaactga atggagcgaa gatgtacgct cgatagg             37

<210> SEQ ID NO 352
<211> LENGTH: 39
<212> TYPE: DNA
<213> ORGANISM: Artificial Sequence
<220> FEATURE:
<223> OTHER INFORMATION: Primer

<400> SEQUENCE: 352
acgcacttga cttgtcttcg aaattctttt tgccatcac           39
```

<210> SEQ ID NO 353
<211> LENGTH: 37
<212> TYPE: DNA
<213> ORGANISM: Artificial Sequence
<220> FEATURE:
<223> OTHER INFORMATION: Primer

<400> SEQUENCE: 353
acccaactga atggagccac aattgaatga aaatgct                                37

<210> SEQ ID NO 354
<211> LENGTH: 39
<212> TYPE: DNA
<213> ORGANISM: Artificial Sequence
<220> FEATURE:
<223> OTHER INFORMATION: Primer

<400> SEQUENCE: 354
acgcacttga cttgtcttcc acgaaacctg tttaccttt                              39

<210> SEQ ID NO 355
<211> LENGTH: 37
<212> TYPE: DNA
<213> ORGANISM: Artificial Sequence
<220> FEATURE:
<223> OTHER INFORMATION: Primer

<400> SEQUENCE: 355
acccaactga atggagcgat attcgacgag ctttctg                                37

<210> SEQ ID NO 356
<211> LENGTH: 39
<212> TYPE: DNA
<213> ORGANISM: Artificial Sequence
<220> FEATURE:
<223> OTHER INFORMATION: Primer

<400> SEQUENCE: 356
acgcacttga cttgtcttct attcatcgtc atcctcctc                              39

<210> SEQ ID NO 357
<211> LENGTH: 37
<212> TYPE: DNA
<213> ORGANISM: Artificial Sequence
<220> FEATURE:
<223> OTHER INFORMATION: Primer

<400> SEQUENCE: 357
acccaactga atggagctat tgaacgcatt gaatcag                                37

<210> SEQ ID NO 358
<211> LENGTH: 39
<212> TYPE: DNA
<213> ORGANISM: Artificial Sequence
<220> FEATURE:
<223> OTHER INFORMATION: Primer

<400> SEQUENCE: 358
acgcacttga cttgtcttct attggtaagc aaaccgtct                              39

<210> SEQ ID NO 359
<211> LENGTH: 37
<212> TYPE: DNA
<213> ORGANISM: Artificial Sequence
<220> FEATURE:

<223> OTHER INFORMATION: Primer

<400> SEQUENCE: 359
acccaactga atggagcggt tcaggacaaa atgtagc      37

<210> SEQ ID NO 360
<211> LENGTH: 39
<212> TYPE: DNA
<213> ORGANISM: Artificial Sequence
<220> FEATURE:
<223> OTHER INFORMATION: Primer

<400> SEQUENCE: 360
acgcacttga cttgtcttct aacttctgaa gcgaaaacc      39

<210> SEQ ID NO 361
<211> LENGTH: 37
<212> TYPE: DNA
<213> ORGANISM: Artificial Sequence
<220> FEATURE:
<223> OTHER INFORMATION: Primer

<400> SEQUENCE: 361
acccaactga atggagcgcg aattttagac gacaatc      37

<210> SEQ ID NO 362
<211> LENGTH: 39
<212> TYPE: DNA
<213> ORGANISM: Artificial Sequence
<220> FEATURE:
<223> OTHER INFORMATION: Primer

<400> SEQUENCE: 362
acgcacttga cttgtcttct aaccgtgctt aattcgttt      39

<210> SEQ ID NO 363
<211> LENGTH: 37
<212> TYPE: DNA
<213> ORGANISM: Artificial Sequence
<220> FEATURE:
<223> OTHER INFORMATION: Primer

<400> SEQUENCE: 363
acccaactga atggagcatt aataaggcga ctggtga      37

<210> SEQ ID NO 364
<211> LENGTH: 39
<212> TYPE: DNA
<213> ORGANISM: Artificial Sequence
<220> FEATURE:
<223> OTHER INFORMATION: Primer

<400> SEQUENCE: 364
acgcacttga cttgtcttct tacccatcca gaatgagac      39

<210> SEQ ID NO 365
<211> LENGTH: 37
<212> TYPE: DNA
<213> ORGANISM: Artificial Sequence
<220> FEATURE:
<223> OTHER INFORMATION: Primer

<400> SEQUENCE: 365
acccaactga atggagcaca attcttaaaa ggcgaca      37

```
<210> SEQ ID NO 366
<211> LENGTH: 39
<212> TYPE: DNA
<213> ORGANISM: Artificial Sequence
<220> FEATURE:
<223> OTHER INFORMATION: Primer

<400> SEQUENCE: 366
acgcacttga cttgtcttct gtagcgtctc cgatatttt                              39

<210> SEQ ID NO 367
<211> LENGTH: 37
<212> TYPE: DNA
<213> ORGANISM: Artificial Sequence
<220> FEATURE:
<223> OTHER INFORMATION: Primer

<400> SEQUENCE: 367
acccaactga atggagccat ggggctttct attatgt                                37

<210> SEQ ID NO 368
<211> LENGTH: 41
<212> TYPE: DNA
<213> ORGANISM: Artificial Sequence
<220> FEATURE:
<223> OTHER INFORMATION: Primer

<400> SEQUENCE: 368
acgcacttga cttgtcttct tcgttctttc ataagtttcc t                           41

<210> SEQ ID NO 369
<211> LENGTH: 37
<212> TYPE: DNA
<213> ORGANISM: Artificial Sequence
<220> FEATURE:
<223> OTHER INFORMATION: Primer

<400> SEQUENCE: 369
acccaactga atggagcttg gagtttgttt tgctttt                                37

<210> SEQ ID NO 370
<211> LENGTH: 40
<212> TYPE: DNA
<213> ORGANISM: Artificial Sequence
<220> FEATURE:
<223> OTHER INFORMATION: Primer

<400> SEQUENCE: 370
acgcacttga cttgtcttcg taacaattaa tccacgtcct                             40

<210> SEQ ID NO 371
<211> LENGTH: 37
<212> TYPE: DNA
<213> ORGANISM: Artificial Sequence
<220> FEATURE:
<223> OTHER INFORMATION: Primer

<400> SEQUENCE: 371
acccaactga atggagctga gcctacctag tgattgg                                37

<210> SEQ ID NO 372
<211> LENGTH: 43
<212> TYPE: DNA
<213> ORGANISM: Artificial Sequence
<220> FEATURE:
<223> OTHER INFORMATION: Primer
```

<400> SEQUENCE: 372
acgcacttga cttgtcttct tggataaatt ccacaaattc ctc        43

<210> SEQ ID NO 373
<211> LENGTH: 37
<212> TYPE: DNA
<213> ORGANISM: Artificial Sequence
<220> FEATURE:
<223> OTHER INFORMATION: Primer

<400> SEQUENCE: 373
acccaactga atggagccgc cagcgtatta tataggt        37

<210> SEQ ID NO 374
<211> LENGTH: 39
<212> TYPE: DNA
<213> ORGANISM: Artificial Sequence
<220> FEATURE:
<223> OTHER INFORMATION: Primer

<400> SEQUENCE: 374
acgcacttga cttgtcttcg ctaattctgg gttgtgttt        39

<210> SEQ ID NO 375
<211> LENGTH: 36
<212> TYPE: DNA
<213> ORGANISM: Artificial Sequence
<220> FEATURE:
<223> OTHER INFORMATION: Primer

<400> SEQUENCE: 375
acccaactga atggagctcg gtaagtatca ccctca        36

<210> SEQ ID NO 376
<211> LENGTH: 38
<212> TYPE: DNA
<213> ORGANISM: Artificial Sequence
<220> FEATURE:
<223> OTHER INFORMATION: Primer

<400> SEQUENCE: 376
acgcacttga cttgtcttct gcttctgtat aacgcatt        38

<210> SEQ ID NO 377
<211> LENGTH: 37
<212> TYPE: DNA
<213> ORGANISM: Artificial Sequence
<220> FEATURE:
<223> OTHER INFORMATION: Primer

<400> SEQUENCE: 377
acccaactga atggagccag tcggtaacgt tattggt        37

<210> SEQ ID NO 378
<211> LENGTH: 39
<212> TYPE: DNA
<213> ORGANISM: Artificial Sequence
<220> FEATURE:
<223> OTHER INFORMATION: Primer

<400> SEQUENCE: 378
acgcacttga cttgtcttct aactcagatg caattggtg        39

<210> SEQ ID NO 379
<211> LENGTH: 37

```
<212> TYPE: DNA
<213> ORGANISM: Artificial Sequence
<220> FEATURE:
<223> OTHER INFORMATION: Primer

<400> SEQUENCE: 379
acccaactga atggagcatt gtagagggtg actctgc                                37

<210> SEQ ID NO 380
<211> LENGTH: 38
<212> TYPE: DNA
<213> ORGANISM: Artificial Sequence
<220> FEATURE:
<223> OTHER INFORMATION: Primer

<400> SEQUENCE: 380
acgcacttga cttgtcttct atcaaaatct ccgccaat                               38

<210> SEQ ID NO 381
<211> LENGTH: 37
<212> TYPE: DNA
<213> ORGANISM: Artificial Sequence
<220> FEATURE:
<223> OTHER INFORMATION: Primer

<400> SEQUENCE: 381
acccaactga atggagcggt tacaggacgg attgata                                37

<210> SEQ ID NO 382
<211> LENGTH: 39
<212> TYPE: DNA
<213> ORGANISM: Artificial Sequence
<220> FEATURE:
<223> OTHER INFORMATION: Primer

<400> SEQUENCE: 382
acgcacttga cttgtcttct cccaccaata tcaaagaac                              39

<210> SEQ ID NO 383
<211> LENGTH: 37
<212> TYPE: DNA
<213> ORGANISM: Artificial Sequence
<220> FEATURE:
<223> OTHER INFORMATION: Primer

<400> SEQUENCE: 383
acccaactga atggagcttc ttcggaagtt ctcagtt                                37

<210> SEQ ID NO 384
<211> LENGTH: 38
<212> TYPE: DNA
<213> ORGANISM: Artificial Sequence
<220> FEATURE:
<223> OTHER INFORMATION: Primer

<400> SEQUENCE: 384
acgcacttga cttgtcttcc ggacacatac gaccatag                               38

<210> SEQ ID NO 385
<211> LENGTH: 37
<212> TYPE: DNA
<213> ORGANISM: Artificial Sequence
<220> FEATURE:
<223> OTHER INFORMATION: Primer

<400> SEQUENCE: 385
```
acccaactga atggagcaag tttgaggtgt ggaaatg                                37

<210> SEQ ID NO 386
<211> LENGTH: 39
<212> TYPE: DNA
<213> ORGANISM: Artificial Sequence
<220> FEATURE:
<223> OTHER INFORMATION: Primer

<400> SEQUENCE: 386
acgcacttga cttgtcttct cgaaatgagt tccaatttt                              39

<210> SEQ ID NO 387
<211> LENGTH: 38
<212> TYPE: DNA
<213> ORGANISM: Artificial Sequence
<220> FEATURE:
<223> OTHER INFORMATION: Primer

<400> SEQUENCE: 387
acccaactga atggagccaa aactaatagg ggagggtg                               38

<210> SEQ ID NO 388
<211> LENGTH: 38
<212> TYPE: DNA
<213> ORGANISM: Artificial Sequence
<220> FEATURE:
<223> OTHER INFORMATION: Primer

<400> SEQUENCE: 388
acgcacttga cttgtcttcc cgagaaccta cctcgtta                               38

<210> SEQ ID NO 389
<211> LENGTH: 37
<212> TYPE: DNA
<213> ORGANISM: Artificial Sequence
<220> FEATURE:
<223> OTHER INFORMATION: Primer

<400> SEQUENCE: 389
acccaactga atggagcagg agatgagagt tttgcac                                37

<210> SEQ ID NO 390
<211> LENGTH: 38
<212> TYPE: DNA
<213> ORGANISM: Artificial Sequence
<220> FEATURE:
<223> OTHER INFORMATION: Primer

<400> SEQUENCE: 390
acgcacttga cttgtcttca cccccataat taccatga                               38

<210> SEQ ID NO 391
<211> LENGTH: 37
<212> TYPE: DNA
<213> ORGANISM: Artificial Sequence
<220> FEATURE:
<223> OTHER INFORMATION: Primer

<400> SEQUENCE: 391
acccaactga atggagccgt tgcgtaagta tgtgcta                                37

<210> SEQ ID NO 392
<211> LENGTH: 39
<212> TYPE: DNA
<213> ORGANISM: Artificial Sequence

```
<220> FEATURE:
<223> OTHER INFORMATION: Primer

<400> SEQUENCE: 392
acgcacttga cttgtcttca ggtggcgtaa ttaacgtag                              39

<210> SEQ ID NO 393
<211> LENGTH: 37
<212> TYPE: DNA
<213> ORGANISM: Artificial Sequence
<220> FEATURE:
<223> OTHER INFORMATION: Primer

<400> SEQUENCE: 393
acccaactga atggagccga aaagttgtcg acctaat                                37

<210> SEQ ID NO 394
<211> LENGTH: 39
<212> TYPE: DNA
<213> ORGANISM: Artificial Sequence
<220> FEATURE:
<223> OTHER INFORMATION: Primer

<400> SEQUENCE: 394
acgcacttga cttgtcttca ctgcgttcac gaagaatag                              39

<210> SEQ ID NO 395
<211> LENGTH: 37
<212> TYPE: DNA
<213> ORGANISM: Artificial Sequence
<220> FEATURE:
<223> OTHER INFORMATION: Primer

<400> SEQUENCE: 395
acccaactga atggagctct cttgattcaa cgtttcc                                37

<210> SEQ ID NO 396
<211> LENGTH: 39
<212> TYPE: DNA
<213> ORGANISM: Artificial Sequence
<220> FEATURE:
<223> OTHER INFORMATION: Primer

<400> SEQUENCE: 396
acgcacttga cttgtcttcg atgcaaaacc aattcactt                              39

<210> SEQ ID NO 397
<211> LENGTH: 37
<212> TYPE: DNA
<213> ORGANISM: Artificial Sequence
<220> FEATURE:
<223> OTHER INFORMATION: Primer

<400> SEQUENCE: 397
acccaactga atggagcgtg aaacatcgct ttttagg                                37

<210> SEQ ID NO 398
<211> LENGTH: 39
<212> TYPE: DNA
<213> ORGANISM: Artificial Sequence
<220> FEATURE:
<223> OTHER INFORMATION: Primer

<400> SEQUENCE: 398
acgcacttga cttgtcttct ccgcaatgat atacttcaa                              39
```

<210> SEQ ID NO 399
<211> LENGTH: 37
<212> TYPE: DNA
<213> ORGANISM: Artificial Sequence
<220> FEATURE:
<223> OTHER INFORMATION: Primer

<400> SEQUENCE: 399
acccaactga atggagcata cggtgaaaat gaagcag                          37

<210> SEQ ID NO 400
<211> LENGTH: 38
<212> TYPE: DNA
<213> ORGANISM: Artificial Sequence
<220> FEATURE:
<223> OTHER INFORMATION: Primer

<400> SEQUENCE: 400
acgcacttga cttgtcttcc gtctttggta atcgttca                         38

<210> SEQ ID NO 401
<211> LENGTH: 37
<212> TYPE: DNA
<213> ORGANISM: Artificial Sequence
<220> FEATURE:
<223> OTHER INFORMATION: Primer

<400> SEQUENCE: 401
acccaactga atggagctta tcgtccattc tttcgtc                          37

<210> SEQ ID NO 402
<211> LENGTH: 39
<212> TYPE: DNA
<213> ORGANISM: Artificial Sequence
<220> FEATURE:
<223> OTHER INFORMATION: Primer

<400> SEQUENCE: 402
acgcacttga cttgtcttca aacctaatga aacgggatt                        39

<210> SEQ ID NO 403
<211> LENGTH: 37
<212> TYPE: DNA
<213> ORGANISM: Artificial Sequence
<220> FEATURE:
<223> OTHER INFORMATION: Primer

<400> SEQUENCE: 403
acccaactga atggagctat gaaaggagcc gtaaaac                          37

<210> SEQ ID NO 404
<211> LENGTH: 39
<212> TYPE: DNA
<213> ORGANISM: Artificial Sequence
<220> FEATURE:
<223> OTHER INFORMATION: Primer

<400> SEQUENCE: 404
acgcacttga cttgtcttct gaatatgaag cggaaaact                        39

<210> SEQ ID NO 405
<211> LENGTH: 37
<212> TYPE: DNA
<213> ORGANISM: Artificial Sequence
<220> FEATURE:
<223> OTHER INFORMATION: Primer

<400> SEQUENCE: 405
acccaactga atggagctcg aacatacctc catttct                              37

<210> SEQ ID NO 406
<211> LENGTH: 39
<212> TYPE: DNA
<213> ORGANISM: Artificial Sequence
<220> FEATURE:
<223> OTHER INFORMATION: Primer

<400> SEQUENCE: 406
acgcacttga cttgtcttca aagatagctt tgcacttgg                            39

<210> SEQ ID NO 407
<211> LENGTH: 37
<212> TYPE: DNA
<213> ORGANISM: Artificial Sequence
<220> FEATURE:
<223> OTHER INFORMATION: Primer

<400> SEQUENCE: 407
acccaactga atggagcaac aagctaaaac cgaacaa                              37

<210> SEQ ID NO 408
<211> LENGTH: 39
<212> TYPE: DNA
<213> ORGANISM: Artificial Sequence
<220> FEATURE:
<223> OTHER INFORMATION: Primer

<400> SEQUENCE: 408
acgcacttga cttgtcttca tagcctcaac tgcttttg                             39

<210> SEQ ID NO 409
<211> LENGTH: 40
<212> TYPE: DNA
<213> ORGANISM: Artificial Sequence
<220> FEATURE:
<223> OTHER INFORMATION: Primer

<400> SEQUENCE: 409
acccaactga atggagcgaa aggagtgcgg gtaataggtt                           40

<210> SEQ ID NO 410
<211> LENGTH: 41
<212> TYPE: DNA
<213> ORGANISM: Artificial Sequence
<220> FEATURE:
<223> OTHER INFORMATION: Primer

<400> SEQUENCE: 410
acgcacttga cttgtcttcg gcctgcaagt ccaatatatg g                         41

<210> SEQ ID NO 411
<211> LENGTH: 37
<212> TYPE: DNA
<213> ORGANISM: Artificial Sequence
<220> FEATURE:
<223> OTHER INFORMATION: Primer

<400> SEQUENCE: 411
acccaactga atggagcgat gcttctgcta tcagstt                              37

<210> SEQ ID NO 412

```
<211> LENGTH: 39
<212> TYPE: DNA
<213> ORGANISM: Artificial Sequence
<220> FEATURE:
<223> OTHER INFORMATION: Primer

<400> SEQUENCE: 412
acgcacttga cttgtcttcg tgtgrctttg aastcttgt                              39

<210> SEQ ID NO 413
<211> LENGTH: 37
<212> TYPE: DNA
<213> ORGANISM: Artificial Sequence
<220> FEATURE:
<223> OTHER INFORMATION: Primer

<400> SEQUENCE: 413
acccaactga atggagcact cgggatactc catactg                               37

<210> SEQ ID NO 414
<211> LENGTH: 37
<212> TYPE: DNA
<213> ORGANISM: Artificial Sequence
<220> FEATURE:
<223> OTHER INFORMATION: Primer

<400> SEQUENCE: 414
acgcacttga cttgtcttcc gaaagcagtg gtcaatc                               37

<210> SEQ ID NO 415
<211> LENGTH: 37
<212> TYPE: DNA
<213> ORGANISM: Artificial Sequence
<220> FEATURE:
<223> OTHER INFORMATION: Primer

<400> SEQUENCE: 415
acccaactga atggagccat gcgctttacg ttatatg                               37

<210> SEQ ID NO 416
<211> LENGTH: 37
<212> TYPE: DNA
<213> ORGANISM: Artificial Sequence
<220> FEATURE:
<223> OTHER INFORMATION: Primer

<400> SEQUENCE: 416
acgcacttga cttgtcttcg cgttctgcac tctgtct                               37

<210> SEQ ID NO 417
<211> LENGTH: 36
<212> TYPE: DNA
<213> ORGANISM: Artificial Sequence
<220> FEATURE:
<223> OTHER INFORMATION: Primer

<400> SEQUENCE: 417
acccaactga atggagcagc gacttccgtg ataaag                                36

<210> SEQ ID NO 418
<211> LENGTH: 38
<212> TYPE: DNA
<213> ORGANISM: Artificial Sequence
<220> FEATURE:
<223> OTHER INFORMATION: Primer

<400> SEQUENCE: 418
```
acgcacttga cttgtcttca ctcaggatac cgtgtggt                                38

<210> SEQ ID NO 419
<211> LENGTH: 37
<212> TYPE: DNA
<213> ORGANISM: Artificial Sequence
<220> FEATURE:
<223> OTHER INFORMATION: Primer

<400> SEQUENCE: 419
acccaactga atggagcttc acgataatcc cctaatg                                 37

<210> SEQ ID NO 420
<211> LENGTH: 38
<212> TYPE: DNA
<213> ORGANISM: Artificial Sequence
<220> FEATURE:
<223> OTHER INFORMATION: Primer

<400> SEQUENCE: 420
acgcacttga cttgtcttct tctgtgctct ggctgata                                38

<210> SEQ ID NO 421
<211> LENGTH: 37
<212> TYPE: DNA
<213> ORGANISM: Artificial Sequence
<220> FEATURE:
<223> OTHER INFORMATION: Primer

<400> SEQUENCE: 421
acccaactga atggagcatt atctgtgccc cttcttt                                 37

<210> SEQ ID NO 422
<211> LENGTH: 38
<212> TYPE: DNA
<213> ORGANISM: Artificial Sequence
<220> FEATURE:
<223> OTHER INFORMATION: Primer

<400> SEQUENCE: 422
acgcacttga cttgtcttcg gagtggatgc cactaaac                                38

<210> SEQ ID NO 423
<211> LENGTH: 37
<212> TYPE: DNA
<213> ORGANISM: Artificial Sequence
<220> FEATURE:
<223> OTHER INFORMATION: Primer

<400> SEQUENCE: 423
acccaactga atggagccct cacacaacaa ttcactg                                 37

<210> SEQ ID NO 424
<211> LENGTH: 39
<212> TYPE: DNA
<213> ORGANISM: Artificial Sequence
<220> FEATURE:
<223> OTHER INFORMATION: Primer

<400> SEQUENCE: 424
acgcacttga cttgtcttct ttttccgaca aatttaagg                               39

<210> SEQ ID NO 425
<211> LENGTH: 37
<212> TYPE: DNA

```
<213> ORGANISM: Artificial Sequence
<220> FEATURE:
<223> OTHER INFORMATION: Primer

<400> SEQUENCE: 425
acccaactga atggagcagc atgaaggttg ctaaaag                              37

<210> SEQ ID NO 426
<211> LENGTH: 39
<212> TYPE: DNA
<213> ORGANISM: Artificial Sequence
<220> FEATURE:
<223> OTHER INFORMATION: Primer

<400> SEQUENCE: 426
acgcacttga cttgtcttcg gtgacttcaa aaccgttag                            39

<210> SEQ ID NO 427
<211> LENGTH: 35
<212> TYPE: DNA
<213> ORGANISM: Artificial Sequence
<220> FEATURE:
<223> OTHER INFORMATION: Primer

<400> SEQUENCE: 427
acccaactga atggagccag taccgacaaa acttc                                35

<210> SEQ ID NO 428
<211> LENGTH: 39
<212> TYPE: DNA
<213> ORGANISM: Artificial Sequence
<220> FEATURE:
<223> OTHER INFORMATION: Primer

<400> SEQUENCE: 428
acgcacttga cttgtcttct ttactactct gaaaacgag                            39

<210> SEQ ID NO 429
<211> LENGTH: 37
<212> TYPE: DNA
<213> ORGANISM: Artificial Sequence
<220> FEATURE:
<223> OTHER INFORMATION: Primer

<400> SEQUENCE: 429
acccaactga atggagcgca ctacaaattt aaatccc                              37

<210> SEQ ID NO 430
<211> LENGTH: 39
<212> TYPE: DNA
<213> ORGANISM: Artificial Sequence
<220> FEATURE:
<223> OTHER INFORMATION: Primer

<400> SEQUENCE: 430
acgcacttga cttgtcttcg tcgattatca acctctatg                            39

<210> SEQ ID NO 431
<211> LENGTH: 37
<212> TYPE: DNA
<213> ORGANISM: Artificial Sequence
<220> FEATURE:
<223> OTHER INFORMATION: Primer

<400> SEQUENCE: 431
acccaactga atggagctta atatcccggc actcata                              37
```

<210> SEQ ID NO 432
<211> LENGTH: 41
<212> TYPE: DNA
<213> ORGANISM: Artificial Sequence
<220> FEATURE:
<223> OTHER INFORMATION: Primer

<400> SEQUENCE: 432
acgcacttga cttgtcttct ccttaactga ataagtgctc a        41

<210> SEQ ID NO 433
<211> LENGTH: 36
<212> TYPE: DNA
<213> ORGANISM: Artificial Sequence
<220> FEATURE:
<223> OTHER INFORMATION: Primer

<400> SEQUENCE: 433
acccaactga atggagcttt aatgaacggt gcctag        36

<210> SEQ ID NO 434
<211> LENGTH: 38
<212> TYPE: DNA
<213> ORGANISM: Artificial Sequence
<220> FEATURE:
<223> OTHER INFORMATION: Primer

<400> SEQUENCE: 434
acgcacttga cttgtcttcg tctgcgtttc tccagtat        38

<210> SEQ ID NO 435
<211> LENGTH: 43
<212> TYPE: DNA
<213> ORGANISM: Artificial Sequence
<220> FEATURE:
<223> OTHER INFORMATION: Primer

<400> SEQUENCE: 435
acccaactga atggagctct ggcctgctaa ataaaaacga acc        43

<210> SEQ ID NO 436
<211> LENGTH: 46
<212> TYPE: DNA
<213> ORGANISM: Artificial Sequence
<220> FEATURE:
<223> OTHER INFORMATION: Primer

<400> SEQUENCE: 436
acgcacttga cttgtcttcc aggcctcagc attttattat ggtgat        46

<210> SEQ ID NO 437
<211> LENGTH: 39
<212> TYPE: DNA
<213> ORGANISM: Artificial Sequence
<220> FEATURE:
<223> OTHER INFORMATION: Primer

<400> SEQUENCE: 437
acccaactga atggagcggg gcggatacct tcacctatg        39

<210> SEQ ID NO 438
<211> LENGTH: 42
<212> TYPE: DNA
<213> ORGANISM: Artificial Sequence
<220> FEATURE:

<223> OTHER INFORMATION: Primer

<400> SEQUENCE: 438
acgcacttga cttgtcttcc tggggttcag tctggacgag at              42

<210> SEQ ID NO 439
<211> LENGTH: 38
<212> TYPE: DNA
<213> ORGANISM: Artificial Sequence
<220> FEATURE:
<223> OTHER INFORMATION: Primer

<400> SEQUENCE: 439
acccaactga atggagcacc atccggcgct aaatcgtc                   38

<210> SEQ ID NO 440
<211> LENGTH: 42
<212> TYPE: DNA
<213> ORGANISM: Artificial Sequence
<220> FEATURE:
<223> OTHER INFORMATION: Primer

<400> SEQUENCE: 440
acgcacttga cttgtcttcg aaatgcgcct ggtaagcaga gt              42

<210> SEQ ID NO 441
<211> LENGTH: 35
<212> TYPE: DNA
<213> ORGANISM: Artificial Sequence
<220> FEATURE:
<223> OTHER INFORMATION: Primer

<400> SEQUENCE: 441
acccaactga atggagcggt aggataacta ccaag                      35

<210> SEQ ID NO 442
<211> LENGTH: 41
<212> TYPE: DNA
<213> ORGANISM: Artificial Sequence
<220> FEATURE:
<223> OTHER INFORMATION: Primer

<400> SEQUENCE: 442
acgcacttga cttgtcttcg tcatgagttt taccaatact c               41

<210> SEQ ID NO 443
<211> LENGTH: 37
<212> TYPE: DNA
<213> ORGANISM: Artificial Sequence
<220> FEATURE:
<223> OTHER INFORMATION: Primer

<400> SEQUENCE: 443
acccaactga atggagcgaa gtggctcatg ttagagg                    37

<210> SEQ ID NO 444
<211> LENGTH: 39
<212> TYPE: DNA
<213> ORGANISM: Artificial Sequence
<220> FEATURE:
<223> OTHER INFORMATION: Primer

<400> SEQUENCE: 444
acgcacttga cttgtcttca gcgagcctat atgtaacca                  39

```
<210> SEQ ID NO 445
<211> LENGTH: 37
<212> TYPE: DNA
<213> ORGANISM: Artificial Sequence
<220> FEATURE:
<223> OTHER INFORMATION: Primer

<400> SEQUENCE: 445
acccaactga atggagcttt aatgtccgtc aacctct                              37

<210> SEQ ID NO 446
<211> LENGTH: 39
<212> TYPE: DNA
<213> ORGANISM: Artificial Sequence
<220> FEATURE:
<223> OTHER INFORMATION: Primer

<400> SEQUENCE: 446
acgcacttga cttgtcttca cgagtttgtg agtcgctat                            39

<210> SEQ ID NO 447
<211> LENGTH: 37
<212> TYPE: DNA
<213> ORGANISM: Artificial Sequence
<220> FEATURE:
<223> OTHER INFORMATION: Primer

<400> SEQUENCE: 447
acccaactga atggagccgg taagaatacg accagag                              37

<210> SEQ ID NO 448
<211> LENGTH: 39
<212> TYPE: DNA
<213> ORGANISM: Artificial Sequence
<220> FEATURE:
<223> OTHER INFORMATION: Primer

<400> SEQUENCE: 448
acgcacttga cttgtcttca gaggatttct tcctccttg                            39

<210> SEQ ID NO 449
<211> LENGTH: 37
<212> TYPE: DNA
<213> ORGANISM: Artificial Sequence
<220> FEATURE:
<223> OTHER INFORMATION: Primer

<400> SEQUENCE: 449
acccaactga atggagcaat tctacaagca cctggaa                              37

<210> SEQ ID NO 450
<211> LENGTH: 39
<212> TYPE: DNA
<213> ORGANISM: Artificial Sequence
<220> FEATURE:
<223> OTHER INFORMATION: Primer

<400> SEQUENCE: 450
acgcacttga cttgtcttct cctattaaaa gcgccatag                            39

<210> SEQ ID NO 451
<211> LENGTH: 37
<212> TYPE: DNA
<213> ORGANISM: Artificial Sequence
<220> FEATURE:
<223> OTHER INFORMATION: Primer
```

<400> SEQUENCE: 451
acccaactga atggagcctt atgcagcaag aggaact                                37

<210> SEQ ID NO 452
<211> LENGTH: 39
<212> TYPE: DNA
<213> ORGANISM: Artificial Sequence
<220> FEATURE:
<223> OTHER INFORMATION: Primer

<400> SEQUENCE: 452
acgcacttga cttgtcttca tacaccggga taggtttct                              39

<210> SEQ ID NO 453
<211> LENGTH: 37
<212> TYPE: DNA
<213> ORGANISM: Artificial Sequence
<220> FEATURE:
<223> OTHER INFORMATION: Primer

<400> SEQUENCE: 453
acccaactga atggagcctg atggaagaga gttcgag                                37

<210> SEQ ID NO 454
<211> LENGTH: 39
<212> TYPE: DNA
<213> ORGANISM: Artificial Sequence
<220> FEATURE:
<223> OTHER INFORMATION: Primer

<400> SEQUENCE: 454
acgcacttga cttgtcttcg tagatataat cagcgccac                              39

<210> SEQ ID NO 455
<211> LENGTH: 37
<212> TYPE: DNA
<213> ORGANISM: Artificial Sequence
<220> FEATURE:
<223> OTHER INFORMATION: Primer

<400> SEQUENCE: 455
acccaactga atggagctgt tacgtacagg ctgtcaa                                37

<210> SEQ ID NO 456
<211> LENGTH: 39
<212> TYPE: DNA
<213> ORGANISM: Artificial Sequence
<220> FEATURE:
<223> OTHER INFORMATION: Primer

<400> SEQUENCE: 456
acgcacttga cttgtcttca tcatatcccg tagcacaag                              39

<210> SEQ ID NO 457
<211> LENGTH: 37
<212> TYPE: DNA
<213> ORGANISM: Artificial Sequence
<220> FEATURE:
<223> OTHER INFORMATION: Primer

<400> SEQUENCE: 457
acccaactga atggagcatc aagctcatct tcaaagc                                37

<210> SEQ ID NO 458
<211> LENGTH: 39

```
<212> TYPE: DNA
<213> ORGANISM: Artificial Sequence
<220> FEATURE:
<223> OTHER INFORMATION: Primer

<400> SEQUENCE: 458
acgcacttga cttgtcttca accatgttca gatccaaaa                              39

<210> SEQ ID NO 459
<211> LENGTH: 37
<212> TYPE: DNA
<213> ORGANISM: Artificial Sequence
<220> FEATURE:
<223> OTHER INFORMATION: Primer

<400> SEQUENCE: 459
acccaactga atggagctac ctctgccaaa aattcat                                37

<210> SEQ ID NO 460
<211> LENGTH: 39
<212> TYPE: DNA
<213> ORGANISM: Artificial Sequence
<220> FEATURE:
<223> OTHER INFORMATION: Primer

<400> SEQUENCE: 460
acgcacttga cttgtcttcg gcatactcaa ggtagtggt                              39

<210> SEQ ID NO 461
<211> LENGTH: 37
<212> TYPE: DNA
<213> ORGANISM: Artificial Sequence
<220> FEATURE:
<223> OTHER INFORMATION: Primer

<400> SEQUENCE: 461
acccaactga atggagctct ttggtagctt gctgact                                37

<210> SEQ ID NO 462
<211> LENGTH: 39
<212> TYPE: DNA
<213> ORGANISM: Artificial Sequence
<220> FEATURE:
<223> OTHER INFORMATION: Primer

<400> SEQUENCE: 462
acgcacttga cttgtcttcc agacgacact tggcttatt                              39

<210> SEQ ID NO 463
<211> LENGTH: 37
<212> TYPE: DNA
<213> ORGANISM: Artificial Sequence
<220> FEATURE:
<223> OTHER INFORMATION: Primer

<400> SEQUENCE: 463
acccaactga atggagccat aacccatcgc aatatct                                37

<210> SEQ ID NO 464
<211> LENGTH: 39
<212> TYPE: DNA
<213> ORGANISM: Artificial Sequence
<220> FEATURE:
<223> OTHER INFORMATION: Primer

<400> SEQUENCE: 464
```

```
acgcacttga cttgtcttca aattatctgt agcggcaaa                               39

<210> SEQ ID NO 465
<211> LENGTH: 37
<212> TYPE: DNA
<213> ORGANISM: Artificial Sequence
<220> FEATURE:
<223> OTHER INFORMATION: Primer

<400> SEQUENCE: 465
acccaactga atggagcgtg tccaacgaaa ccataat                                 37

<210> SEQ ID NO 466
<211> LENGTH: 39
<212> TYPE: DNA
<213> ORGANISM: Artificial Sequence
<220> FEATURE:
<223> OTHER INFORMATION: Primer

<400> SEQUENCE: 466
acgcacttga cttgtcttct ttggttgatt ctgtcagtg                               39

<210> SEQ ID NO 467
<211> LENGTH: 37
<212> TYPE: DNA
<213> ORGANISM: Artificial Sequence
<220> FEATURE:
<223> OTHER INFORMATION: Primer

<400> SEQUENCE: 467
acccaactga atggagcaag cttaactggt gattgga                                 37

<210> SEQ ID NO 468
<211> LENGTH: 39
<212> TYPE: DNA
<213> ORGANISM: Artificial Sequence
<220> FEATURE:
<223> OTHER INFORMATION: Primer

<400> SEQUENCE: 468
acgcacttga cttgtcttcc gcctaacatc ttatctgct                               39

<210> SEQ ID NO 469
<211> LENGTH: 37
<212> TYPE: DNA
<213> ORGANISM: Artificial Sequence
<220> FEATURE:
<223> OTHER INFORMATION: Primer

<400> SEQUENCE: 469
acccaactga atggagcggg tgatgcagta gagaaaa                                 37

<210> SEQ ID NO 470
<211> LENGTH: 39
<212> TYPE: DNA
<213> ORGANISM: Artificial Sequence
<220> FEATURE:
<223> OTHER INFORMATION: Primer

<400> SEQUENCE: 470
acgcacttga cttgtcttct accagatgaa cgaatagcc                               39
```

METHODS AND ASSAYS FOR DETECTION AND SUBTYPING OF MICROBIAL PATHOGENS

CROSS REFERENCE TO RELATED APPLICATIONS

This application is the U.S. National Stage of International Application No. PCT/US2020/015395, filed on Jan. 28, 2020, which claims priority to U.S. Provisional Patent Application No. 62/798,463, filed on Jan. 29, 2019, the contents of each of which are incorporated herein by reference in their entireties.

REFERENCE TO SEQUENCE LISTING SUBMITTED ELECTRONICALLY

The official copy of the sequence listing is submitted electronically via EFS-Web as an ASCII-formatted sequence listing with a file named "91482_239PCT_SeqList_ST25.txt" created on Jan. 27, 2020 and having a size of 83.2 kilobyte, and is filed concurrently with the specification. The sequence listing contained in this ASCII-formatted document is part of the specification and is herein incorporated by reference in its entirety.

TECHNICAL FIELD

This invention relates to methods, primers, assays, and kits for detecting the presence of microbial pathogens in a sample.

BACKGROUND

Throughout recent history, various aggressor nation states and terrorist groups have shown the willingness and/or capability to develop and use biological weapons against war fighters and civilian populations. The ability to detect the agents being developed as well as their virulence and antibiotic resistance profiles, in environmental and clinical materials, would further our capability to detect the development of these agents and their use.

The goal of several federal biosurveillance projects has been the early detection of biothreat agents to prevent or curtail mass civilian or military casualties. These systems have relied upon real-time-PCR to give a binary answer of presence or absence of the target. One challenge has been the complexity of the environmental samples, where tens of thousands of microorganisms exists, many of which are highly similar to the target pathogens. BioWatch is an example where numerous false positive results have been generated due to poorly known near-neighbor species confusing individual assays. While our knowledge of near-neighbors and of the target Biothreat agents is rapidly increasing, it is unrealistic to ever expect complete knowledge of either. DNA sequencing offers great potential, and there is a need for primers, methods, assays, and kits with greater ability to discriminate microbial pathogens in complex environmental and clinical sample matrices.

SUMMARY

Timely and accurate detection and characterization of bacterial biothreat agents is vital for our nation's safety. Current systems for early detection of these agents rely upon single locus Polymerase Chain Reaction (PCR) methods, giving only presence/absence results. This methodology can and has led to false positives due to limited signature validation. The Inventors have developed a multi-agent multi-locus amplicon sequencing protocol encompassing 79 targets aimed at detecting the presence or absence of 5 biothreat agents, as well as the presence and sequence of plasmids, virulence factors, antimicrobial resistance factors, and sequence variant loci for Near Neighbor species differentiation. The agents targeted are *Burkholderia pseudomallei*, *Burkholderia mallei*, *Bacillus anthracis*, *Yersinia pestis*, and *Francisella tularensis*.

The multi-agent assay, consisting of two multiplex amplification reactions, was validated against a diverse subset of target agent and near neighbor panels that were previously used to validate assays targeting individual agents. These panels consisted of 10-14 target agent strains and 11-48 NN strains. Sensitivity was 100% for all target agents, specificity was 91-100%. Targeted amplicon sequencing utilizing a universal amplicon indexing scheme provides a superior alternative to the current single locus PCR systems and enables the detection of multiple biothreat agents across multiple samples with a single sequencing run.

In certain aspects, the present invention provides A method of detecting *Bacillus anthracis* in a sample, comprising detecting at least one *B. anthracis*-specific amplicon in the sample using at least one primer pair selected from the group consisting of: SEQ ID NO: 1 and SEQ ID NO: 2; SEQ ID NO: 3 and SEQ ID NO: 4; SEQ ID NO: 5 and SEQ ID NO: 6; SEQ ID NO: 7 and SEQ ID NO: 8; SEQ ID NO: 9 and SEQ ID NO: 10; SEQ ID NO: 11 and SEQ ID NO: 12; SEQ ID NO: 13 and SEQ ID NO: 14; SEQ ID NO: 15 and SEQ ID NO: 16; SEQ ID NO: 17 and SEQ ID NO: 18; a pair of sequences which are at least 85% identical thereto; and RNA equivalents; wherein the presence of the *B. anthracis*-specific amplicon indicates the presence of *B. anthracis* in the sample, and the absence of the *B. anthracis*-specific amplicon indicates the absence of *B. anthracis* from the sample.

In other aspects, the method further comprises confirming the absence of *B. anthracis* by detecting at least one *B. anthracis* Near Neighbor-specific amplicon using at least one primer pair selected from the group consisting of: SEQ ID NO: 19 and SEQ ID NO: 20; SEQ ID NO: 21 and SEQ ID NO: 22; SEQ ID NO: 23 and SEQ ID NO: 24; a pair of sequences which are at least 85% identical thereto; and RNA equivalents; wherein detecting the *B. anthracis* Near Neighbor-specific amplicon in the sample confirms the absence of *B. anthracis*.

In yet other aspects, the method further comprises confirming the absence of *B. anthracis* by detecting at least one *B. anthracis* Near Neighbor-specific sequence variant (SV) or single nucleotide polymorphism (SNP) using at least one primer pair selected from the group consisting of: SEQ ID NO: 25 and SEQ ID NO: 26; SEQ ID NO: 27 and SEQ ID NO: 28; SEQ ID NO: 49 and SEQ ID NO: 50; SEQ ID NO: 51 and SEQ ID NO: 52; SEQ ID NO: 53 and SEQ ID NO: 54; SEQ ID NO: 55 and SEQ ID NO: 56; SEQ ID NO: 57 and SEQ ID NO: 58; SEQ ID NO: 59 and SEQ ID NO: 60; a pair of sequences which are at least 85% identical thereto; and RNA equivalents; wherein detecting the *B. anthracis* Near Neighbor-specific SV in the sample confirms the absence of *B. anthracis*.

In some aspects, the method further comprises detecting a virulence locus or virulence plasmid in the sample by detecting a virulence-specific amplicon using at least one primer pair selected from the group consisting of: SEQ ID NO: 29 and SEQ ID NO: 30; SEQ ID NO: 31 and SEQ ID NO: 32; SEQ ID NO: 33 and SEQ ID NO: 34; SEQ ID NO: 35 and SEQ ID NO: 36; a pair of sequences which are at least 85% identical thereto; and RNA equivalents; wherein the presence of the virulence-specific amplicon indicates the presence of the virulence locus or virulence plasmid in the sample.

In other aspects, the method further comprises detecting at least one drug resistance single nucleotide polymorphism (SNP) from *B. anthracis* in the sample using at least one primer pair selected from the group consisting of: SEQ ID NO: 37 and SEQ ID NO: 38; SEQ ID NO: 39 and SEQ ID NO: 40; SEQ ID NO: 41 and SEQ ID NO: 42; SEQ ID NO: 43 and SEQ ID NO: 44; SEQ ID NO: 45 and SEQ ID NO: 46; SEQ ID NO: 47 and SEQ ID NO: 48; a pair of sequences which are at least 85% identical thereto; and RNA equivalents. In other aspects, the method further comprises detecting *Burkholderia pseudomallei* and/or *Burkholderia mallei* in the sample by detecting at least one *B. pseudomallei* or *B. mallei*-specific amplicon uses at least one primer pair selected from the group consisting of: SEQ ID NO: 61 and SEQ ID NO: 62; SEQ ID NO: 63 and SEQ ID NO: 64; SEQ ID NO: 65 and SEQ ID NO: 66; SEQ ID NO: 67 and SEQ ID NO: 68; SEQ ID NO: 69 and SEQ ID NO: 70; SEQ ID NO: 71 and SEQ ID NO: 72; SEQ ID NO: 73 and SEQ ID NO: 74; SEQ ID NO: 75 and SEQ ID NO: 76; SEQ ID NO: 77 and SEQ ID NO: 78; SEQ ID NO: 79 and SEQ ID NO: 80; SEQ ID NO: 81 and SEQ ID NO: 82; SEQ ID NO: 83 and SEQ ID NO: 84; SEQ ID NO: 85 and SEQ ID NO: 86; SEQ ID NO: 87 and SEQ ID NO: 88; SEQ ID NO: 89 and SEQ ID NO: 90; SEQ ID NO: 91 and SEQ ID NO: 92; SEQ ID NO: 93 and SEQ ID NO: 94; SEQ ID NO: 95 and SEQ ID NO: 96; SEQ ID NO: 97 and SEQ ID NO: 98; SEQ ID NO: 99 and SEQ ID NO: 100; SEQ ID NO: 101 and SEQ ID NO: 102; SEQ ID NO: 103 and SEQ ID NO: 104; SEQ ID NO: 103 and SEQ ID NO: 104; SEQ ID NO: 105 and SEQ ID NO: 106; SEQ ID NO: 107 and SEQ ID NO: 108; SEQ ID NO: 117 and SEQ ID NO: 118; SEQ ID NO: 119 and SEQ ID NO: 120; SEQ ID NO: 121 and SEQ ID NO: 122; SEQ ID NO: 123 and SEQ ID NO: 124; SEQ ID NO: 125 and SEQ ID NO: 126; a pair of sequences which are at least 85% identical thereto; and RNA equivalents wherein the presence of the *B. pseudomallei* or *B. mallei*-specific amplicon indicates the presence of *B. pseudomallei* and/or *B. mallei* in the sample, and an absence of the *B. pseudomallei* or *B. mallei*-specific amplicon indicates an absence of *B. pseudomallei* and *B. mallei* in the sample.

In certain aspects, the method further comprises confirming the absence of *B. pseudomallei* and *B. mallei* by detecting at least one *B. pseudomallei* or *B. mallei* Near Neighbor-specific amplicon using at least one primer pair selected from the group consisting of: SEQ ID NO: 177 and SEQ ID NO: 178; SEQ ID NO: 179 and SEQ ID NO: 180; SEQ ID NO: 181 and SEQ ID NO: 182; SEQ ID NO: 183 and SEQ ID NO: 184; SEQ ID NO: 185 and SEQ ID NO: 186; SEQ ID NO: 187 and SEQ ID NO: 188; SEQ ID NO: 189 and SEQ ID NO: 190; SEQ ID NO: 191 and SEQ ID NO: 192; SEQ ID NO: 193 and SEQ ID NO: 194; SEQ ID NO: 195 and SEQ ID NO: 196; SEQ ID NO: 197 and SEQ ID NO: 198; SEQ ID NO: 199 and SEQ ID NO: 200; SEQ ID NO: 201 and SEQ ID NO: 202; SEQ ID NO: 203 and SEQ ID NO: 204; SEQ ID NO: 205 and SEQ ID NO: 206; SEQ ID NO: 207 and SEQ ID NO: 208; SEQ ID NO: 207 and SEQ ID NO: 208; SEQ ID NO: 209 and SEQ ID NO: 210; SEQ ID NO: 211 and SEQ ID NO: 212; SEQ ID NO: 213 and SEQ ID NO: 214; SEQ ID NO: 215 and SEQ ID NO: 216; SEQ ID NO: 217 and SEQ ID NO: 218; SEQ ID NO: 219 and SEQ ID NO: 220; SEQ ID NO: 221 and SEQ ID NO: 222; SEQ ID NO: 223 and SEQ ID NO: 224; SEQ ID NO: 225 and SEQ ID NO: 226; SEQ ID NO: 227 and SEQ ID NO: 228; SEQ ID NO: 229 and SEQ ID NO: 230; a pair of sequences which are at least 85% identical thereto; and RNA equivalents; wherein detecting the *B. pseudomallei* or *B. mallei* Near Neighbor-specific amplicon in the sample confirms the absence of *B. pseudomallei* and *B. mallei*.

In yet other aspects, the method further comprises confirming the absence of *B. pseudomallei* and *B. mallei* by detecting at least one *B. pseudomallei* or *B. mallei* Near Neighbor-specific SNP or SV using at least one primer pair selected from the group consisting of: SEQ ID NO: 109 and SEQ ID NO: 110; SEQ ID NO: 111 and SEQ ID NO: 112; SEQ ID NO: 113 and SEQ ID NO: 114; SEQ ID NO: 115 and SEQ ID NO: 116; a pair of sequences which are at least 85% identical thereto; and RNA equivalents; wherein detecting the *B. pseudomallei* or *B. mallei* Near Neighbor-specific SNP or SV in the sample confirms the absence of *B. pseudomallei* and *B. mallei*.

In some aspects, the method further comprises detecting at least one drug resistance SNP or SV from *Burkholderia* spp. in the sample using at least one primer pair selected from the group consisting of: SEQ ID NO: 127 and SEQ ID NO: 128; SEQ ID NO: 129 and SEQ ID NO: 130; SEQ ID NO: 131 and SEQ ID NO: 132; SEQ ID NO: 133 and SEQ ID NO: 134; SEQ ID NO: 135 and SEQ ID NO: 136; SEQ ID NO: 137 and SEQ ID NO: 138; SEQ ID NO: 145 and SEQ ID NO: 146; SEQ ID NO: 147 and SEQ ID NO: 148; SEQ ID NO: 149 and SEQ ID NO: 150; SEQ ID NO: 151 and SEQ ID NO: 152; SEQ ID NO: 153 and SEQ ID NO: 154; a pair of sequences which are at least 85% identical thereto; and RNA equivalents.

In other aspects, the method further comprises detecting *Francisella tularensis* in the sample by detecting at least one *F. tularensis*-specific amplicon using at least one primer pair selected from the group consisting of: SEQ ID NO: 265 and SEQ ID NO: 266; SEQ ID NO: 267 and SEQ ID NO: 268; SEQ ID NO: 269 and SEQ ID NO: 270; a pair of sequences which are at least 85% identical thereto; and RNA equivalents; wherein the presence of the *F. tularensis*-specific amplicon indicates that *F. tularensis* is present in the sample, and an absence of the *F. tularensis*-specific amplicon indicates that *F. tularensis* is absent in the sample.

In yet other aspects, the method further comprises confirming the absence of *F. tularensis* by detecting at least one *F. tularensis* Near Neighbor-specific amplicon using at least one primer pair selected from the group consisting of: SEQ ID NO: 285 and SEQ ID NO: 286; SEQ ID NO: 287 and SEQ ID NO: 288; SEQ ID NO: 289 and SEQ ID NO: 290; SEQ ID NO: 291 and SEQ ID NO: 292; SEQ ID NO: 293 and SEQ ID NO: 294; a pair of sequences which are at least 85% identical thereto; and RNA equivalents; wherein detecting the *F. tularensis* Near Neighbor-specific amplicon in the sample confirms the absence of *F. tularensis*.

In one aspect, the method further comprises confirming the absence of *F. tularensis* by detecting at least one *F. tularensis* Near Neighbor-specific SNP or SV using at least one primer pair selected from the group consisting of: SEQ ID NO: 271 and SEQ ID NO: 272; SEQ ID NO: 273 and SEQ ID NO: 274; SEQ ID NO: 275 and SEQ ID NO: 276; SEQ ID NO: 277 and SEQ ID NO: 278; SEQ ID NO: 279 and SEQ ID NO: 280; SEQ ID NO: 281 and SEQ ID NO: 282; SEQ ID NO: 283 and SEQ ID NO: 284; a pair of sequences which are at least 85% identical thereto; and RNA equivalents; wherein detecting the *F. tularensis* Near Neighbor-specific SNP or SV in the sample confirms the absence of *F. tularensis*.

In another aspect, the method further comprises detecting *Yersinia pestis* in the sample by detecting at least one *Y. pestis*-specific amplicon using at least one primer pair selected from the group consisting of: SEQ ID NO: 231 and SEQ ID NO: 232; SEQ ID NO: 233 and SEQ ID NO: 234; SEQ ID NO: 235 and SEQ ID NO: 236; SEQ ID NO: 237 and SEQ ID NO: 238; a pair of sequences which are at least 85% identical thereto; and RNA equivalents; wherein the presence of the *Y. pestis*-specific amplicon indicates the presence of *Y. pestis* in the sample, and an absence of the *Y. pestis*-specific amplicon indicates an absence of *Y. pestis* in the sample.

In still another aspect, the method further comprises confirming the absence of *Y. pestis* by detecting at least one *Y. pestis* Near Neighbor-specific SNP or SV using at least one primer pair selected from the group consisting of: SEQ ID NO: 249 and SEQ ID NO: 250; SEQ ID NO: 251 and SEQ ID NO: 252; SEQ ID NO: 253 and SEQ ID NO: 254; SEQ ID NO: 255 and SEQ ID NO: 256; SEQ ID NO: 257 and SEQ ID NO: 258; SEQ ID NO: 259 and SEQ ID NO: 260; SEQ ID NO: 261 and SEQ ID NO: 262; a pair of sequences which are at least 85% identical thereto; and RNA equivalents; wherein detecting the *Y. pestis* Near Neighbor-specific SNP or SV confirms the absence of *Y. pestis*.

In certain aspects, the method further comprises confirming the absence of *Y. pestis* by detecting at least one *Y. pestis* Near Neighbor-specific amplicon using at least one primer pair selected from the group consisting of: SEQ ID NO: 263 and SEQ ID NO: 264; a pair of sequences which are at least 85% identical thereto; and RNA equivalents; wherein detecting the *Y. pestis* Near Neighbor-specific amplicon confirms the absence of *Y. pestis*.

In other aspects, the method further comprises characterizing and/or subtyping *Y. pestis* in the sample by detecting at least one amplicon using at least one primer pair selected from the group consisting of: SEQ ID NO: 239 and SEQ ID NO: 240; SEQ ID NO: 241 and SEQ ID NO: 242; SEQ ID NO: 243 and SEQ ID NO: 244; SEQ ID NO: 245 and SEQ ID NO: 246; SEQ ID NO: 247 and SEQ ID NO: 248; a pair of sequences which are at least 85% identical thereto; and RNA equivalents.

In some aspects, the amplicons are generated with at least one multiplex amplification reaction. In other aspects, the amplicons are generated with at least two, at least three, at least four, or at least five multiplex amplification reactions.

In other aspects, the amplicon, SNP or SV is determined using next-generation sequencing. In one aspect, each primer in the at least one primer pair comprises a universal tail sequence. In some aspects, the universal tail sequence comprises SEQ ID NO: 301 or SEQ ID NO: 303.

In certain aspects, the amplicon is present when a locus read count of the amplicon is at least 10 sequence reads covering at least 75% of a corresponding amplicon reference sequence.

In other aspects, sequence analysis of sequence read alignments is performed to determine whether a target species, Near Neighbor species, virulence or antibiotic resistance allele is present in the sample, wherein the target species is *Bacillus anthracis, Burkholderia pseudomallei, Burkholderia mallei, Francisella tularensis*, or *Yersinia pestis*.

In one embodiment, the sample is an environmental sample. In another embodiment, the sample is a biological sample obtained from a subject.

In certain embodiments, the method further comprises administering an effective amount of at least one antibiotic to the subject, wherein the at least one antibiotic is selected from the group consisting of a fluoroquinolone, an aminoglycoside, a glycopeptide, a lincosamide, a macrolide/ketolide, a cephalosporin, a monobactam, a nitroimidazole, a penicillin, a streptogramin, a tetracycline, and a physiologically acceptable salt, prodrug, or combination thereof.

In another embodiment, the at least one antibiotic is not a fluoroquinolone if a gyrA drug resistance SNP is detected; and/or the at least one antibiotic is not a fluoroquinolone if a parC drug resistance SNP is detected; and/or the at least one antibiotic is not a fluoroquinolone or an aminocoumarin if a gyrB drug resistance SNP is detected; and/or the at least one antibiotic is not a rifamycin if a rpoB drug resistance SNP is detected; and/or the at least one antibiotic is not a β-lactam if a penA drug resistance SNP is detected; and/or the at least one antibiotic is not a trimethoprim and sulfamethoxazole combination, co-trimoxazole, if a folM drug resistance SV is detected; and/or the at least one antibiotic is not a trimethoprim and sulfamethoxazole combination, co-trimoxazole, if a bpeT drug resistance SV is detected; and/or the at least one antibiotic is not a trimethoprim and sulfamethoxazole combination, co-trimoxazole, if a bpeS drug resistance SV is detected.

BRIEF DESCRIPTION OF THE DRAWINGS

FIG. 1A depicts sequence ready multi-locus amplification. The universal indexing strategy comprising universal tails is described in U.S. Publication No. 2016/0326572, the contents of which are incorporated herein by reference. FIG. 1B depicts sequencing and bioinformatic analysis.

Figure 3A:
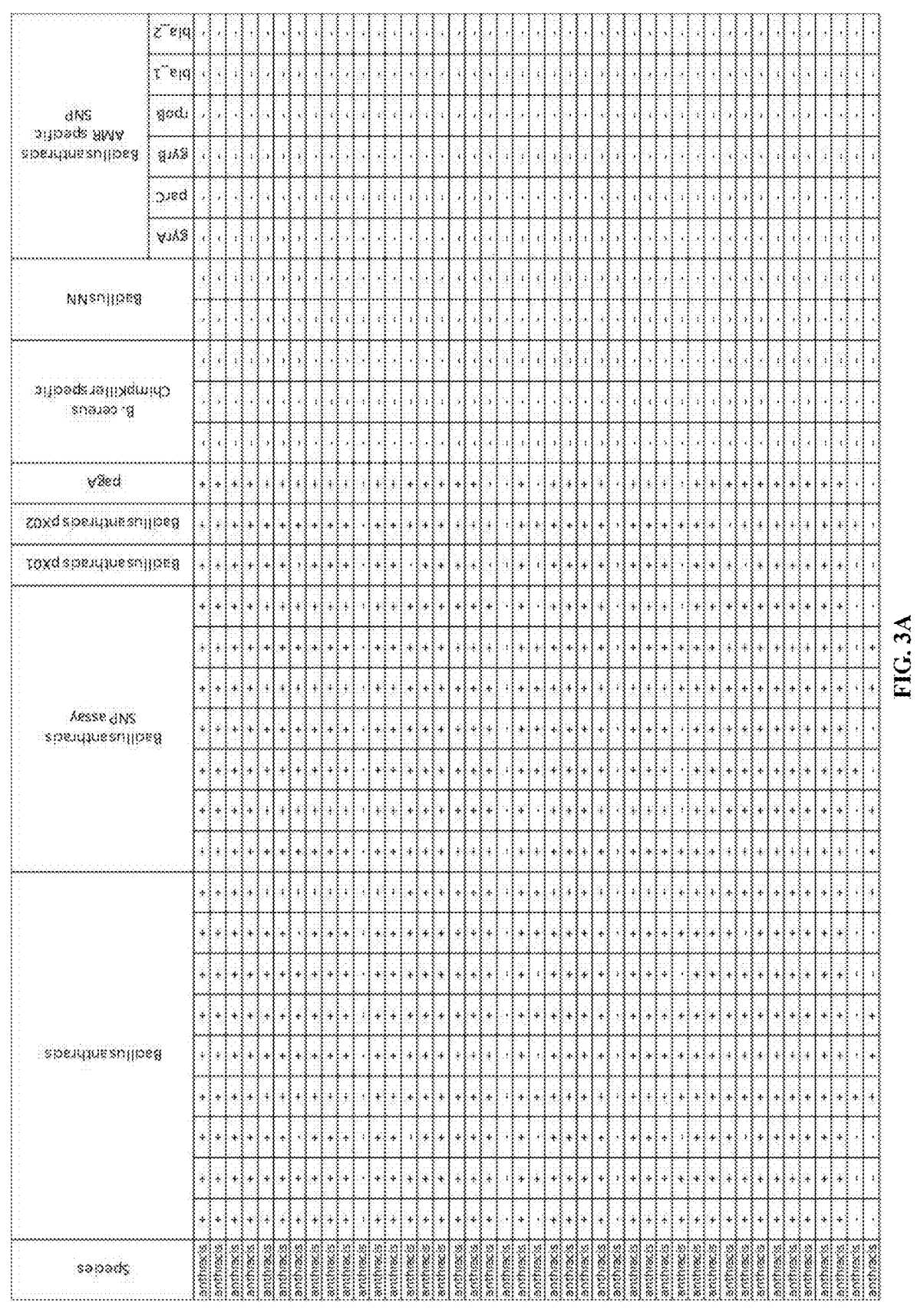
Figure 3B:
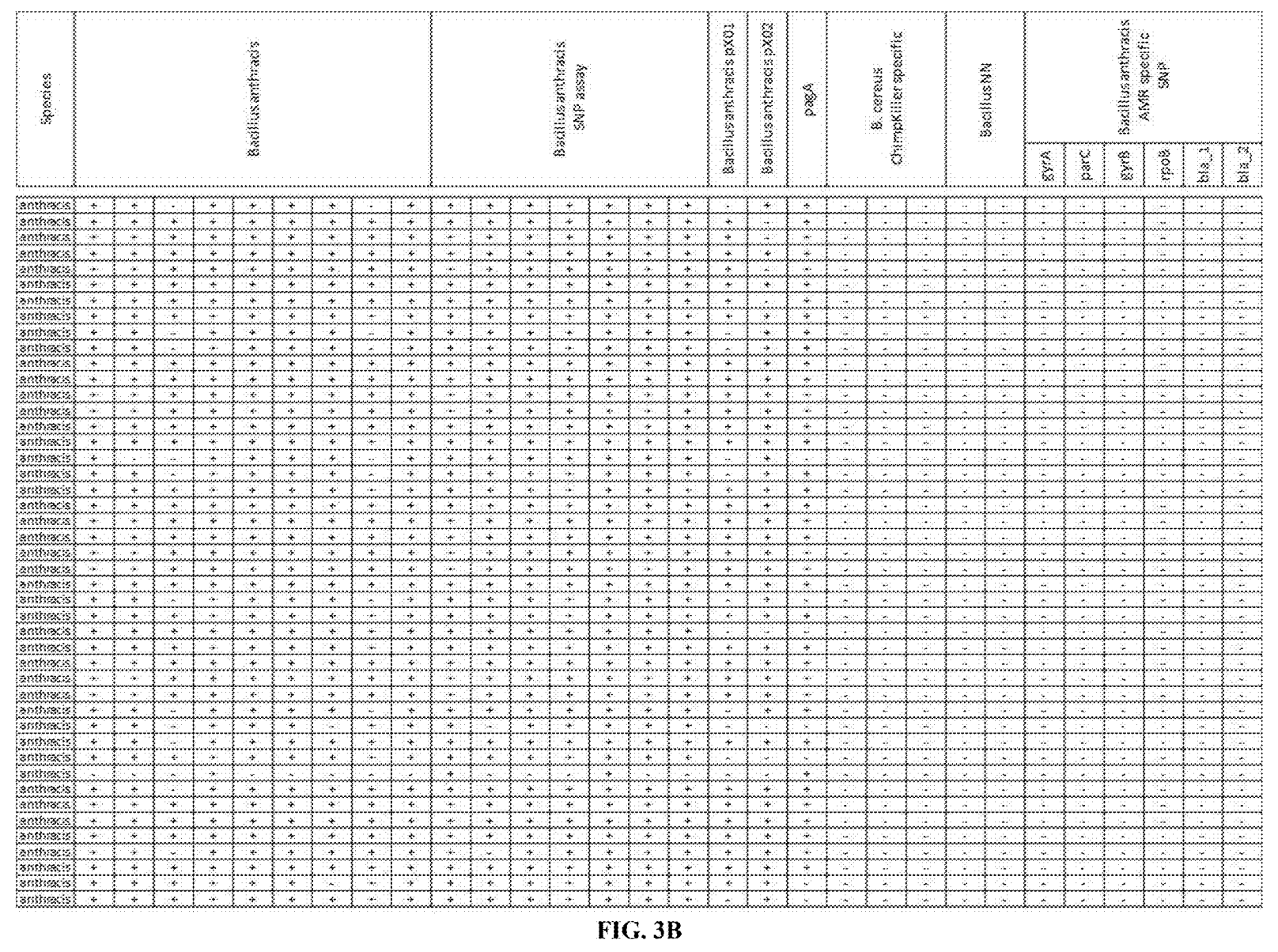
Figure 3C:
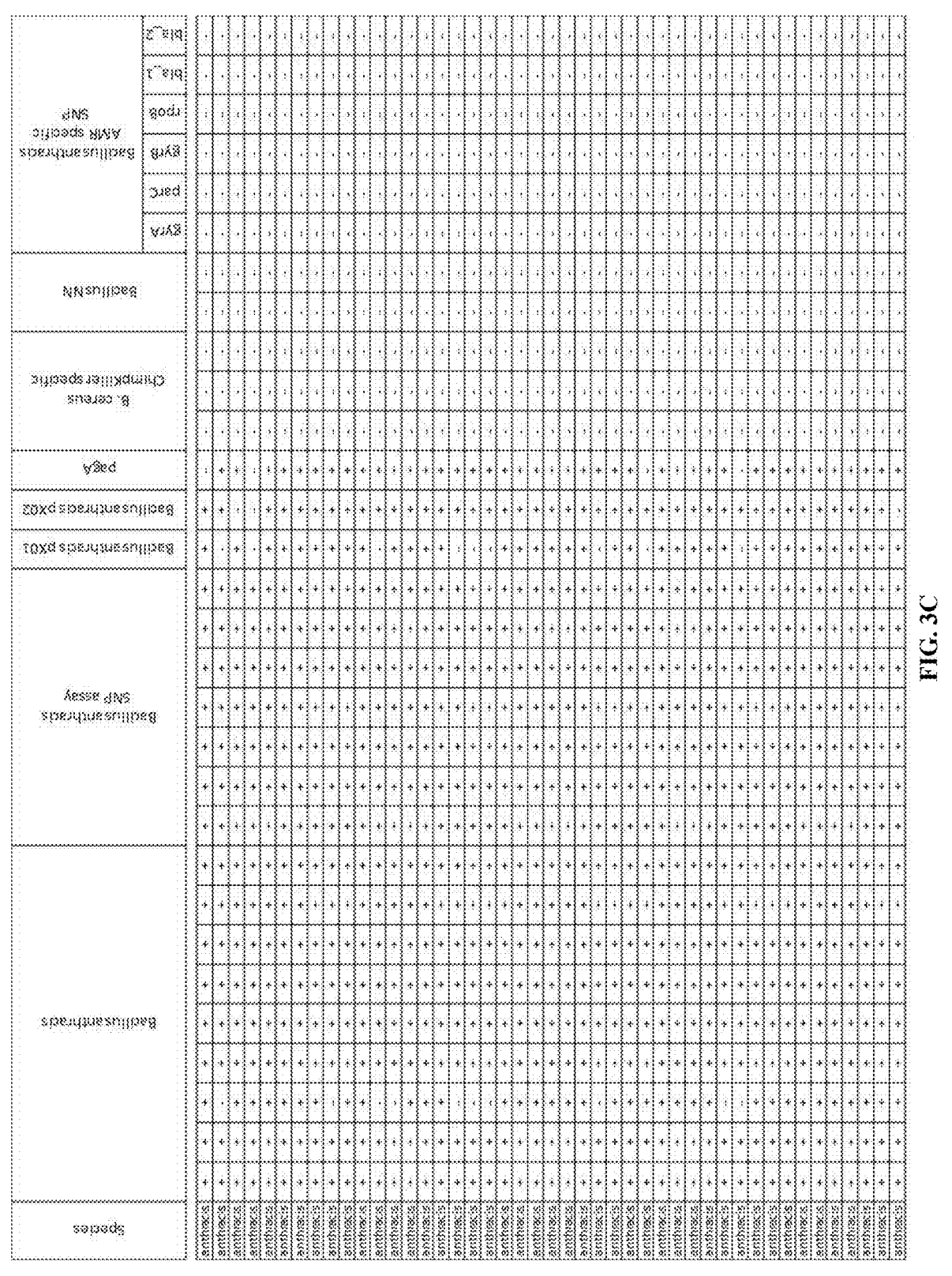
Figure 3D:
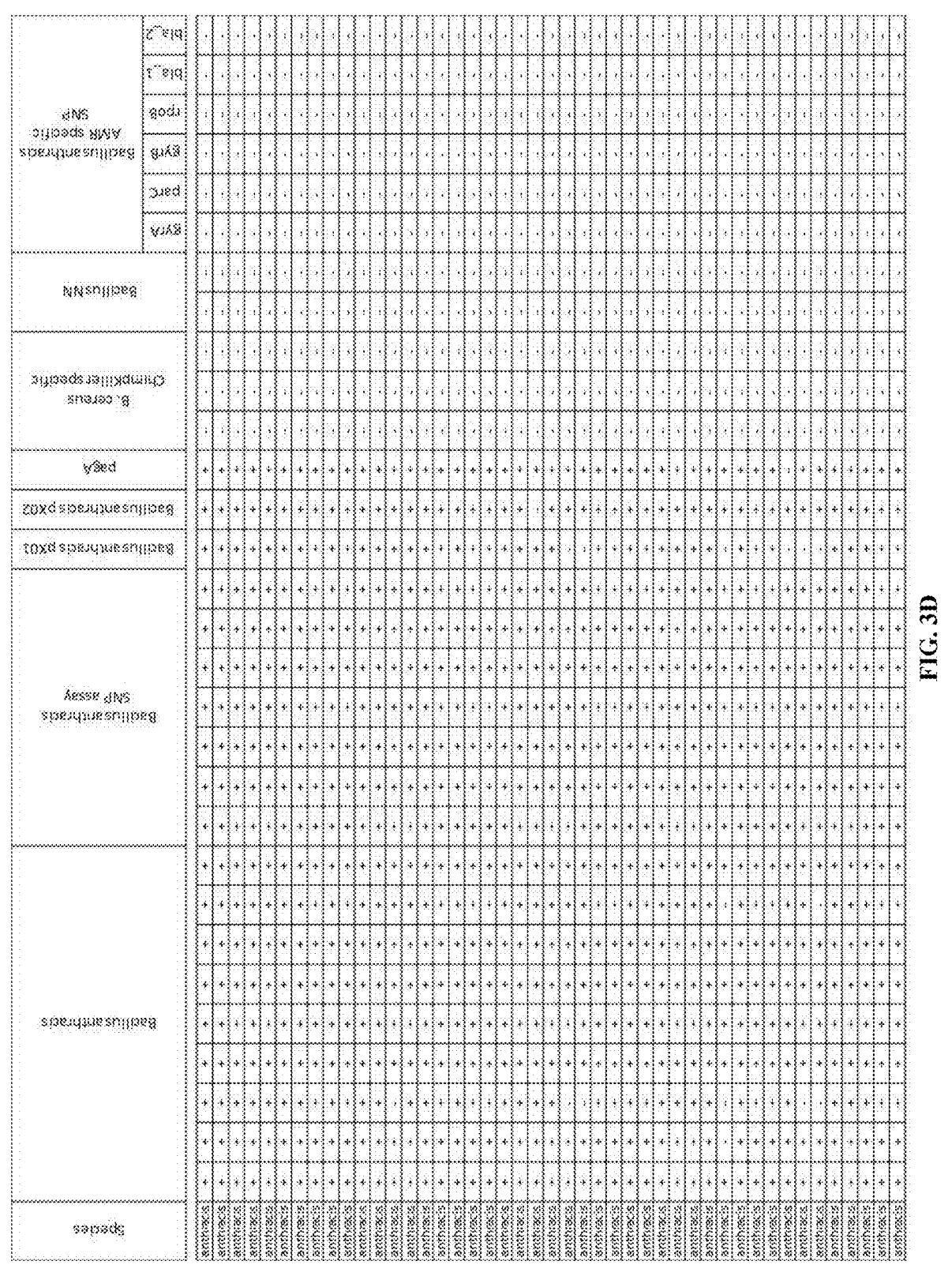
Figure 3E:
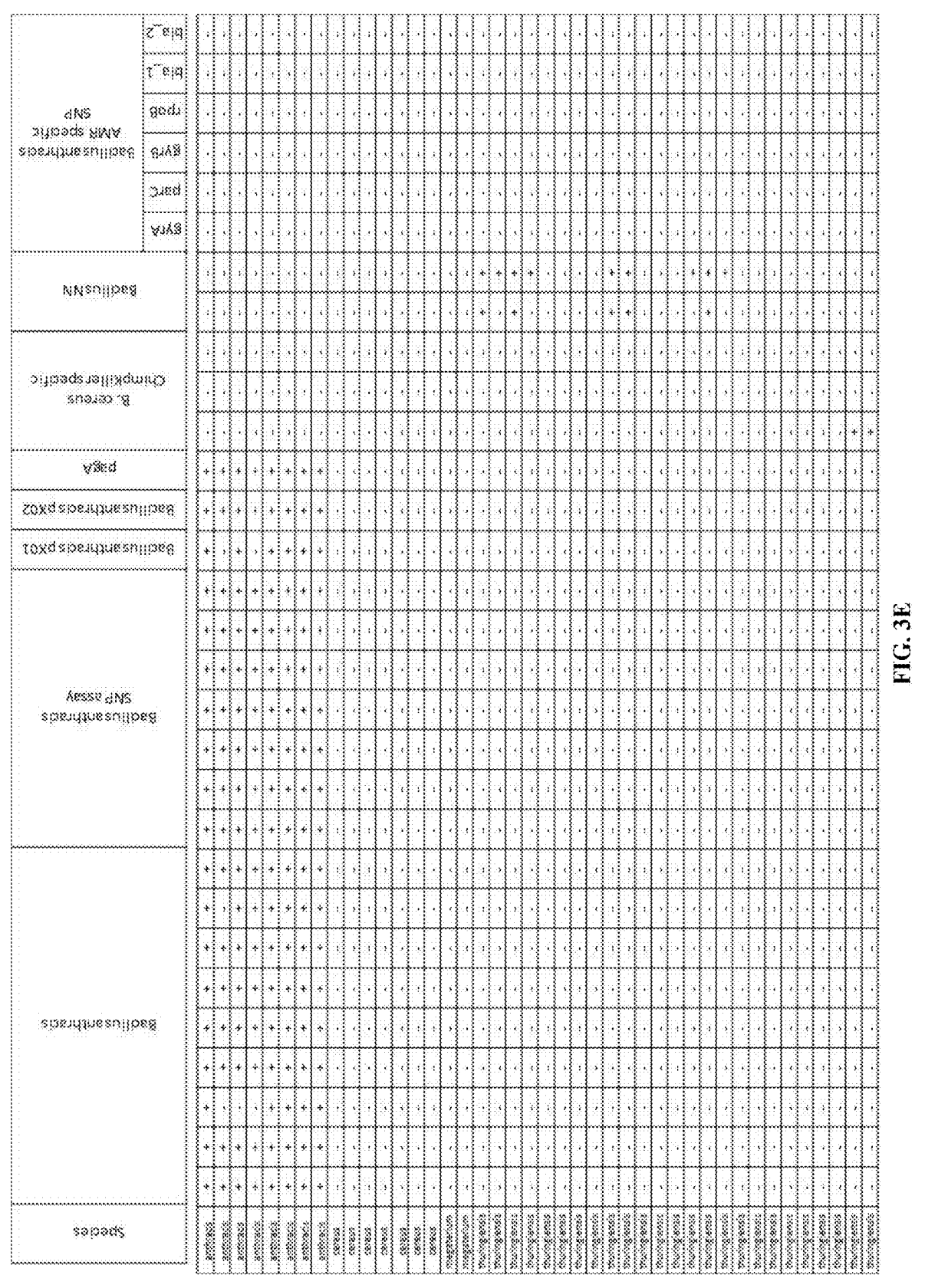

FIGS. 3A-3E. An ASAP output result table, showing a subset of results from a large diverse sample set (693 isolates). The ASAP output demonstrates a general presence/absence for each select agent isolate or near neighbor isolate tested using UI-AmpSeq assays specific for *B. anthraces*, known virulence determinants, near neighbor (NN) species, and antimicrobial resistance (AMR) targets.

Figure 4A:
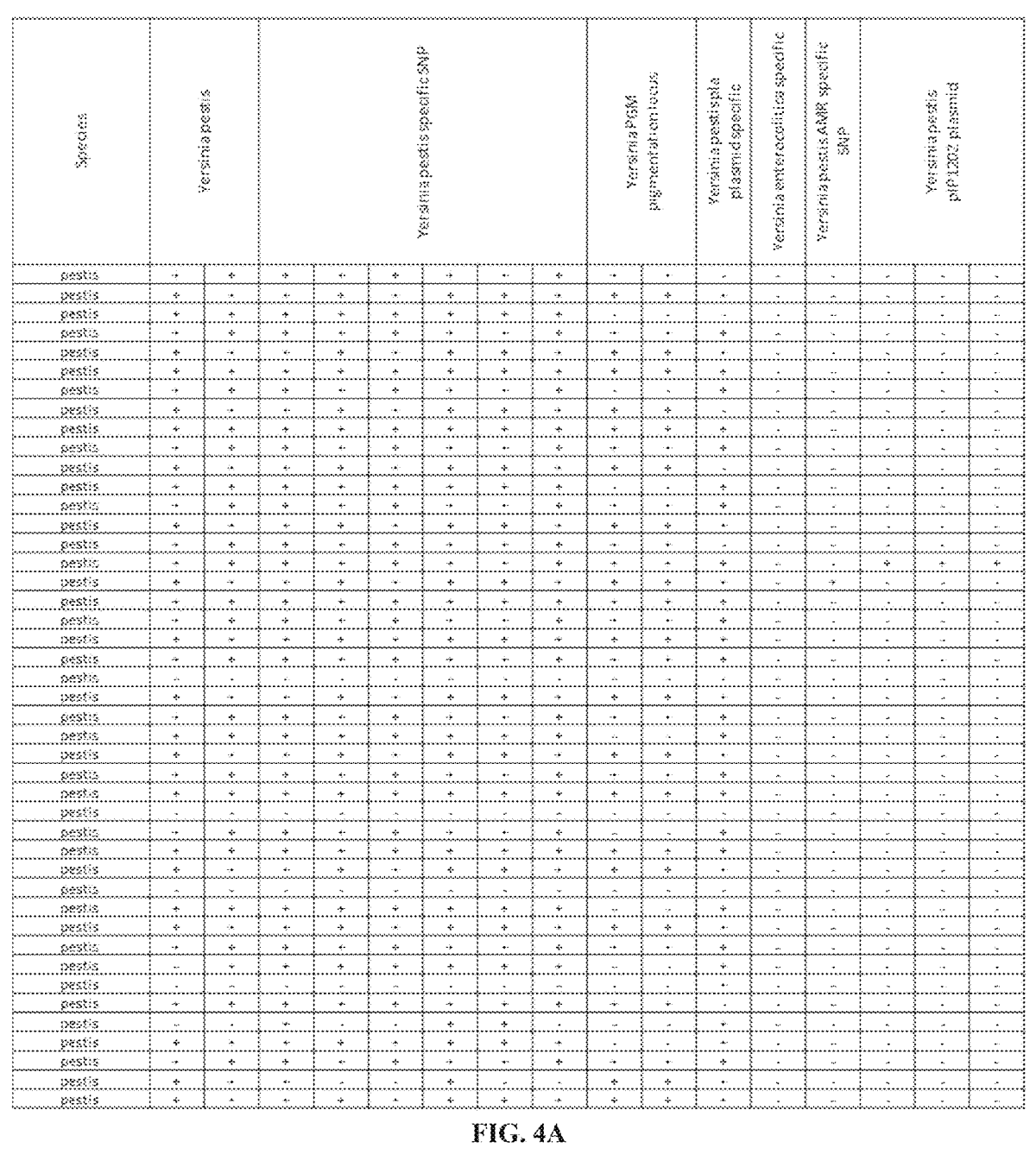

FIGS. 4A-4D An ASAP output result table, showing a subset of results from a large diverse sample set (693 isolates). The ASAP output demonstrates a general presence/absence for each select agent isolate or near neighbor isolate tested using UI-AmpSeq assays specific for *Y. pestis*, known virulence determinants, near neighbor (NN) species, and antimicrobial resistance (AMR) targets.

Figure 5B:
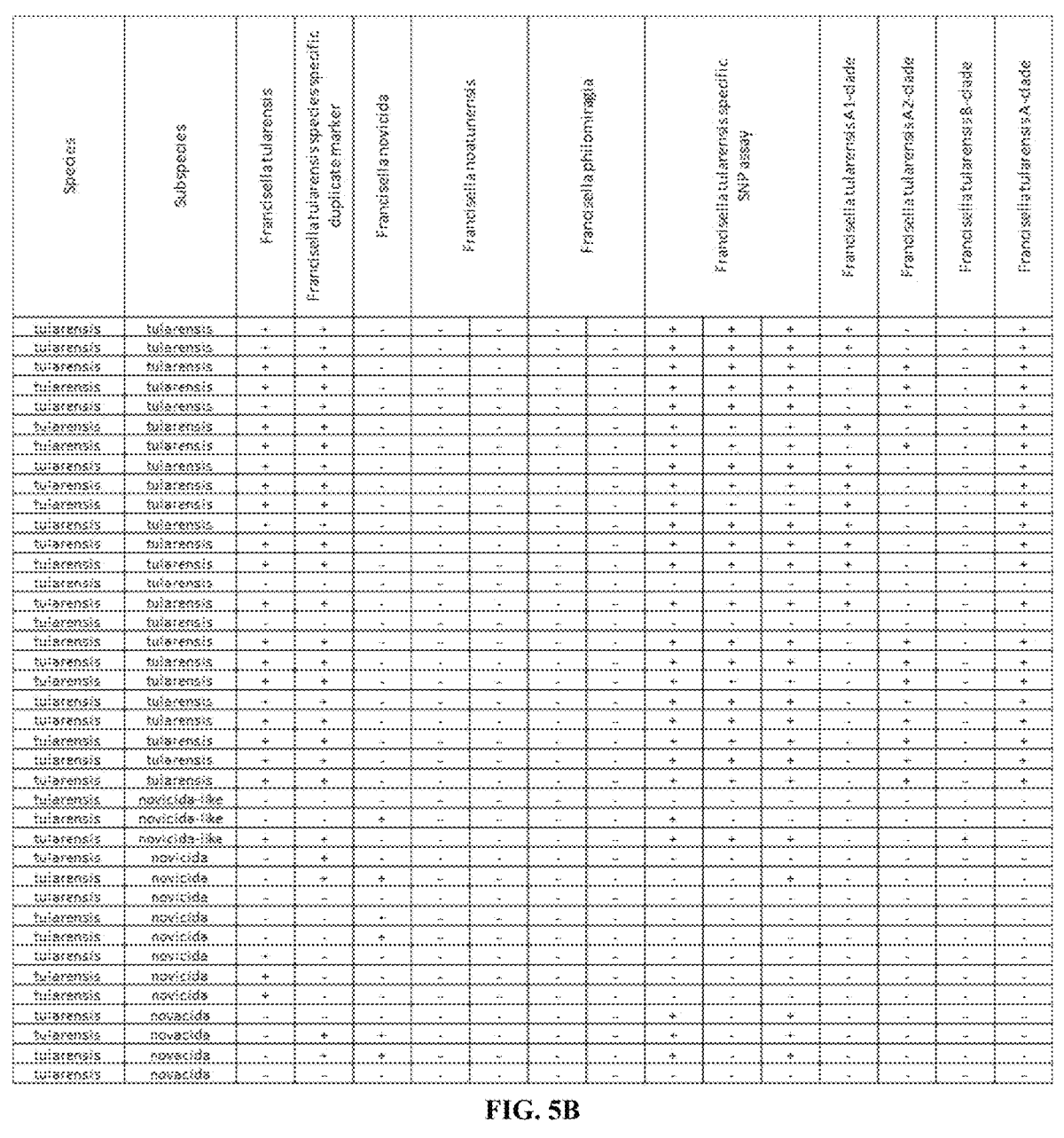

FIGS. 5A-5E An ASAP output result table, showing a subset of results from a large diverse sample set (693 isolates). The ASAP output demonstrates a general presence/absence for each select agent isolate or near neighbor isolate tested using UI-AmpSeq assays specific for *F. tularensis*, known virulence determinants, near neighbor (NN) species, and antimicrobial resistance (AMR) targets.

Figure 6A:
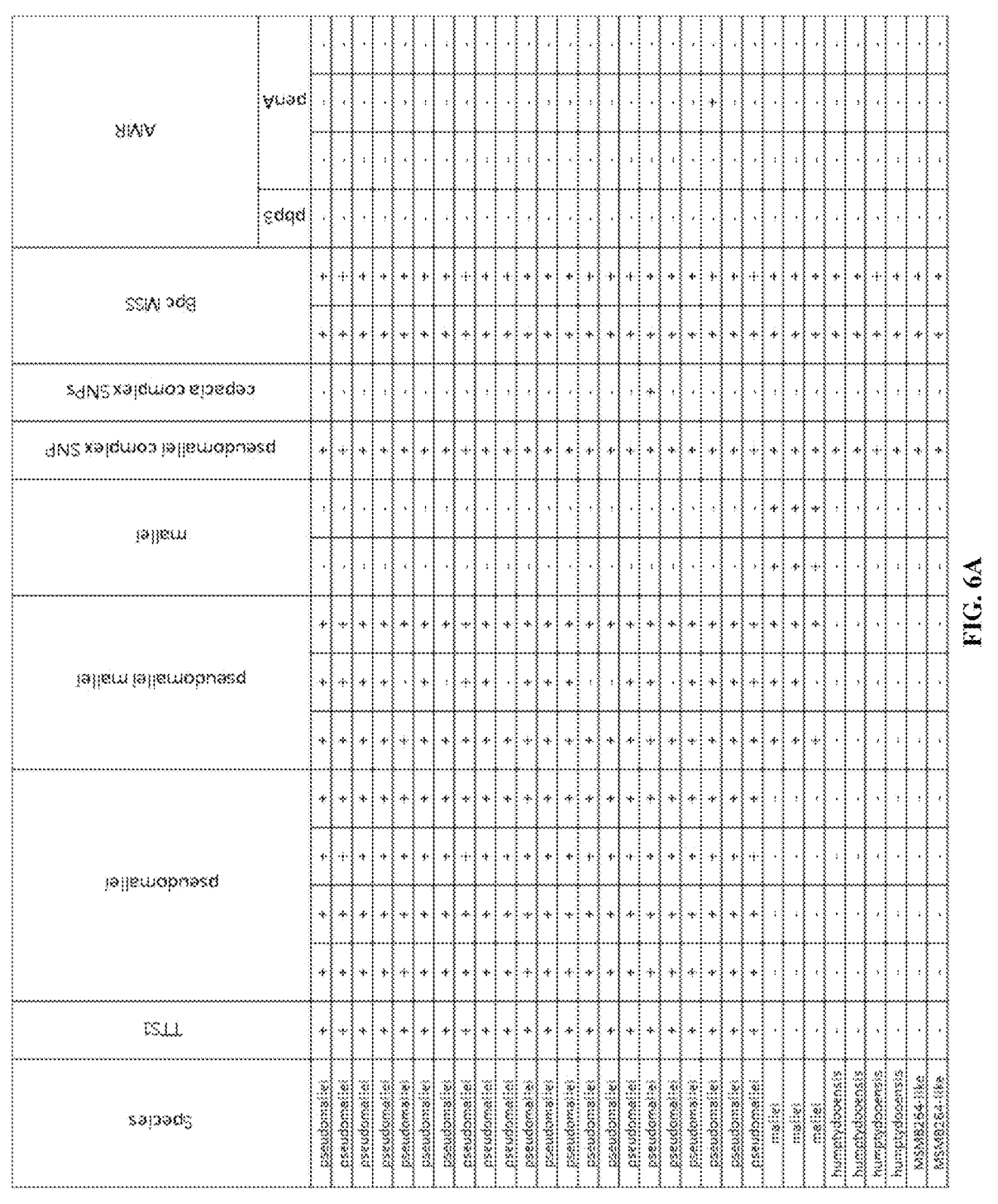
Figure 6B:
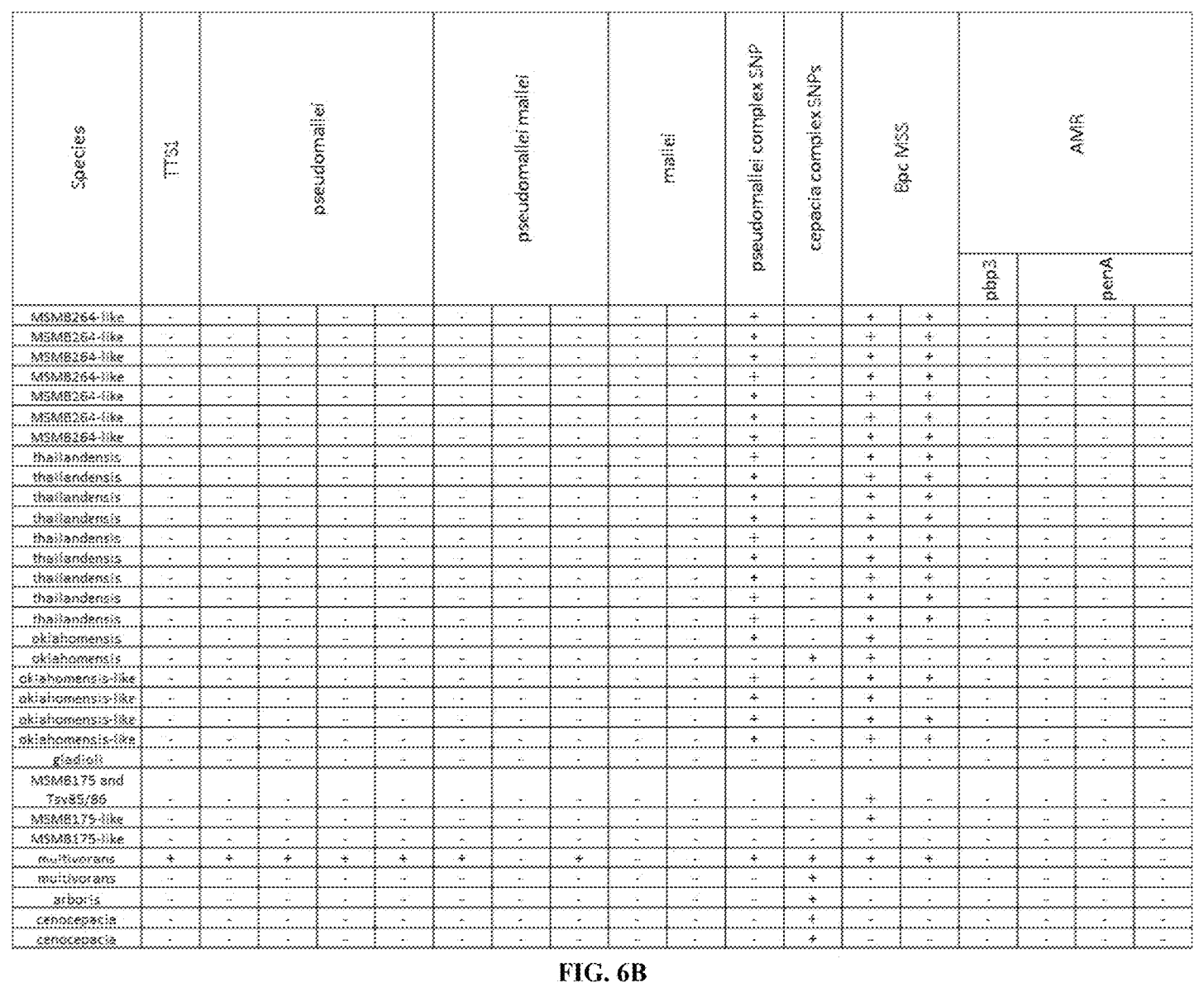
Figure 6C:
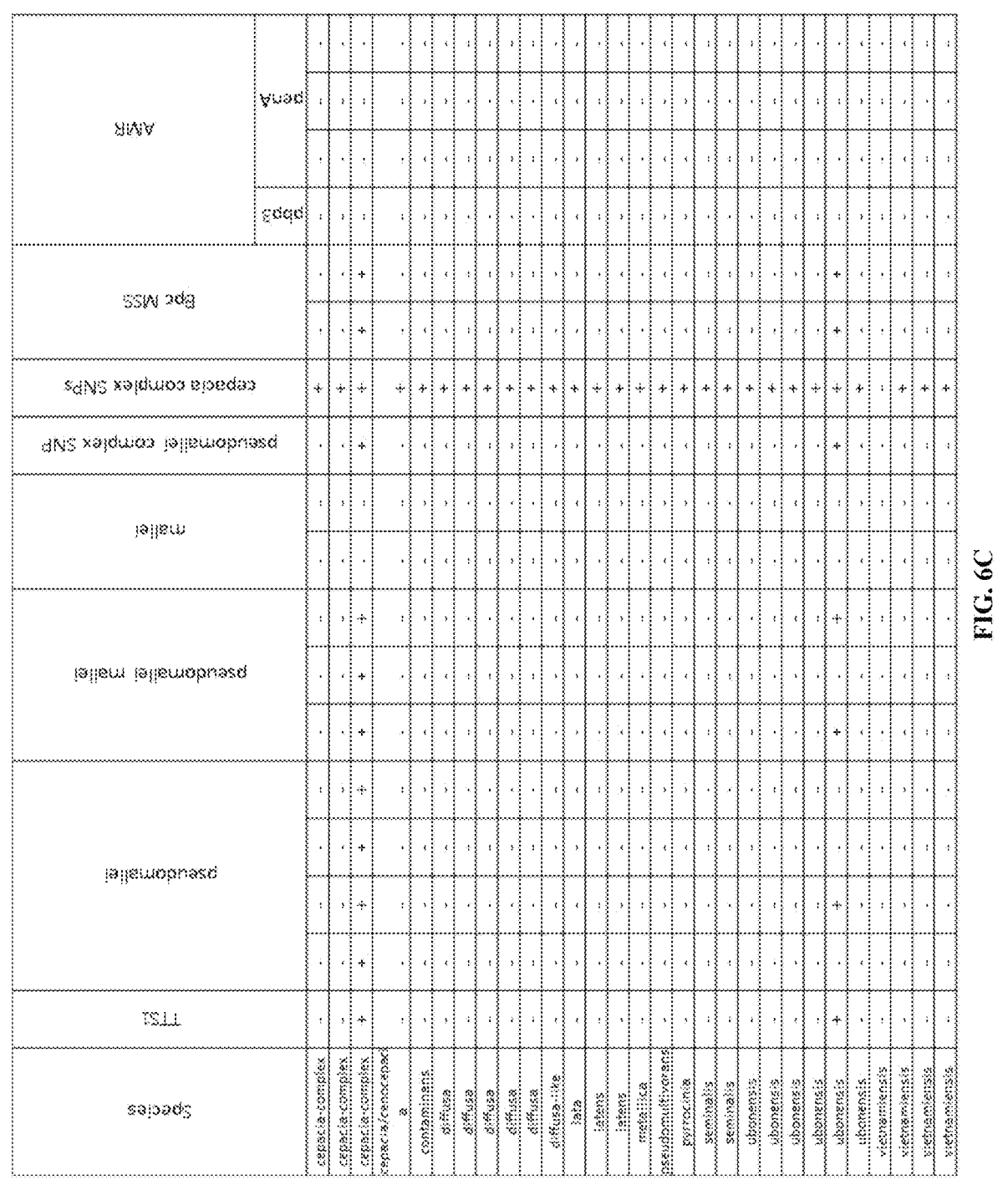

FIGS. 6A-6C An ASAP output result table, showing a subset of results from a large diverse sample set (693 isolates). The ASAP output demonstrates a general presence/ absence for each select agent isolate or near neighbor isolate tested using UI-AmpSeq assays specific B. pseudomallei, B. mallei*, known virulence determinants, near neighbor (NN) species, and antimicrobial resistance (AMR) targets.

Figure 7:
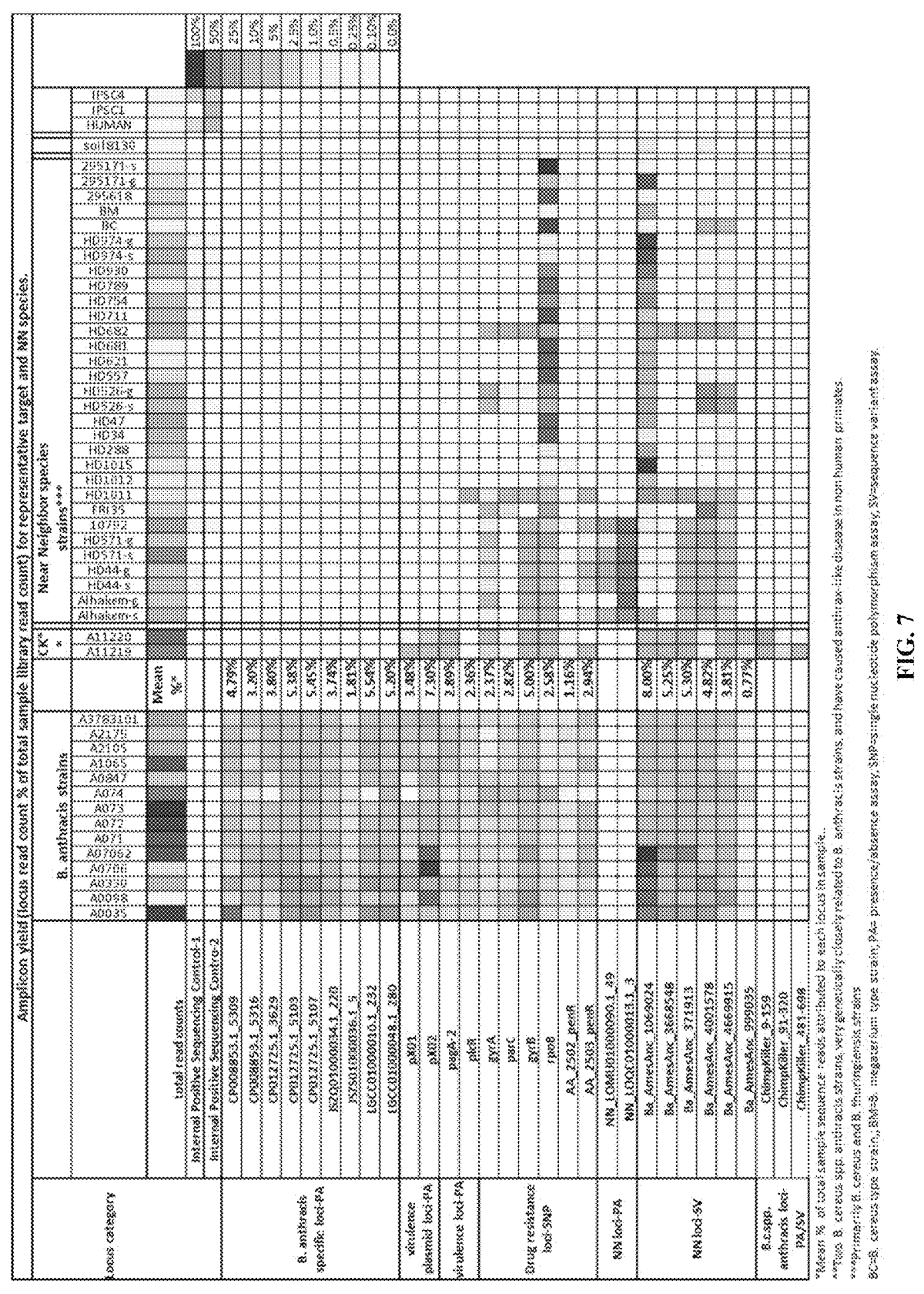

FIG. 7. Sensitivity and specificity results for *B. anthracis* assay, including amplicon yield (locus read count % of total sample library read count) for representative target and NN species.

Figure 8B:
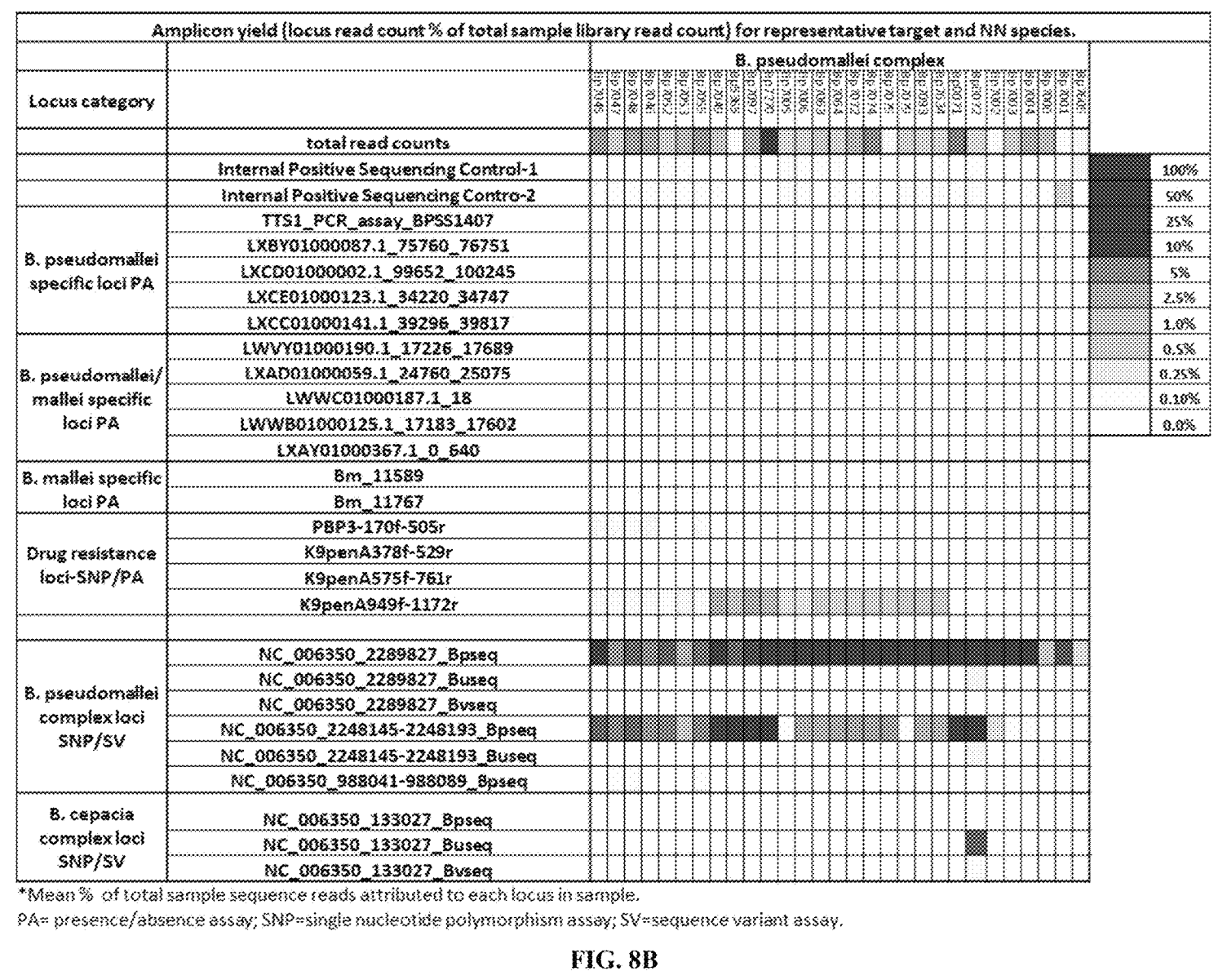

FIGS. 8A-8C. Sensitivity and specificity results for *B. pseudomallei/mallei* assay, including amplicon yield (locus read count % of total sample library read count) for representative target and NN species.

Figure 9:
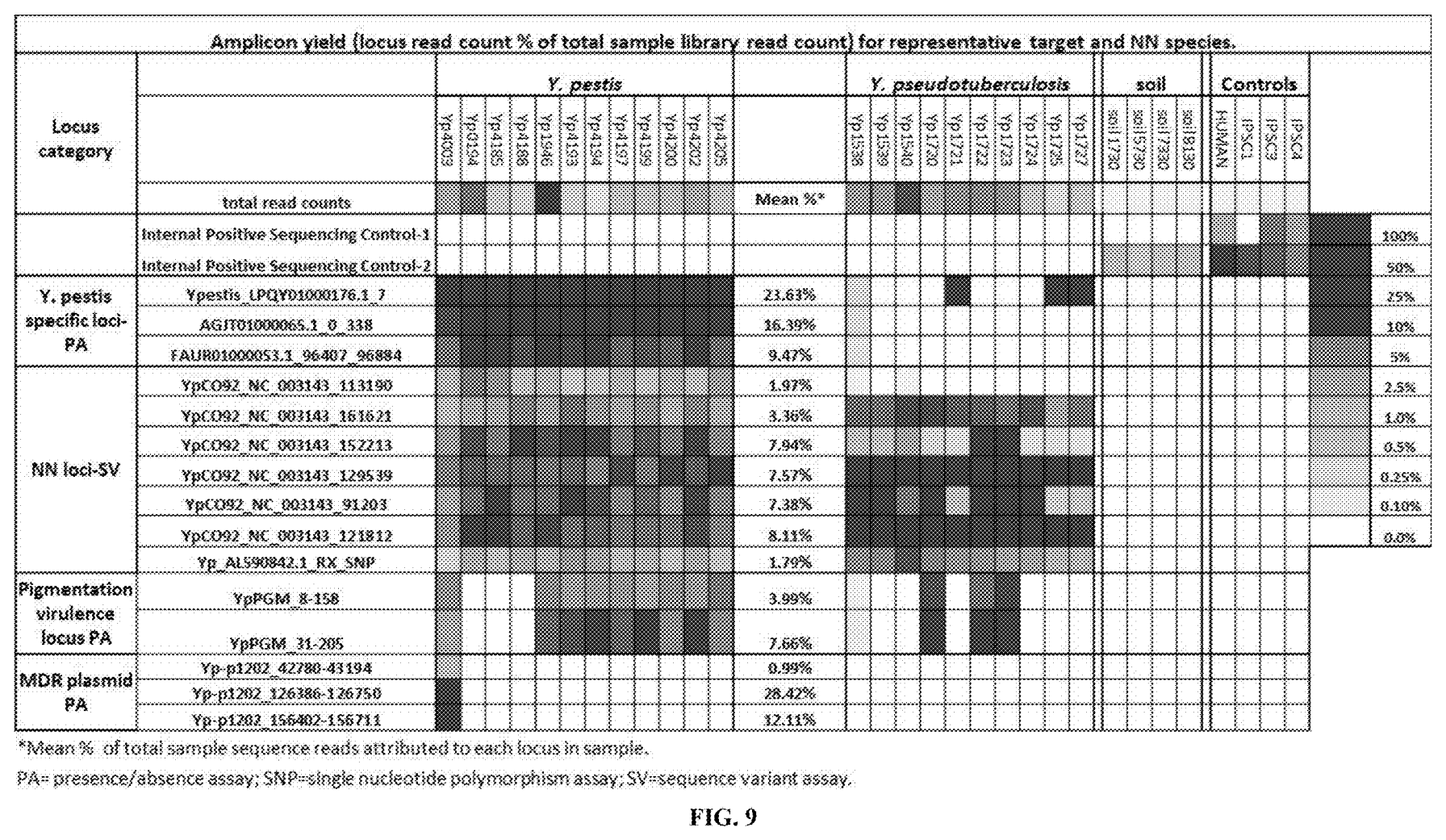

FIG. 9. Sensitivity and specificity results for *Y. pestis* assay, including amplicon yield (locus read count % of total sample library read count) for representative target and NN species.

FIG. 10. Sensitivity and specificity results for *F. tularensis* assay, including amplicon yield (locus read count % of total sample library read count) for representative target and NN species.

FIG. 11 An Example Clinical Plate layout. The black wells are samples.

DETAILED DESCRIPTION

Definitions

As used herein, the verb "comprise" as is used in this description and in the claims and its conjugations are used in its non-limiting sense to mean that items following the word are included, but items not specifically mentioned are not excluded.

As used herein, reference to an element by the indefinite article "a" or "an" does not exclude the possibility that more than one of the elements are present, unless the context clearly requires that there is one and only one of the elements. The indefinite article "a" or "an" thus usually means "at least one."

The sample in this method is preferably a biological sample from a subject. The term "sample" or "biological sample" or "environmental sample" is used in its broadest sense. Depending upon the embodiment of the invention, for example, a sample may comprise a bodily fluid including whole blood, serum, plasma, urine, saliva, cerebral spinal fluid, semen, vaginal fluid, pulmonary fluid, tears, perspiration, mucus and the like; an extract from a cell, chromosome, organelle, or membrane isolated from a cell; a cell; genomic DNA, RNA, or cDNA, in solution or bound to a substrate; a tissue; a tissue print, or any other material isolated in whole or in part from a living subject or organism. Biological samples may also include sections of tissues such as biopsy and autopsy samples, and frozen sections taken for histologic purposes such as blood, plasma, serum, sputum, stool, tears, mucus, hair, skin, and the like. Biological samples also include explants and primary and/or transformed cell cultures derived from patient tissues. In some embodiments, sample may comprise a portion of a non-animal organism, such as a plant (e.g., castor beans or derivatives thereof). In other embodiments, the sample comprises soil, water, air or other environmental material.

In some embodiments, sample or biological sample may include a bodily tissue, fluid, or any other specimen that may be obtained from a living organism that may comprise additional living organisms. By way of example only, in some embodiments, sample or biological sample may include a specimen from a first organism (e.g., a human) that may further comprise an additional organism (e.g., bacteria, including pathogenic or non-pathogenic/commensal bacteria, viruses, parasites, fungi, including pathogenic or non-pathogenic fungi, etc.). In some embodiments, the additional organism may be separately cultured after isolation of the sample to provide additional starting materials for downstream analyses, in some embodiments, the sample or biological sample may comprise a direct portion of the additional, non-human organism and the host organism (e.g., a biopsy or sputum sample that contains human cells and bacteria).

Some embodiments of the invention may comprise a multiplex assay. As used herein, the term "multiplex" refers to the production of more than one amplicon, PCR product, PCR fragment, amplification product, etc. in a single reaction vessel. In other words, multiplex is to be construed as the amplification of more than one target-specific sequences within a PCR reaction or assay within the same PCR assay mixture (e.g., more than one amplicon is produced within a single vessel that contains all of the reagents necessary to perform a PCR reaction). In some embodiments, a step prior to performing the PCR (or RT-PCR, quantitative RT-PCR, etc.) reaction can occur such that sets of primers and/or primers and probes are designed, produced, and optimized within a given set of reaction conditions to ensure proper amplicon production during the performance of the PCR.

BioThreatSeq

Currently, there are two approaches being used to identifying specimens in the environment. The first approach, metagenomics, tries to sequence "all" of the DNA in a sample and then to unravel its content computationally. Sequencing "all" of the DNA is difficult, slow, and very expensive. The computational approaches are improving but still contain many flaws that lead to false conclusions. A recent sensationalized report of DNA from anthrax and plague bacteria in the NYC subways illustrates the pitfalls of such endeavors (Mason et al., Cell Systems). Significant amounts of data are produced with metagenomics but frequently not enough for informative signatures to differentiate pathogens from near neighbors. Deep sequencing of single specimens may cost nearly $1,000 and take several weeks to generate. It is clearly not ready at this time for implementation for biosurveillance.

The second approach, amplicon sequencing, involves the deep (>5,000×) sequencing of the 16S gene PCR amplicon to identify individual components of mixed bacterial communities. While the PCR primers are not specific, the intervening sequences can be highly informative and can be used to discriminate among bacterial taxa. Unfortunately for biothreat detection, the 16S gene has insufficient discrimination power to differentiate biothreat pathogens from their near neighbors. Discrimination power is a function of gene diversity and the 16S has low or no diversity among closely related bacteria. It cannot effectively identify a biothreat agent or distinguish from near-neighbor species.

Increasing the amplicon discrimination power can be accomplished through comparative genomic analysis to identify diverse genomics regions. This is most effective when large genome databases are available and can be highly predictive of success once implemented. In clinical diagnostics, this approach is being used to identify multiple pathogens and to predict their virulence and resistance to antibiotics. PCR primers specific to a pathogen genera or species is sufficient, if there is additional DNA sequence information that can be leveraged for precise agent identification. Multiplex systems of several hundred amplicons are becoming common and provide coverage for dozens of pathogens. Sample preparation that works for real-time-PCR also works for this technology, so currently sampling schemes would adapt well to this type of assay. A multiple amplicon sequencing system would be easily adapted to changing targets with addition of new amplicons. Because of the multiplex nature of the assay, redundant amplicons can easily be included to verify the identification of a biothreat agent and even provide a differential identification of a near-neighbor species. Variation within the amplicons can be analyzed to identify drug resistance, virulence factors and subtype to the strain level.

Figure 1A:
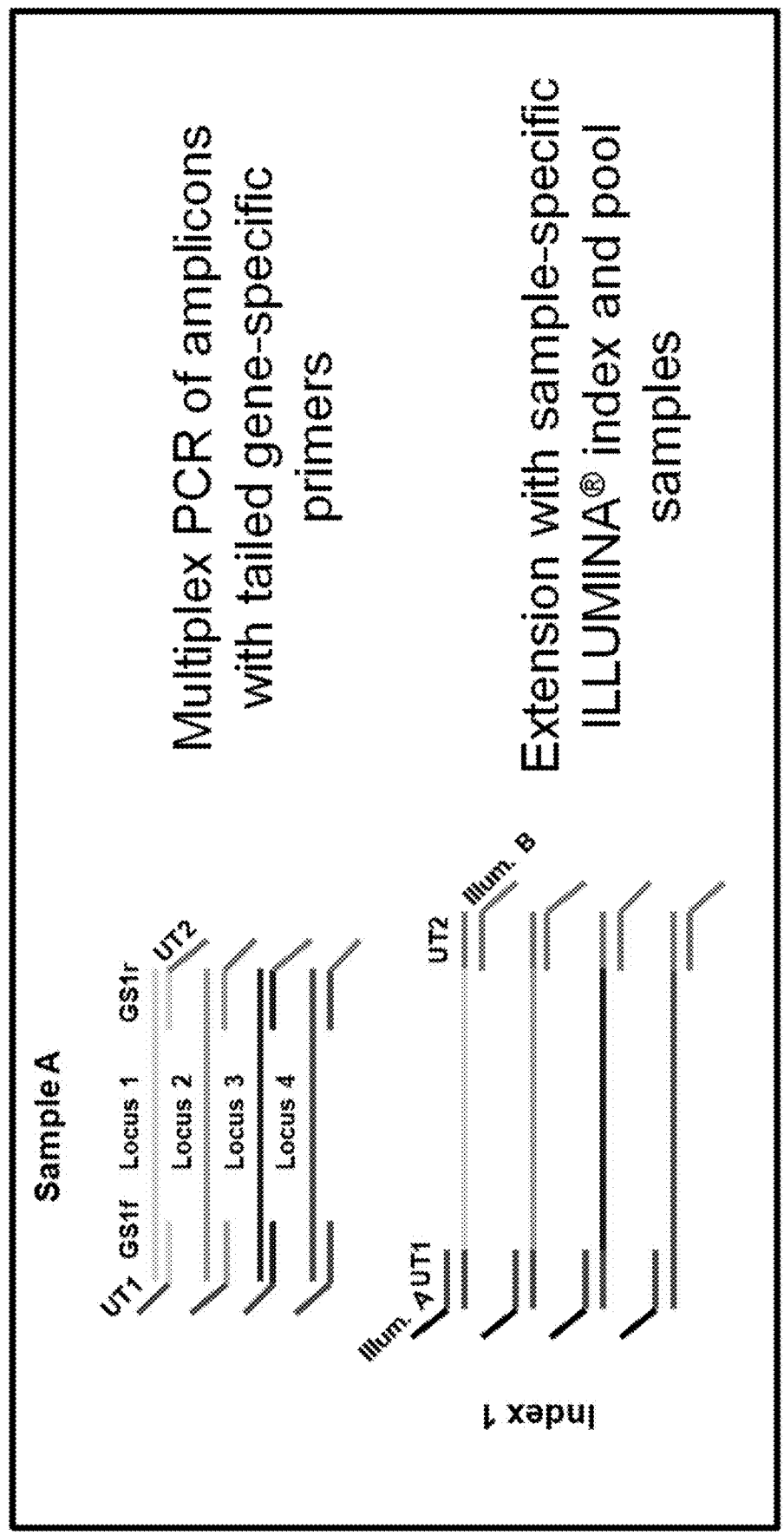
FIGS. 1A and 1B depict a universal index multiplex amplicon sequencing assay (UI-AmpSeq). Gene-specific primers containing universal tails (UT) amplify gene-specific targets. An ILLUMINA® extension PCR is run on these tailed PCR amplicons using ILLUMINA® indices containing complementary sequences to the UT, which allow for amplicon sequencing on an ILLUMINA® platform.
Figure 1B:
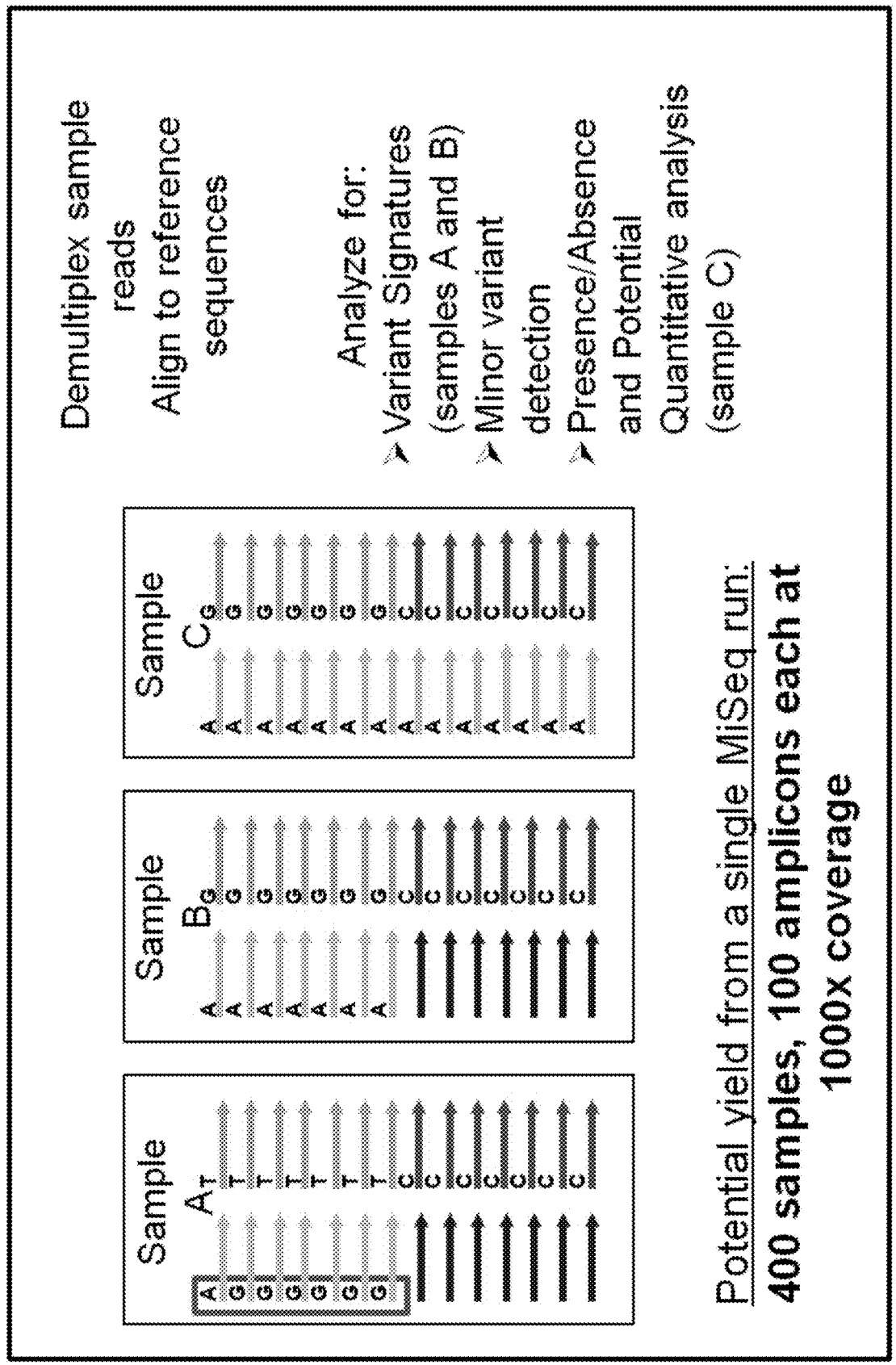
Figure 2:
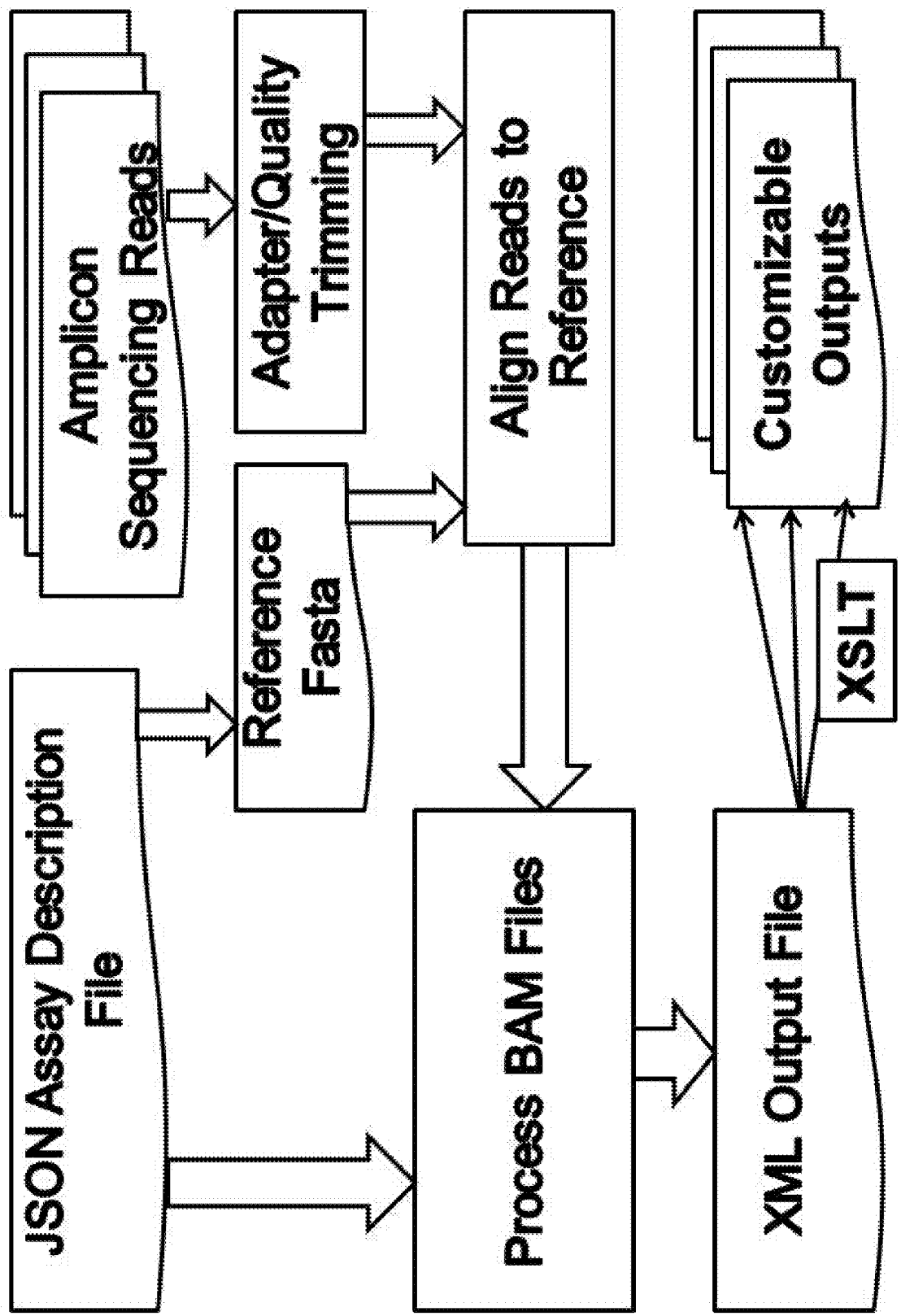
FIG. 2 depicts an ASAP analysis. Enhanced Amplicon Sequencing Analysis pipeline (ASAP) allows the user to quickly analyze read data for specific targets and provides a detailed report output file. The ASAP bioinformatics method is described in U.S. Publication No. 2018/0173843, the contents of which are incorporated herein by reference.
Figure 8C:
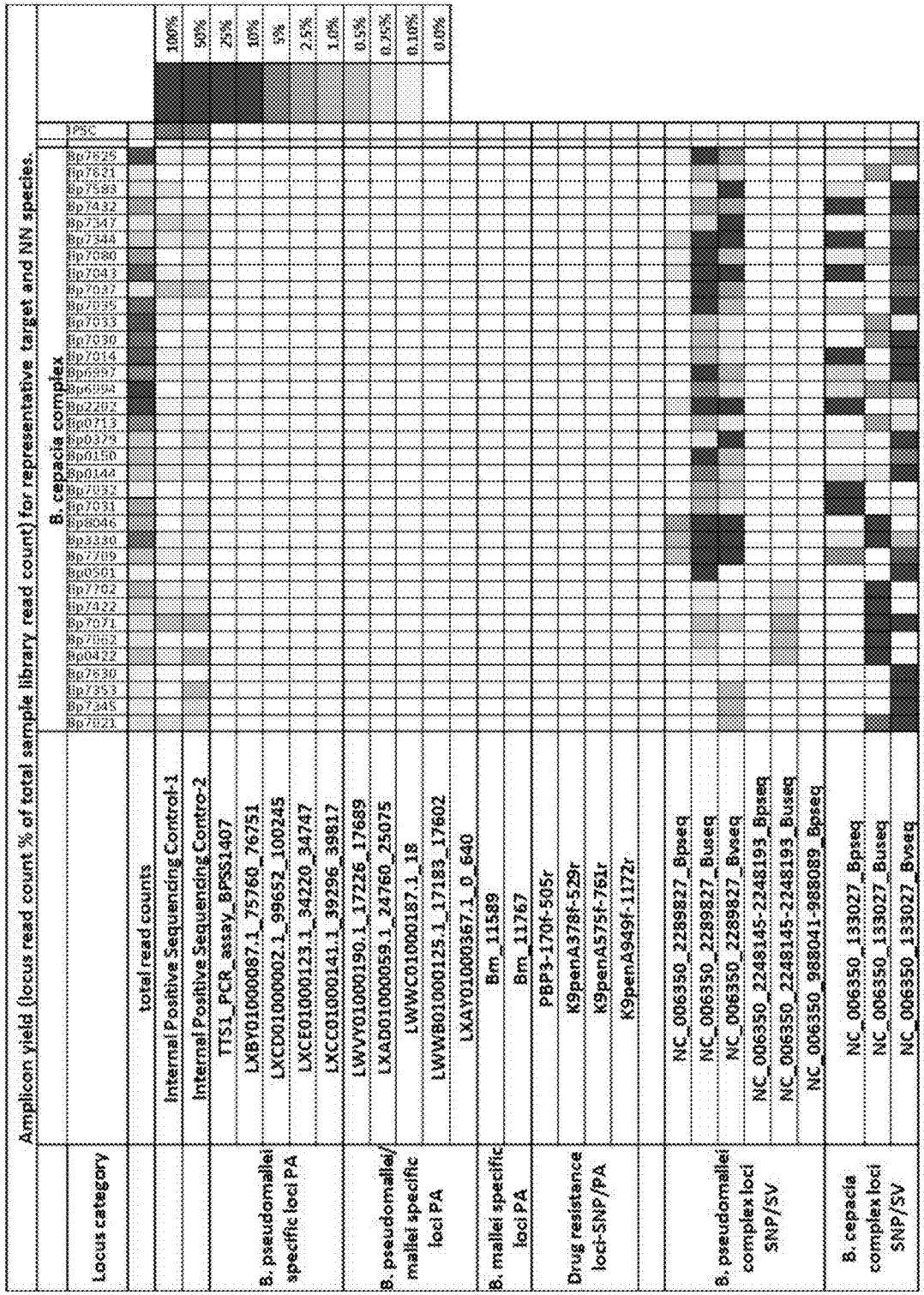

The ideal multiple amplicon sequencing system for identifying major biothreat agents should distinguish between the biothreat agent and its near-neighbor species using both amplification positive/negative criteria and qualitative analysis of sequence within the amplicons. This latter analysis provides strain identification and drug susceptibility identification. The analytical system should be supported by an automated interpretive software that generates actionable reports. Such a system includes quality assurance data to identify sample and/or process issues rapidly, to limit the effect of QC issues on final results.

"BioThreatSeq" detects a presence, an absence, and/or a clinically important characteristic of nucleic acids from one or more microbial pathogens. BioThreatSeq is based upon very discriminating genetic regions bioinformatically identified using public and private genome sequences from microbial pathogens including but not limited to *Bacillus anthracis, Burkholderia pseudomallei, Burkholderia mallei, Francisella tularensis, Yersinia pestis* and Near Neighbor (NN) species. BioThreatSeq can be used to screen environmental samples for presence of target agent DNA, as well as war fighter and civilian patients for target agent carriage in the event of suspected exposure.

In an embodiment, BioThreatSeq comprises a highly multiplexed amplicon sequencing assay. The assay is a highly informative screening tool capable of simultaneously detecting a presence of a microbial pathogen and a clinically important characteristic of the microbial pathogen without a live culturing step. Non-limiting examples of the clinically important characteristics include: virulence, or antibiotic resistance genetic signatures, etc.

The utility of this assay has been demonstrated on several complex environmental and clinical specimen types including urine, wound swabs, sputum, air, soil, water samples. The superiority of BioThreatSeq over traditional typing techniques include high sensitivity (e.g., a low limit of detection) and high specificity (e.g., discriminating among strains, detecting antimicrobial resistance, and profiling virulence signatures, etc.) in target agent detection. BioThreatSeq is also highly adaptable to new content, which allows for the flexibility to detect new biothreats agents and signatures. Thus, the assay methodology allows for the expansion of this tool to be used for several other BioThreat agents or applications.

Target Specific Amplicon

The Inventors used comparative genomics to identify a first genomic region that differentiates a target agent from its near neighbor relatives. In the first scenario, the first genomic region is present in all known target strains, and a lack of the first genomic region indicates an absence of the target agent in the sample. In the second scenario, the first genomic region not only is present in all known target strains, but is also absent in near-neighbor species. Thus, a presence of the first genomic region indicates a presence of the target agent in the sample.

In certain non-limiting embodiments, the presence or absence of the first genomic region in the nucleic acids of the sample is determined by PCR using a first forward primer and a first reverse primer. The first forward primer and the first reverse primer amplify a Target Specific Amplicon, i.e., all strains of the threat agent, but not the near neighbors.

Differential Target Amplicons

The Inventors also used comparative genomics to identify a second genomic region that differentiates a target agent from its near neighbor relatives. The second genomic region is present in all strains of the near-neighbor relatives, but will not be in the target. Thus, a presence of the second genomic region indicates an absence of the target agent in the sample.

In certain non-limiting embodiments, the presence or absence of the second genomic region in the nucleic acids of the sample is determined by PCR using a second forward primer and a second reverse primer. The second forward primer and second reverse primer amplify Differential Target Amplicons, i.e., all strains of the near neighbors, but not the threat agent. Differential identification assays can be included in the multiplex assay to help nullify any false positive results. This optional step offers interpretive value in complex species.

The Inventors determined the exclusivity and inclusivity of the first forward and the first reverse primers in silico across all available threat agents (*Bacillus anthracis, Burkholderia pseudomallei, Burkholderia mallei, Francisella tularensis,* and *Yersinia pestis*) and near neighbor genomes. The in-silico validation included genomes from common contaminants such as humans. Because a large number of genomics sequences exist for both target and non-target organisms, the in-silico validation step eliminates any primers that are non-exclusive to the biothreat target. The assay primers were tested against the target and near-neighbor DNA templates to validate them under actual assay conditions.

Primer Design

The design of the first forward primer, the first reverse primer, the second forward primer, and the second reverse primer is consistent with a standard PCR method but is amendable to analysis using next-generation sequencing methods. This requirement includes the addition of "barcodes" to allow for indexing of samples for combining into single DNA sequencing batches. The technical details are provided in the PCT Patent Application entitled "Systems And Methods for Universal Tail-Based Indexing Strategies for Amplicon Sequencing" (International Application Number: PCT/US2014/064890; International Publication Number: WO 2015/070187 A2), the contents of which are hereby incorporated in their entirety.

The Inventors determined the exclusivity and inclusivity of the second forward and the second reverse primers in silico across all available threat agents (*Bacillus anthracis, Burkholderia pseudomallei, Burkholderia mallei, Francisella tularensis,* and *Yersinia pestis*) and near neighbor genomes. The in-silico validation included genomes from common contaminants such as humans and soil DNA. Because a large number of genomics sequences exist for both target and non-target organisms, the in-silico validation step eliminates any primers that are non-exclusive to the near-neighbor species. The assay primers were tested against the target and near-neighbor DNA templates to validate them under actual assay conditions.

In the third scenario, the first genomic region is present in all known target strains and at least one near-neighbor species. In this case, producing an exclusive amplicon is not feasible and the combination of amplification and internal sequence is needed to distinguish target from near-neighbors. In the absence of exclusive-target amplification, the amplicon sequence could provide definitive identification of the target and non-target agents.

The Inventors has defined the phylogenetic structure of the first genomic region that includes both the target agent and its near neighbors and identified a variable internal sequence region which allows for: (1) differentiation of near neighbor from target species, (2) strain identification, (3) drug susceptibility identification, and/or (4) virulence prediction.

Performance of the Multiplex Assays

The Inventors have developed combined multi-agent amplicon sequencing assays for 2, 3, 4, 5, 6, or 7 biothreat agents and validated them under laboratory conditions. For the combined biothreat agent assays, important test parameters such as linearity, LOD, sensitivity, specificity, quantitative performance (absolute and relative), contaminant interference, performance with environmental samples (spikes), etc. have been determined.

Software

The Inventors have developed software that analyzes $B.$ $anthracis$ amplicon sequence data and provides actionable information (i.e., agent presence with confidence metrics, presence of virulence and antibiotic resistance factors, phylogenetic classification, etc.). The Inventors have also developed software that analyzes $B.$ $anthracis$ and other target agent ($F.$ $tularensis,$ $Y.$ $pestis,$ $B.$ $mallei,$ $B.$ $pseudomallei,$ $Brucella$ $melitensis$, and $B.$ $abortus$) and allow for on-site and remote reporting.

BTSeq comprises target agent and near neighbor (NN) species identification assays, antimicrobial resistance (AMR) assays, virulence gene assays, and uses TGen North's amplicon sequencing analysis pipeline (ASAP) to report results.

Use of the disclosed amplicon sequencing tool can be used to screen environmental samples for presence of target agent DNA, as well as war fighter and civilian patients for target agent carriage in the event of suspected exposure.

In some embodiments, the present invention relates to a method of detecting $Bacillus$ $anthracis$ in a sample, comprising detecting at least one $B.$ $anthracis$-specific amplicon selected from the group consisting of: CP008853.1_5309, CP008853.1_5316, CP012725.1_3629, CP012725.1_5103, CP012725.1_5107, JSZQ01000034.1_220, JSZS01000036.1_5, LGCC01000010.1_232, and LGCC01000048.1_280 in the sample, wherein the presence of the $B.$ $anthracis$-specific amplicon indicates the presence of $B.$ $anthracis$ in the sample, and an absence of the $B.$ $anthracis$-specific amplicon indicates an absence of $B.$ $anthracis$ in the sample.

In other embodiments, the disclosed methods further comprise confirming the absence of $B.$ $anthracis$ by detecting at least one $B.$ $anthracis$ Near Neighbor-specific amplicon selected from the group consisting of: NN_LOMU01000090.1_49, NN_LOQC01000013.1_3, and ChimpKiller_9-159 in the sample, wherein detecting the $B.$ $anthracis$ Near Neighbor-specific amplicon confirms the absence of $B.$ $anthracis.$ In yet other embodiments, the disclosed methods further comprise characterizing and/or subtyping $B.$ $anthracis$ by detecting at least one amplicon, single nucleotide polymorphism (SNP) or sequence variant (SV) selected from the group consisting of: ChimpKiller_91-320, ChimpKiller_481-698, plcR, pagA, pX01, pX01, gyrA, parC, gyrB, rpoB, AA_2502, AA_2503, Ba_AmesAnc_4669915, Ba_AmesAnc_4001578, Ba_AmesAnc_1069024, Ba_AmesAnc_3668548, Ba_AmesAnc_371913, and Ba_AmesAnc_999035 in the sample.

In certain aspects, the disclosed methods further comprise characterizing and/or subtyping $B.$ $anthracis$ by detecting at least one amplicon, single nucleotide polymorphism (SNP) or sequence variant (SV) selected from the group consisting of: ChimpKiller_91-320, ChimpKiller_481-698, plcR, pagA, pX01, pX01, gyrA, parC, gyrB, rpoB, AA_2502, AA_2503, Ba_AmesAnc_4669915, Ba_AmesAnc_4001578, Ba_AmesAnc_1069024, Ba_AmesAnc_3668548, Ba_AmesAnc_371913, and Ba_AmesAnc_999035 in the sample.

In other aspects, the present invention relates to a method of detecting $Burkholderia$ $pseudomallei$ and/or $Burkholderia$ $mallei$ in a sample by detecting at least one $B.$ $pseudomallei$ or $B.$ $mallei$-specific amplicon selected from the group consisting of: LWWC01000187.1_18, LWWB01000125.1_17183_17602, LXAY01000367.1_0_640, LWVY01000190.1_17226_17689, and LXAD01000059.1_24760_25075, wherein the presence of the $B.$ $pseudomallei$ or $B.$ $mallei$-specific amplicon indicates the presence of $B.$ $pseudomallei$ and/or $B.$ $mallei$ in the sample, and an absence of the $B.$ $pseudomallei$ or $B.$ $mallei$-specific amplicon indicates an absence of $B.$ $pseudomallei$ and $B.$ $mallei$ in the sample.

In some embodiments, the present invention provides a method of detecting $Burkholderia$ $pseudomallei$ and/or $Burkholderia$ $mallei$ in the sample by detecting at least one $B.$ $pseudomallei$ or $B.$ $mallei$-specific amplicon selected from the group consisting of: LWWC01000187.1_18, LWWB01000125.1_17183_17602, LXAY01000367.1_0_640, LWVY01000190.1_17226_17689, and LXAD01000059.1_24760_25075, wherein the presence of the $B.$ $pseudomallei$ or $B.$ $mallei$-specific amplicon indicates the presence of $B.$ $pseudomallei$ and/or $B.$ $mallei$ in the sample, and an absence of the $B.$ $pseudomallei$ or $B.$ $mallei$-specific amplicon indicates an absence of $B.$ $pseudomallei$ and $B.$ $mallei$ in the sample.

In other embodiments, the present invention provides a method of detecting $B.$ $pseudomallei$ in a sample by detecting at least one $B.$ $pseudomallei$-specific amplicon selected from the group consisting of: TTS1 BPSS1407, LXCC01000141.1 39296 39817, LXBY01000087.1_75760_76751, LXCD01000002.1_99652_100245, and LXCE01000123.1_34220_34747 (, wherein the presence of the $B.$ $pseudomallei$-specific amplicon indicates the presence of $B.$ $pseudomallei$ in the sample, and an absence of the $B.$ $pseudomallei$-specific amplicon indicates an absence of $B.$ $pseudomallei$ in the sample.

In yet other embodiments, the present invention provides a method of detecting $B.$ $mallei$ in the sample by detecting at least one $B.$ $mallei$-specific amplicon selected from the group consisting of: Bm 11589 and Bm 11767, wherein the presence of the $B.$ $mallei$-specific amplicon indicates the presence of $B.$ $mallei$ in the sample, and an absence of the $B.$ $mallei$-specific amplicon indicates an absence of $B.$ $mallei$ in the sample.

In certain aspects, the disclosed methods further comprise characterizing and/or subtyping $B.$ $pseudomallei$ and/or $B.$ $mallei$ by detecting at least one one amplicon, single nucleotide polymorphism (SNP) or sequence variant (SV) selected from the group consisting of: K9penA378-529, K9penA575-761, K9penA949-1172, pbp3-1, and pbp3-2 in the sample.

In other aspects, the disclosed methods further comprise confirming the absence of B. pseudomallei and B. mallei by detecting at least one B. pseudomallei or B. mallei Near Neighbor-specific single nucleotide polymorphism (SNP) or sequence variant (SV) selected from the group consisting of: NC 006350 2289827, NC 006350 133027, NC 006350 2248145-2248193, and NC 006350 988041-988089 in the sample, wherein detecting the B. pseudomallei or B. mallei Near Neighbor-specific single nucleotide polymorphism (SNP) or sequence variant (SV) confirms the absence of B. pseudomallei and B. mallei.

In yet other aspects, the present invention provides a method of detecting Francisella tularensis in a sample by detecting at least one F. tularensis-specific amplicon selected from the group consisting of: F. tularensis_CP000915.1_1782, F. tularensis_CP000915.1-731, and Ft_dup_CP000915.1_197, wherein the presence of the F. tularensis-specific amplicon indicates that F. tularensis is present in the sample, and an absence of the F. tularensis-specific amplicon indicates that F. tularensis is absent in the sample.

In some aspects, the disclosed methods further comprise confirming the absence of F. tularensis by detecting at least one F. tularensis Near Neighbor-specific amplicon selected from the group consisting of: F. tnovicida_CP009607.1, F. philom_CP009444.1_569, and F. philom_CP009444.1_285 in the sample, wherein detecting the F. tularensis Near Neighbor-specific amplicon confirms the absence of F. tularensis.

In other aspects, the disclosed methods further comprise confirming the absence of F. tularensis by detecting at least one F. tularensis Near Neighbor-specific SNP or SV selected from the group consisting of: FtA1, FtA2, FtB, FtA, FtLVS_AM233362_1646546, FtLVS_AM233362_1643765, and FtLVS_AM233362_1562618 in the sample, wherein detecting the F. tularensis Near Neighbor-specific polymorphism confirms the absence of F. tularensis.

In yet other aspects, the present invention provides a method of detecting Yersinia pestis in the sample by detecting at least one Y. pestis-specific amplicon selected from the group consisting of: Y. pestis_LPQY01000176.1_7, AGJT01000065.1_0_338, and FAUR01000053.1_96407_96884, wherein the presence of the Y. pestis-specific amplicon indicates the presence of Y. pestis in the sample, and an absence of the Y. pestis-specific amplicon indicates an absence of Y. pestis in the sample.

In one embodiment, the disclosed methods further comprise confirming the absence of Y. pestis by detecting at least one Y. pestis Near Neighbor-specific SNP or SV selected from the group consisting of:
YpCO92_NC_003143_113190,
YpCO92_NC_003143_161621,
YpCO92_NC_003143_152213,
YpCO92_NC_003143_129539,
YpCO92_NC_003143_91203,
YpCO92_NC_003143_121812, and
Yp_AL590842.1_RX_SNP in the sample, wherein detecting the Y. pestis Near Neighbor-specific SNP or SV confirms the absence of Y. pestis.

In another embodiment, the disclosed methods further comprise characterizing and/or subtyping Y. pestis by detecting at least one amplicon selected from the group consisting of: YpPGM_AL031866.1_81, YpPGM_31-205, Yp-p1202_42780-43194, Yp-p1202_126386-126750, and Yp-p1202_156402-156711 in the sample.

In some embodiments, the presence or absence of B. anthracis in a sample is detected by identifying a specific mutation in the PlcR gene, a single base change at position 640, a nonsense mutation, which creates a dysfunctional protein. In other embodiments, the presence or absence of B. anthracis in a sample is detected by identifying the pXO1 and/or pXO2 plasmids.

PlcR is a global transcriptional regulator which controls most of the secreted virulence factors in B. cereus and B. thuringiensis. It is chromosomally encoded and is ubiquitous throughout the cell (Agaisse, H. et al. (June 1999). "PlcR is a pleiotropic regulator of extracellular virulence factor gene expression in Bacillus thuringiensis". Molecular Microbiology. 32 (5): 1043-53). In B. anthracis, however, the plcR gene contains a single base change at position 640, a nonsense mutation, which creates a dysfunctional protein. While 1% of the B. cereus group carries an inactivated plcR gene, none of them carries the specific mutation found only in B. anthracis (Slamti, L. et al. (June 2004). "Distinct mutations in PlcR explain why some strains of the Bacillus cereus group are nonhemolytic". Journal of Bacteriology. 186 (11): 3531-8).

The lack of PlcR in B. anthracis is a principle characteristic differentiating it from other members of the B. cereus group. While B. cereus and B. thuringiensis depend on the plcR gene for expression of their virulence factors, B. anthracis relies on the pXO1 and pXO2 plasmids for its virulence (Kolsto, A. et al. (October 2009). "What Sets Bacillus anthracis Apart from Other Bacillus Species?" Annual Review of Microbiology. 63 (1): 451-476). Bacillus cereus biovar anthracis, i.e. B. cereus with the two plasmids, is also capable of causing anthrax.

In various embodiments, the disclosed methods identify an antibiotic resistance gene selected from a beta-lactamase gene, such as blaOXA, encoding extended spectrum OM class D beta-lactamases, blaCTX-M 82, blaCFX A4, encoding extended spectrum class A serine beta-lactamases, and AmpC, encoding the extended spectrum cephalosporin-resistant class C beta-lactamases; a multidrug efflux transporter system gene such as acrE, encoding a component of the AcrEF-ToIC multidrug efflux transporter system (Lau and Zgurskaya, 2005, J. Bacteriol. 187:7815); baeR, encoding a response regulator of the MdtABC multidrug efflux transporter system (Nagakubo et al., 2002, J. Bacteriol. 184:4161); emrY, encoding a component of the EmrKY-ToIC multidrug efflux transporter system (Tanabe et al., 1997, J. Gen. Appl. Microbiol. 43:257); mdtD, encoding a component of the MdtABC multidrug efflux transporter system (Nagakubo et al., 2002, J. Bacteriol. 184:4161); and mdtN, encoding a multidrug resistance efflux pump from the major facilitator superfamily (Sulavik et al., 2001, Antimicrob. Agents Chemother. 45:1126); pbp2, encoding penicillin binding protein 2 (Bharat et al., 2015, Antimicrob. Agents Chemother. 59:5003); pbp4, encoding penicillin binding protein 4 (Sun et al., 2014, PLoS One 9:e97202); andaminoglycoside_strA (Scholz et al., 1989, Gene 75:271) encodes an aminoglycoside phosphotransferase, and Tetracycline_tet39 (Agerso and Guardabassi, 2005, J. Antimicrob. Chemother. 55:566) encodes a component of a tetracycline efflux pump.

Other antibiotic resistance genes are provided in the Antibiotic Resistance Genes Database (ARDB), see Nucl. Acids Res. (2009) 37 (suppl 1): D443-D447, the World Wide Web (www) at ardb.cbcb.umd.edu, Antimicrob. Agents Chemother. July 2013 vol. 57 no. 7 3348-3357, and the NCBI database (the World Wide Web (www) at ncbi.nlm.nih.gov), the entire contents of which are hereby incorporated by reference.

In various embodiments, the antibiotic resistance gene is one or more of the genes shown below:

Aminocoumarins:
  Aminocournarin-resistant DNA topoisomerases
  Aminocournarin-resistant GyrB, ParE, ParY
Aminoglycosides:
  Aminoglycoside acetyltransferases
  AAC(1), AAC(2), AAC(3), AAC(6')
  Aminoglycosi de nucleotidyltransferases
  ANT(2"), ANT(3"), ANT(4), ANT(6), ANT(9)
  Aminoglycoside phosphotransferases
  APH(2"), APH(3"), APH(3'), APH(4), APH(6), APH(7"), APH(9)
  16S rRNA methyltransferases
  ArmA, RaitA, RrntB, RrniC, Sgrn
β-Lactams:
  Class A β-lactamases
  AER, BLA1, CTX-M, KPC, SHV, TEM, etc.
  Class B (metallo-)β-lactamases
  BlaB, CcrA, IMP, NDM, VIM, etc.
  Class C β-lactamases
  ACT, AmpC, CMY, LAT, PDC, etc.
  Class D β-lactamases
  OXA β-lactamase
  mecA (methicillin-resistant PBP2)
  Mutant porin proteins conferring antibiotic resistance
  Antibiotic-resistant Omp36, OmpF, PIB (por)
Genes Modulating β-Lactam Resistance:
  bla (blaI, blaR1) and mec (mecI, mecR1) operons
Chloramphenicol:
  Chloramphenicol acetyitransferase (CAT)
  Chloramphenicol phosphotransferase
Ethambutol:
  Ethambutol-resistant arabinosyltransferase (FrnbB)
Mupirocin:
  Mupirocin-resistant isoleucyl-tRNA synthetases
  MupA, MupB
    Peptide Antibiotics:
    Integral membrane protein MpriF
Phenicol:
  Cfr 23S rRNA methyltransferase
Rifampin:
  Rifampin ADP-ribosyitransferase (Arr)
  Rifampin glycosyltransferase
  Rifampin monooxygenase
  Rifampin phosphotransferase
  Rifampin resistance RNA polymerase-binding proteins
  DnaA, RbpA
  Rifampin-resistant beta-subunit of RNA polymerase (RpoB)
Streptogramins:
  Cfr 23S rRNA methyltransferase
  Erm 23S rRNA methyltransferases
  ErmA, ErmB, Erm(31), etc.
  Streptogramin resistance ATP-binding cassette (ABC) efflux pumps
  Lsa, MsrA, Vga, VgaB
  Streptogramin Vgb lyase
  Vat acetyltransferase
Fitioroquirmiones:
  Fluoroquinolone acetyltransferase
  Fluoroquinolone-resistant DNA topoisomerases
  Fluoroquinolone-resistant GyrA, GyrB, ParC
  Quinolone resistance protein (Qnr)
Fosfomycin:
  Fosfomycin phosphotransferases
  FomA, FomB, FosC
  Fosfomycin thiol transferases
  FosA, FosB, FosX
Glycopeptides:
  VanA, VanB, VanD, VanR, VanS, etc.
Lincosamides:
  Cfr 23S rRNA methyltransferase
  Erm 23SrRNA methyltransferases
  ErmA, ErmB, Em(31), etc.
  Lincosamide nucleotidyltransferase (Lin)
Linezolid:
  Cfr 23S rRNA methyltransferase
Macrolides:
  Cfr 23S rRNA methyltransferase
  Erm 23S rRNA methyltransferases
  ErmA, ErmB, Erm(31),
  Macrolide esterases
  EreA, EreB
  Macrolide glycosyltransferases
  GimA, Mgt, Ole
  Macrolide phosphotransferases (MPH)
  MPH(2')-I, MPH(2')-II
  Macrolide resistance efflux pumps
  MefA, MefE, Mel
Streptothricin:
  Streptothricin acetyltransferase (sat)
Sulfonamides:
  Sulfonamide-resistant dihydropteroate synthases
  Sul1, Sul2, Sul3, sulfonamide-resistant FolP
Tetracyclines:
  Mutant porin PIB (por) with reduced permeability
  Tetracycline inactivation enzyme TetX
  Tetracycline resistance major facilitator supeifamily (MFS) efflux pumps
  TetA, TetB, TetC, Tet30, Tet31, etc.
  Tetracycline resistance ribosomal protection proteins
  TetM, TetO, TetQ, Tet32, Tet36, etc.
Efflux Pumps Conferring Antibiotic Resistance:
  ABC antibiotic efflux pump
  MacAR-TolC, MsbA, MsrA, VgaB, etc.
  MFS antibiotic efflux pump
  EmrD, EmrAB-TolC, NorB, GepA, etc.
  Multidrug and toxic compound extrusion (MATE) transporter
  MepA
  Resistance-nodulation-cell division (RND) efflux pump
  AdeABC, AcrD, MexAB-OprM, mtrCDE, etc.
  Small multidrug resistance (SMR) antibiotic efflux pump
  EmrE
Genes Modulating Antibiotic Efflux:
  adeR, acrR, baeSR, mexR, phoPQ, mtrR
Multidrug Resistance:
  plasmid plP1202

In certain aspects, the disclosed methods the sample is obtained from a subject and the method further comprises administering at least one antibiotic to the subject.

In one aspect, the at least one antibiotic is a fluoroquinolone. Non-limiting fluoroquinolones for use as described herein include levofloxacin, ofloxacin, ciprofloxacin, enoxacin, gatifloxacin, gemifloxacin, grepafloxacin, besifloxacin, lomefloxacin, moxifloxacin, norfloxacin, ofloxacin, pefloxacin, sparfloxacin, garenoxacin, trovafloxacin, sitafloxacin, and DX-619.

In another aspect, the at least one antibiotic is an aminoglycoside such as amikacin, gentamycin, kanamycin, neomycin, netilmicin, paromomycin, streptomycin, or tobramycin.

In another aspect, the at least one antibiotic is a carbapenem such as ertapenem, imipenem, meropenem, or chloramphenicol.

In another aspect, the at least one antibiotic is a glycopeptide such as vancomycin.

In another aspect, the at least one antibiotic is a lincosamide such as clindamycin.

In another aspect, the at least one antibiotic is a macrolide/ketolide such as azithromycin, clarithromycin, dirithromycin, erythromycin, or telithromycin.

In another aspect, the at least one antibiotic is a cephalosporin such as (1st generation) cefadroxil, cefazolin, cephalexin, cephalothin, cephapirin, and cephradine; or (2nd generation) cefaclor, cefamandole, cefonicid, cefotetan, cefoxitin, cefprozil, cefuroxime, and loracarbef, or (3rd generation) cefdinir, cefditoren, cefixime, cefoperazone, cefotaxime, cefpodoxime, ceftazidime, ceftibuten, ceftizoxime, and ceftriaxone, or (4th generation) cefepime.

In another aspect, the at least one antibiotic is a monobactam such as aztreonam.

In another aspect, the at least one antibiotic is a nitroimidazole such as metronidazole.

In another aspect, the at least one antibiotic is an oxazolidinone such as linezolid.

In another aspect, the at least one antibiotic is a penicillin such as amoxicillin, amoxicillin/clavulanate, ampicillin, ampicillin/sulbactam, bacampicillin, carbenicillin, cloxacillin, dicloxacillin, methicillin, mezlocillin, nafcillin, oxacillin, penicillin G, penicillin V, piperacillin, piperacillin/tazobactam, ticarcillin, or ticarcillin/clavulanate.

In another aspect, the at least one antibiotic is a streptogramin such as quinupristin/dalfopristin.

In another aspect, the at least one antibiotic is a tetracycline such as demeclocycline, doxycycline, minocycline, or tetracycline.

In another aspect, the at least one antibiotic is a β-lactam such as a penicillin, cephalosporin, carbapenem, or monobactam.

The at least one antibiotic may be a physiologically acceptable salt, prodrug, or combination of any one of the aforementioned antibiotics.

The following examples are given for purely illustrative and non-limiting purposes of the present invention.

EXAMPLES

Example 1. Detecting the Presence of Nucleic Acids from *Burkholderia*

This protocol describes procedures for: (1) PCR amplification of multiplexed *Burkholderia* targets; (2) Index extension PCR to prepare amplicons for MiSeq (ILLUMINA® sequencer); (3) SequelPrep™ Normalization Plate Kit (ThermoFisher); and (4) Agencourt AMPure XP bead cleanup for PCR purification (Beckman Coulter).

Universal-tailed gene-specific primers are pooled together in a "primer mix" in amounts relative to each other to help reduce PCR bias. Make the primer mixture by combining the primers and 1×TE (e.g., according to Table 8). Vortex and spin down each primer stock. The primer mixture can be stored at −20° C. Plan and arrange the layout of where the samples will go on a 96-well plate. If clinical samples are being processed, make sure to space the samples on the plate accordingly. FIG. 11 can be used as an example clinical plate layout. Black wells are samples. Combine the following volumes of reagents as described in Table 10, except IPSC to create the *Burkholderia* Multiplex Master Mix. Reagents should be thawed and mixed before use. Vortexing PCR mastermix should be avoided to prevent damaging the enzymes in the mixture.

To prepare *Burkholderia* Multiplex, on experimental day, thaw out an aliquot of Internal Plasmid Sequencing Control (IPSC) at 10ˆ6 copies per uL, dilute down to 10ˆ3 copies per uL by three serial dilutions of 1 to 10. Make dilutions in tubes for better vortexing & spinning. For single reaction no-template control (NTC) reaction, add 12.5 μL Q5 2× HotStart, 5 μL 5M Betaine, and 4.5 μL Diluted Primer Mix. For single reaction, add 12.5 μL Q5 2× HotStart, 5 μL 5M Betaine, 1 μL IPSC 1000 copies per μL, and 4.5 μL Diluted Primer Mix. To prepare for Master Mix reaction, add 2475 μL Q5 2× HotStart, 990 μL 5M Betaine, 198 μL IPSC 1000 copies per μL, and 891 μL Diluted Primer.

Gently mix template DNA and spin down (Do not vortex genomic DNA). Add 2□L of template DNA to its appropriate well, along with 2□L $H_2O$ for IPSC, and 3□L $H_2O$ for NTC. Seal plate with a thermocycler seal. Spin down the plate. Using a heated lid, put plate on thermocycler and run the following parameters:

| Step | Repeats | Temperature (° C.) | Time |
|---|---|---|---|
| initial denaturation | 1 | 98 | 5 min |
| denaturation | 35 | 98 | 30 sec |
| annealing | | 68 | 15 sec |
| extension | | 72 | 20 sec |
| final extension | 1 | 72 | 2 min |
| cooling | 1 | 10 | forever |

Spin plates (*Burkholderia* target plate and *Bacillus, Yersinia, Francisella* target plate) down once the thermocycler finishes.

Prepare AMPure Beads. Prepare 10 mM Tris-HCl 0.05% Tween-20 in $H_2O$ by adding 400 μL 10 mM Tris-HCl, 20 μL 0.05% Tween-20, and 39.580 mL Molecular Grade $H_2O$, and heat to 50° C. Equilibrate the bead to Room Temperature for 30 minutes. Add beads in a 1:1 ratio with reaction volume to each well (30 μL) and mix well by pipetting. Incubate the bead/reaction mixture for 5 minutes. Place the 96-well plate onto a magnetic stand, incubate for another 5 minutes. Aspirate supernatant out of wells without disturbing the beads. If beads were disturbed, let them incubate for another 2 minutes. Be sure to remove as much liquid as you can. Twice wash the beads by adding 80% EtOH (32 ml 100% Ethanol, and 8 ml Molecular Grade $H_2O$) to completely cover beads (~200 μL) and incubate for 30 seconds. Aspirate. Fully remove liquids after the wash. Move plate off magnetic stand and allow beads to dry. Be sure to keep a close watch on the beads. If the beads start to crack, the DNA will be difficult to elute out. Move plate off the magnetic stand and add 32.54 heated 10 mM Tris-HCl 0.05% Tween-20 in $H_2O$ to the wells, mix well. Incubate for 2 minutes. Move plate to magnetic stand and incubate for 2 minutes. Remove 304 of supernatant and transfer it to a new well, do not disturb or transfer any beads.

*Burkholderia, Bacillus, Francisella*, and *Yersinia* AmpSeq amplicons require two bead cleanups before Extension PCR. Repeat steps 12-21.

Detecting the Presence of Nucleic Acids from *Bacillus anthracis, Yersinia*, and *Francisella* UT-AmpSeq PCR and Bead Cleanup.

1. PCR amplification of multiplexed *Bacillus*, *Yersinia*, and *Francisella* targets. Universal-tailed gene-specific primers are pooled together in a "primer mix" in amounts relative to each other to help reduce PCR bias. These amounts have been previously optimized. Please follow the Primer Mix parameters to create the needed mix for the multiplex currently in use.
2. Index extension PCR to prepare amplicons for MiSeq (ILLUMINA® sequencer). Enter the total number of samples in the box below. Primer Mix Parameters, # of Samples
3. SequelPrep™ Normalization Plate Kit (ThermoFisher).
4. Agencourt AMPure XP bead cleanup for PCR purification (Beckman Coulter).

Protocol

SOP for *Burkholderia* UT-AmpSeq PCR and Bead Cleanup
This SOP describes procedures for the following:
1. PCR amplification of multiplexed *Burkholderia* targets
2. Index extension PCR to prepare amplicons for MiSeq (ILLUMINA® sequencer)
3. SequelPrep™ Normalization Plate Kit (ThermoFisher)
4. Agencourt AMPure XP bead cleanup for PCR purification (Beckman Coulter)

Figure 11:
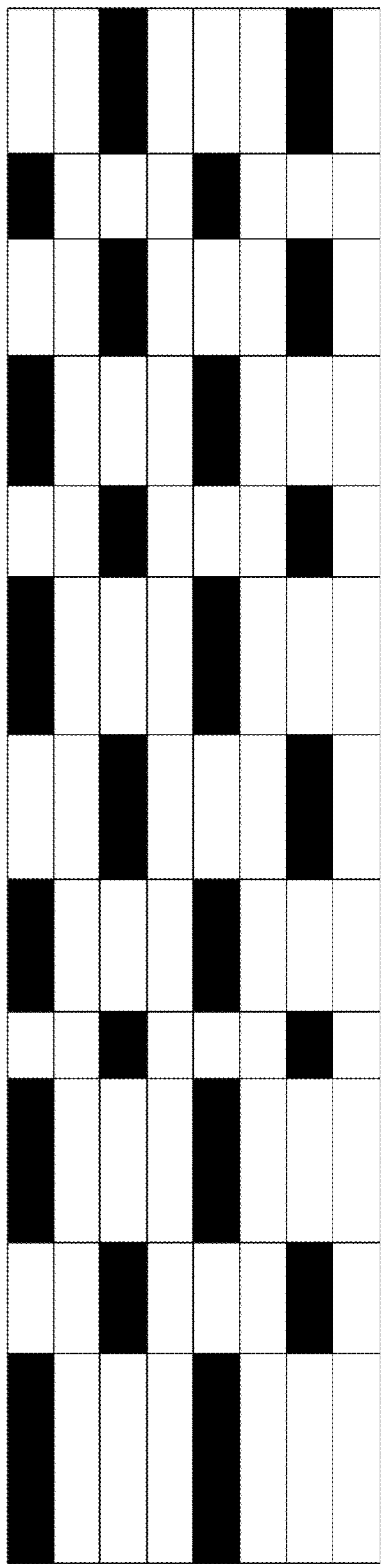

Steps and Procedures
1. Universal-tailed gene-specific primers are pooled together in a "primer mix" in amounts relative to each other to help reduce PCR bias. These amounts have been previously optimized.
Please follow the Primer Mix parameters to create the needed mix for the multiplex currently in use
2. Enter the total number of samples in the box below.
Primer Mix Parameters
# of Samples
180
ensure that all values in column K "How much starting primer conc. to add in mix stock" are above 2.0u1 and not highlighted in red
3a. Make the primer mixture by combining the following primers.
3b. Vortex and spin down each primer stock.
3c. Using the "Start (uM)" concentration primer stock of each primer, add the volume from "Amount to add (uL)" into a 1.7 mL microcentrifuge tube, unless "Total (uL)" at bottom of table is above 1200, then split volume evenly across necessary tubes. Vortex to mix and spin.
(Refer to Table 8)
4a. This mixture can be stored at −20° C. for future use. To use mixture, let thaw, vortex and spin down.
4b. If using mixture previously made, write down the initials of the person who made it and when: Initials _____ Date _____
5. Plan and arrange the layout of where your samples will go on a 96-well plate. If you are processing clinical samples make sure to space your samples on the plate accordingly. 6. Use the Plate Maps sheet for convenience and record keeping.
(Refer to FIG. 11).
6a. Reagents should be thawed and mixed before use. Avoid vortexing PCR mastermix as this can damage the enzymes in the mixture.
6b. Combine the following volumes of reagents as described in the following table except IPSC to create the *Burkholderia* Multiplex Master Mix

| *Burkholderia* Multiplex Reagent | uL for single reaction | uL addition in Master Mix |
|---|---|---|
| Q5 2x HotStart | 12.5 | 2475 |
| Betaine 5M | 5 | 990 |
| IPSC 1000 copies/uL | 1 | 198 |
| Diluted Primer Mix | 4.5 | 891 |
| | | 4554 |

6c. Add 22 uL of *Burkholderia* Multiplex Master Mix without IPSC to any NTC reactions you are processing
7a. Thaw out an aliquot of Internal Plasmid Sequencing Control (IPSC) at 10^6 copies per uL. Dilute this down to 10^3 copies/uL by three serial dilutions of 1 to 10. Make dilutions in tubes for better vortexing & spinning Make this fresh the day of.
7b. Add volume with the # of NTCs subtracted of 10^3 copies/uL IPSC to master mix. For example, if you had 3 NTCs that you had aliquoted master mix for, and the above table indicated 9 uL of IPSC be added, you would add 6 instead.
7d. Mix well and spin down
7e. Add 23 uL of Master Mix to each appropriate well on your plate
8a. Gently mix template DNA and spin down (Do not vortex genomic DNA)
8b. Add 2 uL of template DNA to its appropriate well, along with 2 uL $H_2O$ for IPSC, and 3 uL $H_2O$ for NTC
8c. Seal plate with a thermocycler seal
8d. Spin down plate
9. Using a heated lid, put plate on thermocycler and run the following parameters

| Step: | Reps: | Temp: | Time: |
|---|---|---|---|
| initial denaturation | 1 | 98 | 5 min |
| denaturation | 35 | 98 | 30 sec |
| annealing | | 68 | 15 sec |
| extension | | 72 | 20 sec |
| final extension | 1 | 72 | 2 min |
| cooling | 1 | 10 | forever |

10. During this time, take out AMPure Beads to equilibrate them to Room Temperature for 30 minutes and heat some 10 mM Tris-HCl 0.05% Tween-20 in $H_2O$ to 50 C.

| 10 mM Tris-HCl 0.05% Tween-20 in H2O Example Formula | |
|---|---|
| 10 mM Tris-HCl | 400 uL |
| 0.05% Tween-20 | 20 uL |
| Molecular Grade H2O | 39.580 mL |
| 80% Ethanol in H2O | |
| 100% Ethanol | 32 mL |
| MBG H2O | 8 mL |

11. Spin plates (*Burkholderia* target plate and *Bacillus, Yersinia, Francisella* target plate) down once the thermocycler finishes
12. Combine 15 uL of *Burkholderia* target reaction with 15 uL of *Bacillus, Yersinia, Francisella* target reaction
13. Add beads in a 1:1 ratio with reaction volume to each well (30 uL) and mix well by pipette
14. Incubate the bead/reaction mixture for 5 minutes 15. Place 96-well plate onto a magnetic stand, incubate for another 5 minutes
16. Aspirate supernatant out of wells without disturbing the beads. If beads ARE disturbed, let them incubate for another 2 minutes. Be sure to remove as much liquid as you can
17a. Add 80% EtOH to completely cover beads (~200 uL) and incubate for 30 seconds. Aspirate.
17b. Repeat 16a and remove as much liquid as you can (two washes total), following with a 20 uL pipette to ensure full removal
18. Move plate off magnetic stand and allow beads to dry. Be sure to keep a close watch on the beads. If the beads start to crack, the DNA will be harder to elute out.
19. Move plate off the magnetic stand and add 32.5 uL heated 10 mM Tris-HCl 0.05% Tween-20 in $H_2O$ to the wells, mix well
20. Incubate for 2 minutes
21. Move plate to magnetic stand and incubate for 2 minutes
22. Remove 30 uL of supernatant and transfer it to a new well, do not disturb or transfer any beads
22. *Burkholderia, Bacillus, Francisella*, and *Yersinia* AmpSeq amplicons require two bead cleanups before Extension PCR. Repeat steps 12-21
23. Store amplicons at −20 C Index Extension PCR
24. Thaw, gently mix, and spin down the following reagents in the following amounts for the Index Extension of the Target Amplicons
* Amounts are in respect to number of samples entered in Step 2

| Index Extension Master Mix Reagent | uL | Lot# |
|---|---|---|
| 2x Kapa Hifi | 2475 | |
| Betaine 5M | 990 | |
| Molecular Grade H2O | 693 | |

25. Combine the above volumes together, mix gently, and spin down.
26a. Each reaction will require a unique pair of index primers (UT1 and UT2), prepare a chart of what indexes will be used and where
26b. Thaw, vortex, and spin down the stock 10 uM aliquots of each index that will be used for this run
26c. If some tubes appear empty, create a new 10 uM aliquot of that index. Dilute in TE.
27. Once all indexes are accounted for, add 21 uL of Index Extension Master Mix to each appropriate well in a 96-well plate
28. Add 1 uL of each 10 uM index to its appropriate well
29a. After all UT1 and UT2 indexes have been added to their wells add 2 uL of CLEANED AMPLICONS
29b. The following should now be in each reaction well

| 12.5 uL | 2x Kapa Hifi |
|---|---|
| 3.5 uL | H2O |
| 5 uL | 5M Betaine |
| 2 uL | DNA |
| 1 uL | 10 uM UT1 |
| 1 uL | 10 uM UT2 |
| 25 uL | |

30. Seal the plate with a thermocycler seal
31. Spin down plate
32a. Using a heated lid, put plate on thermocycler and run the following parameters

| Step: | Reps: | Temp: | Time: |
|---|---|---|---|
| initial denaturation | 1 | 98 | 2 min |
| denaturation | 8 | 98 | 30 sec |
| annealing | | 60 | 20 sec |
| extension | | 72 | 30 sec |
| final extension | 1 | 72 | 2 min |
| cooling | 1 | 10 | forever |

32b. After the PCR has completed, spin down plate
33a. Samples will be cleaned and normalized using the Invitrogen SequalPrep system
33b. In a new plate, add equal amounts of illext DNA template and SequalPrep Normalization Binding Buffer
33c. Mix completely by pipette mixing several times, take care not to etch the sides of the well with the pipette tip
33d. Incubate the plate for 1 hour at room temperature to allow binding of DNA to the plate surface (longer than 1 hr is acceptable but will not increase binding or final elution concentration, can be overnight)
33e. Aspirate the liquid from the wells
33f. Add 50 uL Sequal Prep Normalization Wash Buffer, mix by pipetting up and down twice
33g. Completely aspirate the buffer, a small amount of residual Wash Buffer (1-3 uL) is typical
33h. Add 20 uL SequalPrep Normalization Elution Buffer to each well of the plate, mix by pipette
33i. Incubate at room temperature for 5 minutes
33j. Transfer samples to a new plate
34a. Samples should all be normalized now so pool them together in equal volumes
34b. The final DNA concentration will be fairly low, so perform an AMPure XP bead cleanup on the pool at a 1:1 ratio of pool to beads (be sure to note total volume of pooled samples)
34c. However, when eluting the DNA off the beads with heated Tris-Tween use ⅒ the initial pool volume used
35. Store DNA at −20 C SOP for *Bacillus, Yersinia*, and *Francisella* UT-AmpSeq PCR and Bead Cleanup
This SOP describes procedures for the following:
1. PCR amplification of multiplexed *Bacillus, Yersinia*, and *Francisella* targets
2. Index extension PCR to prepare amplicons for MiSeq (ILLUMINA® sequencer)
3. SequelPrep™ Normalization Plate Kit (ThermoFisher)
4. Agencourt AMPure XP bead cleanup for PCR purification (Beckman Coulter)

Steps and Procedures
1. Universal-tailed gene-specific primers are pooled together in a "primer mix" in amounts relative to each other to help reduce PCR bias. These amounts have been previously optimized.
Please Follow the Primer Mix Parameters to Create the Needed Mix for the Multiplex Currently in use
2. Enter the total number of samples in the box below.
Primer Mix Parameters
# of Samples
180
ensure that all values in column K "How much starting primer conc. to add in mix stock" are above 2.0u1 and not highlighted in red 3a. Make the primer mixture by combining the following primers.
3b. Vortex and spin down each primer stock.
3c. Using the "Start (uM)" concentration primer stock of each primer, add the volume from "Amount to add (uL)" into a 1.7 mL microcentrifuge tube, unless "Total (uL)" at bottom of table is above 1200, then split volume evenly across necessary tubes. Vortex to mix and spin.
(Refer to Table 10)
4a. This mixture can be stored at −20° C. for future use. To use mixture, let thaw, vortex and spin down.
4b. If using mixture previously made, write down the initials of the person who made it and when: Initials_____ Date_____
5. Plan and arrange the layout of where your samples will go on a 96-well plate. If you are processing clinical samples make sure to space your samples on the plate accordingly.
6. Use the Plate Maps sheet for convenience and record keeping.
(Refer to FIG. 11).
6a. Reagents should be thawed and mixed before use. Avoid vortexing PCR mastermix as this can damage the enzymes in the mixture.
6b. Combine the following volumes of reagents as described in the following table except IPSC to create the *Bacillus, Francisella*, and *Yersinia* Multiplex Master Mix

| *Bacillus, Francisella, Yersinia* Multiplex Reagent | uL for single reaction | uL addition in Master Mix |
| --- | --- | --- |
| Q5 2x HotStart | 12.5 | 2475 |
| H2O | 5 | 990 |
| IPSC 1000 copies/uL | 1 | 198 |
| Diluted Primer Mix | 4.5 | 891 |
|  |  | 4554 |

6c. Add 22 uL of *Burkholderia* Multiplex Master Mix without IPSC to any NTC reactions you are processing
7a. Thaw out an aliquot of Internal Plasmid Sequencing Control (IPSC) at 10^6 copies per uL. Dilute this down to 10^2 copies/uL by three serial dilutions of 1 to 10. Make dilutions in tubes for better vortexing & spinning Make this fresh the day of.
7b. Add volume with the # of NTCs subtracted of 10^2 copies/uL IPSC to master mix. For example, if you had 3 NTCs that you had aliquoted master mix for, and the above table indicated 9 uL of IPSC be added, you would add 6 instead.
7d. Mix well and spin down
7e. Add 23 uL of Master Mix to each appropriate well on your plate
8a. Gently mix template DNA and spin down (Do not vortex genomic DNA)
8b. Add 2 uL of template DNA to its appropriate well, along with 2 uL $H_2O$ for IPSC, and 3 uL $H_2O$ for NTC
8c. Seal plate with a thermocycler seal
8d. Spin down plate
9. Using a heated lid, put plate on thermocycler and run the following parameters

| Step: | Reps: | Temp: | Time: |
| --- | --- | --- | --- |
| initial denaturation | 1 | 98 | 5 min |
| denaturation | 35 | 98 | 30 sec |
| annealing |  | 55 | 15 sec |
| extension |  | 72 | 20 sec |
| final extension | 1 | 72 | 2 min |
| cooling | 1 | 10 | forever |

10. During this time, take out AMPure Beads to equilibrate them to Room Temperature for 30 minutes and heat some 10 mM Tris-HCl 0.05% Tween-20 in $H_2O$ to 50 C

| 10 mM Tris-HCl 0.05% Tween-20 in H2O Example Formula | |
| --- | --- |
| 10 mM Tris-HCl | 400 uL |
| 0.05% Tween-20 | 20 uL |
| Molecular Grade H2O | 39.580 mL |

| 80% Ethanol in H2O | |
| --- | --- |
| 100% Ethanol | 32 mL |
| MBG H2O | 8 mL |

11. Spin plates (*Burkholderia* target plate and *Bacillus, Yersinia, Francisella* target plate) down once the thermocycler finishes
12. Combine 15 uL of *Burkholderia* target reaction with 15 uL of *Bacillus, Yersinia, Francisella* target reaction
13. Add beads in a 1:1 ratio with reaction volume to each well (30 uL) and mix well by pipette
14. Incubate the bead/reaction mixture for 5 minutes
15. Place 96-well plate onto a magnetic stand, incubate for another 5 minutes
16. Aspirate supernatant out of wells without disturbing the beads. If beads ARE disturbed, let them incubate for another 2 minutes. Be sure to remove as much liquid as you can
17a. Add 80% EtOH to completely cover beads (~200 uL) and incubate for 30 seconds.
Aspirate.
17b. Repeat 16a and remove as much liquid as you can (two washes total), following with a 20 uL pipette to ensure full removal
18. Move plate off magnetic stand and allow beads to dry. Be sure to keep a close watch on the beads. If the beads start to crack, the DNA will be harder to elute out.
19. Move plate off the magnetic stand and add 32.5 uL heated 10 mM Tris-HCl 0.05% Tween-20 in $H_2O$ to the wells, mix well
20. Incubate for 2 minutes
21. Move plate to magnetic stand and incubate for 2 minutes
22. Remove 30 uL of supernatant and transfer it to a new well, do not disturb or transfer any beads
22. *Burkholderia, Bacillus, Francisella*, and *Yersinia* AmpSeq amplicons require two bead cleanups before Extension PCR. Repeat steps 12-21
23. Store amplicons at −20 C
Index Extension PCR
24. Thaw, gently mix, and spin down the following reagents in the following amounts for the Index Extension of the Target Amplicons
*Amounts are in respect to number of samples entered in Step 2

| Index Extension Master Mix Reagent | uL |
|---|---|
| 2x Kapa Hifi | 2475 |
| Betaine 5M | 990 |
| Molecular Grade H2O | 693 |
| | 4158 |
| Lot# | |

25. Combine the above volumes together, mix gently, and spin down.
26a. Each reaction will require a unique pair of index primers (UT1 and UT2), prepare a chart of what indexes will be used and where
26b. Thaw, vortex, and spin down the stock 10 uM aliquots of each index that will be used for this run
26c. If some tubes appear empty, create a new 10 uM aliquot of that index. Dilute in TE.
27. Once all indexes are accounted for, add 21 uL of Index Extension Master Mix to each appropriate well in a 96-well plate
28. Add 1 uL of each 10 uM index to its appropriate well
29a. After all UT1 and UT2 indexes have been added to their wells add 2 uL of CLEANED AMPLICONS
29b. The following should now be in each reaction well

| 12.5 uL | 2x Kapa Hifi |
| 3.5 uL | H2O |
| 5 uL | 5M Betaine |
| 2 uL | DNA |
| 1 uL | 10 uM UT1 |
| 1 uL | 10 uM UT2 |
| 25 uL | |

30. Seal the plate with a thermocycler seal
31. Spin down plate
32. Using a heated lid, put plate on thermocycler and run the following parameters

| Step: | Reps: | Temp: | Time: |
|---|---|---|---|
| initial denaturation | 1 | 98 | 2 min |
| denaturation | 8 | 98 | 30 sec |
| annealing | | 60 | 20 sec |
| extension | | 72 | 30 sec |
| final extension | 1 | 72 | 2 min |
| cooling | 1 | 10 | forever |

32b. After the PCR has completed, spin down plate
33a. Samples will be cleaned and normalized using the Invitrogen SequalPrep system
33b. In a new plate, add equal amounts of illext DNA template and SequalPrep Normalization Binding Buffer
33c. Mix completely by pipette mixing several times, take care not to etch the sides of the well with the pipette tip
33d. Incubate the plate for 1 hour at room temperature to allow binding of DNA to the plate surface (longer than 1 hr is acceptable but will not increase binding or final elution concentration, can be overnight)
33e. Aspirate the liquid from the wells
33f. Add 50 uL Sequal Prep Normalization Wash Buffer, mix by pipetting up and down twice
33g. Completely aspirate the buffer, a small amount of residual Wash Buffer (1-3 uL) is typical
33h. Add 20 uL SequalPrep Normalization Elution Buffer to each well of the plate, mix by pipette
33i. Incubate at room temperature for 5 minutes
33j. Transfer samples to a new plate
34a. Samples should all be normalized now so pool them together in equal volumes
34b. The final DNA concentration will be fairly low, so perform an AMPure XP bead cleanup on the pool at a 1:1 ratio of pool to beads (be sure to note total volume of pooled samples)
34c. However, when eluting the DNA off the beads with heated Tris-Tween use 1/10 the initial pool volume used
35. Store DNA at −20 C

*Burkholderia pseudomallei, Burkholderia mallei, Bacillus anthracis, Yersinia pestis* and *Francisella tularensis* are all Tier 1 select agents, posing a potentially severe threat to public health.[1]

Current surveillance methods rely upon single locus PCR techniques that allow for only presence/absence of SA results.

Has been known to lead to false positives, especially due to the complexity of environmental samples including huge numbers of microorganisms, many of which can be highly similar target pathogens.

Constantly working to develop technologies that significantly improve the identification of biological contaminants in varying sample types Both sequencing costs and sequencing time are decreasing.[2]

Targeted amplicon sequencing can provide the necessary information at a fraction of the cost of WGS.

Targeted amplicon sequencing can also provide a more manageable data set for researchers with less background in bioinformatics with an appropriate processing tool.

Summary

With the cost of sequencing decreasing and the ability to combine higher and higher numbers of samples on a single run, amplicon sequencing provides a cost effective alternative to individual PCR methods.

A screening panel of target organism strains as well as near neighbor strains allowed for differentiation with 100% sensitivity for all target agents and 91-100% specificity.

Future Directions

Limit of detection testing across a subset of target organisms in a pristine sample.

Limit of detection testing across a subset of target organisms in samples with environmental and human backgrounds.

Testing on other sequencing platforms.

REFERENCES

[1] Select Agents and Toxins Regulations. 42 C.F.R. Part 73.3 HHS Select Agents and Toxins

[2] Goodwin S, McPherson J D, McCombie W R. Coming of age: ten years of next-generation sequencing technologies. Nat Rev Genet. 2016

TABLE 1

| BTseq Loci Summary | | | | |
|---|---|---|---|---|
| | B. anthracis | B. pseudomallei/ mallei | F. tularensis | Y. pestis |
| Target Species Loci PA | 9 | 12* | 3 | 3 |
| NN Species Loci PA | 4 | 0 | 3 | 0 |
| NN Species Loci SNP/SV | 7 | 9 | 7 | 7 |
| AMR Loci | 6 | 4 | 0 | 3 |
| Virulence/Plasmid Loci | 4 | 0 | 0 | 2 |
| Total | 30 | 25 | 13 | 15 |

*Five loci amplify both Bp and Bm

TABLE 2

SNPs for detecting the presence of nucleic acids from *Bacillus anthracis*.

| LocusID | Ba_AmesAnc | | | | | | |
|---|---|---|---|---|---|---|---|
| | 1069024::91 | 1712462::85 | 3668548::88 | 371913::77 | 388555::108 | 3981642::97 | 4001578::113 |
| Reference | T | C | C | T | A | A | C |
| Ba_A0098_S45_L001 | T | C | C | T | A | A | C |
| Ba_A0330_S46_L001 | T | C | C | T | A | A | C |
| Ba_A0490_S47_L001 | T | C | C | T | A | A | C |
| Ba_A0605_S48_L001 | T | C | C | T | A | A | C |
| Ba_A0615_S49_L001 | T | C | C | T | A | A | C |
| Ba_A0706_S50_L001 | T | C | C | T | A | A | C |
| Ba_A071_S52_L001 | T | C | C | T | A | A | C |
| Ba_A072_S58_L001 | T | C | C | T | A | A | C |
| Ba_A073_S59_L001 | T | C | C | T | A | A | C |
| Ba_A074_S60_L001 | T | C | C | T | A | A | C |
| Ba_A0767_S51_L001 | T | C | C | T | A | A | C |
| Ba_A0847_S53_L001 | T | C | C | T | A | A | C |
| Ba_A1085_S54_L001 | T | C | C | T | A | A | C |
| Ba_A2010_S55_L001 | T | C | C | T | A | A | C |
| Ba_A2105_S56_L001 | T | C | C | T | A | A | C |
| Ba_A2175_S57_L001 | T | C | C | T | A | A | C |
| Ba_NN295171-grainy_S63_L001 | A | X | X | X | X | X | T |
| Ba_NN295171-smooth_S70_L001 | X | X | X | X | X | X | X |
| Ba_NN295618_S71_L001 | X | X | X | X | X | X | X |
| Ba_NNAI-hakem-grainy_S77_L001 | X | X | X | X | X | X | X |
| Ba_NNAI-hakem-smooth_S64_L001 | A | X | X | C | G | G | T |
| Ba_NNATCC10792_S62_L001 | A | X | X | C | G | G | T |
| Ba_NNATCC13402_S76_L001 | X | X | X | X | X | X | X |
| Ba_NNATCC31293_S74_L001 | X | X | X | X | X | X | T |
| Ba_NNBacillus-cereus_S69_L001 | X | X | X | X | X | X | X |
| Ba_NNBacillus-megaterium_S75_L001 | A | X | X | X | X | X | T |
| Ba_NNFRI33_S72_L001 | X | X | X | X | X | X | X |
| Ba_NNFRI35_S73_L001 | A | X | X | X | G | G | T |
| Ba_NNHD-1011_S93_L001 | A | X | T | C | G | G | T |
| Ba_NNHD-1012_S94_L001 | A | X | X | C | X | X | T |
| Ba_NNHD-1015_S61_L001 | A | X | X | X | X | G | T |
| Ba_NNHD-288_S81_L001 | A | X | X | C | G | G | T |
| Ba_NNHD-34_S78_L001 | X | X | X | X | X | X | T |
| Ba_NNHD-44-grainy_S79_L001 | X | X | X | C | X | G | T |
| Ba_NNHD-44-smooth_—S66_L001 | X | X | X | X | X | X | X |
| Ba_NNHD-47_S80_L001 | A | X | X | C | G | X | T |
| Ba_NNHD-526-grainy_S82_L001 | A | X | X | T | X | G | T |

TABLE 2-continued

SNPs for detecting the presence of nucleic acids from *Bacillus anthracis*.

| | | | | | | | |
|---|---|---|---|---|---|---|---|
| Ba_NNHD-526-smooth_—S67_L001 | A | T | X | C | G | G | T |
| Ba_NNHD-557_S83_L001 | X | X | X | X | X | X | T |
| Ba_NNHD-571-grainy_S84_L001 | A | X | T | C | G | G | T |
| Ba_NNHD-571-smooth_S65_L001 | A | X | T | C | G | G | T |
| Ba_NNHD-621_S85_L001 | X | X | X | X | X | X | T |
| Ba_NNHD-681_S86_L001 | A | X | X | X | G | X | T |
| Ba_NNHD-682_S87_L001 | X | X | X | X | X | X | X |
| Ba_NNHD-711_S88_L001 | X | X | X | X | X | X | X |
| Ba_NNHD-754_S89_L001 | A | X | X | X | X | X | T |
| Ba_NNHD-789_S90_L001 | X | X | X | X | X | X | X |
| Ba_NNHD-930_S91_L001 | A | X | X | X | G | X | T |
| Ba_NNHD-974-grainy_S92_L001 | A | X | X | X | G | G | T |
| Ba_NNHD-974-smooth_S68_L001 | A | X | X | X | G | G | T |
| Ba_NNNTC_Ba_1_S95_L001 | X | X | X | X | X | X | X |
| Ba_NNNTC_Ba_2_S96_L001 | X | X | X | X | X | X | X |
| F1057_S97_L001 | X | X | X | X | X | X | X |
| F1062_S98_L001 | X | X | X | X | X | X | X |
| NTC_Ft1_S99_L001 | X | X | X | X | X | X | X |
| NTC_Ft2_S100_L001 | X | X | X | X | X | X | X |
| NTC_Yp1_55_S104_L001 | X | X | X | X | X | X | X |
| NTC_Yp2_55_S105_L001 | X | X | X | X | X | X | C |
| NTC_Yp3_60_S109_L001 | X | X | X | X | X | X | C |
| NTC_Yp4_60_S110_L001 | X | X | X | X | X | X | C |
| NTC_Yp5_65_S114_L001 | X | X | X | X | X | X | C |
| NTC_Yp6_65_S115_L001 | X | X | X | X | X | X | C |
| Yp1763_55_S101_L001 | X | X | X | X | X | X | X |
| Yp1763_60_S106_L00 | X | X | X | X | X | X | X |
| Yp1763_65_S111_L001 | X | X | X | X | X | X | X |
| Yp2051_55_S102_L001 | X | X | X | X | X | X | X |
| Yp2051_60_S107_L001 | X | X | X | X | X | X | X |
| Yp2051_65_S112_L001 | X | X | X | X | X | X | X |
| Yp2126_55_S103_L001 | X | X | X | X | X | X | X |
| Yp2126_60_S108_L001 | X | X | X | X | X | X | X |
| Yp2126_65_S113_L001 | X | X | X | X | X | X | X |

| | Ba_AmesAnc | | | | |
|---|---|---|---|---|---|
| LocusID | 4087624::116 | 4669915::40 | 734209::105 | 999035::79 | plcR::147 |
| Reference | G | T | T | G | A |
| Ba_A0098_S45_L001 | G | T | T | G | A |
| Ba_A0330_S46_L001 | G | T | T | G | A |
| Ba_A0490_S47_L001 | G | T | T | G | A |
| Ba_A0605_S48_L001 | G | T | T | G | A |
| Ba_A0615_S49_L001 | G | T | T | G | A |
| Ba_A0706_S50_L001 | G | T | T | G | A |
| Ba_A071_S52_L001 | G | T | T | G | A |
| Ba_A072_S58_L001 | G | T | T | G | A |
| Ba_A073_S59_L001 | G | T | T | G | A |
| Ba_A074_S60_L001 | G | T | T | G | A |
| Ba_A0767_S51_L001 | G | T | T | G | A |
| Ba_A0847_S53_L001 | G | T | T | G | A |
| Ba_A1085_S54_L001 | G | T | T | G | A |
| Ba_A2010_S55_L001 | G | T | T | G | A |
| Ba_A2105_S56_L001 | G | T | T | G | A |
| Ba_A2175_S57_L001 | G | T | T | G | A |
| Ba_NN295171-grainy_S63_L001 | X | X | X | A | X |
| Ba_NN295171-smooth_S70_L001 | X | X | X | X | X |
| Ba_NN295618_S71_L001 | X | X | X | X | X |
| Ba_NNAI-hakem-grainy_S77_L001 | X | X | X | X | X |
| Ba_NNAI-hakem-smooth_S64_L001 | T | C | C | A | X |

TABLE 2-continued

SNPs for detecting the presence of nucleic acids from *Bacillus anthracis*.

| | | | | | |
|---|---|---|---|---|---|
| Ba_NNATCC10792_S62_L001 | T | C | C | A | C |
| Ba_NNATCC13402_S76_L001 | X | X | X | X | X |
| Ba_NNATCC31293_S74_L001 | X | X | X | X | X |
| Ba_NNB*acillus-cereus*_S69_L001 | X | X | X | X | X |
| Ba_NN*Bacillus-megaterium*_S75_L001 | X | X | X | X | X |
| Ba_NNFRI33_S72_L001 | X | X | X | X | X |
| Ba_NNFRI35_S73_L001 | T | C | X | A | C |
| Ba_NNHD-1011_S93_L001 | T | C | C | A | C |
| Ba_NNHD-1012_S94_L001 | T | C | X | A | C |
| Ba_NNHD-1015_S61_L001 | X | C | X | A | X |
| Ba_NNHD-288_S81_L001 | X | C | C | A | X |
| Ba_NNHD-34_S78_L001 | X | X | X | X | X |
| Ba_NNHD-44-grainy_S79_L001 | X | C | X | X | C |
| Ba_NNHD-44-smooth_—S66_L001 | X | X | X | X | X |
| Ba_NNHD-47_S80_L001 | X | C | X | A | X |
| Ba_NNHD-526-grainy_S82_L001 | X | C | X | X | A |
| Ba_NNHD-526-smooth_—S67_L001 | T | C | X | A | X |
| Ba_NNHD-557_S83_L001 | X | X | X | X | X |
| Ba_NNHD-571-grainy_S84_L001 | T | C | C | A | C |
| Ba_NNHD-571-smooth_S65_L001 | T | C | C | A | C |
| Ba_NNHD-621_S85_L001 | X | X | X | X | X |
| Ba_NNHD-681_S86_L001 | X | C | X | A | X |
| Ba_NNHD-682_S87_L001 | X | X | X | X | X |
| Ba_NNHD-711_S88_L001 | X | X | X | X | X |
| Ba_NNHD-754_S89_L001 | X | C | X | A | X |
| Ba_NNHD-789_S90_L001 | X | X | X | X | X |
| Ba_NNHD-930_S91_L001 | X | C | X | A | X |
| Ba_NNHD-974-grainy_S92_L001 | X | C | X | X | X |
| Ba_NNHD-974-smooth_S68_L001 | X | C | X | X | X |
| Ba_NNNTC_Ba_1_S95_L001 | X | X | X | X | X |
| Ba_NNNTC_Ba_2_S96_L001 | X | X | X | X | X |
| F1057_S97_L001 | X | X | X | X | X |
| F1062_S98_L001 | X | X | X | X | X |
| NTC_Ft1_S99_L001 | X | X | X | X | X |
| NTC_Ft2_S100_L001 | X | X | X | X | X |
| NTC_Yp1_55_S104_L001 | X | X | X | X | X |
| NTC_Yp2_55_S105_L001 | X | X | X | X | A |
| NTC_Yp3_60_S109_L001 | X | X | X | X | X |
| NTC_Yp4_60_S110_L001 | X | X | X | X | A |
| NTC_Yp5_65_S114_L001 | X | X | X | X | X |
| NTC_Yp6_65_S115_L001 | X | X | X | X | A |
| Yp1763_55_S101_L001 | X | X | X | X | X |
| Yp1763_60_S106_L00 | X | X | X | X | X |
| Yp1763_65_S111_L001 | X | X | X | X | X |
| Yp2051_55_S102_L001 | X | X | X | X | X |
| Yp2051_60_S107_L001 | X | X | X | X | X |
| Yp2051_65_S112_L001 | X | X | X | X | X |
| Yp2126_55_S103_L001 | X | X | X | X | X |
| Yp2126_60_S108_L001 | X | X | X | X | X |
| Yp2126_65_S113_L001 | X | X | X | X | X |

TABLE 3

Primers for detecting the presence of nucleic acids from *Bacillus anthracis*.

| Assay name | Assay Type | Target species/gene | | primer name | sequence (5' -> 3') | SEQ ID NO |
|---|---|---|---|---|---|---|
| CP008853.1_5309 | PA | *B. anthracis* | F | Ba-specific-3F_UT1 | ACGTCAGGTGATTATTGGAC | 1 |
| | | | R | Ba-specific-3R_UT2 | CAACAATTATATCCGCCATT | 2 |
| CP008853.1_5316 | PA | *B. anthracis* | F | Ba-specific-5F_UT1 | GAAGATGTACGCTCGATAGG | 3 |
| | | | R | Ba-specific-5R_UT2 | GAAATTCTTTTTGCCATCAC | 4 |
| CP012725.1_3629 | PA | *B. anthracis* | F | Ba-specific-6F_UT1 | CACAATTGAATGAAAATGCT | 5 |
| | | | R | Ba-specific-6R_UT2 | CACGAAACCTGTTTACCTTT | 6 |
| CP012725.1_5103 | PA | *B. anthracis* | F | Ba-specific-8F_UT1 | GATATTCGACGAGCTTTCTG | 7 |
| | | | R | Ba-specific-8R_UT2 | TATTCATCGTCATCCTCCTC | 8 |
| CP012725.1_5107 | PA | *B. anthracis* | F | Ba-specific-9F_UT1 | TATTGAACGCATTGAATCAG | 9 |
| | | | R | Ba-specific-9R_UT2 | TATTGGTAAGCAAACCGTCT | 10 |
| JSZQ01000034.1_220 | PA | *B. anthracis* | F | Ba-specific-11F_UT1 | GGTTCAGGACAAAATGTAGC | 11 |
| | | | R | Ba-specific-11R_UT2 | TAACTTCTGAAGCGAAAACC | 12 |
| JSZS01000036.1_5 | PA | *B. anthracis* | F | Ba-specific-12F_UT1 | GCGAATTTTAGACGACAATC | 13 |
| | | | R | Ba-specific-12R_UT2 | TAACCGTGCTTAATTCGTTT | 14 |
| LGCC01000010.1_232 | PA | *B. anthracis* | F | Ba-specific-14F_UT1 | ATTAATAAGGCGACTGGTGA | 15 |
| | | | R | Ba-specific-14R_UT2 | TTACCCATCCAGAATGAGAC | 16 |
| LGCC01000048.1_280 | PA | *B. anthracis* | F | Ba-specific-16F_UT1 | ACAATTCTTAAAAGGCGACA | 17 |
| | | | R | Ba-specific-16R_UT2 | TGTAGCGTCTCCGATATTTT | 18 |
| NN_LOMU01000090.1_49 | PA | near neighbor species | F | Ba-specific-20F_UT1 | CATGGGGCTTTCTATTATGT | 19 |
| | | | R | Ba-specific-20R_UT2 | TTCGTTCTTTCATAAGTTTCCT | 20 |
| NN_LOQC01000013.1_3 | PA | near neighbor species | F | Ba-specific-22F_UT1 | TTGGAGTTTGTTTTGCTTTT | 21 |
| | | | R | Ba-specific-22Rv2_UT2 | GTAACAATTAATCCACGTCCT | 22 |
| ChimpKiller_9-159 | PA | *B. cereus* spp. *anthracis* | F | ChimpKiller_9F | TTATCGTCCATTCTTTCGTC | 23 |
| | | | R | ChimpKiller_159R | AAACCTAATGAAACGGGATT | 24 |
| ChimpKiller_91-320 | SV | *B. cereus* spp. *anthracis* | F | ChimpKiller_91F | TATGAAAGGAGCCGTAAAAC | 25 |
| | | | R | ChimpKiller_320R | TGAATATGAAGCGGAAAACT | 26 |
| ChimpKiller_481-698 | SV | *B. cereus* spp. *anthracis* | F | ChimpKiller_481F | TCGAACATACCTCCATTTCT | 27 |
| | | | R | ChimpKiller_698R | AAAGATAGCTTTGCACTTGG | 28 |
| plcR | PA | Virulence locus plcR | F | Ba-specific-1F_UT1 | TTTTTCGTAAGCATCTTCAA | 29 |
| | | | R | Ba-specific-1R_UT2 | TTTGATGTGAAGGTGAGACA | 30 |
| pagA | PA | Virulence locus pagA | F | 801F_pagAv3_UT1 | GGTTACAGGACGGATTGATA | 31 |
| | | | R | 1042R_pagAv3_UT2 | TCCCACCAATATCAAAGAAC | 32 |
| pX01 | PA | Virulence plasmid | F | pX01_113F_UT1 | TGAGCCTACCTAGTGATTGG | 33 |
| pX01 | | | R | pX01-315Rv2_UT2 | TTGGATAAATTCCACAAATTCCTC | 34 |
| pX02 | PA | Virulence plasmid pX02 | F | pX02_101F_UT1 | CGCCAGCGTATTATATAGGT | 35 |
| | | | R | pX02_269R_UT2 | GCTAATTCTGGGTTGTGTTT | 36 |
| gyrA | SNP | Drug resistance SNP gyrA | F | gyrA_28Fv2_UT1 | TCGGTAAGTATCACCCTCA | 37 |
| | | | R | gyrA_182Ry2_UT2 | TGCTTCTGTATAACGCATT | 38 |
| parC | SNP | Drug resistance SNP parC | F | parC_1F_UT1 | CAGTCGGTAACGTTATTGGT | 39 |
| | | | R | parC_197R_UT2 | TAACTCAGATGCAATTGGTG | 40 |
| gyrB | SNP | Drug resistance SNP gyrB | F | gyrB_8F_UT1 | ATTGTAGAGGGTGACTCTGC | 41 |
| | | | R | gyrB_194R_UT2 | TATCAAAATCTCCGCCAAT | 42 |
| rpoB | SNP | Drug resistance SNP rpoB | F | rpoB_29F_UT1 | TTCTTCGGAAGTTCTCAGTT | 43 |
| | | | R | rpoB_196R_UT2 | CGGACACATACGACCATAG | 44 |
| AA_2502 | SNP | Drug resistance SNP | F | AA_2502_UT1 | AAGTTTGAGGTGTGGAAATG | 45 |
| | | | R | AA_2502_UT2 | TCGAAATGAGTTCCAATTTT | 46 |
| AA_2503 | SNP | Drug resistance SNP | F | AA_2503v2_UT1 | CAAAACTAATAGGGGAGGGTG | 47 |
| | | | R | AA_2503_UT2 | CCGAGAACCTACCTCGTTA | 48 |

TABLE 3-continued

Primers for detecting the presence of nucleic acids from *Bacillus anthracis*.

| Assay name | Assay Type | Target species/gene | primer name | sequence (5' -> 3') | SEQ ID NO |
|---|---|---|---|---|---|
| Ba_AmesAnc_4669915 | SV | near neighbor species | F Ba&NN32_F | AGGAGATGAGAGTTTTGCAC | 49 |
| | | | R Ba&NN32_R | ACCCCCATAATTACCATGA | 50 |
| Ba_AmesAnc_4001578 | SV | near neighbor species | F Ba&NN33_F | CGTTGCGTAAGTATGTGCTA | 51 |
| | | | R Ba&NN33_R | AGGTGGCGTAATTAACGTAG | 52 |
| Ba_AmesAnc_1069024 | SV | near neighbor species | F Ba&NN37_F | CGAAAAGTTGTCGACCTAAT | 53 |
| | | | R Ba&NN37_R | ACTGCGTTCACGAAGAATAG | 54 |
| Ba_AmesAnc_3668548 | SV | near neighbor species | F Ba&NN38_F | TCTCTTGATTCAACGTTTCC | 55 |
| | | | R Ba&NN38_R | GATGCAAAACCAATTCACTT | 56 |
| Ba_AmesAnc_371913 | SV | near neighbor species | F Ba&NN40_F | GTGAAACATCGCTTTTTAGG | 57 |
| | | | R Ba&NN40_R | TCCGCAATGATATACTTCAA | 58 |
| Ba_AmesAnc_999035 | SV | near neighbor species | F Ba&NN41_F | ATACGGTGAAAATGAAGCAG | 59 |
| | | | R Ba&NN41_R | CGTCTTTGGTAATCGTTCA | 60 |

TABLE 4

Primers for detecting the presence of nucleic acids from *Burkholderia*.

| Assay name | Assay Type | Target species/gene | primer name | sequence (5' -> 3') | SEQ ID NO: |
|---|---|---|---|---|---|
| TTS1_BPSS1407 | PA | TTS1 | F BpAmpSeq_1_F | TCGTCGTCACCGGGATGGTC | 61 |
| | | | R BpAmpSeq_1_R | GGCCTTTGCCCGCATACTCG | 62 |
| LXCC01000141.1_39296_39817 | PA | *B. pseudomallei* | F BpAmpSeq_3_F | TCGCAWGAAGTGCGTTGCCG | 63 |
| | | | R BpAmpSeq_3_R | GCCGCTTGCGAAGCGATGAT | 64 |
| LXBY01000087.1_75760_76751 | PA | *B. pseudomallei* | F BpAmpSeq_4_F | CGCGCTTGCCCAACTACCAG | 65 |
| | | | R BpAmpSeq_4_R | GCGCAACGGTGCGAGACAAT | 66 |
| LXCD01000002.1_99652_100245 | PA | *B. pseudomallei* | F BpAmpSeq_5_F | AATCCATGCATGTCGYGCCC | 67 |
| | | | R BpAmpSeq_5_R | GCGATCGCTCAACGGGCTTC | 68 |
| LXCE01000123.1_34220_34747 | PA | *B. pseudomallei* | F BpAmpSeq_6_F | TCGCATTTGCAYACGCTCCC | 69 |
| | | | R BpAmpSeq_6_R | AGTGCGCAAACTTGGCGAGG | 70 |
| BpCEN586498 | PA | *pseudomallei* | F BpCEN586498_F102 | CACCGAAAGATTTCAGTTCCGCCTCATTCA | 71 |
| | | | R BpCEN586498_R388 | GGCCGTCGATGGTTTCGTCGGTTTTC | 72 |
| BpCEN617822 | PA | *pseudomallei* | F BpCEN617822_F43 | TGCATTGAGCACGGCACGCAGATTC | 73 |
| | | | R BpCEN617822_R260 | GAAAAATTTATCGGATCGAGCACCATGGTTTG | 74 |
| BpCEN972235 | PA | *pseudomallei* | F BpCEN972235_F107 | ATACGCGGCGCGGCTCATTTCG | 75 |
| | | | R BpCEN972235_R305 | GCGTCGCGCTCGTCGATACGGTCA | 76 |
| BpCEN70178 | PA | *pseudomallei* | F BpCEN70178-2F | TGCGCAGCGAGTGGTTCAGGTTGTC | 77 |
| | | | R BpCEN70178-182R | CGACGATACGGATACGGCACGGAAGC | 78 |

TABLE 4-continued

Primers for detecting the presence of nucleic acids from *Burkholderia*.

| Assay name | Assay Type | Target species/ gene | primer name | sequence (5' -> 3') | SEQ ID NO: |
|---|---|---|---|---|---|
| BpCEN508364 | PA | *pseudomallei* | F UT1-BpCEN508364_F37 | CCGCGCCGGCCGCAGACC | 79 |
| | | | R UT2-BpCEN508364_R184 | CGGGCGTGCCGGACTCCTCGTC | 80 |
| LWWC01000187.1_18 | PA | *B. pseudomallei mallei* | F BpAmpSeq_8_F | CCTTTGCGGCAAGCGTCGAA | 81 |
| | | | R BpAmpSeq_8_R | GAGCCAACGCACATGGACGG | 82 |
| LWWB01000125.1_17183_17602 | PA | *B. pseudomallei mallei* | F BpAmpSeq_10_F | CCAGTCGGGCCGGGAAAAAC | 83 |
| | | | R BpAmpSeq_10_R | GGCGGCAAAAGCGTCGATGA | 84 |
| LXAY01000367.1_0_640 | PA | *B. pseudomallei mallei* | F BpAmpSeq_11_F | GCCGGAACCGTCGAGCATTG | 85 |
| | | | R BpAmpSeq_11_R | TGGATTCGACTGCCTCCGCT | 86 |
| LWVY01000190.1_17226_17689 | PA | *B. pseudomallei mallei* | F BpAmpSeq_12_F | TCGATATCCGCCGTCTCGCC | 87 |
| | | | R BpAmpSeq_1_R | ATGTGTCGGTGGGCTTCGGT | 88 |
| LXAD01000059.1_24760_25075 | PA | *B. pseudomallei mallei* | F BpAmpSeq_13_F | GAAAGGCGATGTGCCGAGCG | 89 |
| | | | R BpAmpSeq_13_R | TTCGGAGAAGCGCCAAACGC | 90 |
| BpmCEN322640 | PA | *pseudomallei/mallei* | F BpCEN322640_F2 | CGCGGACAGCATCGATTACGTGAATC | 91 |
| | | | R BpCEN32264_R2 | CCGCCGAATCCGATGCTCAATTTC | 92 |
| BpmCEN1761486 | PA | *pseudomallei/mallei* | F BpmCEN1761486_F1 | GACCTGCAGCAGGTATTCGACATTATCGTTC | 93 |
| | | | R BpCEN1761486_R1 | AGCTTCGCATACAGCACTTCCGCCAG | 94 |
| BpmCEN1235988 | PA | *pseudomallei/mallei* | F BpmCEN1235988_F1 | GCGCTGCCCGTTTCACCACTGG | 95 |
| | | | R BpmCEN1235988_R1 | CGTGACGCCGTCGGGAAAGATCATC | 96 |
| BpmCEN1565214 | PA | *pseudomallei/mallei* | F BpmCEN1565214_F1 | CTGACCGAACGATGGCTGGAGATACATGC | 97 |
| | | | R BpmCEN1565214_R1 | CAAATGGGAAGCGAGCTCCCTTCCGA | 98 |
| BpmCEN276339-1 | PA | *pseudomallei/mallei* | F BpmCEN276339-1_F1 | CGGACGCCTGTCGCCCGAAACCTAT | 99 |
| | | | R BpmCEN276339-1_R1 | CGCGAGCACGCCGAGCGACAT | 100 |
| BpmCEN276339-2 | PA | *pseudomallei/mallei* | F BpmCEN276339-2_F1 | CGTCGACGCCCCGGGCTTTCTG | 101 |
| | | | R BpmCEN276339-2_R1 | CGCCGCGCACCGGTTTCAATC | 102 |
| BpmCEN894337 | PA | *pseudomallei/mallei* | F BpmCEN894337_F_1 | CGAAAATAATTTTCGGCCGGCGCAC | 103 |
| | | | R BpmCEN894337_R1 | CGACAGGCATCGGGCGACTACTACCAG | 104 |
| BpmCEN1722622 | PA | *pseudomallei/mallei* | F UT2-Bpm_CEN1722622-f1 | CAACGGGCGAGTTTGCAACGGAATC | 105 |
| | | | R UT1-Bpm_CEN1722622-1-1 | GCCGGCTTGGCTTCGTCCTTGTC | 106 |
| BpmCEN357268 | PA | *pseudomallei/mallei* | F UT1-Bpm_CEN357268-f1 | CGGCATGCGCGGCCGAATC | 107 |
| | | | R UT2-Bpm_CEN357268-r1 | ATCGCGCCCTGCAGCGAGCAC | 108 |

TABLE 4-continued

Primers for detecting the presence of nucleic acids from *Burkholderia*.

| Assay name | Assay Type | Target species/ gene | primer name | sequence (5' -

TABLE 4-continued

Primers for detecting the presence of nucleic acids from *Burkholderia*.

| Assay name | Assay Type | Target species/ gene | primer name | sequence (5' -> 3') | SEQ ID NO: |
|---|---|---|---|---|---|
| penA_P167S | SNP | penA | F K9penA881fUT1 | GCTGTGCGCGGCGACG CTTCAGTA | 137 |
| | | | R K9penA1258rUT2 | CCGATGTCGTTCGCCG TTCCGTAGTC | 138 |
| PBP3-170f-505r | PA | penA | F PBP3-170f3UT1 | ATCCGCCGTCCCGCCC AGCAATAG | 139 |
| | | | R PBP3-505r3UT2 | GGGTTCGCCCAGATTT CGTAGGTGGTGAG | 140 |
| pbp3-1 | PA | pbp3 | F K9pbp336fUT1 | TCGCCGTTTCACGCCC CGCAAC | 141 |
| | | | R K9PBP3331rUT2 | GCGCCGAACGCGAGG AACACGA | 142 |
| pbp3-2 | PA | pbp3 | F K9pbp31292fUT1 | GCTCGCGAAGCTCGCG CTGAACC | 143 |
| | | | R K9PBP31527rUT2 | GGATCGTGCCGTCGCC CGCATAC | 144 |
| V15G_R20 | SV | folM pteredine reductase | F 1026pter371fU | ACAAGCCCGGYGTCGTCG AGATGGTGAC | 145 |
| | | | R 1026pter636rUT2 | CGCGTCGGCCGAAYG GTCGTAGT | 146 |
| bpeT HTH | SV | bpeT HTH region | F bpeT_-76fUT1 | AATCGTCGGCTGCGTC GCCTTCA | 147 |
| | | | R bpeT_596rUT2 | CGGGTAGCGTGAGTG GAATTCGCAGAG | 148 |
| bpeT substrate binding | SV | bpeT substrate binding region | F bpeT_695fUT1 | CCTCGAAGGCTTCGGG CTGATCCAG | 149 |
| | | | R bpeT_1014rUT2 | GACTAACCGCTTACGC CACCCACTCGTTC | 150 |
| bpeS HTH | SV | bpeS HTH region | F bpeS_-83fUT1 | AAAGCGAATAGTCGC GAAGCGGCTTGA | 151 |
| | | | R bpeS_230rUT2 | GCGATCTCGGTGATGA TCTTGATGCAGTG | 152 |
| bpeS substrate binding | SV | bpeS substrate binding region | F bpeS_648fUT1 | AACGGCGGCGTGACC GTCAACG | 153 |
| | | | R bpeS_977rUT2 | CGCTACGCGGCCACCT GCCC | 154 |
| bimA | PA | bimA | F Bpvir_bimA_407F | CGGAGCTTCAGAACA ACCCGCGTGTAAC | 155 |
| | | | R Bpvir_bimA_654R | CCTTCGGACCTTTTCC CGCAACTGGC | 156 |
| cheD | PA | cheD | F Bpvir_cheD_29F | AATTCGGCCGGCAGGC GGTACG | 157 |
| | | | R Bpvir_cheD_297R | CGCGCGCAGCCGGCAT TTG | 158 |
| fhaB1long | PA | fhaB1long | F Bpvir_fhaB1long_8410F | CCCTTCGGTCCCCACC AGAAAAATTCG | 159 |
| | | | R Bpvir_fhaB1long_8599R | AGCCGTACAGGCCAAT GCAGCCATCTATG | 160 |
| fhaB1short | PA | fhaB1short | F Bpvir_fhaB1short_63F | GCGCCGCGTGTTCGTG ACCTTGTC | 161 |
| | | | R Bpvir_fhaB1short_316R | CGCTGATCGGCGCATC GGACAC | 162 |
| fhaB2 | PA | fhaB2 | F Bpvir_fhaB2_1812F | ATCGTGATATCGCCGG TTCCTGGTTGTG | 163 |
| | | | R Bpvir_fhaB2_2100R | CACGTTTGGCGGCAGT GCAAGGTGTAG | 164 |

TABLE 4-continued

Primers for detecting the presence of nucleic acids from *Burkholderia*.

| Assay name | Assay Type | Target species/ gene | primer name | sequence (5' -> 3') | SEQ ID NO: |
|---|---|---|---|---|---|
| fhaB3 | PA | fhaB3 | F Bpvir_fhaB3_3966F | TCTGCTGATCGGCCTTCGCCAGATAYAC | 165 |
| | | | R Bpvir_fhaB3_4324R | GCGGATGAACAATTTCCTGTCGAGCGACTATTAC | 166 |
| LPSA | PA | LPSA | F Bpvir_LPSA_1087F | GCAGGGCGCCTTGATATCCGCTATGAG | 167 |
| | | | R Bpvir_LPSA_1407R | CGGCGCAAGGTTCTCCTGCCACATC | 168 |
| LPSb1 | PA | LPSb1 | F Bpvir_LP_Sb1_65F | GTGTGATCGACKGCGTCCTCCCTGAG | 169 |
| | | | R Bpvir_LPSb1_256R | CAAGCCGCTGATACCCGTGTCGCTG | 170 |
| LPSb2 | PA | LPSb2 | F Bpvir_LPSb2_88F | GCGCTTCTCGGTGGGTACGAAAAACAGC | 171 |
| | | | R Bpvir_LPSb2_400R | CGAGTCGGCCAAGATCATTCAGGACCAG | 172 |
| wcbj | PA | wcbj | F Bpvir_wcbj_252F | CACCTTGACACTGATCCGCGGCGTAG | 173 |
| | | | R Bpvir_wcbj_508R | CTTCCTTCGCACAACCGAGCAAATACTGAGTAAATC | 174 |
| ylf | PA | ylf | F Bpvir_ylf_865F | GATCTTGCGACCGATGCTCAGCGTGTG | 175 |
| | | | R Bpvir_ylf_1153R | TGGCGCGGGCCAAGGATATCAGTTC | 176 |
| thai_small_15666 | PA | *thailandensis* (small clade) | F thai_small_15666_3F_UT1 | GCCTTACGCCTTCGGGATCG | 177 |
| | | | R thai_small_15666_342R_UT2 | GAATGCGCTCACCCGATGCT | 178 |
| thai_small_28301 | PA | *thailandensis* (small clade) | F thai_small_28301_11F_UT1 | AGCAAGCCATCCGCGTCATC | 179 |
| | | | R thai_small_28301_297R_UT2 | CAGGATGCCACCGTTGGTGA | 180 |
| thai_large_48054 | PA | *thailandensis* (large clade) | F thai_large_48054_286F | GCCACAGGCATGGTGAGCAA | 181 |
| | | | R thai_large_48054_534R | CGGCATTCCCTCAATCACGAA | 182 |
| thai_all_110625 | PA | *thailandensis* | F thai_all_110625_212F | CTGCGTCCCAAACCGACGA | 183 |
| | | | R thai_all_110625_512R | CCGTCGATGCCACGAATGAA | 184 |
| humpty_7099 | PA | *humptydooensis* | F humpty_7099_510F | CCCCAAAAATCCCGCTCTGG | 185 |
| | | | R humpty_7099_762R | CGGCACAAAGCCGGTGAAAG | 186 |
| humpty_45647 | PA | *humptydooensis* | F HUMPTY_45647_173F_UT1 | TGCCGTTCAGTTGGGCCTTT | 187 |
| | | | R HUMPTY_45647_390R_UT2 | TGCCGCTTCCAACTGCTTCA | 188 |
| humpty_7093 | PA | *humptydooensis* | F HUMPTY_7093_48F_UT1 | GGGCGGGCCAATCTTTTCTG | 189 |
| | | | R HUMPTY_7093_381R_UT2 | TCCGCGATGTGACCAAACGA | 190 |
| humpty_38764 | PA | *humptydooensis* | F humpty_38764_44F | TCGGAGATTCCGACGGACCA | 191 |
| | | | R humpty_38764_390R | CCGCATATCGCCCTGACACA | 192 |

TABLE 4-continued

Primers for detecting the presence of nucleic acids from *Burkholderia*.

| Assay name | Assay Type | Target species/ gene | | primer name | sequence (5' -> 3') | SEQ ID NO: |
|---|---|---|---|---|---|---|
| okla_24632 | PA | *oklahomensis* | F | OK_24632_724F_UT1 | GGCACCGACGTGCAAAAAGC | 193 |
| | | | R | OK_24632_996R_UT2 | GGCCGATCTCGGCACTACGA | 194 |
| okla_5812 | PA | *oklahomensis* | F | okla_5812_382F | GCGGGGTACGGGCTAACCAA | 195 |
| | | | R | okla_5812_700R | TCCGTACGCTCGCCACAACA | 196 |
| okla_3784 | PA | *oklahomensis* | F | okla_3784_454F | GCAAAGGCGCCAGGAAACAA | 197 |
| | | | R | okla_3784_742R | ACCGCCCCGATTGACCAAGT | 198 |
| okla_like_18345 | PA | *oklahomensis*-like | F | OK_like_18345_56F_UT1 | TCCAGGCGGTTCTCCGATTG | 199 |
| | | | R | OK_like_18345_372R_UT2 | GTTGCCGATGTCGAGGCACA | 200 |
| okla_like_18342 | PA | *oklahomensis*-like | F | OK_like_18342_361F_UT1 | TCTTCGGCGAGCGTCTACGG | 201 |
| | | | R | OK_like_18342_685R_UT2 | CGCGTCGGACGAGTGTCGTA | 202 |
| MSMB175_14005 | PA | MSMB175 group | F | MSMB175_14005_422F | GGCTCACACGGCTGGGTCAT | 203 |
| | | | R | MSMB175_14005_746R | ACGGCGTTTGGACCACGAG | 204 |
| MSMB175_1868 | PA | MSMB175 group | F | MSMB175_1868_197F_UT1 | CCGCCTACTGGTGGCAGGTG | 205 |
| | | | R | MSMB175_1868_480R_UT2 | GCCAGTCCCGGGAAGGAGTG | 206 |
| MSMB175_8900 | PA | MSMB175 group | F | MSMB175_8900_29F_UT1 | GCTCATCCTGCCAGGCCAGT | 207 |
| | | | R | MSMB175_8900_345R_UT2 | GATACCCACCGCCGGAACCT | 208 |
| MSMB175_9798 | PA | MSMB175 group | F | MSMB175_9798_517F_UT1 | AGCGGCGGATTATGGGCACT | 209 |
| | | | R | MSMB175_9798_782R_UT2 | ACGCTGGGGCTGTTTTGCAG | 210 |
| MSMB264_34074 | PA | MSMB264 group | F | MSMB264_34074_554F | CGCCCTTCGAGCTTGCTTCC | 211 |
| | | | R | MSMB264_34074_778R | CCGCAACAGGTGGCTTCTGAC | 212 |
| MSMB264_4163 | PA | MSMB264 group | F | MSMB264_4163_252F | CGTTGCCCCCGCCCACGTAG | 213 |
| | | | R | MSMB264_4163_596R | CCGTGTGGCGCGTCCTCCAT | 214 |
| vietnam_61292 | PA | *vietnamiensis* | F | vietnam_61292_183F | TGGGCTCATCCTCGCAAAGC | 215 |
| | | | R | vietnam_61292_527R | ACGCGCTCGGTGGAAAACAG | 216 |
| vietnam_98057 | PA | *vietnamiensis* | F | vietnam_98057_111F | TCACACCATGGGCTCCGAGA | 217 |
| | | | R | vietnam_98057_460R | CGGGCGGGTAGACGAGTTCC | 218 |
| vietnam_226017 | PA | *vietnamiensis* | F | vietnam_226017_33F_UT1 | ACCACGAGTGTGTGCGGCATT | 219 |
| | | | R | vietnam_226017_285R_UT2 | GCGCTCGATGGTTCCCGAAG | 220 |
| ubon_small_102920 | PA | *ubonensis* (small clade) | F | ubon_small_102920_511F | CTTGCCTTCCAGGCGCACAT | 221 |
| | | | R | ubon_small_102920_802R | TGCCAAGCGGAAGCTCCTTG | 222 |

TABLE 4-continued

Primers for detecting the presence of nucleic acids from *Burkholderia*.

| Assay name | Assay Type | Target species/ gene | primer name | sequence (5' -> 3') | SEQ ID NO: |
|---|---|---|---|---|---|
| ubon_small_111449 | PA | *ubonensis* (small clade) | F ubon_small_111449_167F_UT1 | UGCCGTGTCCGCATGATCCTC | 223 |
| | | | R ubon_small_111449_431R_UT2 | CGCTCCAGTGCGTTGTCGAG | 224 |
| ubon_large_1438777 | PA | *ubonensis* (large clade) | F ubon_large_41F_1438777_B_RP | HCACTGTTCGCATCGGTATTC | 225 |
| | | | R ubon_large_240R_1438777_BH_RP | CTYGCCGTGTCCGTCACGACAAG | 226 |
| ubon_all_1328624 | PA | *ubonensis* | F ubon_all_1328624_220F | GGCGCCTTCTGGTGGTCCTT | 227 |
| | | | R ubon_all_1328624_563R | TGGCTTTGCGACCAGTCGTG | 228 |
| cepacia_1208120 | PA | *cepacia*-complex | F cepacia_1208120_1F | ATGGCAARGATTCTKGTRG | 229 |
| | | | R cepacia_1208120_311R | TTCACGATCCAGCCCTT | 230 |

TABLE 5

Primers for detecting the presence of nucleic acids from *Yersinia*.

| Assay name | Assay Type | Target species/ gene | primer name | sequence (5'->3') | SEQ ID NO: |
|---|---|---|---|---|---|
| Ypestis_LPQY01000176.1_7 | PA | *Y. pestis* | F Yp&NN1_F | AACAAGCTAAAACCGAACAA | 231 |
| | | | R Yp&NN1_R | ATAGCCTCAACTGCTTTTTG | 232 |
| AGJT01000065.1_0_338 | PA | *Y. pestis* | F Yp&NN11_F | CAGTACCGACAAAACTTC | 233 |
| | | | R Yp&NN11_R | TTTACTACTCTGAAAACGAG | 234 |
| FAUR01000053.1_96407_96884 | PA | *Y. pestis* | F Yp&NN12_F | GCACTACAAATTTAAATCCC | 235 |
| | | | R Yp&NN12_R | GTCGATTATCAACCTCTATG | 236 |
| Wagner_Yp_pla_Forward | PA | *Y. pestis* | F Yp&NN2_F | GAAAGGAGTGCGGGTAATAGGTT | 237 |
| | | | R Yp&NN2_R | GGCCTGCAAGTCCAATATATGG | 238 |
| YpPGM_8-158 | PA | Virulence locus PGM | F YpPGM_8F | TTAATATCCCGGCACTCATA | 239 |
| | | | R YpPGM_158R | TCCTTAACTGAATAAGTGCTCA | 240 |
| YpPGM_31-205 | PA | Virulence locus PGM | F YpPGM_31Fv2 | TTTAATGAACGGTGCCTAG | 241 |
| | | | R YpPGM_205Rv2 | GTCTGCGTTTCTCCAGTAT | 242 |
| Yp-p1202_42780-43194 | PA | Drug Resistance plasmid p1P1202 | F Yp-p1202_42780F-UT1 | TCTGGCCTGCTAAATAAAAACGAACC | 243 |
| | | | R Yp-p1202_43194R-UT2 | CAGGCCTCAGCATTTTATTATGGTGAT | 244 |
| Yp-p1202_126386-126750 | PA | Drug Resistance plasmid p1P1202 | F Yp-p1202_126386F-UT1 | GGGGCGGATACCTTCACCTATG | 245 |
| | | | R Yp-p1202_126750R-UT2 | CTGGGGTTCAGTCTGGACGAGAT | 246 |
| Yp-p1202_156402-156711 | PA | Drug Resistance plasmid p1P1202 | F Yp-p1202_156402F2-UT1 | ACCATCCGGCGCTAAATCGTC | 247 |
| | | | R Yp-p1202_156711R-UT2 | GAAATGCGCCTGGTAAGCAGAGT | 248 |
| YpCO92_NC_003143_113190 | SV | near neighbor species | F Yp&NN4_F | ACTCGGGATACTCCATACTG | 249 |
| | | | R Yp&NN4_R | CGAAAGCAGTGGTCAATC | 250 |
| YpCO92_NC_003143_161621 | SV | near neighbor species | F Yp&NN5_F | CATGCGCTTTACGTTATATG | 251 |
| | | | R Yp&NN5_R | GCGTTCTGCACTCTGTCT | 252 |
| YpCO92_NC_003143_152213 | SV | near neighbor species | F Yp&NN6_F | AGCGACTTCCGTGATAAAG | 253 |
| | | | R Yp&NN6_R | ACTCAGGATACCGTGTGGT | 254 |

TABLE 5-continued

Primers for detecting the presence of nucleic acids from Yersinia.

| Assay name | Assay Type | Target species/gene | primer name | sequence (5'->3') | SEQ ID NO: |
|---|---|---|---|---|---|
| YpCO92_NC_003143_129539 | SV | near neighbor species | F Yp&NN7_F | TTCACGATAATCCCCTAATG | 255 |
| | | | R Yp&NN7_R | TTCTGTGCTCTGGCTGATA | 256 |
| YpCO92_NC_003143_91203 | SV | near neighbor species | F Yp&NN8_F | ATTATCTGTGCCCCTTCTTT | 257 |
| | | | R Yp&NN8_R | GGAGTGGATGCCACTAAAC | 258 |
| YpCO92_NC_003143_121812 | SV | near neighbor species | F Yp&NN9_F | CCTCACACAACAATTCACTG | 259 |
| | | | R Yp&NN9_R | TTTTTCCGACAAATTTAAGG | 260 |
| Yp_AL590842.1_RX_SNP | SV | near neighbor species | F Yp&NN10_F | AGCATGAAGGTTGCTAAAAG | 261 |
| | | | R Yp&NN10_R | GGTGACTTCAAAACCGTTAG | 262 |
| Yentero_FR729477.2_1623 | PA | Y. enterocolitics | F Yp&NN3_F | GATGCTTCTGCTATCAGSTT | 263 |
| | | | R Yp&NN3_R | GTGTGRCTTTGAASTCTTGT | 264 |

TABLE 6

Primers for detecting the presence of nucleic acids from Francisella.

| Assay name | Assay Type | Target species/gene | primer name | sequence (5'->3') | SEQ ID NO: |
|---|---|---|---|---|---|
| Ftularensis_CP000915.1_1782 | PA | F. tularensis | F Ft&NN2_F | GAAGTGGCTCATGTTAGAGG | 265 |
| | | | R Ft&NN2_R | AGCRGAGCCTATATGTAACCA | 266 |
| Ftularensis_CP000915.1_731 | PA | F. tularensis | F Ft&NN3_F | TTTAATGTCCGTCAACCTCT | 267 |
| | | | R Ft&NN3_R | ACGAGTTTGTGAGTCGCTAT | 268 |
| Ft_dup_CP000915.1_197 | PA | F. tularensis | F Ft&NN8_F | TGTTACGTACAGGCTGTCAA | 269 |
| | | | R Ft&NN8_R | ATCATATCCCGTAGCACAAG | 270 |
| FtA1 | SNP | FtA1 Clade | F 9F_FtA1_UT1 | CATAACCCATCGCAATATCT | 271 |
| | | | R 246R_FtA1_UT2 | AAATTATCTGTAGCGGCAAA | 272 |
| FtA2 | SNP | FtA2 Clade | F 34F_FtA2_UT1 | GTGTCCAACGAAACCATAAT | 273 |
| | | | R 169R_FtA2_UT2 | TTTGGTTGATTCTGTCAGTG | 274 |
| FtB | SNP | FtB Clade | F 28F_FtB_UT1 | AAGCTTAACTGGTGATTGGA | 275 |
| | | | R 173R_FtB_UT2 | CGCCTAACATCTTATCTGCT | 276 |
| FtA | SNP | FtA Clade | F 14F_FtA_UT1 | GGGTGATGCAGTAGAGAAAA | 277 |
| | | | R 207R_FtA_UT2 | TACCAGATGAACGAATAGCC | 278 |
| FtLVS_AM233362_1646546 | SV | near neighbor species | F Ft&NN9_F | ATCAAGCTCATCTTCAAAGC | 279 |
| | | | R Ft&NN9_R | AACCATGTTCAGATCCAAAA | 280 |
| FtLVS_AM233362_1643765 | SV | near neighbor species | F Ft&NN10_F | TACCTCTGCCAAAAATTCAT | 281 |
| | | | R Ft&NN10_R | GGCATACTCAAGGTAGTGGT | 282 |
| FtLVS_AM233362_1562618 | SV | near neighbor species | F Ft&NN11_F | TCTTTGGTAGCTTGCTGACT | 283 |
| | | | R Ft&NN11_R | CAGACGACACTTGGCTTATT | 284 |
| Ftnovicida_CP009607.1 | PA | F. tularensis spp. Novicida | F Ft&NN1_F | GGTAGGATAACTACCAAG | 285 |
| | | | R Ft&NN1_R | GTCATGAGTTTTACCAATACTC | 286 |
| Fphilom_CP009444.1_569 | PA | F. philomiragia | F Ft&NN6_F | CTTATGCAGCAAGAGGAACT | 287 |
| | | | R Ft&NN6_R | ATACACCGGGATAGGTTTCT | 288 |
| Fphilom_CP009444.1_285 | PA | F. philomiragia | F Ft&NN7_F | CTGATGGAAGAGAGTTCGAG | 289 |
| | | | R Ft&NN7_Rv2 | GTAGATATAATCAGCGCCAC | 290 |
| Fnoatunensis_CP003402.1_1749 | PA | F. noatunensis | F Ft&NN4_F | CGGTAAGAATACGACCAGAG | 291 |
| | | | R Ft&NN4_R | AGAGGATTTCTTCCTCCTTG | 292 |
| Fnoatunensis_CP003402.1_424 | PA | F. noatunensis | F Ft&NN5_F | AATTCTACAAGCACCTGGAA | 293 |
| | | | R Ft&NN5_R | TCCTATTAAAAGCGCCATAG | 294 |

TABLE 7

Primers for Sequence Control.

| Assay name | Target species/gene | Forward primer name | Forward sequence (5'->3') | SEQ ID NO | Reverse primer name | Reverse sequence 5'->3') | SEQ ID NO |
|---|---|---|---|---|---|---|---|
| IPSC-1 | sequencing control | UT1-IPSC-f1 | GGGCGGACGAAAACCCTTGAGCACAG | 295 | UT2-IPSC-r1 | GCCGGGATGCCTTACCTAGACGCAATGA | 298 |
| IPSC-1 | sequencing control | UT1-IPSC-f1v2 | GCTCGGGCGGACGAAAACCCTTGA | 296 | UT2-IPSC-r1 | GCCGGGATGCCTTACCTAGACGCAATGA | 299 |
| IPSC-2 | sequencing control | UT1-IPSC-f2 | GCGGCAGCCGTTGAGGCAAAAGTGATAC | 297 | UT2-IPSC-r2 | CGAGTTCCGTCCGGTTAAGCGTGACAGTC | 300 |

Forward sequence w/UT: ACCCAACTGAATGGAGC (SEQ ID NO: 301) at 5' of the forward sequence, e.g., UT1-IPSC-f1: ACCCAACTGAATGGAGCGGGCGGACGAAAACCCTTGAGCACAG (SEQ ID NO: 302)
Reverse sequence w/UT: ACGCACTTGACTTGTCTTC (SEQ ID NO: 303) at 5' of the reverse sequence, e.g., UT2-IPSC-r1: ACGCACTTGACTTGTCTTCGCCGGGATGCCTTACCTAGACGCAATGA (SEQ ID NO: 304)

TABLE 8

Preparation of Primer Mixture for detecting the presence of nucleic acids from *Burkholderia*.

| Assay name | Primer | Target | Start (uM) | Desired final uM in rxn. | uM in mix stock (final uM × 5.56) | Volume needed in Mix stock (uL) | starting primer conc. to add in mix stock | Recalculated final conc. of primer in a single rxn. |
|---|---|---|---|---|---|---|---|---|
| TTS1_BPSS1407 | BpAmpSeq_1_F | TTS1 | 100 | 0.10 | 0.56 | 0.03 | 5.0 | 0.10 |
| TTS1_BPSS1407 | BpAmpSeq_1_R | TTS1 | 100 | 0.10 | 0.56 | 0.03 | 5.0 | 0.10 |
| LXCC01000141.1_39296_39817 | BpAmpSeq_3_F | *pseudomallei* | 100 | 0.20 | 1.11 | 0.05 | 9.9 | 0.20 |
| LXCC01000141.1_39296_39817 | BpAmpSeq_3_R | *pseudomallei* | 100 | 0.20 | 1.11 | 0.05 | 9.9 | 0.20 |
| LXBY01000087.1_75760_76751 | BpAmpSeq_4_F | *pseudomallei* | 100 | 0.20 | 1.11 | 0.05 | 9.9 | 0.20 |
| LXBY01000087.1_75760_76751 | BpAmpSeq_4_R | *pseudomallei* | 100 | 0.20 | 1.11 | 0.05 | 9.9 | 0.20 |
| LXCD01000002.1_99652_100245 | BpAmpSeq_5_F | *pseudomallei* | 100 | 0.40 | 2.22 | 0.10 | 19.8 | 0.40 |
| LXCD01000002.1_99652_100245 | BpAmpSeq_5_R | *pseudomallei* | 100 | 0.40 | 2.22 | 0.10 | 19.8 | 0.40 |
| LXCE01000123.1_34220_34747 | BpAmpSeq_6_F | *pseudomallei* | 100 | 0.40 | 2.22 | 0.10 | 19.8 | 0.40 |
| LXCE01000123.1_34220_34747 | BpAmpSeq_6_R | *pseudomallei* | 100 | 0.40 | 2.22 | 0.10 | 19.8 | 0.40 |
| LWWC01000187.1_18 | BpAmpSeq_8_F | *pseudomallei mallei* | 100 | 0.30 | 1.67 | 0.08 | 14.9 | 0.30 |
| LWWC01000187.1_18 | BpAmpSeq_8_R | *pseudomallei mallei* | 100 | 0.30 | 1.67 | 0.08 | 14.9 | 0.30 |
| LWWB01000125.1_17183_17602 | BpAmpSeq_10_F | *pseudomallei mallei* | 100 | 0.20 | 1.11 | 0.05 | 9.9 | 0.20 |
| LWWB01000125.1_17183_17602 | BpAmpSeq_10_R | *pseudomallei mallei* | 100 | 0.20 | 1.11 | 0.05 | 9.9 | 0.20 |
| LXAY1000367.1_0_640 | BpAmpSeq_11_F | *pseudomallei mallei* | 100 | 0.10 | 0.56 | 0.03 | 5.0 | 0.10 |
| LXAY01000367.1_0_640 | BpAmpSeq_11_R | *pseudomallei mallei* | 100 | 0.10 | 0.56 | 0.03 | 5.0 | 0.10 |
| LWVY01000190.1_17226_17689 | BpAmpSeq_12_F | *pseudomallei mallei* | 100 | 0.40 | 2.22 | 0.10 | 19.8 | 0.40 |
| LWVY01000190.1_17226_17689 | BpAmpSeq_12_R | *pseudomallei mallei* | 100 | 0.40 | 2.22 | 0.10 | 19.8 | 0.40 |
| LXAD01000059.1_24760_25075 | BpAmpSeq_13_F | *pseudomallei mallei* | 100 | 0.30 | 1.67 | 0.08 | 14.9 | 0.30 |
| LXAD01000059.1_24760_25075 | BpAmpSeq_13_R | *pseudomallei mallei* | 100 | 0.30 | 1.67 | 0.08 | 14.9 | 0.30 |
| NC_006350_2289827 | BpAmpSeq_16_F | *pseudomallei* complex SNP | 100 | 0.40 | 2.22 | 0.10 | 19.8 | 0.40 |
| NC_006350_2289827 | BpAmpSeq_16_R | *pseudomallei* complex SNP | 100 | 0.40 | 2.22 | 0.10 | 19.8 | 0.40 |
| NC_006350_133027 | BpAmpSeq_18_F | *cepacia* complex SNPs | 100 | 0.20 | 1.11 | 0.05 | 9.9 | 0.20 |
| NC_006350_133027 | BpAmpSeq_18_R | *cepacia* complex SNPs | 100 | 0.20 | 1.11 | 0.05 | 9.9 | 0.20 |
| NC_006350_2248145-2248193 | BpAmpSeq_19_F | Bpc MSS | 100 | 0.40 | 2.22 | 0.10 | 19.8 | 0.40 |
| NC_006350_2248145-2248193 | BpAmpSeq_19_R | Bpc MSS | 100 | 0.40 | 2.22 | 0.10 | 19.8 | 0.40 |
| NC_006350_988041-988089 | BpAmpSeq_20_F | Bpc MSS | 100 | 0.20 | 1.11 | 0.05 | 9.9 | 0.20 |
| NC_006350_988041-988089 | BpAmpSeq_20_R | Bpc MSS | 100 | 0.20 | 1.11 | 0.05 | 9.9 | 0.20 |
| Bm_11589 | BpAmpSeq_21_F | *mallei* | 100 | 0.40 | 2.22 | 0.10 | 19.8 | 0.40 |
| Bm_11589 | BpAmpSeq_21_R | *mallei* | 100 | 0.40 | 2.22 | 0.10 | 19.8 | 0.40 |
| Bm_11767 | BpAmpSeq_22_F | *mallei* | 100 | 0.40 | 2.22 | 0.10 | 19.8 | 0.40 |
| Bm_11767 | BpAmpSeq_22_R | *mallei* | 100 | 0.40 | 2.22 | 0.10 | 19.8 | 0.40 |
| PBP3-170-505 | BpAmpSeq_24_F | pbp3 | 100 | 0.20 | 1.11 | 0.05 | 9.9 | 0.20 |
| PBP3-170-505 | BpAmpSeq_24_R | pbp3 | 100 | 0.20 | 1.11 | 0.05 | 9.9 | 0.20 |
| K9penA378-529 | BpAmpSeq_26_F | penA | 100 | 0.10 | 0.56 | 0.03 | 5.0 | 0.10 |
| K9penA378-529 | BpAmpSeq_26_R | penA | 100 | 0.10 | 0.56 | 0.03 | 5.0 | 0.10 |
| K9penA575-761 | BpAmpSeq_27_F | penA | 100 | 0.10 | 0.56 | 0.03 | 5.0 | 0.10 |
| K9penA575-761 | BpAmpSeq_27_R | penA | 100 | 0.10 | 0.56 | 0.03 | 5.0 | 0.10 |
| K9penA949-1172 | BpAmpSeq_28_F | penA | 100 | 0.10 | 0.56 | 0.03 | 5.0 | 0.10 |
| K9penA949-1172 | BpAmpSeq_28_R | penA | 100 | 0.10 | 0.56 | 0.03 | 5.0 | 0.10 |
| IPSC | IPSC-f1v2 | IPSC | 20 | 0.05 | 0.28 | 0.06 | 12.4 | 0.05 |
| IPSC | IPSC-r1 | IPSC | 20 | 0.05 | 0.28 | 0.06 | 12.4 | 0.05 |

Volume of primer mix in a single rxn: 4.5 uL.

Desired volume of primer mix stock: 891 uL.

TABLE 10

Preparation of Primer Mixture for detecting the presence of nucleic acids from SOP
for *Bacillus*, *Yersinia*, and *Francisella* UT-AmpSeq PCR and Bead Cleanup

| Primer name | Assay name | Start (uM) | Volume of primer mix in a single rxn (uL) | Desired final uM in rxn. | uM in mix stock (final uM × 5.56) | Volume needed in Mix stock (uL) | Desired volume of Primer mix stock (uL) | How much starting primer conc. to add in mix stock | Re-calculated final conc. Of primer in a single rxn. |
|---|---|---|---|---|---|---|---|---|---|
| Ba-specific-1F_UT1 | plcR | 100 | 4.5 | 0.1 | 0.56 | 0.03 | 891 | 5 | 0 |
| Ba-specific-1R_UT2 | plcR | 100 | | 0.1 | 0.56 | 0.03 | | 5 | 0 |
| Ba-specific-3F_UT1 | CP008853.1_5309 | 500 | | 0.2 | 1.11 | 0.01 | | 2 | 0 |
| Ba-specific-3R_UT2 | CP008853.1_5309 | 500 | | 0.2 | 1.11 | 0.01 | | 2 | 0 |
| Ba-specific-5F_UT1 | CP008853.1_5316 | 500 | | 0.2 | 1.11 | 0.01 | | 2 | 0 |
| Ba-specific-5R_UT2 | CP008853.1_5316 | 500 | | 0.2 | 1.11 | 0.01 | | 2 | 0 |
| Ba-specific-6F_UT1 | CP012725.1_3629 | 500 | | 1.6 | 8.9 | 0.08 | | 15.9 | 0 |
| Ba-specific-6R_UT2 | CP012725.1_3629 | 500 | | 1.6 | 8.9 | 0.08 | | 15.9 | 0 |
| Ba-specific-8F_UT1 | CP012725.1_5103 | 100 | | 0.1 | 0.56 | 0.03 | | 5 | 0 |
| Ba-specific-8R_UT2 | CP012725.1_5103 | 100 | | 0.1 | 0.56 | 0.03 | | 5 | 0 |
| Ba-specific-9F_UT1 | CP012725.1_5107 | 100 | | 0.1 | 0.56 | 0.03 | | 5 | 0 |
| Ba-specific-9R_UT2 | CP012725.1_5107 | 100 | | 0.1 | 0.56 | 0.03 | | 5 | 0 |
| Ba-specific-11F_UT1 | JSZQ01000034.1_220 | 100 | | 0.1 | 0.56 | 0.03 | | 5 | 0 |
| Ba-specific-11R_UT2 | JSZQ01000034.1_220 | 100 | | 0.1 | 0.56 | 0.03 | | 5 | 0 |
| Ba-specific-12F_UT1 | JSZS01000036.15 | 100 | | 0.1 | 0.56 | 0.03 | | 5 | 0 |
| Ba-specific-12R_UT2 | JSZS01000036.15 | 100 | | 0.1 | 0.56 | 0.03 | | 5 | 0 |
| Ba-specific-14F_UT1 | LGCC01000010.1_232 | 500 | | 0.4 | 2.22 | 0.02 | | 4 | 0 |
| Ba-specific-14R_UT2 | LGCC01000010.1_232 | 500 | | 0.4 | 2.22 | 0.02 | | 4 | 0 |
| Ba-specific-16F_UT1 | LGCC01000048.1_280 | 100 | | 0.1 | 0.56 | 0.03 | | 5 | 0 |
| Ba-specific-16R_UT2 | LGCC01000048.1_280 | 100 | | 0.1 | 0.56 | 0.03 | | 5 | 0 |
| Ba-specific-20F_UT1 | NN_LOMU01000090.1_49 | 500 | | 1 | 5.56 | 0.05 | | 9.9 | 0 |
| Ba-specific-20R_UT2 | NN_LOMU01000090.1_49 | 500 | | 1 | 5.56 | 0.05 | | 9.9 | 0 |
| Ba-specific-22F_UT1 | NN_LOQC01000013.1_3 | 500 | | 0.2 | 1.11 | 0.01 | | 2 | 0 |
| Ba-specific-22Rv2_UT2 | NN_LOQC01000013.1_3 | 500 | | 0.2 | 1.11 | 0.01 | | 2 | 0 |
| pX01_113F_UT1 | pX01 | 500 | | 0.8 | 4.45 | 0.04 | | 7.9 | 0 |
| pX01-315Rv2_UT2 | pX01 | 500 | | 0.8 | 4.45 | 0.04 | | 7.9 | 0 |
| pX02_101F_UT1 | pX02 | 100 | | 0.1 | 0.56 | 0.03 | | 5 | 0 |
| pX02_269R_UT2 | pX02 | 100 | | 0.1 | 0.56 | 0.03 | | 5 | 0 |
| gyrA_28Fv2_UT1 | gyrA | 50 | | 0.05 | 0.28 | 0.03 | | 5 | 0 |
| gyrA_182Rv2_UT2 | gyrA | 50 | | 0.05 | 0.28 | 0.03 | | 5 | 0 |
| parC_1F_UT1 | parC | 100 | | 0.05 | 0.28 | 0.01 | | 2.5 | 0 |
| parC_197R_UT2 | parC | 100 | | 0.05 | 0.28 | 0.01 | | 2.5 | 0 |
| gyrB_8F_UT1 | gyrB | 100 | | 0.1 | 0.56 | 0.03 | | 5 | 0 |
| gyrB_194R_UT2 | gyrB | 100 | | 0.1 | 0.56 | 0.03 | | 5 | 0 |
| 801F_pagAv3_UT1 | pagAv3 | 100 | | 0.1 | 0.56 | 0.03 | | 5 | 0 |
| 1042R_pagAv3_UT2 | pagAv3 | 100 | | 0.1 | 0.56 | 0.03 | | 5 | 0 |
| rpoB_29F_UT1 | rpoB | 50 | | 0.05 | 0.28 | 0.03 | | 5 | 0 |
| rpoB_196R_UT2 | rpoB | 50 | | 0.05 | 0.28 | 0.03 | | 5 | 0 |
| AA_2502_UT1 | AA_2502 | 500 | | 0.8 | 4.45 | 0.04 | | 7.9 | 0 |
| AA_2502_UT2 | AA_2502 | 500 | | 0.8 | 4.45 | 0.04 | | 7.9 | 0 |
| AA_2503v2_UT1 | AA_2503 | 500 | | 0.8 | 4.45 | 0.04 | | 7.9 | 0 |
| AA_2503_UT2 | AA_2503 | 500 | | 0.8 | 4.45 | 0.04 | | 7.9 | 0 |
| Ba&NN32_F | Ba_AmesAnc_4669915 | 100 | | 0.1 | 0.56 | 0.03 | | 5 | 0 |
| Ba&NN32_R | Ba_AmesAnc_4669915 | 100 | | 0.1 | 0.56 | 0.03 | | 5 | 0 |
| Ba&NN33_F | Ba_AmesAnc_4001578 | 100 | | 0.05 | 0.28 | 0.01 | | 2.5 | 0 |
| Ba&NN33_R | Ba_AmesAnc_4001578 | 100 | | 0.05 | 0.28 | 0.01 | | 2.5 | 0 |
| Ba&NN37_F | Ba_AmesAnc_1069024 | 500 | | 0.2 | 1.11 | 0.01 | | 2 | 0 |
| Ba&NN37_R | Ba_AmesAnc_1069024 | 500 | | 0.2 | 1.11 | 0.01 | | 2 | 0 |
| Ba&NN38_F | Ba_AmesAnc_3668548 | 500 | | 0.2 | 1.11 | 0.01 | | 2 | 0 |
| Ba&NN38_R | Ba_AmesAnc_3668548 | 500 | | 0.2 | 1.11 | 0.01 | | 2 | 0 |
| Ba&NN40_F | Ba_AmesAnc_371913 | 500 | | 0.2 | 1.11 | 0.01 | | 2 | 0 |
| Ba&NN40_R | Ba_AmesAnc_371913 | 500 | | 0.2 | 1.11 | 0.01 | | 2 | 0 |
| Ba&NN41_F | Ba_AmesAnc_999035 | 100 | | 0.05 | 0.28 | 0.01 | | 2.5 | 0 |
| Ba&NN41_R | Ba_AmesAnc_999035 | 100 | | 0.05 | 0.28 | 0.01 | | 2.5 | 0 |
| ChimpKiller_9F | ChimpKiller_9-159 | 100 | | 0.1 | 0.56 | 0.03 | | 5 | 0 |
| ChimpKiller_159R | ChimpKiller_9-159 | 100 | | 0.1 | 0.56 | 0.03 | | 5 | 0 |
| ChimpKiller_91F | ChimpKiller_91-320 | 500 | | 0.8 | 4.45 | 0.04 | | 7.9 | 0 |
| ChimpKiller_320R | ChimpKiller_91-320 | 500 | | 0.8 | 4.45 | 0.04 | | 7.9 | 0 |
| ChimpKiller_481F | ChimpKiller_481-698 | 500 | | 0.8 | 4.45 | 0.04 | | 7.9 | 0 |
| ChimpKiller_698R | ChimpKiller_481-698 | 500 | | 0.8 | 4.45 | 0.04 | | 7.9 | 0 |
| Yp&NN1_F | *Ypestis*_LPQY01000176.1_7 | 500 | | 0.2 | 1.11 | 0.01 | | 2 | 0 |
| Yp&NN1_R | *Ypestis*_LPQY01000176.1_7 | 500 | | 0.2 | 1.11 | 0.01 | | 2 | 0 |
| Yp&NN2_F | Wagner_Yp_pla_Forward | 100 | | 0.1 | 0.56 | 0.03 | | 5 | 0 |
| Yp&NN2_R | Wagner_Yp_pla_Forward | 100 | | 0.1 | 0.56 | 0.03 | | 5 | 0 |
| Yp&NN3_F | Yentero_FR729477.2_1623 | 500 | | 0.2 | 1.11 | 0.01 | | 2 | 0 |
| Yp&NN3_R | Yentero_FR729477.2_1623 | 500 | | 0.2 | 1.11 | 0.01 | | 2 | 0 |
| Yp&NN4_F | YpCO92_NC_003143_113190 | 500 | | 0.4 | 2.22 | 0.02 | | 4 | 0 |
| Yp&NN4_R | YpCO92_NC_003143_113190 | 500 | | 0.4 | 2.22 | 0.02 | | 4 | 0 |
| Yp&NN5_F | YpCO92_NC_003143_161621 | 100 | | 0.05 | 0.28 | 0.01 | | 2.5 | 0 |
| Yp&NN5_R | YpCO92_NC_003143_161621 | 100 | | 0.05 | 0.28 | 0.01 | | 2.5 | 0 |

TABLE 10-continued

Preparation of Primer Mixture for detecting the presence of nucleic acids from SOP for *Bacillus*, *Yersinia*, and *Francisella* UT-AmpSeq PCR and Bead Cleanup

| Primer name | Assay name | Start (uM) | Volume of primer mix in a single rxn (uL) | Desired final uM in rxn. | uM in mix stock (final uM × 5.56) | Volume needed in Mix stock (uL) | Desired volume of Primer mix stock (uL) | How much starting primer conc. to add in mix stock | Re-calculated final conc. Of primer in a single rxn. |
|---|---|---|---|---|---|---|---|---|---|
| Yp&NN6_F | YpCO92_NC_003143_152213 | 100 | | 0.05 | 0.28 | 0.01 | | 2.5 | 0 |
| Yp&NN6_R | YpCO92_NC_003143_152213 | 100 | | 0.05 | 0.28 | 0.01 | | 2.5 | 0 |
| Yp&NN7_F | YpCO92_NC_003143_129539 | 100 | | 0.1 | 0.56 | 0.03 | | 5 | 0 |
| Yp&NN7_R | YpCO92_NC_003143_129539 | 100 | | 0.1 | 0.56 | 0.03 | | 5 | 0 |
| Yp&NN8_F | YpCO92_NC_003143_91203 | 100 | | 0.05 | 0.28 | 0.01 | | 2.5 | 0 |
| Yp&NN8_R | YpCO92_NC_003143_91203 | 100 | | 0.05 | 0.28 | 0.01 | | 2.5 | 0 |
| Yp&NN9_F | YpCO92_NC_003143_121812 | 100 | | 0.1 | 0.56 | 0.03 | | 5 | 0 |
| Yp&NN9_R | YpCO92_NC_003143_121812 | 100 | | 0.1 | 0.56 | 0.03 | | 5 | 0 |
| Yp&NN10_F | Yp_AL590842.1_RX_SNP | 50 | | 0.05 | 0.28 | 0.03 | | 5 | 0 |
| Yp&NN10_R | Yp_AL590842.1_RX_SNP | 50 | | 0.05 | 0.28 | 0.03 | | 5 | 0 |
| Yp&NN11_F | AGJT01000065.1_0_338 | 100 | | 0.1 | 0.56 | 0.03 | | 5 | 0 |
| Yp&NN11_R | AGJT01000065.1_0_338 | 100 | | 0.1 | 0.56 | 0.03 | | 5 | 0 |
| Yp&NN12_F | FAUR01000053.1_96407_96884 | 100 | | 0.1 | 0.56 | 0.03 | | 5 | 0 |
| Yp&NN12_R | FAUR01000053.1_96407_96884 | 100 | | 0.1 | 0.56 | 0.03 | | 5 | 0 |
| YpPGM_8F | YpPGM_8-158 | 500 | | 0.8 | 4.45 | 0.04 | | 7.9 | 0 |
| YpPGM_158R | YpPGM_8-158 | 500 | | 0.8 | 4.45 | 0.04 | | 7.9 | 0 |
| YpPGM_31Fv2 | YpPGM_31-205 | 50 | | 0.05 | 0.28 | 0.03 | | 5 | 0 |
| YpPGM_205Rv2 | YpPGM_31-205 | 50 | | 0.05 | 0.28 | 0.03 | | 5 | 0 |
| Yp-p1202_42780F-UT1 | Yp-p1202_42780-43194 | 500 | | 0.2 | 1.11 | 0.01 | | 2 | 0 |
| Yp-p1202_43194R-UT2 | Yp-p1202_42780-43194 | 500 | | 0.2 | 1.11 | 0.01 | | 2 | 0 |
| Yp-p1202_126386F-UT1 | Yp-p1202_126386-126750 | 500 | | 0.2 | 1.11 | 0.01 | | 2 | 0 |
| Yp-p1202_126750R-UT2 | Yp-p1202_126386-126750 | 500 | | 0.2 | 1.11 | 0.01 | | 2 | 0 |
| Yp-p1202_156402F2-UT1 | Yp-p1202_156402-156711 | 500 | | 0.2 | 1.11 | 0.01 | | 2 | 0 |
| Yp-p1202_156711R-UT2 | Yp-p1202_156402-156711 | 500 | | 0.2 | 1.11 | 0.01 | | 2 | 0 |
| Ft&NN1_F | *Ftnovicida*_CP009607.1 | 500 | | 0.2 | 1.11 | 0.01 | | 2 | 0 |
| Ft&NN1_R | *Ftnovicida*_CP009607.1 | 500 | | 0.2 | 1.11 | 0.01 | | 2 | 0 |
| Ft&NN2_F | *Ftularensis*_CP000915.1_1782 | 100 | | 0.1 | 0.56 | 0.03 | | 5 | 0 |
| Ft&NN2_R | *Ftularensis*_CP000915.1_1782 | 100 | | 0.1 | 0.56 | 0.03 | | 5 | 0 |
| Ft&NN3_F | *Ftularensis*_CP000915.1_731 | 500 | | 1.6 | 8.9 | 0.08 | | 15.9 | 0 |
| Ft&NN3_R | *Ftularensis*_CP000915.1_731 | 500 | | 1.6 | 8.9 | 0.08 | | 15.9 | 0 |
| Ft&NN4_F | *Fnoatunensis*_CP003402.1_1749 | 500 | | 0.2 | 1.11 | 0.01 | | 2 | 0 |
| Ft&NN4_R | *Fnoatunensis*_CP003402.1_1749 | 500 | | 0.2 | 1.11 | 0.01 | | 2 | 0 |
| Ft&NN5_F | *Fnoatunensis*_CP003402.1_424 | 500 | | 0.2 | 1.11 | 0.01 | | 2 | 0 |
| Ft&NN5_R | *Fnoatunensis*_CP003402.1_424 | 500 | | 0.2 | 1.11 | 0.01 | | 2 | 0 |
| Ft&NN6_F | Fphilom_CP009444.1_569 | 500 | | 0.2 | 1.11 | 0.01 | | 2 | 0 |
| Ft&NN6_R | Fphilom_CP009444.1_569 | 500 | | 0.2 | 1.11 | 0.01 | | 2 | 0 |
| Ft&NN7_F | Fphilom_CP009444.1_285 | 500 | | 0.2 | 1.11 | 0.01 | | 2 | 0 |
| Ft&NN7_Rv2 | Fphilom_CP009444.1_285 | 500 | | 0.2 | 1.11 | 0.01 | | 2 | 0 |
| Ft&NN8_F | Ft_dup_CP000915.1_197 | 100 | | 0.05 | 0.28 | 0.01 | | 2.5 | 0 |
| Ft&NN8_R | Ft_dup_CP000915.1_197 | 100 | | 0.05 | 0.28 | 0.01 | | 2.5 | 0 |
| Ft&NN9_F | FtLVS_AM233362_1646546 | 100 | | 0.05 | 0.28 | 0.01 | | 2.5 | 0 |
| Ft&NN9_R | FtLVS_AM233362_1646546 | 100 | | 0.05 | 0.28 | 0.01 | | 2.5 | 0 |
| Ft&NN10_F | FtLVS_AM233362_1643765 | 100 | | 0.1 | 0.56 | 0.03 | | 5 | 0 |
| Ft&NN10_R | FtLVS_AM233362_1643765 | 100 | | 0.1 | 0.56 | 0.03 | | 5 | 0 |
| Ft&NN11_F | FtLVS_AM233362_1562618 | 100 | | 0.1 | 0.56 | 0.03 | | 5 | 0 |
| Ft&NN11_R | FtLVS_AM233362_1562618 | 100 | | 0.1 | 0.56 | 0.03 | | 5 | 0 |
| 9F_FtA1_UT1 | FtA1 | 100 | | 0.1 | 0.56 | 0.03 | | 5 | 0 |
| 246R_FtA1_UT2 | FtA1 | 100 | | 0.1 | 0.56 | 0.03 | | 5 | 0 |
| 34F_FtA2_UT1 | FtA2 | 100 | | 0.1 | 0.56 | 0.03 | | 5 | 0 |
| 169R_FtA2_UT2 | FtA2 | 100 | | 0.1 | 0.56 | 0.03 | | 5 | 0 |
| 28F_FtB_UT1 | FtB | 100 | | 0.1 | 0.56 | 0.03 | | 5 | 0 |
| 173R_FtB_UT2 | FtB | 100 | | 0.1 | 0.56 | 0.03 | | 5 | 0 |
| 14F_FtA_UT1 | FtA | 100 | | 0.1 | 0.56 | 0.03 | | 5 | 0 |
| 207R_FtA_UT2 | FtA | 100 | | 0.1 | 0.56 | 0.03 | | 5 | 0 |
| IPSC-f2 | IPSC | 20 | | 0.03 | 0.14 | 0.03 | | 6.2 | 0 |
| IPSC-r2 | IPSC | 20 | | 0.03 | 0.14 | 0.03 | | 6.2 | 0 |

580.6 uL total volume of primers 310.4 uL of 1x TE to add to bring up to desired volume of primer mix stock 891.0 Total (uL)

TABLE 11

*Burkholderia primers and primers with Universal Tail (UT).*
*The UT sequence is underlined.*

| Assay name | Target species/ gene | Forward primer name | Forward sequence (5'->3') | SEQ ID NO: | Forward sequence w/UT | SEQ ID NO: |
|---|---|---|---|---|---|---|
| TTS1_BPSS1407 | TTS1 | BpAmpSeq_1_F | TCGTCGTCACCGGGATGGTC | 61 | <u>ACCCAACTGAATGGAGCT</u>CGTCGTCACCGGGATGGTC | 307 |
| | | Reverse primer name | Reverse sequence (5'->3') | | Reverse sequence w/UT | |
| | | BpAmpSeq_1_R | GGCCTTTGCCCGCATACTCG | 62 | <u>ACGCACTTGACTTGTCTTCG</u>GCCTTTGCCCGCATACTCG | 308 |
| | | Forward primer name | Forward sequence (5'->3') | | Forward sequence w/UT | |
| LXCC0 100014 1.1_392 96_398 17 | pseudomallei | BpAmpSeq_3_F | TCGCAWGAAGTGCGTTGCCG | 63 | <u>ACCCAACTGAATGGAGCT</u>CGCAWGAAGTGCGTTGCCG | 309 |
| | | Reverse primer name | Reverse sequence (5'->3') | | Reverse sequence w/UT | |
| | | BpAmpSeq_3_R | GCCGCTTGCGAAGCGATGAT | 64 | <u>ACGCACTTGACTTGTCTTCG</u>CCGCTTGCGAAGCGATGAT | 310 |
| | | Forward primer name | Forward sequence (5'->3') | | Forward sequence w/UT | |
| LXBY0 100008 7.1_757 60_767 51 | pseudomallei | BpAmpSeq_4_F | CGCGCTTGCCCAACTACCAG | 65 | <u>ACCCAACTGAATGGAGCC</u>GCGCTTGCCCAACTACCAG | 311 |
| | | Reverse primer name | Reverse sequence (5'->3') | | Reverse sequence w/UT | |
| | | BpAmpSeq_4_R | GCGCAACGGTGCGAGACAAT | 66 | <u>ACGCACTTGACTTGTCTTCG</u>CGCAACGGTGCGAGACAAT | 312 |
| | | Forward primer name | Forward sequence (5'->3') | | Forward sequence w/UT | |
| LXCD0 100000 2.1_996 52_100 245 | pseudomallei | BpAmpSeq_5_F | AATCCATGCATGTCGYGCCC | 67 | <u>ACCCAACTGAATGGAGCA</u>ATCCATGCATGTCGYGCCC | 313 |
| | | Reverse primer name | Reverse sequence (5'->3') | | Reverse sequence w/UT | |
| | | BpAmpSeq_5_R | GCGATCGCTCAACGGGCTTC | 68 | <u>ACGCACTTGACTTGTCTTCG</u>CGATCGCTCAACGGGCTTC | 314 |
| | | Forward primer name | Forward sequence (5'->3') | | Forward sequence w/UT | |
| LXCE0 100012 3.1_342 20_347 47 | pseudomallei | BpAmpSeq_6_F | TCGCATTTGCAYACGCTCCC | 69 | <u>ACCCAACTGAATGGAGCT</u>CGCATTTGCAYACGCTCCC | 315 |
| | | Reverse primer name | Reverse sequence (5'->3') | | Reverse sequence w/UT | |
| | | BpAmpSeq_6_R | AGTGCGCAAACTTGGCGAGG | 70 | <u>ACGCACTTGACTTGTCTTCA</u>GTGCGCAAACTTGGCGAGG | 316 |
| | | Forward primer name | Forward sequence (5'->3') | | Forward sequence w/UT | |
| LWWC 010001 87.1_18 | pseudomallei mallei | BpAmpSeq_8_F | CCTTTGCGGCAAGCGTCGAA | 81 | <u>ACCCAACTGAATGGAGC TABLE 11-continued Burkholderia primers and primers with Universal Tail (UT).
The UT sequence is underlined.

| Assay name | Target species/ gene | Forward primer name | Forward sequence (5'->3') | SEQ ID NO: | Forward sequence w/UT | SEQ ID NO: |
|---|---|---|---|---|---|---|
| LWWB 010001 25.1_17 183_17 | pseudomallei mallei | BpAmpSeq_10_F | CCAGTCGGGCCGGGAAAAAC | 83 | ACCCAACTGAATGGAGCCCAGTC GGGCCGGGAAAAAC | 319 |
| | | Reverse primer name | Reverse sequence (5'->3') | | Reverse sequence w/UT | |
| 602 | | BpAmpSeq_10_R | GGCGGCAAAAGCGTCGATGA | 84 | ACGCACTTGACTTGTCTTCGGCG GCAAAAGCGTCGATGA | 320 |
| | | Forward primer name | Forward sequence (5'->3') | | Forward sequence w/UT | |
| LXAY0 100036 7.1_0_6 40 | pseudomallei mallei | BpAmpSeq_11_F | GCCGGAACCGTCGAGCATTG | 85 | ACCCAACTGAATGGAGCGCCGG AACCGTCGAGCATTG | 321 |
| | | Reverse primer name | Reverse sequence (5'->3') | | Reverse sequence w/UT | |
| | | BpAmpSeq_11_R | TGGATTCGACTGCCTCCGCT | 86 | ACGCACTTGACTTGTCTTCTGGA TTCGACTGCCTCCGCT | 322 |
| | | Forward primer name | Forward sequence (5'->3') | | Forward sequence w/UT | |
| LWVY 010001 90.1_17 226_17 | pseudomallei mallei | BpAmpSeq_12_F | TCGATATCCGCCGTCTCGCC | 87 | ACCCAACTGAATGGAGCTCGATA TCCGCCGTCTCGCC | 323 |
| | | Reverse primer name | Reverse sequence (5'->3') | | Reverse sequence w/UT | |
| 689 | | BpAmpSeq_12_R | ATGTGTCGGTGGGCTTCGGT | 88 | ACGCACTTGACTTGTCTTCATGT GTCGGTGGGCTTCGGT | 324 |
| | | Forward primer name | Forward sequence (5'->3') | | Forward sequence w/UT | |
| LXAD0 100005 9.1_247 60_250 | pseudomallei mallei | BpAmpSeq_13_F | GAAAGGCGATGTGCCGAGCG | 89 | ACCCAACTGAATGGAGCGAAAG GCGATGTGCCGAGCG | 325 |
| | | Reverse primer name | Reverse sequence (5'->3') | | Reverse sequence w/UT | |
| 75 | | BpAmpSeq_13_R | TTCGGAGAAGCGCCAAACGC | 90 | ACGCACTTGACTTGTCTTCTTCGG AGAAGCGCCAAACGC | 326 |
| | | Forward primer name | Forward sequence (5'->3') | | Forward sequence w/UT | |
| NC_00 6350_2 289827 | pseudomallei complex SNP | BpAmpSeq_16_F | GCCAGCGCATCCACCAACAT | 109 | ACCCAACTGAATGGAGCGCCAGC GCATCCACCAACAT | 327 |
| | | Reverse primer name | Reverse sequence (5'->3') | | Reverse sequence w/UT | |
| | | BpAmpSeq_16_R | AGAGGAAGAAGGGCGAGGCG | 110 | ACGCACTTGACTTGTCTTCAGAG GAAGAAGGGCGAGGCG | 328 |
| | | Forward primer name | Forward sequence (5'->3') | | Forward sequence w/UT | |
| NC_00 6350_1 33027 | cepacia complex SNPs | BpAmpSeq_18_F | CGCGCARYTCGTCGTCCTCG | 111 | ACCCAACTGAATGGAGCCGCGCA RYTCGTCGTCCTCG | 329 |
| | | Reverse primer name | Reverse sequence (5'->3') | | Reverse sequence w/UT | |
| | | BpAmpSeq_18_R | CGAACCTSGTGCMGGTRCAG | 112 | ACGCACTTGACTTGTCTTCCGAA CCTSGTGCMGGTRCAG | 330 |

TABLE 11-continued

Burkholderia primers and primers with Universal Tail (UT).
The UT sequence is underlined.

| Assay name | Target species/ gene | Forward primer name | Forward sequence (5'->3') | Forward sequence w/UT | SEQ ID NO: | SEQ ID NO: |
|---|---|---|---|---|---|---|
| NC_00 6350_2 248145- 224819 3 | Bpc MSS | BpAmpSeq_1 9_F | CACGTTGCCSGGRAARTACG | <u>ACCCAACTGAATGGAGC</u>CACGTT GCCSGGRAARTACG | 113 | 331 |
| | | Reverse primer name | Reverse sequence (5'->3') | Reverse sequence w/UT | | |
| | | BpAmpSeq_1 9_R | CCGTCGACAAGATCGCGCTS | <u>ACGCACTTGACTTGTCTT</u>CCCGTC GACAAGATCGCGCTS | 114 | 332 |
| NC_00 6350_9 88041- 988089 | Bpc MSS | Forward primer name | Forward sequence (5'->3') | Forward sequence w/UT | | |
| | | BpAmpSeq_2 0_F | CAGAACGCGCTRTYCCACG | <u>ACCCAACTGAATGGAGC</u>CAGAA CGCGCTRTYCCACG | 115 | 333 |
| | | Reverse primer name | Reverse sequence (5'->3') | Reverse sequence w/UT | | |
| | | BpAmpSeq_2 0_R | TGCCGCGTGATCCATTGCAT | <u>ACGCACTTGACTTGTCTT</u>CTGCC GCGTGATCCATTGCAT | 116 | 334 |
| Bm_11 589 | mallei | Forward primer name | Forward sequence (5'->3') | Forward sequence w/UT | | |
| | | BpAmpSeq_2 1_F | AGGGGGTGGTTTCCTGAGTG GCGTGAC | <u>ACCCAACTGAATGGAGC</u>AGGGG GTGGTTTCCTGAGTGGCGTGAC | 117 | 335 |
| | | Reverse primer name | Reverse sequence (5'->3') | Reverse sequence w/UT | | |
| | | BpAmpSeq_2 1_R | AGCGGTGTCGACGGGTGGA AAGGATG | <u>ACGCACTTGACTTGTCTT</u>CAGCG GTGTCGACGGGTGGAAAGGATG | 118 | 336 |
| Bm_11 767 | mallei | Forward primer name | Forward sequence (5'->3') | Forward sequence w/UT | | |
| | | BpAmpSeq_2 2_F | ACGGGCGCTTCACGATCTCG GTGTTC | <u>ACCCAACTGAATGGAGC</u>ACGGG CGCTTCACGATCTCGGTGTTC | 119 | 337 |
| | | Reverse primer name | Reverse sequence (5'->3') | Reverse sequence w/UT | | |
| | | BpAmpSeq_2 2_R | GCGCGGCAGTTCGATCAGG CATTTG | <u>ACGCACTTGACTTGTCTT</u>CGCGC GGCAGTTCGATCAGGCATTTG | 120 | 338 |

TABLE 11-continued

Burkholderia primers and primers with Universal Tail (UT). The UT sequence is underlined.

| Assay name | Target species/ gene | Forward primer name | Forward sequence (5'->3') | SEQ ID NO: | Forward sequence w/UT | SEQ ID NO: |
|---|---|---|---|---|---|---|
| K9penA575-761 | penA | BpAmpSeq_27_F | GCTGCGCGGCCAAGCGAAAAACG | 129 | <u>ACGCACTTGACTTGTCTTCGCTG</u>CGCGGCCAAGCGAAAAACG | 343 |
| | | Reverse primer name | Reverse sequence (5'->3') | | Reverse sequence w/UT | |
| | | BpAmpSeq_27_R | CGCGAGGACCGCAGCGCAAAGC | 130 | <u>ACCCAACTGAATGGAGCCGCGA</u>GGACCGCAGCGCAAAGC | 344 |
| | | Forward primer name | Forward sequence (5'->3') | | Forward sequence w/UT | |
| K9penA949-1172 | penA | BpAmpSeq_28_F | GGCCGCAGACCGTCACCGCGTATG | 131 | <u>ACCCAACTGAATGGAGC</u>GGCCGCAGACCGTCACCGCGTATG | 345 |
| | | Reverse primer name | Reverse sequence (5'->3') | | Reverse sequence w/UT | |
| | | BpAmpSeq_28_R | GTCGCCCGTCTTGTTGCCGAGCATC | 132 | <u>ACGCACTTGACTTGTCTTCGTCG</u>CCCGTCTTGTTGCCGAGCATC | 346 |

TABLE 12

Bacillus primers and primers with Universal Tail (UT). The UT sequence is underlined.

| Assay name | Target species/ gene | Forward primer name | Forward sequence (5' -> 3') | SEQ ID NO: | Forward sequence w/UT | SEQ ID NO: |
|---|---|---|---|---|---|---|
| plcR | plcR | Ba-specific-1F_UT1 | TTTTTCGTAAGCATCTTCAA | 29 | <u>ACCCAACTGAATGGAG</u>CTTTTTCGTAAGCATCTTCAA | 347 |
| | | Reverse primer name | Reverse sequence (5' -> 3') | | Reverse sequence w/UT | |
| | | Ba-specific-1RUT2 | TTTGATGTGAAGGTGAGACA | 30 | <u>ACGCACTTGACTTGTCTTC</u>TTTGATGTGAAGGTGAGACA | 348 |
| Assay name | Target species/ gene | Forward primer name | Forward sequence (5' -> 3') | | Forward sequence w/UT | |
| CP008853.1_5309 | | Ba-specific-3F_UT1 | ACGTCAGGTGATTATTGGAC | 1 | <u>ACCCAACTGAATGGAG</u>CACGTCAGGTGATTATTGGAC | 349 |
| | | Reverse primer name | Reverse sequence (5' -> 3') | | Reverse sequence w/UT | |
| | | Ba-specific-3RUT2 | CAACAATTATATCCGCCATT | 2 | <u>ACGCACTTGACTTGTCTTC</u>CAACAATTATATCCGCCATT | 350 |

TABLE 12-continued

Bacillus primers and primers with Universal Tail (UT). The UT sequence is underlined.

| Assay name | Target species/ gene | Forward primer name | Forward sequence (5' -> 3') | SEQ ID NO: | Forward sequence w/UT | SEQ ID NO: |
|---|---|---|---|---|---|---|
| CP(K)88 53.1_ 5316 | | Ba- specific- 5FUT1 | GAAGATGTACGCTCGATAG G | 3 | <u>ACCCAACTGAATGGAGCGAAGA</u>TGTACGCTCGATAGG | 351 |
| | | Reverse primer name | Reverse sequence (5' -> 3') | | Reverse sequence w/UT | |
| | | Ba- specific- 5RUT2 | GAAATTCTTTTTGCCATCAC | 4 | <u>ACGCACTTGACTTGTCTTCGAAA</u>TTCTTTTTGCCATCAC | 352 |

| Assay name | Target species/ gene | Forward primer name | Forward sequence (5' -> 3') | SEQ ID NO: | Forward sequence w/UT | SEQ ID NO: |
|---|---|---|---|---|---|---|
| CP0127 25.1_ 3629 | | Ba- specific- 6F_UT1 | CACAATTGAATGAAAATGCT | 5 | <u>ACCCAACTGAATGGAGC</u>CACAATTGAATGAAAATGCT | 353 |
| | | Reverse primer name | Reverse sequence (5' -> 3') | | Reverse sequence w/UT | |
| | | Ba- specific- 6RUT2 | CACGAAACCTGTTTACCTTT | 6 | <u>ACGCACTTGACTTGTCTTC</u>CACGAAACCTGTTTACCTTT | 354 |

| Assay name | Target species/ gene | Forward primer name | Forward sequence (5' -> 3') | SEQ ID NO: | Forward sequence w/UT | SEQ ID NO: |
|---|---|---|---|---|---|---|
| CP0127 25.1_ 5103 | | Ba- specific- 8F_UT1 | GATATTCGACGAGCTTTCTG | 7 | <u>ACCCAACTGAATGGAGC</u>GATATTCGACGAGCTTTCTG | 355 |
| | | Reverse primer name | Reverse sequence (5' -> 3') | | Reverse sequence w/UT | |
| | | Ba- specific- 8R_UT2 | TATTCATCGTCATCCTCCTC | 8 | <u>ACGCACTTGACTTGTCTTC</u>TATTCATCGTCATCCTCCTC | 356 |

| Assay name | Target species/ gene | Forward primer name | Forward sequence (5' -> 3') | SEQ ID NO: | Forward sequence w/UT | SEQ ID NO: |
|---|---|---|---|---|---|---|
| CP0127 25.1_ 5107 | | Ba- specific- 9F_UT1 | TATTGAACGCATTGAATCAG | 9 | <u>ACCCAACTGAATGGAGC</u>TATTGAACGCATTGAATCAG | 357 |
| | | Reverse primer name | Reverse sequence (5' -> 3') | | Reverse sequence w/UT | |
| | | Ba- specific- 9RUT2 | TATTGGTAAGCAAACCGTCT | 10 | <u>ACGCACTTGACTTGTCTTC</u>TATTGGTAAGCAAACCGTCT | 358 |

TABLE 12-continued

Bacillus primers and primers with Universal Tail (UT). The UT sequence is underlined.

| Assay name | Target species/ gene | Forward primer name | Forward sequence (5' -> 3') | SEQ ID NO: | Forward sequence w/UT | SEQ ID NO: |
|---|---|---|---|---|---|---|
| JSZQ01 000034. 1_220 | | Ba-specific-11F_UT1 | GGTTCAGGACAAAATGTAGC | 11 | <u>ACCCAACTGAATGGAGC</u>GGTTCAGGACAAAATGTAGC | 359 |
| | | Reverse primer name | Reverse sequence (5'-> 3') | | Reverse sequence w/UT | |
| | | Ba-specific-11R_UT2 | TAACTTCTGAAGCGAAAACC | 12 | <u>ACGCACTTGACTTGTCTTCT</u>AACTTCTGAAGCGAAAACC | 360 |

| Assay name | Target species/ gene | Forward primer name | Forward sequence (5' -> 3') | SEQ ID NO: | Forward sequence w/UT | SEQ ID NO: |
|---|---|---|---|---|---|---|
| JSZS010 00036.1_5 | | Ba-specific-12F_UT1 | GCGAATTTTAGACGACAATC | 13 | <u>ACCCAACTGAATGGAGC</u>GCGAATTTTAGACGACAATC | 361 |
| | | Reverse primer name | Reverse sequence (5' -> 3') | | Reverse Sequence w/UT | |
| | | Ba-specific-12RUT2 | TAACCGTGCTTAATTCGTTT | 14 | <u>ACGCACTTGACTTGTCTTCT</u>AACCGTGCTTAATTCGTTT | 362 |

| Assay name | Target species/ gene | Forward primer name | Forward sequence (5' -> 3') | SEQ ID NO: | Forward Sequence w/UT | SEQ ID NO: |
|---|---|---|---|---|---|---|
| LGCC0 1000010.1_ 232 | | Ba-specific-14F_UT1 | ATTAATAAGGCGACTGGTGA | 15 | <u>ACCCAACTGAATGGAGC</u>ATTAATAAGGCGACTGGTGA | 363 |
| | | Reverse primer name | Reverse sequence (5' -> 3') | | Reverse Sequence w/UT | |
| | | Ba-specific-14RUT2 | TTACCCATCCAGAATGAGAC | 16 | <u>ACGCACTTGACTTGTCTTCT</u>TACCCATCCAGAATGAGAC | 364 |

| Assay name | Target species/ gene | Forward primer name | Forward sequence (5' -> 3') | SEQ ID NO: | Forward Sequence w/UT | SEQ ID NO: |
|---|---|---|---|---|---|---|
| LGCC0 1000048.1_ 280 | | Ba-specific-16F_UT1 | ACAATTCTTAAAAGGCGACA | 17 | <u>ACCCAACTGAATGGAGC</u>ACAATTCTrAAAAGGCGACA | 365 |
| | | Reverse primer name | Reverse sequence (5' -> 3') | | Reverse Sequence w/UT | |
| | | Ba-specific-16R_UT2 | TGTAGCGTCTCCGATATTTT | 18 | <u>ACGCACTTGACTTGTCTTCT</u>GTAGCGTCTCCGATATTTT | 366 |

| Assay name | Target species/gene | Forward primer name | Forward sequence (5' -> 3') | SEQ ID NO: | Forward sequence w/ UT | SEQ ID NO: |
|---|---|---|---|---|---|---|
| NNLO MU010000 90.1_49 | | Ba-specific-20FUT1 | CATGGGGCTTTCTATTATGT | 19 | <u>ACCCAACTGAATGGAGC</u>CATGGGGCTTTCTATTATGT | 367 |
| | | Reverse primer name | Reverse sequence (5' -> 3') | | Reverse sequence w/ UT | |

TABLE 12-continued

Bacillus primers and primers with Universal Tail (UT). The UT sequence is underlined.

| Assay name | Target species/gene | Forward primer name | Forward sequence (5' -> 3') | SEQ ID NO: | Forward sequence w/UT | SEQ ID NO: |
|---|---|---|---|---|---|---|
| | | Ba-specific-20R_UT2 | TTCGTTCTTTCATAAGTTTCCT | 20 | <u>ACGCACTTGACTTGTCTTC</u>TTCGTTCTTTCATAAGIF1CCT | 368 |
| Assay name | Target species/gene | Forward primer name | Forward sequence (5' -> 3') | | Forward sequence w/UT | |
| NN_LO QC 0100 0013.1_3 | | Ba-specific-22F_UT1 | TTGGAGTITGTTITGCTTTT | 21 | <u>ACCCAACTGAATGGAGC</u>TTGGAG TTTGTTTTGCTTTT | 369 |
| | | Reverse primer name | Reverse sequence (5' -> 3') | | Reverse sequence w/UT | |
| | | Ba-specific-22Rv2_UT2 | GTAACAATTAATCCACGTCCT | 22 | <u>ACGCACTTGACTTGTCTTC</u>GTAA CAATTAATCCACGTCCT | 370 |
| Assay name | Target species/gene | Forward primer name | Forward sequence (5' -> 3') | | Forward sequence w/UT | |
| pX01 | pX01 | pX01_113F_UT1 | TGAGCCTACCTAGTGATTGG | 33 | <u>ACCCAACTGAATGGAGC</u>TGAGCC TACCTAGTGATTGG | 371 |
| | | Reverse primer name | Reverse sequence (5' -> 3') | | Reverse sequence w/ UT | |
| | | pX01-315Rv2_UT2 | TTGGATAAATTCCACAAATTCCTC | 34 | <u>ACGCACTTGACTTGTCTTC</u>TTGG ATAAATTCCACAAATTCCTC | 372 |
| Assay name | Target species/gene | Forward primer name | Forward sequence (5' -> 3') | | Forward sequence w/UT | |
| pX02 | pX02 | pX02_101F_UT1 | CGCCAGCGTATTATATAGGT | 35 | <u>ACCCAACTGAATGGAGC</u>CGCCAG CGTATTATATAGGT | 373 |
| | | Reverse primer name | Reverse sequence (5' -> 3') | | Reverse sequence w/UT | |
| | | pX02 269R UT2 | GCTAATTCTGGGTTGTGTTT | 36 | <u>ACGCACTTGACTTGTCTTC</u>GCTA ATTCTGGGTTGTGTTT | 374 |
| Assay name | Target species/gene | Forward primer name | Forward sequence (5' -> 3') | | Forward sequence w/UT | |
| gyrA | gyrA | gyrA_28Fv2_UT1 | TCGGTAAGTATCACCCTCA | 37 | <u>ACCCAACTGAATGGAGC</u>TCGGTA AGTATCACCCTCA | 375 |
| | | Reverse primer name | Reverse sequence (5' -> 3') | | Reverse sequence w/ UT | |
| | | gyrA_182Rv2_UT2 | TGCTTCTGTATAACGCATT | 38 | <u>ACGCACTTGACTTGTCTTC</u>TGCTT CTGTATAACGCATT | 376 |
| Assay name | Target species/gene | Forward primer name | Forward sequence (5' -> 3') | | Forward sequence w/UT | |
| parC | parC | parC_1F_UT1 | CAGTCGGTAACGTTATTGGT | 39 | <u>ACCCAACTGAATGGAGC</u>CAGTCG GTAACGTTATTGGT | 377 |
| | | Reverse primer name | Reverse sequence (5' -> 3') | | Reverse sequence w/UT | |
| | | parC_197R_UT2 | TAACTCAGATGCAATTGGTG | 40 | <u>ACGCACTTGACTTGTCTTC</u>TAACT CAGATGCAATTGGTG | 378 |

TABLE 12-continued

Bacillus primers and primers with Universal Tail (UT). The UT sequence is underlined.

| Assay name | Target species/gene | Forward primer name | Forward sequence (5' -> 3') | SEQ ID NO: | Forward sequence w/UT | SEQ ID NO: |
|---|---|---|---|---|---|---|
| gyrB | gyrB | gyrB_8F_UT1 | ATTGTAGAGGGTGACTCTGC | 41 | <u>ACCCAACTGAATGGAGC</u>ATTGTAGAGGGTGACTCTGC | 379 |
| | | Reverse primer name | Reverse sequence (5' -> 3') | | Reverse sequence w/UT | |
| | | gyrB_194R_UT2 | TATCAAAATCTCCGCCAAT | 42 | <u>ACGCACTTGACTTGTCTT</u>CTATCAAAATCTCCGCCAAT | 380 |
| Assay name | Target species/gene | Forward primer name | Forward sequence (5' -> 3') | | Forward sequence w/UT | |
| pagA | pagA | 801F_pagAv3_UT1 | GGTTACAGGACGGATTGATA | 31 | <u>ACCCAACTGAATGGAGC</u>GGTTACAGGACGGATTGATA | 381 |
| | | Reverse primer name | Reverse sequence (5' -> 3') | | Reverse sequence w/UT | |
| | | 1042R_pagAv3UT2 | TCCCACCAATATCAAAGAAC | 32 | <u>ACGCACTTGACTTGTCTT</u>CTCCCACCAATATCAAAGAAC | 382 |
| Assay name | Target species/gene | Forward primer name | Forward sequence (5' -> 3') | | Forward sequence w/UT | |
| rpoB | rpoB | rpoB_29F_UT1 | TTCTTCGGAAGTTCTCAGTT | 43 | <u>ACCCAACTGAATGGAGC</u>TTCTTCGGAAGTTCTCAGTT | 383 |
| | | Reverse primer name | Reverse sequence (5' -> 3') | | Reverse sequence w/UT | |
| | | rpoB_196R_UT2 | CGGACACATACGACCATAG | 44 | <u>ACGCACTTGACTTGTCTT</u>CCGGACACATACGACCATAG | 384 |
| Assay name | Target species/gene | Forward primer name | Forward sequence (5' -> 3') | | Forward sequence w/UT | |
| AA_2502 | | AA_2502_UT1 | AAGTTTGAGGTGTGGAAATG | 45 | <u>ACCCAACTGAATGGAGC</u>AAGTTTGAGGTGTGGAAATG | 385 |
| | | Reverse primer name | Reverse sequence (5' -> 3') | | Reverse sequence w/UT | |
| | | AA_2502_UT2 | TCGAAATGAGTTCCAATTTT | 46 | <u>ACGCACTTGACTTGTCTT</u>CTCGAAATGAGTTCCAATTTT | 386 |
| Assay name | Target species/gene | Forward primer name | Forward sequence (5' -> 3') | | Forward sequence w/UT | |
| AA_2503 | | AA_2503v2_UT1 | CAAAACTAATAGGGGAGGGTG | 47 | <u>ACCCAACTGAATGGAGC</u>CAAAACTAATAGGGGAGGGTG | 387 |
| | | Reverse primer name | Reverse sequence (5' -> 3') | | Reverse sequence w/UT | |
| | | AA_2503_UT2 | CCGAGAACCTACCTCGTTA | 48 | <u>ACGCACTTGACTTGTCTT</u>CCCGAGAACCTACCTCGTTA | 388 |
| Assay name | Target species/gene | Forward primer name | Forward sequence (5' -> 3') | | Forward sequence w/UT | |
| Ba_AmesAnc_4669915 | | Ba&NN32_F | AGGAGATGAGAGTTTTGCAC | 49 | <u>ACCCAACTGAATGGAGC</u>AGGAGATGAGAGTTTTGCAC | 389 |
| | | Reverse primer name | Reverse sequence (5' -> 3') | | Reverse sequence w/UT | |
| | | Ba&NN32_R | ACCCCCATAATTACCATGA | 50 | <u>ACGCACTTGACTTGTCTT</u>CACCCCCATAATTACCATGA | 390 |

TABLE 12-continued

*Bacillus* primers and primers with Universal Tail (UT). The UT sequence is underlined.

| Assay name | Target species/gene | Forward primer name | Forward sequence (5' -> 3') | SEQ ID NO: | Forward sequence w/UT | SEQ ID NO: |
|---|---|---|---|---|---|---|
| Ba_AmesAnc_4001578 | | Ba&NN33_F | CGTTGCGTAAGTATGTGCTA | 51 | <u>ACCCAACTGAATGGAGCC</u>GTTGCGTAAGTATGTGCTA | 391 |
| | | Reverse primer name | Reverse sequence (5' -> 3') | | Reverse sequence w/UT | |
| | | Ba&NN33_R | AGGTGGCGTAATTAACGTAG | 52 | <u>ACGCACTTGACTTGTCTTC</u>AGGTGGCGTAATTAACGTAG | 392 |
| Assay name | Target species/gene | Forward primer name | Forward sequence (5' -> 3') | | Forward sequence w/UT | |
| Ba_AmesAnc_1069024 | | Ba&NN37_F | CGAAAAGTTGTCGACCTAAT | 53 | <u>ACCCAACTGAATGGAGCC</u>GAAAAGTTGTCGACCTAAT | 393 |
| | | Reverse primer name | Reverse sequence (5' -> 3') | | Reverse sequence w/UT | |
| | | Ba&NN37_R | ACTGCGTTCACGAAGAATAG | 54 | <u>ACGCACTTGACTTGTCTTC</u>ACTGCGTTCACGAAGAATAG | 394 |
| Assay name | Target species/gene | Forward primer name | Forward sequence (5' -> 3') | | Forward sequence w/UT | |
| Ba_AmesAnc_3668548 | | Ba&NN38_F | TCTCTTGATTCAACGTTTCC | 55 | <u>ACCCAACTGAATGGAGCT</u>CTCTTGATTCAACGTTTCC | 395 |
| | | Reverse primer name | Reverse sequence (5' -> 3') | | Reverse sequence w/UT | |
| | | Ba&NN38_R | GATGCAAAACCAATTCACTT | 56 | <u>ACGCACTTGACTTGTCTTC</u>GATGCAAAACCAATTCACTT | 396 |
| Assay name | Target species/gene | Forward primer name | Forward sequence (5' -> 3') | | Forward sequence w/UT | |
| Ba_AmesAnc_371913 | | Ba&NN40_F | GTGAAACATCGCTTTTTAGG | 57 | <u>ACCCAACTGAATGGAGC</u>GTGAAACATCGCTTTTTAGG | 397 |
| | | Reverse primer name | Reverse sequence (5' -> 3') | | Reverse sequence w/UT | |
| | | Ba&NN40_R | TCCGCAATGATATACTTCAA | 58 | <u>ACGCACTTGACTTGTCTTC</u>TCCGCAATGATATACTTCAA | 398 |
| Assay name | Target species/gene | Forward primer name | Forward sequence (5' -> 3') | | Forward sequence w/UT | |
| BaA_mesAnc_999035 | | Ba&NN41_F | ATACGGTGAAAATGAAGCAG | 59 | <u>ACCCAACTGAATGGAGC</u>ATACGGTGAAAATGAAGCAG | 399 |
| | | Reverse primer name | Reverse sequence (5' -> 3') | | Reverse sequence w/UT | |
| | | Ba&NN41_R | CGTCTTTGGTAATCGTTCA | 60 | <u>ACGCACTTGACTTGTCTTC</u>CGTCTTTGGTAATCGTTCA | 400 |
| Assay name | Target species/gene | Forward primer name | Forward sequence (5' -> 3') | | Forward sequence w/UT | |
| ChimpKiller_9-159 | | ChimpKiller_9F | TTATCGTCCATTCTTTCGTC | 23 | <u>ACCCAACTGAATGGAGC</u>TTATCGTCCATTCTTTCGTC | 401 |
| | | Reverse primer name | Reverse sequence (5' -> 3') | | Reverse sequence w/UT | |
| | | ChimpKiller_159R | AAACCTAATGAAACGGGATT | 24 | <u>ACGCACTTGACTTGTCTTC</u>AAACCTAATGAAACGGGATT | 402 |

TABLE 12-continued

Bacillus primers and primers with Universal Tail (UT). The UT sequence is underlined.

| Assay name | Target species/gene | Forward primer name | Forward sequence (5' -> 3') | SEQ ID NO: | Forward sequence w/UT | SEQ ID NO: |
|---|---|---|---|---|---|---|
| ChimpKiller_ 91-320 | | ChimpKiller_ 91F | TATGAAAGGAGCCGTAAAA C | 25 | <u>ACCCAACTGAATGGAGCT</u>ATGAA AGGAGCCGTAAAAC | 403 |
| | | Reverse primer name | Reverse sequence (5' -> 3') | | Reverse sequence w/UT | |
| | | ChimpKiller_ 320R | TGAATATGAAGCGGAAAAC T | 26 | <u>ACGCACTTGACTTGTCTT</u>CTGAA TATGAAGCGGAAAACT | 404 |
| Assay name | Target species/gene | Forward primer name | Forward sequence (5' -> 3') | | Forward sequence w/UT | |
| ChimpKiller_ 481-698 | | ChimpKiller_ 481F | TCGAACATACCTCCATTTCT | 27 | <u>ACCCAACTGAATGGAGCT</u>CGAAC ATACCTCCATTTCT | 405 |
| | | Reverse primer name | Reverse sequence (5' -> 3') | | Reverse sequence w/UT | |
| | | ChimpKiller_ 698R | AAAGATAGCTTTGCACTTGG | 28 | <u>ACGCACTTGACTTGTCTT</u>CAAAG ATAGCTTTGCACTTGG | 406 |

TABLE 13

Yersinia primers and primers with Universal Tail (UT). The UT sequence is underlined.

| Assay name | Target species/gene | Forward primer name | Forward sequence (5' -> 3') | SEQ ID NO: | Forward sequence w/UT | SEQ ID NO: |
|---|---|---|---|---|---|---|
| Ypestis_LPQY 01000176.1_7 | | Yp&NN1_F | AACAAGCTAAAACCGAACA A | 231 | <u>ACCCAACTGAATGGAGC</u>AACAA GCTAAAACCGAACAA | 407 |
| | | Reverse primer name | Reverse sequence (5' -> 3') | | Reverse sequence w/UT | |
| | | Yp&NN1_R | ATAGCCTCAACTGCTTTTG | 232 | <u>ACGCACTTGACTTGTCTT</u>CATAG CCTCAACTGCTTTTG | 408 |
| Assay name | Target species/gene | Forward primer name | Forward sequence (5' -> 3') | | Forward sequence w/UT | |
| Wagner_Yp_ pla_Forward | | Yp&NN2_F | GAAAGGAGTGCGGGTAATA GGTT | 237 | <u>ACCCAACTGAATGGAGC</u>GAAAG GAGTGCGGGTAATAGGTT | 409 |
| | | Reverse primer name | Reverse sequence (5' -> 3') | | Reverse sequence w/UT | |
| | | Yp&NN2_R | GGCCTGCAAGTCCAATATA TGG | 238 | <u>ACGCACTTGACTTGTCTT</u>CGGCC TGCAAGTCCAATATATGG | 410 |
| Assay name | Target species/gene | Forward primer name | Forward sequence (5' -> 3') | | Forward sequence w/UT | |
| YenteroFR72 9477.2_623 | | Yp&NN3_F | GATGCTTCTGCTATCAGSTT | 263 | <u>ACCCAACTGAATGGAGC</u>GATGCT TCTGCTATCAGSTT | 411 |
| | | Reverse primer name | Reverse sequence (5' -> 3') | | Reverse sequence w/UT | |
| | | Yp&NN3_R | GTGTGRCTTTGAASTCTTGT | 264 | <u>ACGCACTTGACTTGTCTT</u>CGTGT GRCTTTGAASTCTTGT | 412 |

TABLE 13-continued

Yersinia primers and primers with Universal Tail (UT). The UT sequence is underlined.

| Assay name | Target species/gene | Forward primer name | Forward sequence (5' -> 3') | SEQ ID NO: | Forward sequence w/UT | SEQ ID NO: |
|---|---|---|---|---|---|---|
| YPCO92_NC_003143_113190 | | Yp&NN4_F | ACTCGGGATACTCCATACTG | 249 | <u>ACCCAACTGAATGGAGC</u>ACTCGGGATACTCCATACTG | 413 |
| | | Reverse primer name | Reverse sequence (5' -> 3') | | Reverse sequence w/UT | |
| | | Yp&NN4_R | CGAAAGCAGTGGTCAATC | 250 | <u>ACGCACTTGACTTGTCTTC</u>CGAAAGCAGTGGTCAATC | 414 |
| Assay name | Target species/gene | Forward primer name | Forward sequence (5' -> 3') | | Forward sequence w/UT | |
| YPCO92_NC_003143_161621 | | Yp&NN5_F | CATGCGCTTTACGTTATATG | 251 | <u>ACCCAACTGAATGGAGC</u>CATGCGCTTTACGTTATATG | 415 |
| | | Reverse primer name | Reverse sequence (5' -> 3') | | Reverse sequence w/UT | |
| | | Yp&NN5_R | GCGTTCTGCACTCTGTCT | 252 | <u>ACGCACTTGACTTGTCTTC</u>GCGTTCTGCACTCTGTCT | 416 |
| Assay name | Target species/gene | Forward primer name | Forward sequence (5' -> 3') | | Forward sequence w/UT | |
| YPCO92_NC_003143_152213 | | Yp&NN6_F | AGCGACTTCCGTGATAAAG | 253 | <u>ACCC'AACTGAATGGAGC</u>AGCGACTTCCGTGATAAAG | 417 |
| | | Reverse primer name | Reverse sequence (5' -> 3') | | Reverse sequence w/UT | |
| | | Yp&NN6_R | ACTCAGGATACCGTGTGGT | 254 | <u>ACGCACTTGACTTGTCTTC</u>ACTCAGGATACCGTGTGGT | 418 |
| Assay name | Target species/gene | Forward primer name | Forward sequence (5' -> 3') | | Forward sequence w/UT | |
| YPCO92_NC_003143_129539 | | Yp&NN7_F | TTCACGATAATCCCCTAATG | 255 | <u>ACCCAACTGAATGGAGC</u>TTCACGATAATCCCCTAATG | 419 |
| | | Reverse primer name | Reverse sequence (5' -> 3') | | Reverse sequence w/UT | |
| | | Yp&NN7_R | TTCTGTGCTCTGGCTGATA | 256 | <u>ACGCACTTGACTTGTCTTC</u>TTCTGTGCTCTGGCTGATA | 420 |
| Assay name | Target species/gene | Forward primer name | Forward sequence (5' -> 3') | | Forward sequence w/UT | |
| YPCO92_NC_003143_91203 | | Yp&NN8_F | ATTATCTGTGCCCCTTCTTT | 257 | <u>ACCCAACTGAATGGAGC</u>ATTATCTGTGCCCCTTCTTT | 421 |
| | | Reverse primer name | Reverse sequence (5' -> 3') | | Reverse sequence w/UT | |
| | | Yp&NN8_R | GGAGTGGATGCCACTAAAC | 258 | <u>ACGCACTTGACTTGTCTTC</u>GGAGTGGATGCCACTAAAC | 422 |
| Assay name | Target species/gene | Forward primer name | Forward sequence (5' -> 3') | | Forward sequence w/UT | |
| YpC092_NC_003143_121812 | | Yp&NN9_F | CCTCACACAACAATTCACTG | 259 | <u>ACCCAACTGAATGGAGC</u>CCTCACACAACAATTCACTG | 423 |
| | | Reverse primer name | Reverse sequence (5' -> 3') | | Reverse sequence w/UT | |
| | | Yp&NN9_R | TTTTTCCGACAAATTTAAGG | 260 | <u>ACGCACTTGACTTGTCTTC</u>TTTTTCCGACAAATTTAAGG | 424 |

TABLE 13-continued

Yersinia primers and primers with Universal Tail (UT). The UT sequence is underlined.

| Assay name | Target species/gene | Forward primer name | Forward sequence (5' -> 3') | SEQ ID NO: | Forward sequence w/UT | SEQ ID NO: |
|---|---|---|---|---|---|---|
| Yp_AL590842.1_RX_SNP | | Yp&NN10_F | AGCATGAAGGTTGCTAAAAG | 261 | <u>ACCCAACTGAATGGAGC</u>AGCATGAAGGTTGCTAAAAG | 425 |
| | | Reverse primer name | Reverse sequence (5' -> 3') | | Reverse sequence w/UT | |
| | | Yp&NN10_R | GGTGACTTCAAAACCGTTAG | 262 | <u>ACGCACTTGACTTGTCTTC</u>GGTGACTTCAAAACCGTTAG | 426 |
| Assay name | Target species/gene | Forward primer name | Forward sequence (5' -> 3') | | Forward sequence w/UT | |
| AGJT01000065.1_0_338 | | Yp&NN11_F | CAGTACCGACAAAACTTC | 233 | <u>ACCCAACTGAATGGAGC</u>CAGTACCGACAAAACTTC | 427 |
| | | Reverse primer name | Reverse sequence (5' -> 3') | | Reverse sequence w/UT | |
| | | Yp&NN11_R | TTTACTACTCTGAAAACGAG | 234 | <u>ACGCACTTGACTTGTCTTC</u>TTTACTACTCTGAAAACGAG | 428 |
| Assay name | Target species/gene | Forward primer name | Forward sequence (5' -> 3') | | Forward sequence w/UT | |
| FAURO1000053.1_9640_796884 | | Yp&NN12_F | GCACTACAAATTTAAATCCC | 235 | <u>ACCCAACTGAATGGAGC</u>GCACTACAAATTTAAATCCC | 429 |
| | | Reverse primer name | Reverse sequence (5' -> 3') | | Reverse sequence w/UT | |
| | | Yp&NN12_R | GTCGATTATCAACCTCTATG | 236 | <u>ACGCACTTGACTTGTCTTC</u>GTCGATTATCAACCTCTATG | 430 |
| Assay name | Target species/gene | Forward primer name | Forward sequence (5' -> 3') | | Forward sequence w/UT | |
| YpPGM_8-158 | PGM | YpPGM_8F | TTAATATCCCGGCACTCATA | 239 | <u>ACCCAACTGAATGGAGC</u>TTAATATCCCGGCACTCATA | 431 |
| | | Reverse primer name | Reverse sequence (5' -> 3') | | Reverse sequence w/UT | |
| | | YpPGM_158R | TCCTTAACTGAATAAGTGCTCA | 240 | <u>ACGCACTTGACTTGTCTTC</u>TCCTTAACTGAATAAGTGCTCA | 432 |
| Assay name | Target species/gene | Forward primer name | Forward sequence (5' -> 3') | | Forward sequence w/UT | |
| YpPGM_31-205 | PGM | YpPGM_31Fv2 | TTTAATGAACGGTGCCTAG | 241 | <u>ACCCAACTGAATGGAGC</u>TTTAATGAACGGTGCCTAG | 433 |
| | | Reverse primer name | Reverse sequence (5' -> 3') | | Reverse sequence w/UT | |
| | | YpPGM_205Rv2 | GTCTGCGTTTCTCCAGTAT | 242 | <u>ACGCACTTGACTTGTCTTC</u>GTCTGCGTTTCTCCAGTAT | 434 |
| Assay name | Target species/gene | Forward primer name | Forward sequence (5' -> 3') | | Forward sequence w/UT | |
| Yp-p1202_42780-43194 | p1P1202 | Yp-P1202_42780F-UT1 | TCTGGCCTGCTAAATAAAAACGAACC | 243 | <u>ACCCAACTGAAIGGAGC</u>TCTGGCCTGCTAAATAAAAACGAACC | 435 |

TABLE 13-continued

Yersinia primers and primers with Universal Tail (UT). The UT sequence is underlined.

| | | | | | SEQ ID NO: | | SEQ ID NO: |
|---|---|---|---|---|---|---|---|
| | | Reverse primer name | Reverse sequence (5' -> 3') | | | Reverse sequence w/UT | |
| | | Yp-p1202_43194 R-UT2 | CAGGCCTCAGCATTTTATT ATGGTGAT | | 244 | <u>ACGCACTTGACTTGTCTTC</u>CAGG CCTCAGCATTTTATTATGGTGAT | 436 |
| Assay name | Target species/gene | Forward primer name | Forward sequence (5' -> 3') | | | Forward sequence w/UT | |
| Yp-p1202_1 26386-126750 | p1P1202 | Yp-P1202_12638 6F-UT1 | GGGGCGGATACCTTCACCT ATG | | 245 | <u>ACCCAACTGAATGGAGCGGGGC</u> GGATACCTTCACCTATG | 437 |
| | | Reverse primer name | Reverse sequence (5' -> 3') | | | Reverse sequence w/UT | |
| | | Yp-p1202_126750R-UT2 | CTGGGGTTCAGTCTGGACG AGAT | | 246 | <u>ACGCACTTGACTTGTCTTC</u>CTGG GGTTCAGTCTGGACGAGAT | 438 |
| Assay name | Target species/gene | Forward primer name | Forward sequence (5' -> 3') | | | Forward sequence w/UT | |
| Yp-p1202_156402-156711 | p1P1202 | Yp-p1202_15640 2F2-UT1 | ACCATCCGGCGCTAAATCG TC | | 247 | <u>ACCCAACTGAATGGAGC</u>ACCATC CGGCGCTAAATCGTC | 439 |
| | | Reverse primer name | Reverse sequence (5' -> 3') | | | Reverse sequence w/UT | |
| | | Yp-p1202_15671 1R-UT2 | GAAATGCGCCTGGTAAGCA GAGT | | 248 | <u>ACGCACTTGACTTGTCTTC</u>GAAA TGCGCCTGGTAAGCAGAGT | 440 |

TABLE 14

Francisella primers and primers with Universal Tail (UT). The UT sequence is underlined.

| | | | | | SEQ ID NO: | | SEQ ID NO: |
|---|---|---|---|---|---|---|---|
| Assay name | Target species/gene | Forward primer name | Forward sequence (5' -> 3') | | | Forward sequence w/UT | |
| Ftnovicida_ CP009607.1 | | Ft&NN1_F | GGTAGGATAACTACCAAG | | 285 | <u>ACCCAACTGAATGGAGC</u>GGTAG GATAACTACCAAG | 441 |
| | | Reverse primer name | Reverse sequence (5' -> 3') | | | Reverse sequence w/UT | |
| | | Ft&NN1_R | GTCATGAGTTTTACCAATA CTC | | 286 | <u>ACGCACTTGACTTGTCTTC</u>GTCAT GAGTTTTACCAATACTC | 442 |
| Assay name | Target species/gene | Forward primer name | Forward sequence (5' -> 3') | | | Forward sequence w/UT | |
| Ftularensis_CP0 00915.1_1782 | | Ft&NN2_F | GAAGTGGCTCATGTTAGAG G | | 265 | <u>ACCCAACTGAATGGAGC</u>GAAGT GGCTCATGTTAGAGG | 443 |
| | | Reverse primer name | Reverse sequence (5' -> 3') | | | Reverse sequence w/UT | |
| | | Ft&NN2_R | AGCGAGCCTATATGTAACC A | | 266 | <u>ACGCACTTGACTTGTCTTC</u>AGCG AGCCTATATGTAACCA | 444 |

TABLE 14-continued

Francisella primers and primers with Universal Tail (UT). The UT sequence is underlined.

| Assay name | Target species/gene | Forward primer name | Forward sequence (5' -> 3') | SEQ ID NO: | Forward sequence w/UT | SEQ ID NO: |
|---|---|---|---|---|---|---|
| Ftularensis_CP000915.1_731 | | Ft&NN3_F | TTTAATGTCCGTCAACCTCT | 267 | <u>ACCCAACTGAATGGAGC</u>TTTAATGTCCGTCAACCTCT | 445 |
| | | Reverse primer name | Reverse sequence (5' -> 3') | | Reverse sequence w/UT | |
| | | Ft&NN3_R | ACGAGTTTGTGAGTCGCTAT | 268 | <u>ACGCACTTGACTTGTCTTC</u>ACGAGTTTGTGAGTCGCTAT | 446 |
| Assay name | Target species/gene | Forward primer name | Forward sequence (5' -> 3') | | Forward sequence w/UT | |
| Fnoatunensis_CP003402.1_1749 | | Ft&NN4_F | CGGTAAGAATACGACCAGAG | 291 | <u>ACCCAACTGAATGGAGC</u>CGGTAAGAATACGACCAGAG | 447 |
| | | Reverse primer name | Reverse sequence (5' -> 3') | | Reverse sequence w/UT | |
| | | Ft&NN4_R | AGAGGATTTCTTCCTCCTTG | 292 | <u>ACGCACTTGACTTGTCTTC</u>AGAGGATTTCTTCCTCCTTG | 448 |
| Assay name | Target species/gene | Forward primer name | Forward sequence (5' -> 3') | | Forward sequence w/UT | |
| Fnoatunensis_CP003402.1_424 | | Ft&NN5_F | AATTCTACAAGCACCTGGAA | 293 | <u>ACCCAACTGAATGGAGC</u>AATTCTACAAGCACCTGGAA | 449 |
| | | Reverse primer name | Reverse sequence (5' -> 3') | | Reverse sequence w/UT | |
| | | Ft&NN5R | TCCTATTAAAAGCGCCATAG | 294 | <u>ACGCACTTGACTTGTCTTC</u>TCCTATTAAAAGCGCCATAG | 450 |
| Assay name | Target species/gene | Forward primer name | Forward sequence (5' -> 3') | | Forward sequence w/UT | |
| Fphilom_CP009444.1_569 | | Ft&NN6F | CTTATGCAGCAAGAGGAACT | 287 | <u>ACCCAACTGAATGGAGC</u>CTTATGCAGCAAGAGGAACT | 451 |
| | | Reverse primer name | Reverse sequence (5' -> 3') | | Reverse sequence w/UT | |
| | | Ft&NN6_R | ATACACCGGGATAGGTTTCT | 288 | <u>ACGCACTTGACTTGTCTTC</u>ATACACCGGGATAGGTTTCT | 452 |
| Assay name | Target species/gene | Forward primer name | Forward sequence (5' -> 3') | | Forward sequence w/UT | |
| Fphilom_CP009444.1_285 | | Ft&NN7_F | CTGATGGAAGAGAGTTCGAG | 289 | <u>ACCCAACTGAATGGAGC</u>CTGATGGAAGAGAGTTCGAG | 453 |
| | | Reverse primer name | Reverse sequence (5' -> 3') | | Reverse sequence w/UT | |
| | | Ft&NN7_Rv2 | GTAGATATAATCAGCGCCAC | 290 | <u>ACGCACTTGACTTGTCTTC</u>GTAGATATAATCAGCGCCAC | 454 |
| Assay name | Target species/gene | Forward primer name | Forward sequence (5' -> 3') | | Forward sequence w/UT | |
| Ft_dup_CP000915.1_197 | | Ft&NN8_F | TGTTACGTACAGGCTGTCAA | 269 | <u>ACCCAACTGAATGGAGC</u>TGTTACGTACAGGCTGTCAA | 455 |
| | | Reverse primer name | Reverse sequence (5' -> 3') | | Reverse sequence w/UT | |
| | | Ft&NN8_R | ATCATATCCCGTAGCACAAG | 270 | <u>ACGCACTTGACTTGTCTTC</u>ATCATATCCCGTAGCACAAG | 456 |

TABLE 14-continued

Francisella primers and primers with Universal Tail (UT). The UT sequence is underlined.

| Assay name | Target species/gene | Forward primer name | Forward sequence (5' -> 3') | Forward sequence w/UT | SEQ ID NO: | SEQ ID NO: |
|---|---|---|---|---|---|---|
| FtLVS_AM2333 62_1646546 | | Ft&NN9_F | ATCAAGCTCATCTTCAAAGC | 279 | <u>ACCCAACTGAATGGAGC</u>ATCAAG CTCATCTTCAAAGC | 457 |
| | | Reverse primer name | Reverse sequence (5' -> 3') | Reverse sequence w/UT | | |
| | | Ft&NN9_R | AACCATGTTCAGATCCAAAA | 280 | <u>ACGCACTTGACTTGTCTTC</u>AACC ATGTTCAGATCCAAAA | 458 |
| Assay name | Target species/gene | Forward primer name | Forward sequence (5' -> 3') | Forward sequence w/UT | | |
| FtLVS_AM2333 62_1643765 | | Ft&NN10_F | TACCTCTGCCAAAAATTCAT | 281 | <u>ACCCAACTGAATGGAGC</u>TACCTC TGCCAAAAATTCAT | 459 |
| | | Reverse primer name | Reverse sequence (5' -> 3') | Reverse sequence w/UT | | |
| | | Ft&NN10_R | GGCATACTCAAGGTAGTGGT | 282 | <u>ACGCACTTGACTTGTCTTC</u>GGCA TACTCAAGGTAGTGGT | 460 |
| Assay name | Target species/gene | Forward primer name | Forward sequence (5' -> 3') | Forward sequence w/UT | | |
| FtLVS_AM2333 62_1562618 | | Ft&NN11_F | TCTTTGGTAGCTTGCTGACT | 283 | <u>ACCCAACTGAATGGAGC</u>TCTTTG GTAGCTTGCTGACT | 461 |
| | | Reverse primer name | Reverse sequence (5' -> 3') | Reverse sequence w/UT | | |
| | | Ft&NN11_R | CAGACGACACTTGGCTTATT | 284 | <u>ACGCACTTGACTTGTCTTC</u>CAGA CGACACTTGGCTTATT | 462 |
| Assay name | Target species/gene | Forward primer name | Forward sequence (5'-> 3') | Forward sequence w/UT | | |
| FtA1 | FtA1 | 9F_FtA1_UT 1 | CATAACCCATCGCAATATCT | 271 | <u>ACCCAACTGAATGGAGC</u>CATAAC CCATCGCAATATCT | 463 |
| | | Reverse primer name | Reverse sequence (5' -> 3') | Reverse sequence w/UT | | |
| | | 246R_FtA1_ UT2 | AAATTATCTGTAGCGGCAAA | 272 | <u>ACGCACTTGACTTGTCTTC</u>AAAT TATCTGTAGCGGCAAA | 464 |
| Assay name | Target species/gene | Forward primer name | Forward sequence (5' -> 3') | Forward sequence w/UT | | |
| FtA2 | FtA2 | 34F_FtA2_U T1 | GTGTCCAACGAAACCATAAT | 273 | <u>ACCCAACTGAATGGAGC</u>GTGTCC AACGAAACCATAAT | 465 |
| | | Reverse primer name | Reverse sequence (5' -> 3') | Reverse sequence w/UT | | |
| | | 169R_FtA2_ UT2 | TTTGGTTGATTCTGTCAGTG | 274 | <u>ACGCACTTGACTTGTCTTC</u>TTTGG TTGATTCTGTCAGTG | 466 |
| Assay name | Target species/gene | Forward primer name | Forward sequence (5' -> 3') | Forward sequence w/UT | | |
| FtB | FtB | 28F_FtB_UT 1 | AAGCTTAACTGGTGATTGGA | 275 | <u>ACCCAACTGAATGGAGC</u>AAGCTT AACTGGTGATTGGA | 467 |
| | | Reverse primer name | Reverse sequence (5' -> 3') | Reverse sequence w/UT | | |
| | | 173R_FtB_U T2 | CGCCTAACATCTTATCTGCT | 276 | <u>ACGCACTTGACTTGTCTTC</u>CGCCT AACATCTTATCTGCT | 468 |

TABLE 14-continued

Francisella primers and primers with Universal Tail (UT). The UT sequence is underlined.

| Assay name | Target species/gene | Forward primer name | Forward sequence (5' -> 3') | Forward sequence w/UT | SEQ ID NO: | SEQ ID NO: |
|---|---|---|---|---|---|---|
| FtA | FtA | 14F_FtA_UT1 | GGGTGATGCAGTAGAGAAA A | 277 | <u>ACCCAACTGAATGGAGCGGGTG</u>ATGCAGTAGAGAAAA | 469 |
| | | Reverse primer name | Reverse sequence (5' -> 3') | | | Reverse sequence w/UT |
| | | 207R_FtA_UT2 | TACCAGATGAACGAATAGC C | 278 | <u>ACGCACTTGACTTGTCTTCTACC</u>AGATGAACGAATAGCC | 470 |

All headings are for the convenience of the reader and should not be used to limit the meaning of the text that follows the heading, unless so specified.

Unless defined otherwise, all technical and scientific terms herein have the same meaning as commonly understood by one of ordinary skill in the art to which this invention belongs. Although any methods and materials, similar or equivalent to those described herein, can be used in the practice or testing of the present invention, the preferred methods and materials are described herein. All publications, patents, and patent publications cited are incorporated by reference in their entirety for all purposes.

The publications discussed herein are provided solely for their disclosure prior to the filing date of the present application. Nothing herein is to be construed as an admission that the present invention is not entitled to antedate such publication by virtue of prior invention.

While the invention has been described in connection with specific embodiments thereof, it will be understood that it is capable of further modifications and this application is intended to cover any variations, uses, or adaptations of the invention following, in general, the principles of the invention and including such departures from the present disclosure as come within known or customary practice within the art to which the invention pertains and as may be applied to the essential features hereinbefore set forth and as follows in the scope of the appended claims.

What is claimed is:

1. A method of detecting *Bacillus anthracis* in a sample, comprising:
   generating one or more amplicons from the sample using at least one primer pair comprising a forward and reverse primer in at least one amplification reaction;
   sequencing the one or more amplicons using next-generation sequencing; and
   detecting at least one *B. anthracis*-specific amplicon in the sequenced amplicons, wherein each forward and reverse primer comprise a forward and reverse sequence selected from the group consisting of:
   SEQ ID NO: 1 and SEQ ID NO: 2;
   SEQ ID NO: 3 and SEQ ID NO: 4;
   SEQ ID NO: 5 and SEQ ID NO: 6;
   SEQ ID NO: 7 and SEQ ID NO: 8;
   SEQ ID NO: 9 and SEQ ID NO: 10;
   SEQ ID NO: 11 and SEQ ID NO: 12;
   SEQ ID NO: 13 and SEQ ID NO: 14;
   SEQ ID NO: 15 and SEQ ID NO: 16; and
   SEQ ID NO: 17 and SEQ ID NO: 18;
   wherein the presence of the at least one *B. anthracis*-specific amplicon indicates the presence of *B. anthracis* in the sample, and the absence of the at least one *B. anthracis*-specific amplicon indicates the absence of *B. anthracis* from the sample.

2. The method of claim 1, further comprising confirming the absence of *B. anthracis* by detecting at least one *B. anthracis* Near Neighbor-specific amplicon using at least one primer pair comprising a forward and reverse primer comprising a forward and reverse sequence selected from the group consisting of:
   SEQ ID NO: 19 and SEQ ID NO: 20;
   SEQ ID NO: 21 and SEQ ID NO: 22; and
   SEQ ID NO: 23 and SEQ ID NO: 24;
   wherein detecting at least one *B. anthracis* Near Neighbor-specific amplicon in the sample confirms the absence of *B. anthracis*.

3. The method of claim 1, further comprising confirming the absence of *B. anthracis* by detecting at least one *B. anthracis* Near Neighbor-specific sequence variant (SV) or single nucleotide polymorphism (SNP) using at least one primer pair comprising a forward and reverse primer comprising a forward and reverse sequence selected from the group consisting of:
   SEQ ID NO: 25 and SEQ ID NO: 26;
   SEQ ID NO: 27 and SEQ ID NO: 28;
   SEQ ID NO: 49 and SEQ ID NO: 50;
   SEQ ID NO: 51 and SEQ ID NO: 52;
   SEQ ID NO: 53 and SEQ ID NO: 54;
   SEQ ID NO: 55 and SEQ ID NO: 56;
   SEQ ID NO: 57 and SEQ ID NO: 58; and
   SEQ ID NO: 59 and SEQ ID NO: 60;
   wherein detecting at least one *B. anthracis* Near Neighbor-specific SV in the sample confirms the absence of *B. anthracis*.

4. The method of claim 1, further comprising detecting a virulence locus or virulence plasmid in the sample by detecting a virulence-specific amplicon using at least one primer pair comprising a forward and reverse primer comprising a forward and reverse sequence selected from the group consisting of:
   SEQ ID NO: 29 and SEQ ID NO: 30;
   SEQ ID NO: 31 and SEQ ID NO: 32;
   SEQ ID NO: 33 and SEQ ID NO: 34; and
   SEQ ID NO: 35 and SEQ ID NO: 36;
   wherein the presence of the virulence-specific amplicon indicates the presence of the virulence locus or virulence plasmid in the sample.

5. The method of claim 1, further comprising detecting at least one drug resistance single nucleotide polymorphism (SNP) from *B. anthracis* in the sample using at least one primer pair comprising a forward and reverse primer comprising a forward and reverse sequence selected from the group consisting of:
   SEQ ID NO: 37 and SEQ ID NO: 38;
   SEQ ID NO: 39 and SEQ ID NO: 40;
   SEQ ID NO: 41 and SEQ ID NO: 42;
   SEQ ID NO: 43 and SEQ ID NO: 44;
   SEQ ID NO: 45 and SEQ ID NO: 46; and
   SEQ ID NO: 47 and SEQ ID NO: 48.

6. The method of claim 1, further comprising detecting *Burkholderia pseudomallei* and/or *Burkholderia mallei* in the sample by detecting at least one *B. pseudomallei* or *B. mallei*-specific amplicon using at least one primer pair comprising a forward and reverse primer comprising a forward and reverse sequence selected from the group consisting of:
   SEQ ID NO: 61 and SEQ ID NO: 62;
   SEQ ID NO: 63 and SEQ ID NO: 64;
   SEQ ID NO: 65 and SEQ ID NO: 66;
   SEQ ID NO: 67 and SEQ ID NO: 68;
   SEQ ID NO: 69 and SEQ ID NO: 70;
   SEQ ID NO: 71 and SEQ ID NO: 72;
   SEQ ID NO: 73 and SEQ ID NO: 74;
   SEQ ID NO: 75 and SEQ ID NO: 76;
   SEQ ID NO: 77 and SEQ ID NO: 78;
   SEQ ID NO: 79 and SEQ ID NO: 80;
   SEQ ID NO: 81 and SEQ ID NO: 82;
   SEQ ID NO: 83 and SEQ ID NO: 84;
   SEQ ID NO: 85 and SEQ ID NO: 86;
   SEQ ID NO: 87 and SEQ ID NO: 88;
   SEQ ID NO: 89 and SEQ ID NO: 90;
   SEQ ID NO: 91 and SEQ ID NO: 92;
   SEQ ID NO: 93 and SEQ ID NO: 94;
   SEQ ID NO: 95 and SEQ ID NO: 96;
   SEQ ID NO: 97 and SEQ ID NO: 98;
   SEQ ID NO: 99 and SEQ ID NO: 100;
   SEQ ID NO: 101 and SEQ ID NO: 102;
   SEQ ID NO: 103 and SEQ ID NO: 104;
   SEQ ID NO: 103 and SEQ ID NO: 104;
   SEQ ID NO: 105 and SEQ ID NO: 106;
   SEQ ID NO: 107 and SEQ ID NO: 108;
   SEQ ID NO: 117 and SEQ ID NO: 118;
   SEQ ID NO: 119 and SEQ ID NO: 120;
   SEQ ID NO: 121 and SEQ ID NO: 122;
   SEQ ID NO: 123 and SEQ ID NO: 124; and
   SEQ ID NO: 125 and SEQ ID NO: 126;
   wherein the presence of the at least one *B. pseudomallei* or *B. mallei*-specific amplicon indicates the presence of *B. pseudomallei* and/or *B. mallei* in the sample, and an absence of the at least one *B. pseudomallei* or *B. mallei*-specific amplicon indicates an absence of *B. pseudomallei* and *B. mallei* in the sample.

7. The method of claim 6, further comprising confirming the absence of *B. pseudomallei* and *B. mallei* by detecting at least one *B. pseudomallei* or *B. mallei* Near Neighbor-specific amplicon using at least one primer pair comprising a forward and reverse primer comprising a forward and reverse sequence selected from the group consisting of:
   SEQ ID NO: 177 and SEQ ID NO: 178;
   SEQ ID NO: 179 and SEQ ID NO: 180;
   SEQ ID NO: 181 and SEQ ID NO: 182;

SEQ ID NO: 183 and SEQ ID NO: 184;
SEQ ID NO: 185 and SEQ ID NO: 186;
SEQ ID NO: 187 and SEQ ID NO: 188;
SEQ ID NO: 189 and SEQ ID NO: 190;
SEQ ID NO: 191 and SEQ ID NO: 192;
SEQ ID NO: 193 and SEQ ID NO: 194;
SEQ ID NO: 195 and SEQ ID NO: 196;
SEQ ID NO: 197 and SEQ ID NO: 198;
SEQ ID NO: 199 and SEQ ID NO: 200;
SEQ ID NO: 201 and SEQ ID NO: 202;
SEQ ID NO: 203 and SEQ ID NO: 204;
SEQ ID NO: 205 and SEQ ID NO: 206;
SEQ ID NO: 207 and SEQ ID NO: 208;
SEQ ID NO: 207 and SEQ ID NO: 208;
SEQ ID NO: 209 and SEQ ID NO: 210;
SEQ ID NO: 211 and SEQ ID NO: 212;
SEQ ID NO: 213 and SEQ ID NO: 214;
SEQ ID NO: 215 and SEQ ID NO: 216;
SEQ ID NO: 217 and SEQ ID NO: 218;
SEQ ID NO: 219 and SEQ ID NO: 220;
SEQ ID NO: 221 and SEQ ID NO: 222;
SEQ ID NO: 223 and SEQ ID NO: 224;
SEQ ID NO: 225 and SEQ ID NO: 226;
SEQ ID NO: 227 and SEQ ID NO: 228; and
SEQ ID NO: 229 and SEQ ID NO: 230;
wherein detecting at least one *B. pseudomallei* or *B. mallei* Near Neighbor-specific amplicon in the sample confirms the absence of *B. pseudomallei* and *B. mallei*.

8. The method of claim 6, further comprising confirming the absence of *B. pseudomallei* and *B. mallei* by detecting at least one *B. pseudomallei* or *B. mallei* Near Neighbor-specific SNP or SV using at least one primer pair comprising a forward and reverse primer comprising a forward and reverse sequence selected from the group consisting of:
SEQ ID NO: 109 and SEQ ID NO: 110;
SEQ ID NO: 111 and SEQ ID NO: 112;
SEQ ID NO: 113 and SEQ ID NO: 114; and
SEQ ID NO: 115 and SEQ ID NO: 116;
wherein detecting at least one *B. pseudomallei* or *B. mallei* Near Neighbor-specific SNP or SV in the sample confirms the absence of *B. pseudomallei* and *B. mallei*.

9. The method of claim 6, further comprising detecting at least one drug resistance SNP or SV from *Burkholderia* spp. in the sample using at least one primer pair comprising a forward and reverse primer comprising a forward and reverse sequence selected from the group consisting of:
SEQ ID NO: 127 and SEQ ID NO: 128;
SEQ ID NO: 129 and SEQ ID NO: 130;
SEQ ID NO: 131 and SEQ ID NO: 132;
SEQ ID NO: 133 and SEQ ID NO: 134;
SEQ ID NO: 135 and SEQ ID NO: 136;
SEQ ID NO: 137 and SEQ ID NO: 138;
SEQ ID NO: 145 and SEQ ID NO: 146;
SEQ ID NO: 147 and SEQ ID NO: 148;
SEQ ID NO: 149 and SEQ ID NO: 150;
SEQ ID NO: 151 and SEQ ID NO: 152; and
SEQ ID NO: 153 and SEQ ID NO: 154.

10. The method of claim 1, further comprising detecting *Francisella tularensis* in the sample by detecting at least one *F. tularensis*-specific amplicon using at least one primer pair comprising a forward and reverse primer comprising a forward and reverse sequence selected from the group consisting of:
SEQ ID NO: 265 and SEQ ID NO: 266;
SEQ ID NO: 267 and SEQ ID NO: 268; and
SEQ ID NO: 269 and SEQ ID NO: 270;
wherein the presence of the at least one *F. tularensis*-specific amplicon indicates that *F. tularensis* is present in the sample, and an absence of the at least one *F. tularensis*-specific amplicon indicates that *F. tularensis* is absent in the sample.

11. The method of claim 10, further comprising confirming the absence of *F. tularensis* by detecting at least one *F. tularensis* Near Neighbor-specific amplicon using at least one primer pair comprising a forward and reverse primer comprising a forward and reverse sequence selected from the group consisting of:
SEQ ID NO: 285 and SEQ ID NO: 286;
SEQ ID NO: 287 and SEQ ID NO: 288;
SEQ ID NO: 289 and SEQ ID NO: 290;
SEQ ID NO: 291 and SEQ ID NO: 292; and
SEQ ID NO: 293 and SEQ ID NO: 294;
wherein detecting at least one *F. tularensis* Near Neighbor-specific amplicon in the sample confirms the absence of *F. tularensis*.

12. The method of claim 10, further comprising confirming the absence of *F. tularensis* by detecting at least one *F. tularensis* Near Neighbor-specific SNP or SV using at least one primer pair comprising a forward and reverse primer comprising a forward and reverse sequence selected from the group consisting of:
SEQ ID NO: 271 and SEQ ID NO: 272;
SEQ ID NO: 273 and SEQ ID NO: 274;
SEQ ID NO: 275 and SEQ ID NO: 276;
SEQ ID NO: 277 and SEQ ID NO: 278;
SEQ ID NO: 279 and SEQ ID NO: 280;
SEQ ID NO: 281 and SEQ ID NO: 282; and
SEQ ID NO: 283 and SEQ ID NO: 284;
wherein detecting at least one *F. tularensis* Near Neighbor-specific SNP or SV in the sample confirms the absence of *F. tularensis*.

13. The method of claim 1, further comprising detecting *Yersinia pestis* in the sample by detecting at least one *Y. pestis*-specific amplicon using at least one primer pair comprising a forward and reverse primer comprising a forward and reverse sequence selected from the group consisting of:
SEQ ID NO: 231 and SEQ ID NO: 232;
SEQ ID NO: 233 and SEQ ID NO: 234;
SEQ ID NO: 235 and SEQ ID NO: 236; and
SEQ ID NO: 237 and SEQ ID NO: 238;
wherein the presence of at least one *Y. pestis*-specific amplicon indicates the presence of *Y. pestis* in the sample, and an absence of at least one *Y. pestis*-specific amplicon indicates an absence of *Y. pestis* in the sample.

14. The method of claim 13, further comprising confirming the absence of *Y. pestis* by detecting at least one *Y. pestis* Near Neighbor-specific SNP or SV using at least one primer pair comprising a forward and reverse primer comprising a forward and reverse sequence selected from the group consisting of:
SEQ ID NO: 249 and SEQ ID NO: 250;
SEQ ID NO: 251 and SEQ ID NO: 252;
SEQ ID NO: 253 and SEQ ID NO: 254;
SEQ ID NO: 255 and SEQ ID NO: 256;
SEQ ID NO: 257 and SEQ ID NO: 258;
SEQ ID NO: 259 and SEQ ID NO: 260; and
SEQ ID NO: 261 and SEQ ID NO: 262;
wherein detecting at least one *Y. pestis* Near Neighbor-specific SNP or SV confirms the absence of *Y. pestis*.

15. The method of claim 13, further comprising confirming the absence of *Y. pestis* by detecting at least one *Y. pestis* Near Neighbor-specific amplicon using at least one primer pair comprising a forward and reverse primer comprising a forward and reverse sequence selected from the group consisting of:

SEQ ID NO: 263 and SEQ ID NO: 264;
wherein detecting at least one *Y. pestis* Near Neighbor-specific amplicon confirms the absence of *Y. pestis*.

16. The method of claim 13, further comprising characterizing and/or subtyping *Y. pestis* in the sample by detecting at least one amplicon using at least one primer pair comprising a forward and reverse primer comprising a forward and reverse sequence selected from the group consisting of:

SEQ ID NO: 239 and SEQ ID NO: 240;
SEQ ID NO: 241 and SEQ ID NO: 242;
SEQ ID NO: 243 and SEQ ID NO: 244;
SEQ ID NO: 245 and SEQ ID NO: 246; and
SEQ ID NO: 247 and SEQ ID NO: 248.

17. The method of claim 1, wherein the one or more amplicons are generated with at least one multiplex amplification reaction; and each primer in the at least one primer pair comprises a universal tail sequence.

18. The method of claim 17, wherein the at least one amplicon is present when a locus read count of the at least one amplicon is at least 10 sequence reads covering at least 75% of a corresponding amplicon reference sequence, and the universal tail sequence for each forward and reverse primer comprises SEQ ID NO: 301 and SEQ ID NO: 303.

19. The method of claim 1, wherein the sample is a biological sample obtained from a subject and further comprising administering an effective amount of at least one antibiotic to the subject, wherein the at least one antibiotic is selected from the group consisting of a fluoroquinolone, an aminoglycoside, a glycopeptide, a lincosamide, a macrolide/ketolide, a cephalosporin, a monobactam, a nitroimidazole, a penicillin, a streptogramin, a tetracycline, and a physiologically acceptable salt, prodrug, or combination thereof.

20. The method of 19, wherein the at least one antibiotic is not a fluoroquinolone if a gyrA drug resistance SNP is detected; and/or the at least one antibiotic is not a fluoroquinolone if a parC drug resistance SNP is detected; and/or the at least one antibiotic is not a fluoroquinolone or an aminocoumarin if a gyrB drug resistance SNP is detected; and/or the at least one antibiotic is not a rifamycin if a rpoB drug resistance SNP is detected; and/or the at least one antibiotic is not a β-lactam if a penA drug resistance SNP is detected; and/or the at least one antibiotic is not a trimethoprim and sulfamethoxazole combination, co-trimoxazole, if a folM drug resistance SV is detected; and/or the at least one antibiotic is not a trimethoprim and sulfamethoxazole combination, co-trimoxazole, if a bpeT drug resistance SV is detected; and/or the at least one antibiotic is not a trimethoprim and sulfamethoxazole combination, co-trimoxazole, if a bpeS drug resistance SV is detected.

* * * * *